US008916355B2

(12) United States Patent
Anderson et al.

(10) Patent No.: US 8,916,355 B2
(45) Date of Patent: Dec. 23, 2014

(54) PAIN SIGNALING MOLECULES

(75) Inventors: David J. Anderson, Altadena, CA (US);
Xinzhong Dong, Pasadena, CA (US);
Mark Zylka, Pasadena, CA (US);
Sang-kyou Han, Arcadia, CA (US);
Melvin I. Simon, San Marino, CA (US)

(73) Assignee: California Institute of Technology, Pasadena, CA (US)

( * ) Notice: Subject to any disclaimer, the term of this patent is extended or adjusted under 35 U.S.C. 154(b) by 1179 days.

(21) Appl. No.: 11/703,062

(22) Filed: Feb. 5, 2007

(65) Prior Publication Data
US 2007/0196873 A1 Aug. 23, 2007

Related U.S. Application Data

(63) Continuation of application No. 10/957,135, filed on Sep. 30, 2004, now abandoned, which is a continuation of application No. 10/183,116, filed on Jun. 26, 2002, now abandoned, which is a continuation-in-part of application No. 09/849,869, filed on May 4, 2001, now abandoned, which is a continuation of application No. 09/704,707, filed on Nov. 3, 2000, now Pat. No. 7,691,604.

(60) Provisional application No. 60/202,027, filed on May 4, 2000, provisional application No. 60/222,344, filed on Aug. 1, 2000, provisional application No. 60/285,493, filed on Apr. 19, 2001.

(51) Int. Cl.
G01N 33/567 (2006.01)
G01N 33/50 (2006.01)
G01N 33/543 (2006.01)
C07K 14/705 (2006.01)
A61K 38/00 (2006.01)

(52) U.S. Cl.
CPC ........... C07K 14/70571 (2013.01); A61K 38/00 (2013.01); G01N 33/5082 (2013.01); G01N 33/5041 (2013.01); G01N 33/5058 (2013.01); G01N 33/54366 (2013.01); G01N 2333/726 (2013.01); G01N 2500/02 (2013.01); C07K 14/705 (2013.01)
USPC .......................................... 435/7.2; 436/501

(58) Field of Classification Search
None
See application file for complete search history.

(56) References Cited

U.S. PATENT DOCUMENTS

| 5,516,659 | A | 5/1996 | Nii et al. |
| 5,525,718 | A | 6/1996 | Ohashi et al. |
| 5,738,999 | A | 4/1998 | Segerson et al. |
| 6,228,616 | B1 | 5/2001 | Bandman et al. |
| 6,696,257 | B1 | 2/2004 | Ahmad et al. |
| 2004/0014169 | A1 | 1/2004 | Vogeli et al. |

FOREIGN PATENT DOCUMENTS

| JP | 2000-23676 | 1/2000 |
| JP | 2000-23677 | 1/2000 |
| WO | WO 99/32519 | 7/1999 |
| WO | WO 00/20455 | 4/2000 |
| WO | WO 00/20456 | 4/2000 |
| WO | WO 00/20580 | 4/2000 |
| WO | WO 00/41724 | 7/2000 |
| WO | WO 00/64928 | 11/2000 |
| WO | WO 01/16159 | 3/2001 |
| WO | WO 01/19983 A1 | 3/2001 |
| WO | WO 01/36471 A2 | 5/2001 |
| WO | WO 01/36473 | 5/2001 |
| WO | WO 01/44472 | 6/2001 |
| WO | WO 01/48015 A2 | 7/2001 |
| WO | WO 01/48188 | 7/2001 |
| WO | WO 01/48189 | 7/2001 |
| WO | WO 01/57085 A2 | 8/2001 |
| WO | WO 01/57190 | 8/2001 |
| WO | WO 01/60999 | 8/2001 |
| WO | WO 01/62788 | 8/2001 |
| WO | WO 01/62797 | 8/2001 |
| WO | WO 01/66750 | 9/2001 |
| WO | WO 01/70814 | 9/2001 |
| WO | WO 01/72838 | 10/2001 |
| WO | WO 01/74902 | 10/2001 |
| WO | WO 01/83555 | 11/2001 |
| WO | WO 01/83745 | 11/2001 |
| WO | WO 01/83748 | 11/2001 |
| WO | WO 01/85791 | 11/2001 |
| WO | WO 01/98351 | 12/2001 |
| WO | WO 02/00699 | 1/2002 |
| WO | WO 02/10387 | 2/2002 |

OTHER PUBLICATIONS

Ross et al. RTA, a candidate G protein-coupled receptor: Cloning, sequencing, and tissue distribution. Apr. 1990, P.N.A.S. 87(8):3052-3056.*
Fluhmann et al. A human orphan calcitonin receptor-like structure. Jan. 5, 1995, B.B.R.C. 206(1):341-347.*
Eva et al. Molecular cloning of a novel G protein-coupled receptor that may belong to the neuropeptide receptor family. Oct. 1990, FEBS Letters 271(1,2):81-84.*
Gantz et al. Cloning and chromosomal location of a gene (GPR18) encoding a novel seven transmembrane receptor highly expressed in spleen and testis. 1997, Genomics 42:462-466.*
Zhou et al. Molecular cloning and characterization of an adenosine receptor: The A3 adenosine receptor. Aug. 1992, P.N.A.S. 89(16):7432-7436.*

(Continued)

Primary Examiner — John Ulm
(74) Attorney, Agent, or Firm — Knobbe, Martens, Olson & Bear LLP

(57) ABSTRACT

The invention relates generally to novel genes expressed in normal but not Neurogenin-1-deficient animals. The invention relates specifically to a novel family of G protein-coupled receptors and a novel family of two-transmembrane segment proteins that are expressed in dorsal root ganglia, and a method of screening for genes specifically expressed in nociceptive sensory neurons.

10 Claims, 28 Drawing Sheets

(56) References Cited

OTHER PUBLICATIONS

Adler et al., "A Novel Family of Mammalian Taste Receptors," *Cell*, vol. 100, pp. 693-702 (2000).
Aimes et al., "Cloning, expression, and characterization of chicken tissue inhibitor metalloproteinase-2 (TIMP-2) in normal and transformed chicken embryo fibroblasts," *J. Cell. Physiol.*, 174(3):342-352 (1998).
Ambrose et al., "Genomic organization of the mouse dystrobrevin gene: Comparative analysis with the dystrophin gene," *Genomics*, 3993): 359-369 (1997).
Barnett et al., "Nucleotide sequence and predicted functions of the entire *Sinorhizobium leiloti* pSynnA megaplasmid," *Proc. Natl. Acad. Sci. U.S.A.*, 98(17);9883-9888 (2001).
Bork et al., "Sequences and topology deriving biological knowledge from genomic sequences," *Current Opinion in Structural Biology*, vol. 8, pp. 331-332 (1998).
Breitbart et al., "Complete nucleotide sequence of the fast skeletal troponin T gene," *J. Mol. Biol.*, 188(2):313-324 (1986).
Breitbart et al., "Intricate combinatorial patterns of excon splicing generate multiple regulated troponin T isoforms from a single gene," *Cell*, 41(1):67-82 (1985).
Buck et al., "A Novel Multigene Family May Encode Odorant Receptors: A Molecular Basis for Odor Recognition," *Cell*, vol. 65, pp. 175-187 (1991).
Cao et al., "Primary afferent tachykinins are required to experience moderate to intense pain," *Nature*, vol. 392, pp. 390-394 (1998).
Carninci et al., "High-efficiency full-length cDNA cloning," *Methods in enzymology*, 303: 19-44 (1999).
Caterina et al., "Impaired Nociception and Pain Sensation in Mice Lacking the Capsaicin Receptor," *Science*, vol. 288, pp. 306-313 (2000).
Caterina et al., "Sense and specificity: a molecular identity for nociceptors," *Current Opinion in Neurobiology*, vol. 9, pp. 525-530 (1999).
Caterina et al., "The capsaicin receptor: a heat-activated ion channel in the pain pathway," *Nature*, vol. 389, pp. 816-824 (1997).
Chandrashekar et al., "T2Rs Function as Bitter Taste Receptor," *Cell*, vol. 100, pp. 703-711 (2000).
Chuang et al., "A 29 kDa intracellular chloride channel p64h1 is associated with largew dense-core vesicles in rat hippocampal neurons," *J. Neurosci.*, 19(8):2919-2928 (1999).
Deguchi et al., "A novel multiple PDZ domain-containing molecule interacting with N-methyl-D-aspartate receptors and neuronal cell addhesion proteins," *J. Biol. Chem.*, 273(33):21105-21110 (1998).
Dempsey et al., "The human HNRPD locus maps to 4q21 and encodes a highly conserved protein," *Genomics*, 49(3):378-384 (1998).
Dong et al., "A diverse family of gpcrs expressed in specific subsets of nociceptive sensory neurons," *Cell*, 106(5):619-632 (2001).
Dulac et al., "A Novel Family of Genes Encoding Putative Pheromone Receptors in Mammals," *Cell*, vol. 83, pp. 195-206 (1995).
Edwards, J.C., "A novel p64-related Cl-channel: subcellular distribution and nephron segment-specific expression," *Am. J. Physiol.*, 276(3): F398-F408 (1999).
Friedel et al., "A Novel 7-Transmembrane Receptor Expressed in Nerve Growth Factor-Dependent Sensory Neurons," *Molecular and Cellular Neuroscience*, vol. 17, pp. 31-40 (2001).
Garfinkel et al., "Cloning and characterization of cDNA sequences corresponding to myosin light chains 1, 2, and 3, troponin-C, troponin-T, alpha-tropomyosin, and alpha-actin," *J. Biol. Chem.*, 257(18):11078-11086 (1982).
GenBank Database E ntry: Accession No. AY042215, "*Homo sapiens* G protein-coupled receptor (MRGX3) gene, complete cds," Dong et al., Released Sep. 14, 2001.
GenBank Database Entry: AB014605, "*Homo sapiens* mRNA for KIAA0705 protein, complete cds," Ohara et al., Feb. 6, 1999.
GenBank Database Entry: AB019373, "*Mus musculus* mRNA for ERK5, complete cds," Kamakura et al., Released Oct. 13, 1999.
GenBank Database Entry: AB020734, "*Oryzias latipes* gene for polypeptide elongation factor 1 alpha, complete cds," Kinoshita, M., Released Jun. 3, 1999.
GenBank Database Entry: AB029485, "*Mus musculus* ARIP1 mRNA for activin receptor interacting protein 1, complete cds," Shoji et al., Released Mar. 2, 2000.
GenBank Database Entry: AB032996, "*Homo sapiens* mRNA for KIAA1170 protein, partial cds," Ohara et al., Released Nov. 11, 1999.
GenBank Database Entry: AB051486, "*Homo sapiens* mRNA for KIAA1699 protein, partial cds," Ohara et al., Released Feb. 7, 2001.
GenBank Database Entry: Accession No. AF004664, "*Gallus gallus* tissue inhibitor of metalloproteinase-2 precursor (TIMP-2) mRNA, complete cds," Aimes et al., Released Sep. 28, 2001.
GenBank Database Entry: Accession No. AX099247, "Sequence 1 from Patent WO0119983," Deleersnijder et al., Released Apr. 2, 2001.
GenBank Database Entry: Accession No. AX147812, "Sequence 57 from Patent WO0136473," Vogeli et al., Released Jun. 8, 2001.
GenBank Database Entry: Accession No. AX147824, "Sequence 69 from Patent WO0136473," Vogeli et al., Released Jun. 8, 2001.
GenBank Database Entry: Accession No. AX148178, "Sequence 19 from Patent WO0136471," Chen et al., Released Jun. 8, 2001.
GenBank Database Entry: Accession No. AX148188, "Sequence 29 from Patent WO0136471," Chen et al., Released Jun. 8, 2001.
GenBank Database Entry: Accession No. AX188692, "Sequence 3 from Patent WO0148015," Lind et al., Released Aug. 8, 2001.
GenBank Database Entry: Accession No. AX188700, "Sequence 11 from Patent WO0148015," Lind et al., Released Aug. 8, 2001.
GenBank Database Entry: Accession No. AY042193, "*Mus musculus* G protein-coupled receptor (MrgA3) mRNA, complete cds," Dong et al., Released Oct. 15, 2001.
GenBank Database Entry: Accession No. AY042194, "*Mus musculus* RF-amide G protein-coupled receptor (Mrga4) mRNA, complete cds," Dong et al., Released Sep. 14, 2001.
GenBank Database Entry: Accession No. AY042197, "*Mus musculus* G protein-coupled receptor (MrgA7) gene, complete cds," Dong et al., Released Sep. 14, 2001.
GenBank Database Entry: Accession No. AY042199, "*Mus musculus* G protein-coupled receptor (MrgB1) gene, complete cds," Dong et al., Released Sep. 14, 2001.
GenBank Database Entry: Accession No. AY042213, "*Homo sapiens* G protein-coupled receptor (MRGX1) gene, complete cds,"Dong et al.; Released Sep. 14, 2001.
GenBank Database Entry: Accession No. AY042214, "*Homo sapiens* G protein-coupled receptor (MRGX2) gene, complete ods," Dong et al., Released Sep. 14, 2001.
GenBank Database Entry: Accession No. AY042216, "*Homo sapiens* G protein-coupled receptor (MRGX4) gene, complete cds,"Dong et al.; Released Sep. 14, 2001.
GenBank Database Entry: Accession No. E31936, "Seven-pass transmembrane receptor proetin ERG9," Tsuyoshi et al., Released Feb. 7, 2001.
GenBank Database Entry: Accession No. M15202, "*Rattus norvegicus* troponin T class proteins, alternatively spliced products, complete cds," Released Jun. 12, 2000.
GenBank Database Entry: Accession No. XM_004872, "*Homo sapiens* atrophin-1 interacting protein 1; activin receptor interacting protein 1 (KIAA0705), mRNA," Released Oct. 16, 2001.
GenBank Database Entry: Accession No. XM_017189, "*Homo sapiens* atrophin-1 interacting protein 1; activin receptor interacting protein 1 (KIAA070), mRNA," Releasd Oct. 16, 2001.
GenBank Database Entry: AE000874, "Methanobacteriunn thermoautotrophicum from bases 922625 to 934189 (section 80 of 148) of the complete genome," Smith, D.R., Released Nov. 15, 1997.
GenBank Database Entry: Accession No. AE004000, "*Xylella fastidiosa* 9a5c, section 146 of 229 of the complete genome," Simpson et al., Released Jun. 15, 2001.
GenBank Database Entry: AE004551, "*Pseudomonas aeruginosa* PA01, section 112 of 529 of the complete genome," Stover et al., Released Aug. 30, 2000.
GenBank Database Entry: AE007228, "*Sinorhizobium meliloti* plasmid pSymA section 34 of 121 of the complete plasmid sequence," Barnett et al., Released Aug. 15, 2001.

(56) References Cited

OTHER PUBLICATIONS

GenBank Database Entry: AF022982, "*Caenorhabditis elegans* cosmid T23B12, complete sequence," Waterson, R., Released Sep. 14, 2001.
GenBank Database Entry: AF034863, "*Rattus norvegicus* synaptic scaffolding molecule (S-SCAM) mRNA, complete cds," Hirao et al., Released Aug. 10, 1998.
GenBank Database Entry: AF038563, "*Homo sapiens* membrane associated guanylate kinase 2 (MAGI-2) mRNA, complete cds," Wood et al., Released Sep. 16, 1999.
GenBank Database Entry: AF057160, "*Homo sapiens* putative poly (ADP-ribosyl) transferase (PARPL) mRNA, complete cds," Still, I.H., Released Feb. 8, 2000.
GenBank Database Entry: AF080475, "*Homo sapiens* thyroglobulin gene, exon 39," Rivolta et al., Released May 9, 2000.
GenBank Database Entry: AF100956, "*Mus musculus* major histocompatibility locus class II region; Fas-binding protein Daxx (DAXX) gene, partial cds; Bing1 (BING1), tapasin (tapasin), RaIGDS-like factor (RFL), KE2 (KE2), BING4 (BING4), beta1,3-galactosyl transferase (beta1,3-galactosyl transferase), ribosomal protein subunit S18 (RPS18), Sacm21 (Sacm21), H2K1 (b) (H2-K1 (b)), RING1 (RING1), KE6a (KE6a), KE4 (KE4), RXRbeta (RXRbeta), collagen alpha-2 (XI) (COLA11A2), H2-) alpha (H2-Oalpha), RING3 (RING3), H2-M alpha (XI) (COLA11A2), H2-) alpha (H2-Oalpha), RING3 (RING3), H2-M alpha (H2-M alpha), H2-M beta 2 (H2-M beta2), and H2-M beta1 (H2-M beta1) genes, complete cds; and LMP2 gene, partial cds,"Rowen et al., Released Nov. 3, 1998.
GenBank Database Entry: AF109196, "*Homo sapiens* intracellular chloride channel p64H1 mRNA, complete cds," Chuang et al., Released Apr. 20, 1999.
GenBank Database Entry: AF109907, "*Homo sapiens* S164 gene, partial cds; PS1 and hypothetical protein genes, complete cds; and S171 gene, partial cds," Rowen, L., Released Dec. 23, 1998.
GenBank Database Entry: AF126159, "*Mus musculus* big MAP kinase 1a (BMK1) mRNA, alternatively spliced, complete cds," Luo et al., Released Apr. 2, 2001.
GenBank Database Entry: AF126160, "*Mus musculus* big MP kinase 1B (BMK1) mRNA, alternatively spliced, complete cds," Luo et al., Released Apr. 2, 2001.
GenBank Database Entry: AF126161, "*Mus musculus* big MAP kinase 1B(BMK1) mRNA, alternatively spliced," Luo et al., Released Apr. 2, 2001.
GenBank Database Entry: AF130819, "*Rattus norvegicus* S-SCAm beta mRNA, complete cds," Hirao et al., Released Jan. 27, 2000.
GenBank Database Entry: AF132734, "*Homo sapiens* REC8 mRNA, partial cds," Luo et al., Released May 1, 2000.
GenBank Database Entry: AF158255, "*Homo sapiens* vault protein mRNA, complete cds," Kickhoefer et al., Sep. 14, 1999.
GenBank Database Entry: AF177217, "*Canis familiaris* matrix metalloproteinase-2 (MMP-2) mRNA, partial cds," Jahic et al., Released May 4, 2000.
GenBank Database Entry: AF205032, "*Carpodacus mexicanus* Came-DAB1 and serine-threonine kinase genes, complete sequence," Hess et al., Released Sep. 25, 2000.
GenBank Database Entry: AF241798, "*Mus musculus* 2 P domain potasium channel (Kcnk3) gene, exon 2 and complete cds," Goldstein, S.A.N., Released Jul. 3, 2000.
Genbank Database Entry: AF261146, Description: NID:8547318 *Branchiostoma floride* homeoprotein (EmxA) mRNA, complete cds, Williams et al., Released Oct. 16, 2000.
GenBank Database Entry: AF319553, "*Homo sapiens* TNFRSF19L mRNA, complete cds," Sica et al., Released Jul. 25, 2001.
GenBank Database Entry: AF324792, "*Ehrlichia canis* phosphoribosylaminoimidazole carboxylase (purK) gene, complete cds; major outer membrane protein gene cluster 2, complete sequence; and u6 gene, partial cds," Ohashi et al., Released Apr. 11, 2001.

GenBank Database Entry: AF349460, "*Ovis aries* uterine milk protein gene, 5' flanking region, 5' UTR and partial cds," Fleming et al., Released May 12, 2001.
GenBank Database Entry: AF380839, "*Homo sapiens* secretory protein SEC8 mRNA, complete cds," Sha et al., Released May 28, 2001.
GenBank Database Entry: AJ005424, "*Rattus norvegicus* mRNA for BMK1/ERK5 protein, partial," Yang, C.C., Released Oct. 2, 1998.
GenBank Database Entry: AJ011907. "*Klebsiella pneumoniae* DNA sequence for transposon Tn5711, partial," Albiger et al., Released Oct. 14, 1998.
GenBank Database Entry: AK001624, "*Homo sapiens* cDNA FLJ10762 fis, clone NT2RP4000008, moderately similar to Chlorine Channel Protein P64," Isogai et al., Released Aug. 31, 2001.
GenBank Database Entry: AK011625, "*Mus Musculus* 10 days embryo cDNA, RIKEN full-length enriched library, clone:2610029P10, full insert sequence," Adachi et al., Released Jul. 5, 2001.
GenBank Database Entry: AK019862, "*Mus musculus* 11 days pregnant adult female ovary and uterus cDNA, RIKEN full-length enriched library, clone: 5031400M07, full insert sequence," Adachi et al., Released Jul. 5, 2001.
GenBank Database Entry: AK022751, "*Homo sapiens* cDNA FLJ12689 fis' clone NT2RM4002565, highly similar to *Mus musculus* Sec8 mRNA," Isogai et al., Released Sep. 29, 2000.
GenBank Database Entry: AK027688, "*Homo sapiens* cDNA FLJ14782 fis, clone NT2RP4000524, highly similar to *Mus musculus* Sec8 mRNA," Isogai et al., Released May 15, 2001.
GenBank Database Entry: AK027899, "*Homo sapiens* cDNA FLJ14993 fis, clone Y79AA1001874, weakly similar to OX40L Receptor Precursor," Isogai et al., Released May 15, 2001.
GenBank Database Entry: AL117424, "*Homo sapiens* mRNA; cDNA DKFZp566G223 (from clone DKFZp566G223); complete cds," Koehner et al., Released Mar. 10, 2001.
GenBank Database Entry: AL122012, "*Leishmania major* Friedlin chromosome 23 cosmid L8342, complete cds," Masuy et al., Released Dec. 15, 1999.
GenBank Database Entry: AL357523, "*Streptomyces coelicolor* cosmid 9C5," Cerdeno et al., Released Jun. 1, 2000.
GenBank Database Entry: AP000510, "*Homo sapiens* genomic DNA, chromosome 6p21.3, HLA Class I region, section 9/20," Hirakawa et al., Released Aug. 22, 2001.
GenBank Database Entry: AP001137, "*Homo sapiens* genomic DNA, chromosome 21q21.1-q21.2, LL56-APP region, clone: B812P3," Hattori et al., Released Jan. 26, 2001.
GenBank Database Entry: AP001278, "*Oryza sativa* genomic DNA, chromosome 1, clone: P0434D08," Sasaki et al., Released Nov. 22, 2000.
GenBank Database Entry: AP001539, "*Oryza sativa* genomic DNA, chromosome 1, clone: P0708G02," Sasaki et al., Released Jul. 28, 2000.
GenBank Database Entry: AP001667, "*Homo sapiens* genomic DNA, chromosome 21q, section 11/105," Hattor et al., Released May 30, 2000.
GenBank Database Entry: AP001681, "*Homo sapiens* genomic DNA, chromosome 21Q, section 25/105," Hattori et al., Released May 30, 2000.
GenBank Database Entry: AP001800, "*Oryza sativa* genomic DNA, chromosome 1, PAC clone: P0443E05," Sasaki et al., Released Jul. 15, 2000.
GenBank Database Entry: AP002835, "*Oryza sativa* genomic DNA, chromosome 1, PAC clone: P0417G05," Sasaki et al., Released Feb. 7, 2001.
GenBank Database Entry: AP003011, "*Mesorhizobium loti* DNA, complete genome, section 18/21," Kaneko et al., Released May 15, 2001.
GenBank Database Entry: AR001253, "Sequence 1 from patent US 5738999," Released Dec. 4, 1998.
GenBank Database Entry: AR149778, "Sequence 2 from patent US 6228616," Released Aug. 8, 2001.
GenBank Database Entry: AX147794, "Sequence 39 from Patent WO01346818," Released Jun. 8, 2001.
GenBank Database Entry: AX167357, "Sequence 1 from Patent WO0144472," Released Jul. 3, 2001.

(56) References Cited

OTHER PUBLICATIONS

GenBank Database Entry: AX188734, "Sequence 45 from Patent WO0148015," Released Aug. 6, 2001.
GenBank Database Entry: AX230115, "Sequence 2 from Patent WO0162797," Released Sep. 11, 2001.
GenBank Database Entry: AX230151, "Sequence 28 from patent W)0162797," Released Sep. 11, 2001.
GenBank Database Entry: AX233369, "Sequence 12 from patent WO0162788," Released Sep. 11, 2001.
GenBank Database Entry: AY042195, "*Mus musculus* G protein-coupled receptor (MrgA5) gene, complete cds," Dong et al., Released Sep. 14, 2001.
GenBank Database Entry: AY042198, "*Mus musculus* G protein-coupled receptor (MrgA8) gene, complete cds," Dong et al., Released Sep. 14, 2001.
GenBank Database Entry: AY042210, "*Mus musculus* G protein-coupled receptor (MrgE) gene, complete cds," Dong et al., Released Sep. 14, 2001.
GenBank Database Entry: BC002058, "*Mus musculus*, Similar to zinc finger protein 101, clone MGC:6101 Image: 3593763, mRNA, complete cds," Strausberg, R., Released Jul. 12, 2001.
GenBank Database Entry: BC007404, "*Homo sapiens*, Similar to mitogen-activated protein kinase 7, clone MGC:2148 Image:3009873, mRNA, complete cds," Strausberg, R., Released Jul. 12, 2001.
GenBank Database Entry: BC009963, "*Homo sapiens*, mitogen-activated protein kinase 7, cline MGC:15371 Image:4300124, mRNA, complete cds," Strausberg, R., Released Jul. 12, 2001.
GenBank Database Entry: BC010610, "*Homo sapiens*, clone Image:4214515, mRNA, partial cds," Strausberg, R., Released Jul. 12, 2001.
GenBank Database Entry: BC012444, "*Homo sapiens*, Similar to chloride intracellular channel 4, clone MGC: 8812 Image: 3861372, mRNA, complete cds," Strausberg, R., Released Aug. 20, 2001.
GenBank Database Entry: BC013201, "*Homo sapiens*, Similar to chromosome 6 open reading frame 31, clone MGC:18030 Image:3924575, mRNA, complete cds," Strausberg, R., Released Aug. 29, 2001.
GenBank Database Entry: D16817, "*Rattus norvegicus* mRnA for metabotropic glutamate receptor mGluR7, complete cds," Okamoto, N., Released Feb. 1, 2000.
GenBank Database Entry: D79999, "*Homo sapiens* mRNA for KIAA0177 protein, parital cds," Ohara et al., Released Oct. 6, 2001.
GenBank Database Entry: E05718, "Asparaginilendopeptidase gene," Released Sep. 29, 1997.
GenBank Database Entry: E31933, Seven-pass transmembrane receptor protein ERG5, Released Feb. 7, 2001.
GenBank Database Entry: L19109, "*Rattus noregicus* (clone R2(CT1)) heparin-binding fibroblast growth factor receptor 2 (intracellular domain) mRNA, 3' end," released Jun. 26, 1996.
GenBank Database Entry: L19110., "Rat (clone R2(CT2)) heparin-binding fibroblast growth factor receptor 2 (intracellular domain) mRNA, 3'end," Released Aug. 26, 1993.
GenBank Database Entry: I20815, "Sequence 10 from patent US 5,516,659," Released Oct. 7, 1996.
GenBank Database Entry: I22095, "Sequence 11 from patent US 5525718," Released Oct. 7, 1996.
GenBank Database Entry: LMFP265, "*Leishmania major* Friedlin chromosome 13 PAC P265," Robben et al., Released Sep. 4, 2001.
GenBank Database Entry: M21027, "*Ovis aries* uterine milk protein precursor a mRNA, complete cds," Released Oct. 20, 2000.
GenBank Database Entry: NC_000868, "*Pyrococcus abyssi*, complete genome," Released Jul. 9, 2001.
GenBank Database Entry: NC_000916, "Methanobacterium thermoautotrophicum delta H complete genome," Released Sep. 19, 2001.
GenBank Database Entry: NM_001949, "*Homo sapiens* transcription factor 3 (E2F3) mRNA, complete cds," Released Feb. 6, 2001.
GenBank Database Entry: NM_002138, "*Homo sapiens* heterogeneous nuclear ribonucleoprotein D (AU-rich element RNA-binding protein 1, 37kD) (HNRPD), transcript variant 3, mRNA," Released May 16, 2001.
GenBank Database Entry: NM_002138, "*Homo sapiens* heterogeneous nuclear ribonucleoprotein D (AU-rich element RNA-binding protein 1, 37kD) (HNRPD), transcript variant 3, mRNA)," Released May 16, 2001.
GenBank Database Entry: NM_002377, "*Homo sapiens* MAS1 oncogene (MAS1), mRNA," Released Oct. 31, 2000.
GenBank Database Entry: nm_006437, "*Homo sapiens* ADP-ribosyltransferase (NAD+; poly (ADP-ribose) polymerase)-like 1 (ADPRTL1), mRNA," Released Feb. 3, 2001.
GenBank Database Entry: NM_006765, "*Homo sapiens* Putative prostate cancer tumor suppressor (N33), mRNA," Released Nov. 2, 2000.
GenBank Database Entry: NM_012508, "*Rattus norvegicus* ATPase isoform 2. NA+K+ transporting, beta polypeptide 2 (Atp2b2), mRNA," Released Nov. 1, 2000.
Genbank Database Entry: NM_014287, "*Homo sapiens* pM5 protein (PM5), mRNA," Released Nov. 2, 2000.
GenBank Database Entry: NM_031369, "*Homo sapiens* heterogeneous nuclear ribonucleoprotein D (AU-rich element RNA-binding protein 1, 37kD) (HNRPD), transcript variant 2, mRNA," Released May 16, 2001.
GenBank Database Entry: NM_031370, "*Homo sapiens* heterogeneous nuclear ribonucleoprotein D (AU-rich element RNA-binding protein 1, 37 kD) (HNRPD), transcript variant 1, mRNA," Released May 16, 2001.
GenBank Database Entry: NM_032975, "*Homo sapiens* dystrobrevin, alpha (DTNA), transcript variant alpha, mRNA," Released Jul. 19, 2001.
GenBank Database Entry: NM_032980, "*Homo sapiens* dystrobrevin, alpha (DTNA), transcript variant alpha, mRNA," Released Jul. 19, 2001.
GenBank Database Entry: U25278, "Human ERK5 mRNA, complete cds," Zhou, G., Released Nov. 16, 1995.
GenBank Database Entry: U29725, "Human BMK1 alpha kinase mRNA, complete cds," Lee et al., Released Dec. 5, 1995.
GenBank Database Entry: U29726, "Human BMK1 beta kinase mRNA, complete cds," Lee et al., Released Dec. 5, 1995.
GenBank Database Entry: U29727, "Human BMK1 gamma kinase mRNA, complete cds," Lee et al., Released Dec. 5, 1995.
GenBank Database Entry: X56192, "*D. discoideum* mRNA for ribosomal acidic phosphoprotein P2," Coloma, A., Released Mar. 20, 1991.
GenBank Database Entry: X57398, "Human mRNA for pM5 protein," Templeton, N.S., Released Sep. 26, 2001.
GenBank Database Entry: XM_008323, "*Homo sapiens* mitogen-activated protein kinase 7 (MAPK7), mRNA," Released Oct. 16, 2001.
GenBank Database Entry: XM_010013, "*Homo sapiens* E1A binding protein p300 (EP300), mRNA," Released Oct. 16, 2001.
GenBank Database Entry: XM_012279, "*Homo sapiens* ADP-ribosyltransferase (Nad+; poly (ADP-ribose) polymerase)-like 1 (ADPRTL1), mRNA," Released Oct. 16, 2001.
GenBank Database Entry: XM_012584, "*Homo sapiens* hypothetical gene supported by X57398; NM_014287 (LOC95345), mRNA," Released Aug. 27, 2001.
GenBank Database Entry: XM_016735, "*Homo sapiens* hypothetical protein FLJ21736 (FLJ21736), mRNA," Released Oct. 16,2001.
GenBank Database Entry: XM_027247, "*Homo sapiens* PM5 protein (PM5), mRNA.," Released Oct. 16, 2001.
GenBank Database Entry: XM_027359, "*Homo sapiens* hypothetical gene supported by NM_014287," Released Oct. 16, 2001.
GenBank Database Entry: XM_035133, "*Homo sapients* hypothetical protein FLJ14993, mRNA," Released Oct. 16, 2001.
GenBank Database Entry: XM_037487, "*Homo sapiens* similar to poly (AdP-ribosyl) transferase-like 1; H5 proline-rich; PARP-related;I-alpha-I-related; vault protein, 193-kDa; poly (ADP-ribose) synthetase (*H. sapiens*) (LOC95103), mRNA," Released Aug. 27, 2001.

(56) References Cited

OTHER PUBLICATIONS

GenBank Database Entry: XM_037847, "*Homo sapiens* neurexophilin 3 (NXPH3), mRNA," Released Oct. 16, 2001.
GenBank Database Entry: XM_041759, "*Homo sapiens* corneodesmosin (CDSN), mRNA," Released Aug. 27, 2001.
GenBank Database Entry: XM_043815, "*Homo sapiens* hypothetical protein FLJ21736 (FLJ21736), mRNA," Released Oct. 16, 2001.
GenBank Database Entry: XM_045046, "*Homo sapiens* mitogen-activated protein kinase 7 (MAPK7), mRNA," Released Oct. 16, 2001.
GenBank Database Entry: XM_045047, "*Homo sapiens* mitogen-activated protein kinase 7 (MAPK7), mRNA," Released Oct. 16, 2001.
GenBank Database Entry: XM_045048, "*Homo sapiens* mitogen-activated protein kinase 7 (MAPK7), mRNA," Released Oct. 16, 2001.
GenBank Database Entry: XM_050246, "*Homo sapiens* secretory protein SEC8 (SEC8), mRNA," Released Aug. 27, 2001.
GenBank Database Entry: XM_052950, "*Homo sapiens* mitogen-activated protein kinase 7 (MAPK7), mRNA," Released Oct. 16, 2001.
GenBank Database Entry: XM_053380, "*Homo sapiens* similar to poly (ADP-ribosyl) transferase-like 1; H5 proline-rich; PARP-related; I-alpha-I-related; vault potein, 193-kDa; poly (ADP-ribose) synthetase (*H. sapiens*) (LOC95103), mRNA," Released Aug. 27, 2001.
GenBank Database Entry: XM_054516, "*Homo sapiens* similar to dystrobrevin, alpha (*H. sapiens*)," Released Aug. 28, 2001.
GenBank Database Entry: XM_054519, "*Homo sapiens* similar to dystrobrevin, alpha (*H. sapiens*)," Released Aug. 28, 2001.
GenBank Database Entry: Y15484, "*Canis familiaris* gene encoding retinal guanylate cyclase E," Veske, A., Released Jul. 17, 1998.
GenBank Database Entry: Z50046, "*S. cerevisiae* chromosome IV cosmid 8358," Barrell et al., Released Aug. 11, 1997.
GenBank Database Entry: Z83820, "Human DNA sequence from PAC 215K18 on chromosome X contains ESTs, and STS," Mistry, S., Released Nov. 23, 1999.
GenBank Database Entry: Z84470, "Human DNA sequence from PAC 411B6 on chromosome X," Bird, C., Released Nov. 23, 1999.
GenBank Database Entry: Z84816, "Human DNA sequence from PAC 2A2 on chromosome X contains ESTs," Deadman, R., Released Nov. 23, 1999.
GenBank Database Entry: Z98682, "*Bacillus subtilis* genomic DNA 23.9kB fragment," Glaser et al., Released Aug. 19, 1997.
GenBank Database Entry: Z99111, "*Bacillus subtilis* complete genome (section 8 of 21): from 1394791 to 1603020," Kunst et al., Released Nov. 26, 1997.
GenBank Database Entry: AX188730, "Sequence 41 from Patent WO0148015," Released Aug. 8, 2001.
GenBank Database Entry: E31931, "Seven-pass transmembrane receptor protein ERG5," Released Febuary 7, 2001.
GenBank Database Entry: E31932, "Seven-pass transmembrane receptor protein ERG5," Released Feb. 7, 2001.
GenBank Database Entyr: L11748, "*Methanobacterium thermoautotrophicum* methyl coenzyme M reductase system component A2 gene, complete cds," Released Jun. 12, 1993.
GenBank DatabaseEntry: NC_001136, "*Saccharomyces cerevisiae* chromosome IV, complete chromosome sequence," *Saccharomyces* Genome Database, Released Nov. 3, 2001.
GenBank Databse Entry: AF097330, "*Homo sapiens* H1 chloride channel mRNA, complete cds," Edwards, J.C., Released Jun. 14,1999.
GenBankd Database Entry: XM_045907, "*Homo sapiens* KIAA1170 protein (KIAA1170), mRNA," Released Oct. 16, 2001.
Goffeau et al., "Life with 6000 genes," *Science*, 274(5287):546 (1996).
Gonzalez et al., "Characterization of Gene Expression in Human Trabecular Meshwork Using Single-Pass Sequencing of 1060 Clones," *IOVS*, vol. 41, No. 12, pp. 3678-3693 (2000).

Gouardères et al, "Dual Localization of Neuropeptide FF Receptors in the Rat Dorsal Horn," *Synapse*, vol. 35, pp. 45-52 (2000).
Han et al., "Orphan G protein-coupled receptors MrgA1 and MrgC11 are distinctively activated by RF-amide-related peptides through the $G\alpha_{q/11}$ pathway," *PNAS*, vol. 99, No. 23, pp. 14740-14745 (Nov. 12, 2002).
Hattori et al., "The DNA sequence of human chromosome 21. The chromosome 21 mapping and sequencing consortium," *Nature*, 405(6784):311-319 (2000).
Hess et al., "MHC class II pseudogene and genomic signature of a 32-kb cosmid in the house finch (*Carpodacus mexicanus*)," *Genome Res.*, 10(5): 613-623 (2000).
Hinuma et al., "New neuropeptides containing carboxy-terminal RF amide and their receptor in mammals," *Nature Cell Biology*, vol. 2, pp. 703-708 (2000).
Hirao et al., "Three isoforms of synaptic scaffolding molecule and their characterization. Multimerization between the isoforms and their interaction with N-methyl-D-aspartate receptors and SAP90/PSD-95-associated protein," *J. Biol. Chem.*, 275(4):2966-2972 (2000).
Hirosawa et al., "Characterization of cDnA clones selected by the GeneMark analysis from size-fractionated cDNA libraries from human brain," *DNA Res.*, 6(5):329-33 (1999).
Howard et al., "Orphan G-protein-coupled receptors and natural ligand discover," *Trends in Pharmacological Sciences*, vol. 22, No. 3, pp. 132-140 (Mar. 3, 2001).
Hunt et al., "The Molecular Dynamics of Pain Control," *Nature Reviews*, vol. 2, pp. 83-91 (2001).
Ing and Roberts, "The major progesterone-modulated proteins secreted into the sheep uterus are members of the serpin superfamily of serine protease inhibitors," *J. Biol. Chem.*, 264(6): 3372-3379 (1989).
Ishii et al., "The FEZ1 gene at chromosome 8p22 encodes a leucine-zipper protein, and its expression is altered in multiple human tumors," *Proc. Natl. Acad. Sci. U.S.A.*, 96(7):3928-3933 (1999).
Ishikawa et al., "The complete sequences of 100 new cDNA clones from brain which can code for large proteins in vitro," *Journal DNA Res.*, 5 (3):169-176 (1998).
Ivens et al., "A physical map of the *Leishmania major* Friedlin genome," *Genome Res.*, 8(2):135-145 (1998).
Jackson et al., "The mas oncogene encodes an angiotensin receptor," *Nature*, vol. 335, pp. 437-440 (1988).
Jackson et al., "The mas oncogene encodes an angiotensin receptor," *Nature*, 335(6189):437-440 (1988).
Jacq et al., "The nucleotide sequence of *Saccharyomyces cerevisiae* chromosome IV," *Nature*,387(6632 Suppl):75-78 (1997).
Jean et al., "The nuclear protein PH5P of the inter-alpha-inhibitor superfamily: a missing link between poly (ADP-ribose) polymerase and the inter-alpha-inhibitor family and a novel actor of DNA repair?," *FEBS Lett.*, 446(1):6-8 (1999).
Kajita et al., "The UUAG-specific RNA binding protein, heterogeneous nuclear ribonucleoprotein D0. Common modular structure and binding properties of the x2RBD-Gly family," *J. Biol. Chem.*, 270(38):22167-22175 (1995).
Kamakura et al., "Activation of the protein kinase ERK5/BMK1 by receptor tyrosine kinases. Identification and characterization of a signaling pathway to the nucleus," *J. Biol. Chem.*, 274(37):26563-26571 (1999).
Kaneko et al., "Complete genome structure of the nitrogen-fixing symbiotic bacterium *Mesorhizobium loti*," *DNA Res.*, 7(6):331-338 (2000).
Khurana et al., "(CA) repeat polymorphism in the chromosome 18 encoded dystrophin-like protein," *Hum. Mol. Genet.*, 3950; 841 (1994).
Kickhoefer et al., "The 193-kD vault protein, VDARP, is a novel poly (ADP-ribose) polymerase," *J. Cell Biol.*, 146(5): 917-928 (1999).
Kiledjian et al., "Identification of AUF1 (heterogeneous nuclear ribonucleoprotein D) as a component of the alpha-globin mRNA stability complex," *Mol. Cell. Biol.*, 17(8):4870-4876 (1997).
Kress, M. et al., "Capsaicin, protons and heat: new excitement about nociceptors," *TiPS*, vol. 20, pp. 112—(1999).
Kunst et al., "The complete genome sequence of the gram-positive bacterium *Bacillus subtilis*," *Nature*, 390 (6657):249-256 (1997).

(56) References Cited

OTHER PUBLICATIONS

Lee et al., "Primary structure of BMK1: a new mammalian map kinase," *Biochem. Biophys. Res. Commun.*, 213(2):715-724 (1995).

Lees et al., "The retinoblastoma protein binds to a family of E2F transcription factors," *Mol. Cell. Biol.*, 13(12):7813-7825 (1993).

Lembo et al., "Proenkephalin A gene products activate a new family of sensory neuron-specific GPCRs," *Nature Neuroscience*, vol. 5, No. 3, pp. 201-209 (Mar. 2002).

Loftus et al., "Genome duplications and other features in 12 Mb of DNA sequence from human chromosome 16p and 16q," *Genomics*, 60(3): 295-308 (1999).

Lopes et al., "Roton block and voltage gating are potassium-dependent in the cardiac leak channel kcnk3," *J. Biol. Chem.*, 275(22):16969-16978 (2000).

Ma et al., "NEUROGENIN1 and NEUROGENIN2 control two distinct waves of neurogenesis in developing dorsal root ganglia," *Genes & Development*, vol. 13, pp. 1717-1728 (1999).

MacGrogan et al., "Structure and methylation-associated silencing of a gene within a homozygously deleted region of human chromosome band 8p22," *Genomics*, 3591):55-65 (1996).

Malmberg et al., "Preserved Acute Pain and Reduced Neuropathic Pain in Mice Lacking PKCγ," *Science*, vol. 278, pp. 279-283 (1997).

Marchese et al., "Novel GPCRs and their endogenous ligands: expanding the boundaries of physiology and pharmacology," *TiPS* 20: 370-375 (1999).

Matsunami et al., "A family of candidate taste receptors in human and mouse," *Nature*, vol. 404, pp. 601-604 (2000).

Matsunami et al., "A Multigene Family Encoding a Diverse Array of Putative Pheromone Receptors in Mammals," *Cell*, vol. 90, pp. 775-784 (1997).

Medford et al., "A novel mechanism of alternative RNA splicing for the developmentally regulated generation of troponin T isoforms from a single gene," *Cell*, 28(2):409-421 (1984).

Metzinger et al., "Dystrobrevin deficiency at the sarcolemma of patients with muscular dystrophy," *Hum. Mol. Genet.*, 6(7):1185-1191 (1997).

Michael et al., "Differential Expression of the mRNA for the Vanilloid Receptor Subtype 1 in Cells of the Adult Rat Dorsal Root and Nodose Ganglia and Its Downregulation by Axotomy," *The Journal of Neuroscience*, vol. 19, No. 5, pp. 1844-1854 (1999).

Monnot et al., "Cloning and Functional Characterization of a Novel mas-Related Gene, Modulating Intracellular Angiotensin II Actions," *Molecular Endocrinology*, vol. 5, No. 10, pp. 1477-1487 (1991).

Nagase et al., "Predication of the coding sequences of unidentified human genes. V. The coding sequences of 40 new genes (KIAA0161-KIAA0200) deduced by analysis of cDNA clones from human cell line KG-1," *DNA Res.*, 3(1):17-24 (1996).

Nagase et al., "Predictin of the coding sequences of unidentified human genes. XIX. The complete sequences of 100 new cDNA clones from brain which code for large proteins in vitro," *DNA Res.*, 7(6):347-355 (2000).

Newey et al., "Alternative splicing of dystrobrevin regulates the stoichiometry of syntrophin binding to the dystrophin protein complex," *Curr. Biol.*, 10(20): 1295-1298 (2000).

Ohashi et al., "Analysis of Transcriptionally Active Gene Clusters of Major Outer Membrane Protein Multigene Family in *Ehrlichia canis* and *E. chaffeensis*," *Infect. lnnmun.*, 69(4): 2083-2091 (2001).

Ohashi et al., "Cloning and characterization of nnultigenes encoding the immunodominant 30-kilodalton major outer membrane proteins of *Ehrlichia canis* and application of the recombinant protein for serodiagnosis," *J. Clin. Microbiol.*, 36(9): 2671-2680 (1998).

Okatmoto et al., "Molecular characterization of a new metabotropic glutamate receptor mGluR7 coupled to inhibitory cyclic Amp signal transduction," *J. Biol. Chem.*, 269(2): 1231-1236 (1994).

Ozawa et al., "From dystrophinopathy to sarcoglycanopathy: evolution of a concept of muscular dystrophy," *Muscle Nerve*, 21(4): 421-438 (1998).

Panula et al., "Neuropeptide FF and modulation of pain," *Brain Research*, vol. 848, pp. 191-196 (1999).

Pierce et al., "Differential activities of E2F family members: unique functions in regulating transcription," *Mol. Carcinog.*, 22(3):190-198 (1998).

Price et al., "Structure of a Molluscan Cardioexcitatory Neuropeptide," *Science*, vol. 197, pp. 670-671 (1977).

Prieto et al., "Nucleotide sequence of a cNDA encoding acidic ribosomal phosphoprotein P2 in *Dictyostelium discoideum*," *Nucleic Acids Res.*, 19(6);1341 (1991).

Qiufu et al., "NEUROGENIN1 and NEUROGENIN2 control two distinct waves of neurogenesis in developing dorsal root ganglia," *Genes & Development* 13: 1717-1728 (1999).

Rabin et al., "Human ros1 and mas1 oncogenes located in regions of chromosome 6 associated with tumor-specific rearrangements," *Oncogene Res.*, 1(2):169-178 (1987).

Redenbach et al., "A set of ordered cosmids and a detailed genetic and physical map for the 8 Mb *Streptomyces coelicolor* A3 (2) chromosome," *Mol. Microbiol*, 21(1): 77-96 (1996).

Riesewijk et al., "The MAS proto-oncogene is not imprinted in humans," *Genomics*, 35(2):380-382 (1996).

Ross et al., "RTA, a candidate G protein-coupled receptor: Cloning, sequencing, and tissue distribution," *Proc. Natl. Acad. Sci. USA*, vol. 87, pp. 3052-3056 (1990).

Sadoulet-Puccio et al., "Cloning and characterization of the human homologue of a dystrophin related phosphoprotein found at t he Torpedo electric organ post-synaptic membrane," *Hum. Mol. Genet.*, 5(4):489-498 (1996).

Sadoulet-Puccio et al., "The genomic organization of human dystrobrevin," *Neurogenetics*, 1(1): 37-42 (1997).

Shibata et al., "RIKEN integrated sequence analysis (RISA) system—384-format sequencing pipeline with 384 multicapillary sequencer," *Genome research*, 10(11):1757-1771 (2000).

Shoji et al., "Identification and characterization of a PDZ protein that interacts with activin type II receptors," *J. Biol. Chem.*, 275(8):5485-5492 (2000).

Shull et al., "Molecular cloning of two isoforms of the plasma membrane $Ca^{2+}$-transporting ATPase frm rat brain. Structural and functional domains exhibit similarity to $Na^+,K^+$- and other cation transport ATPases," *J. Biol. Chem.*, 263(18):8646-8657 (1988).

Sica et al., "RELT, a new member of the tumor necrosis factor receptor superfamily, is selectively expressed in hematopoietic tissues and activates transcription factor NF-kappaB," *Blood*, 97(9):2702-2707 (2001).

Simpson et al., "The genome sequence of the plant pathogen *Xylella fastidiosa*. The *Xylella fastidiosa* consortium of the Organization for Nucleotide Sequencing and Analysis," *Nature*, 406(6792):151-157 (2000).

Skolnick et al., "From genes to protein structure and function: novel applications of computational approaches in the genomic era," *TIBTECH*, vol. 18, pp. 34-39 (Jan. 2000).

Smith et al., "Complete genome sequence of *Methanobacterium thermoautotrophicum* detlaH: functional analysis and comparative genomics," *J. Bacteriol.*, 179(22):7135-7155 (1997).

Snider et al, "Tackling Pain at the Source: New Ideas about Nociceptors," *Neuron*, vol. 20, pp. 629-632 (1998).

Still et al., "Identification of a novel gene (ADPRTL1) encoding a potential Poly (ADP-ribosyl) transferase protein," *Genomics*, 62(30: 533-536 (1999).

Stover et al., "Complete genome sequence of *Pseudomonas aeruginosa* PA01, an opportunistic pathogen," *Nature*, 406(6799):959-964 (2000).

Straub et al., "Muscular dystrophies and the dystrophin-glycoprotein complex," *Curr Opin Neurol*, 10(2): 168-175 (1997).

Stucky et al., "Isolectin $B_4$- Positive and -Negative Nociceptors Are Functionally Distinct," *The Journal of Neuroscience*, vol. 19, No. 5, pp. 6497-6505 (1999).

Templeton et al., "Cloning and characterization of a novel human cDnA that has DNA homology to conserved regions of the collagenase gene family," *Genomics*, 12(1):175-6 (1992).

The *C. elegans* Sequencing Consortium, "Genome sequence of the nematode *C. elegans*: a platform for investigating biology," *Science*, 282(5396):2012-2018 (1998).

(56) References Cited

OTHER PUBLICATIONS

The RIKEN Genome Exploration Research Group Phase II Team and the FANTOm Consortium, "Functional annotation of a full-length mouse cDNA collection," *Nature*, 409: 685-690 (2001).

Tominaga et al., "The Cloned Capsaicin Receptor Integrates Multiple Pain-Producing Stimuli," *Neuron*, vol. 21, pp. 531-543 (1998).

Troemel et al., "Divergent Seven Transmembrane Receptors Are Candidate Chemosensory Receptors in C. elegans," *Cell*, vol. 83, pp. 207-218 (1995).

Van Soest et al., "A locus for autosomal recessive *Pseudoxanthoma elasticum*, with penetrance of vascular symptoms in carriers, maps to chromosome 16p13.1," *Genome Res.*, 7(8): 830-834 (1997).

Veske, A., "Organization of the canine gene encoding the E isoform of retinal guanylate cyclase (cGC-E) and exclusion of its involvement in the inherited retinal dystrophy of the Swedish Briard and Briard-beagle dogs," *Biochim. Biophys. Acta*, 1372 (1): 69-77 (1998).

Vilim et al., "Gene for Pain Modulatory Neuropeptide NPFF: Induction in Spinal Cord by Noxious Stimuli," *Molecular Pharmacology*, vol. 55, pp. 804-811 (1999).

Wagner et al., "Localization and physical mapping of genes encoding the A+U-rich element RNA-binding protein AUF1 to human chromosomes 4 and X," *Genomics*, 34(2):219-222 (1996).

Wagner et al., "Structure and genomic organization of the human AUF1 gene: alternative pre-mRNA splicing generates four protein isoforms," *Genomics*, 48(2):195-202 (1998).

Wiemann et al., "Toward a Catalog of Human Genes and Proteins: Sequencing and Analysis of 500 Novel Complete Protein Coding Human cDNAs," *Genome Res.*, 11(3): 422-435 (2001).

Williams et al., "An Amphioxus Emx Homeobox Gene Reveals Duplication During Vertebrate Evolution," *Mol. Biol. Evol.*, 17(10): 1520-1528 (2000).

Wood et al., "Atrophin-1, the DRPLA gene product, interacts with two families of WW domain-containing proteins," *Mol. Cell. Neurosci.*, 11(3):149-160 (1998).

Xu et al., "Effects of (1DMe) NPYF, a synthetic neuropeptide FF analogue, in dfferent pain models," *Peptides*, vol. 20, pp. 1071-1077 (1999).

Yan et al., "Exon skipping causes alteration of the COOH-terminus and deletion of the phospholipase C gamma 1 interaction site in the FGF receptor 2 kinase in normal prostate epithelial cells," *Biochem. Biophys. Res. Commun.*, 194(1): 512-518 (1993).

Yan et al., "Molecular cloning of mouse ERK5/BMK1 splice variants and characterization of ERK5 functional domains," *J. Biol. Chem.*, 276(14);10870-10878 (2001).

Yan et al., "Two-amino acid molecular switch in an epithelial morphogen that regulates binding to two distinct receptors," *Science*, vol. 290, pp. 523-527 (Oct. 20, 2000).

Yang et al., "Interaction of mycoyte enhancer factor 2 (MEF2) with a mitogen-activated protein kinase, ERK5/BMK1," *Nucleic Acids Res.*, 26(20): 4771-4777 (1998).

Yoshida et al., "Biochemical evidence for association of dystrobrevin with the sarcoglycan-sarcospan complex as a basis for understanding sarcoblycanopathy," *Hum. Mol. Genet.*, 9(7):1033-1040 (2000).

Young et al., "Isolation and Characterization of a New Cellular Oncogene Encoding a Protein with Multiple Potential Transmembrane Domains," *Cell*, vol. 45, pp. 711-719 (1986).

Young et al., "Isolation and characterization of a new cellular oncogene encoding a protein with multiple potential transmembrane domains," *Cell*, 45(5):711-710 (1986).

Zhang et al., "Purification, characterization, and cDNA cloning of an AU-rich element RNA-binding protein, AUF1," *Mol. Cell. Biol.*, 13(12):7652-7665 (1993).

Zhou et al., "Components of a new human protein kinase signal transduction pathway," *J. Biol. Chem.*, 270(21):12665-12669 (1995).

Bennett et al., "A Distinct Subgroup of Small DRG Cells Express GDNF Receptor Components and GDNF Is Protective for These Neurons after Nerve Injury," *J. Neuroscience*, 18:3059-3072 (1998).

Boucher et al. "Potent Analgesic Effects of GDNF in Neuropathic Pain States," *Science*, 290:124-127 (2000).

Petruska et al. "Subclassified acutely dissociated cells of rat DRG: histochemistry and patterns of capsaicin-, proton-, and ATP-activated currents," *J. Neurophysiology*, 84:2365-2379 (2000).

Vulchanova et al. "Cytotoxic targeting of isolectin IB4-binding sensory neurons," *Neuroscience*, abstract, 108:143-155 (2001).

Walker, Astra Zeneca presentation at IBC G-protein coupled receptor conference. San Diego, CA, Oct. 14-16, 2002.

Crozier et al., "MrgD activation inhibits KCNQ/M-Currents and contributes to enhanced neuronal excitability," *J. Neurosci.*, 2007, 27(16):4492-4496.

Rau et al., "Mrgprd enhances excitability in specific populations of cutaneous murine polymodal nociceptors," *J. Neurosci.*, 2009, 29:8612-8619.

* cited by examiner

```
mrg3      LCPIWYHCHRPEHTSTVMCAVIWVLSLLICILNSYFCGFLNTQYKNENGCLALNFFTAAYLMLFVVLCLSSLALVA
mrg4      LCPIWYHCHRPEHTSTVMCAVIWVLSLLICILNSYFCGFLNTQYKNENGCLALNFFTAAYLMLFVVLCLSSLALLA
mrg5      LCPIWYHCRRPEHTSTVMCAAIWVLSLLICILDGYFCGYLDNHYFNYSVCQAWDIFIGAYPMFLFVVLCLSTLALLA
mrg6      LCPIWYHCRRPEHTSTVMCAVIWVLSLLICILDGYFCGYLDNHYFNYSVCQAWDIFIGAYPMFLFVVLCLSSLALVA
mrg7      LCPTWYHCRPVHTSTVMCAVIWVLSLLICILNSYFCGFLNTQYKNENGCLALSFFTAAYLMLFVVLCLSSLALLA
mrg8      LCPIWYHCHRPEHTSTIMCVVIWVLSLLICILNRYFCDLFGPKYEINSVCQASEFFIRIYPIFLFVVLCFSTLTLLA
Human1    LWPIWYRCHRPTHLSAVVCVLLWALSLLRSILEWMLCGFLFSGA-DSAWCQTSDFITVAWLIFLCVVLCGSSLVLLI
Human2    LWPIWYRCRRPRHLSAVVCVLLWALSLLLSILEGKFCGFLFSDG-DSGWCQTFDFITAAWLIFLFMVLCGSSLALLV mrg3      RLFCGTGQIKLTRLYVTIMLSILVFLLCGLPFGIHWFLLFKIKDDFHVFDLGFYLASVVLTAINSCANPIIYFFVG
mrg4      RLFCGAGQMKAYQFHVTTLLLFLVTIMLTVIMLTVLVFLLCGLPIAIYCFLLFKIKGDEHVLDVNLYLALEVLTAINSCANPIIYFFVG
mrg5      RLFCGARNMKFTRLFVTIMLTVIMLTVLVFLLCGLPWGITWFLLFWIAPGVFVPDYSPLL---VLTAINSCANPIIYFFVG
mrg6      RLFCGARNMKFTRLFVTIMLTVIMLTVLVFLLCGLPWGITWFLLFWIAPGVFVLDYSPLL---VLTAINSCANPIIYFFVG
mrg7      RLFCGAGQMKLTRFHVTILLTLLVFLLCGLPFVIYCILLFKIKDDFHVLDVNLYLALEVLTAINSCANPIIYFFVG
mrg8      RLFCGAGKKKFTRLFMTIMVTILLFLLCGLPFGIQFFLFIWWLLPWIEGGFSILDYRFFLASLVLTAINSCANPIIYFFVG
human1    RILCGSRKIPLTRLYVTILLTLLTVLVFLLCGLPFGIQFFLFIMIHVDREVLFCHVHLVSIFLSALNSSANPIIYFFVG
human2    RILCGSRGLPLTRLYLTILLTVLVFLLCGLPFGIQWFLIIMWKDSDVLFCHIHPVSVVLSSLNSSANPIIYFFVG
```

| | | | | | | |
|---|---|---|---|---|---|---|
| mrg3  | S | K | S | E | P | |
| mrg4  | N | K | A | E | P | |
| mrg5  | N | K | A | E | P | |
| mrg8  | S | K | A | E | P | |
| mrg9  | N | I | P | K | P | |
| mrg10 | N | K | A | E | L | |
| mrg11 | I | K | A | E | Q | |
| mrg12 | S | K | A | E | P | |

```
mrg3   S K S E P
mrg4   N K A E P
mrg5   S K A E P
mrg8   N I P K E
mrg9   N K A E P
mrg10  I K A E Q
mrg11  S L
mrg12  S K A E P
```

PAIN SIGNALING MOLECULES

This application claims priority under 35 U.S.C. §120 as a continuation of U.S. patent application Ser. No. 10/957,135, filed Sep. 30, 2004 now abandoned, which in turn is a continuation of U.S. patent application Ser. No. 10/183,116, filed Jun. 26, 2002 now abandoned, which in turn is a continuation-in-part of U.S. patent application Ser. No. 09/849,869, filed May 4, 2001 now abandoned, which is a continuation of U.S. patent application Ser. No. 09/704,707, filed Nov. 3, 2000 now U.S. Pat. No. 7,691,604 and under 35 U.S.C. §119(e) to U.S. Provisional Applications 60/202,027, filed May 4, 2000, 60/222,344, filed Aug. 1, 2000, and 60/285,493, filed Apr. 19, 2001, which are herein incorporated by reference in their entirety.

BACKGROUND OF THE INVENTION

1. Field of the Invention

The invention relates generally to novel genes expressed in normal but not Neurogenin-1-deficient animals. The invention relates specifically to a novel family of G protein-coupled receptors and a novel family of two-transmembrane segment proteins that are expressed in dorsal root ganglia, and a method of screening for genes specifically expressed in nociceptive sensory neurons.

2. Description of the Related Art

The treatment of acute and chronic intractable pain is a major target of drug development in the pharmaceutical industry. Pain sensation is mediated by primary sensory neurons in the dorsal root ganglia (DRG), which project peripherally to the skin and centrally to the spinal cord. These neurons express signaling molecules, such as receptors, ion channels and neuropeptides, which are involved in pain sensation. One example is the so-called Vanilloid Receptor-1 (VR-1), which is activated by capsaicin (chili pepper) as well as by heat and acid. Such pain signaling molecules may also influence pain sensation indirectly by acting as positive or negative modulators of the sensory pathway. Searching for drugs that interact with such signaling molecules, for example as receptor agonists or antagonists, is an important approach to the discovery of new therapeutics for the treatment of pain. New candidate signaling molecules expressed by pain-sensing ("nociceptive") sensory neurons are therefore highly desirable targets for new drug screening and drug discovery efforts. The present inventors have previously identified a novel family of basic helix-loop-helix (bHLH) transcription factors, called the Neurogenins (Ngns), which are essential for the development of sensory neurons in the DRG. Different Ngns are required for the development of different subsets of sensory neurons. In particular, Ngn1 is necessary for the development of most if not all nociceptive sensory neurons. In Ngn1$^{-/-}$ mutant mice, although DRG are still present, they are reduced in size and the majority of nociceptive neurons, identified by expression of markers such as trkA and VR-1, are missing (Ma et al. *Genes & Develop*, 13: 1717-1728, (1999)). These results suggested that the isolation of genes expressed in wild-type (normal) but not Ngn1$^{-/-}$ DRG might lead to the identification of novel drug target molecules expressed in differentiating or mature nociceptive sensory neurons.

While pain is usually a natural consequence of tissue injury, as the healing process commences the pain and tenderness associated with the injury resolve. However, some individuals experience pain without an obvious injury or suffer protracted pain after an initial insult. In addition, chronic or intractable pain may occur in association with certain illnesses, such as, for example, bone degenerative diseases, terminal cancer, AIDS, and Reflex sympathetic dystrophy (RSD). Such patients may be unable to receive relief with currently-available pain-relieving (anti-nociceptive) drugs, such as opioid compounds, e.g. morphine, due to problems such as dependence and tolerance. Therefore, there is a great need for novel therapeutic agents for the treatment of pain, in particular chronic pain.

SUMMARY OF THE INVENTION

The present inventors have carried out a screen for genes expressed in wild-type but not Ngn1$^{-/-}$ DRG using positive selection-based differential hybridization. This screen has identified both known signaling molecules involved in nociceptive neuron function, such as VR-1, and novel signaling molecules that are highly specifically expressed in nociceptive sensory neurons. The present invention therefore includes the discovery of new genes that are expressed in normal mice but not in Ngn1 null mutant mice. One family of novel genes isolated from the screen encodes a receptor protein with 7 transmembrane segments, mrg, a characteristic of G protein-coupled receptors. Subsequent staining experiments (see FIG. 2, 2A-D) confirmed that mrg genes were expressed specifically in subsets of nociceptive neurons in DRG. Another novel gene family isolated in this screen, drg-12, encodes a protein with two transmembrane segments.

In particular, the invention includes isolated nucleic acid molecules selected from the group consisting of an isolated nucleic acid molecule comprising a sequence having at least 70% sequence identity to a nucleic acid molecule that encodes the MrgD polypeptide with the amino acid sequence of SEQ ID NO: 49, isolated nucleic acid molecules that hybridize to the complement of a nucleic acid molecule comprising a sequence having at least 70% sequence identity to a nucleic acid molecule that encodes the MrgD polypeptide with the amino acid sequence of SEQ ID NO: 49, an isolated nucleic acid molecule that that hybridizes under stringent conditions to a nucleic acid molecule that encodes the MrgD polypeptide of SEQ ID NO:49 and an isolated nucleic acid molecule that hybridizes to the complement of a nucleic acid molecule that encodes the MrgD polypeptide of SEQ ID NO: 49.

The present invention also includes the nucleic acid molecules described above operably linked to one or more expression control elements, including vectors comprising the isolated nucleic acid molecules. The invention further includes host cells transformed to contain the nucleic acid molecules of the invention and methods for producing a protein comprising the step of culturing a host cell transformed with a nucleic acid molecule of the invention under conditions in which the protein is expressed. The host cells may be prokaryotic cells, such as *E. coli* or eukaryotic cells, such as hamster embyonic kidney (HEK) cells or yeast cells.

The invention further provides an isolated Mrg polypeptide selected from the group consisting of isolated polypeptides encoded by the isolated nucleic acids described above and the human MrgD polypeptide of SEQ ID NO: 35.

The MrgD polypeptide may be fused to a heterologous amino acid sequence, such as an eptiope tag sequence or an immunoglobulin constant domain sequence.

The invention further provides an isolated antibody that specifically binds to a polypeptide of the invention, including monoclonal and polyclonal antibodies, antibody fragments and humanized antibodies.

In another aspect, the invention provides a composition of matter comprising an MrgD polypeptide or an anti-MrgD antibody in admixture with a pharmaceutically acceptable carrier. An article of manufacture is also provided comprising the composition of matter, a container, and instructions for using the composition of matter to alter sensory perception in a mammal.

In a further aspect, the invention provides a method of identifying a compound that can be used to alter pain perception in a mammal. Test compounds are contacted with at least a portion of an MrgD polypeptide of the invention. The MrgD polypeptide or the test compound may be attached to a solid support, such as a microtiter plate. In addition, either the test compound or the MrgD polypeptide is preferably labelled.

Test compounds that are able to form complexes with the MrgD polypeptide are identified. The effects of these compounds is measured in an animal model of pain and compounds that alter pain perception in the animal model are identified as useful in altering pain perception in a mammal. The compound may enhance or decrease the perception of pain.

In one embodiment the MrgD polypeptide is a native human MrgD polypeptide, preferably the MrgD polypeptide of SEQ ID NO: 35.

In another embodiment the MrgD polypeptide may be apresent in a cell membrane or a fraction of a cell membrane prepared from cells expressing the MrgD polypeptide. In a further embodiment, the MrgD polypeptide is present in an immunoadhesin.

The test compounds are preferably selected from the group consisting of peptides, peptide mimetics, antibodies, small organic molecules and small inorganic molecules. In a preferred embodiment the test compounds are peptides. The peptides may be anchored to a solid support by specific binding to an immobilized antibody. In addition, the test compounds may be contained in a cellular extract, particularly a cellular extract prepared from cells known to express an MrgD polypeptide, such as dorsal root ganglion cells.

In another aspect, the invention provides a method of indentifying a compound that binds an MrgD polypeptide by contacting an MrgD polypeptide or fragment with a test compound and a ligand, such as an RFamide peptide, under conditions where binding can occur. Preferably the MrgD polypeptide is contacted with the RFamide peptide prior to being contacted with the test compound. The ability of the test compound to interfere with biding of the RFamide peptide to the MrgD polypeptide is determined.

In one embodiment the MrgD polypeptide is a native human MrgD polypeptide, preferably the MrgD polypeptide of SEQ ID NO: 35.

The invention also provides a method of identifying an MrgD agonist that can be used to alter sensory perception in a mammal. For example, the agonist may be used to enhance or decrease the preception of pain. An MrgD polypeptide is expressed in a host cell capable of producing a second messenger response. In one embodiment the host cell is a eukaryotic cell, preferably a hamster embryonic kidney (HEK) cell, more preferably an HEK cell that expresses Gα15.

The host cell is contacted with one or more test compounds and the second messenger response is measured. Compounds that increase the measured second messenger response are identified as agonists that can be used to alter sensory perception in a mammal. In one embodiment measuring the second messenger response comprises measuring a change in intercellular calcium concentration. This may be done, for example, by using a FURA-2 indicator dye. In another embodiment a second messenger response is measured by measuring the flow of current across the cell membrane.

In another aspect, the invention provides a method for identifying an MrgD polypeptide antagonist that is useful in treating impaired sensory perception in a mammal. In particular the method is useful for identifying antagonists that can alter the perception of pain.

In one embodiment, an MrgD polypeptide, preferably the MrgD polypeptide of SEQ ID NO: 35, is expressed in a host cell capable of producing a second messenger response. The host cell is then contacted with an RFamide peptide and one or more test compounds. The second messenger response is measured, such as by the methods described above, and compounds that alter the second messenger response to the RFamide peptide are identified as agonists that are useful in treating impaired sensory perception, such as pain.

In yet another aspect, the present invention provides a method of identifying an anti-MrgD agonist antibody that can be used to alter the perception of pain in a mammal. In one embodiment the anti-MrgD agonist antibody the method is used to identify anti-MrgD agonist antibodies that can be used to treat pain in a mammal that is suffering from pain.

In a preferred embodiment, candidate antibodies are prepared that specifically bind to an MrgD polypeptide, more preferably to the MrgD polypeptide of SEQ ID NO: 35. An MrgD polypeptide, preferably the MrgD polypeptide of SEQ ID NO: 35, is expressed in a host cell known to be capable of producing a second messenger response. The host cell is then contacted with a candidate antibody and the second messenger response is measured. Antibodies that increase the second messenger response are identified as agonist antibodies that can be used to treat pain in a mammal.

The invention also provides a method of treating pain in a mammal, comprising administering to the mammal an MrgD agonist. In one embodiment, the agonist is an agonist of the human MrgD polypeptide of SEQ ID NO: 35.

BRIEF DESCRIPTION OF THE DRAWINGS

FIG. 1A shows the alignment of a homologous region of the amino acid sequences of SEQ ID NO: 2, 4, 6, 8, 10 and 12, and also of two human members of the mrg family (SEQ ID NOS: 16 and 18).

FIGS. 1B-D indicate that mrgs define a Novel G protein-couple receptor Gene Family. Amino acid sequences of eight mouse full-length mrg genes were aligned using ClustalW. The sequence depicted are: mrg3 (SEQ ID NO: 2), mrg4 (SEQ ID NO: 4), mrg5 (SEQ ID NO: 6), mrg8 (SEQ ID NO: 12), mrg9 (SEQ ID NO: 21), mrg10 (SEQ ID NO: 23), mrg11 (SEQ ID NO: 25), and mrg12 (SEQ ID NO: 27). Identical residues in >50% of the predicted proteins are darkly shaded; conservative substitutions are highlighted in light gray. The approximate locations of predicted transmembrane domain 1-7 are indicated on top of the sequences as TM1-TM7. The predicted extracellular and cytoplasmic domains are indicated as E1-E7 and C1-C7 respectively.

The microscopy images of in situ hybridization in FIG. 2 show the localization of antisense staining against a nucleotide of SEQ ID NO: 2 ("mrg3") and of SEQ ID NO: 4 ("mrg4") in transverse sections of dorsal root ganglia (DRG) from newborn wild type (WT) and Neurogenin1 null mutant (Ngn1$^{-/-}$) mice. White dashed lines outline the DRG and black dashed lines outline the spinal cord. Note that in the Ngn1$^{-/-}$ mutant, the size of the DRG is severely reduced due to the loss of nociceptive sensory neurons, identified using three other independent markers (trkA; VR-1 and SNS-TTXi (Ma et al., (1999)). mrg3 is expressed in a subset of DRG in WT mice (A) but is absent in the Ngn1$^{-/-}$ DRG (B). mrg4 is expressed in a smaller subset of DRG than that of mrg3 (C).

It is also absent in the Ngn1$^{-/-}$ DRG (D). The loss of mrg-expressing neurons in the Ngn1$^{-/-}$ DRG indicates that these neurons are likely to be nociceptive.

Figure 2A:
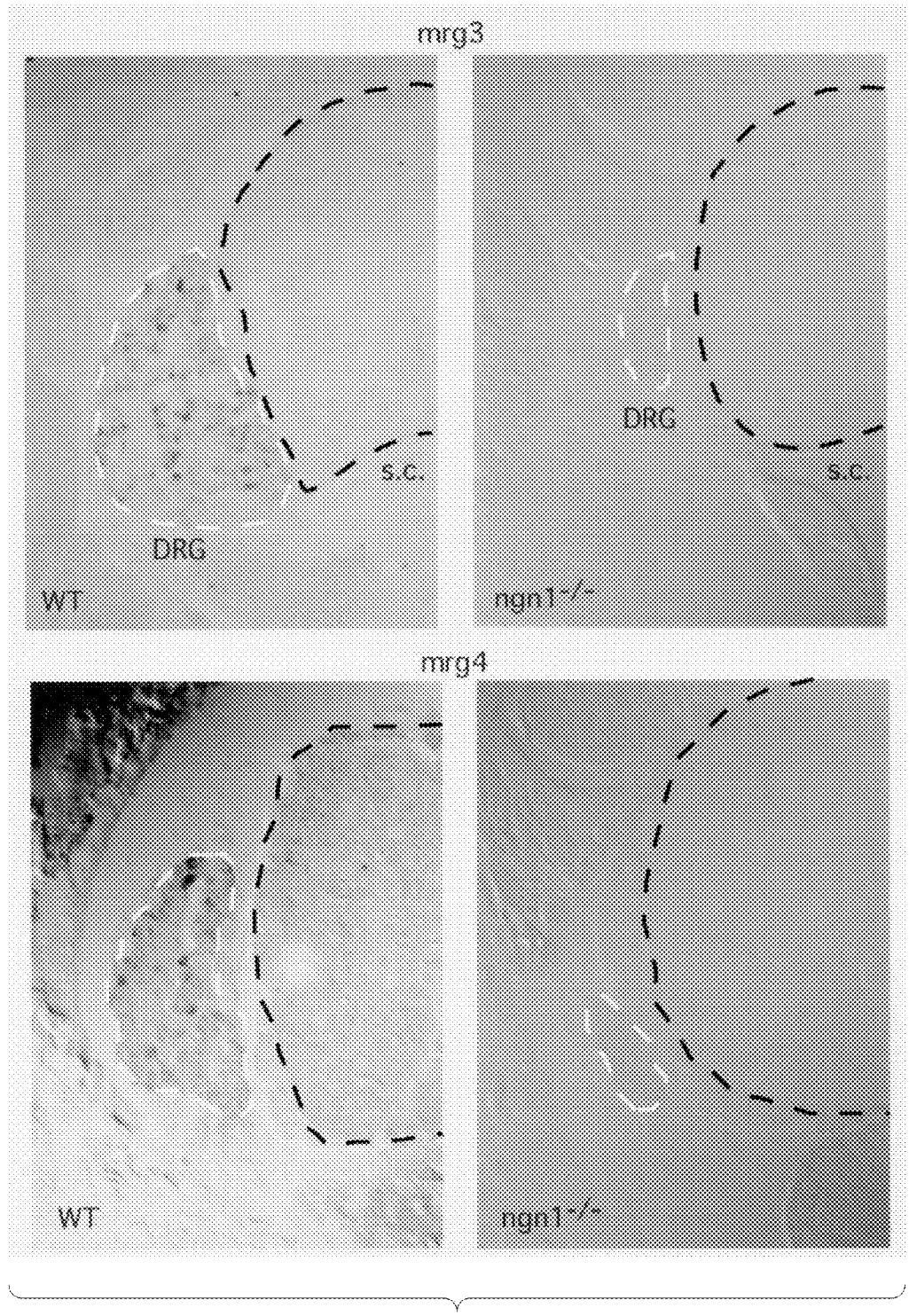

FIG. 2A shows expression of mrgs in subsets of dorsal root ganglia (DRG) neurons. Frozen transverse sections of DRG from wild-type (a-i) and ngn1$^{-/-}$ (j) mutant new born mice were annealed with antisense digoxigenin RNA probes, and hybridization was visualized with an alkailine phosphatase-conjugated antibody. Positive signals are shown as dark purple stainings. TrkA is expressed in a large portion of wild-type DRG neurons (a) but absent in ngn1$^{-/-}$ (data not shown). Each of the eight mrg genes (b-i) is expressed in a small subset of neurons in wild-type DRG in completely absent in ngn1$^{-/-}$ DRG (j and data not shown). Black dash line outlines the ngn1$^{-/-}$ mutant DRG.

Figure 2B:
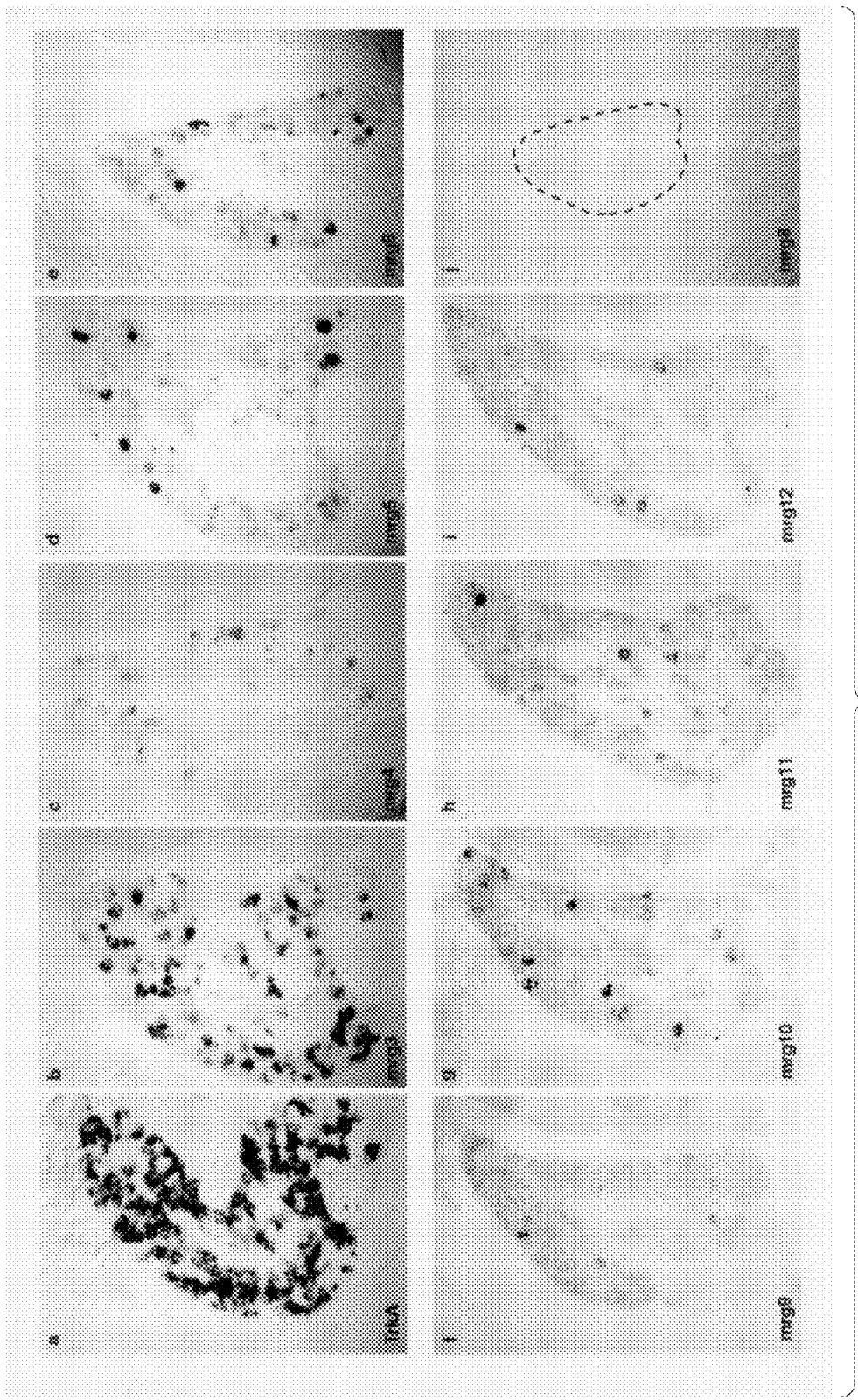

FIG. 2B shows that mrgs are expressed by TrkA$^+$ nociceptive neurons. Double labeling technique was used to colocalize TrkA (b,e) and mrgs (a,d) in DRG neurons. During the double labeling experiments frozen sections of wild-type DRG were undergone in situ hybridizations with either mrg3 (a-c) or mrg5 (d-f) fluorescein-labeled antisense RNA probes followed by anti-TrkA antibody immunostaining. The same two frames (a and b, d and e) were digitally superimposed to reveal the extent of colocalization (c, f). The white arrowheads indicate examples of double positive cells.

Figure 2C:
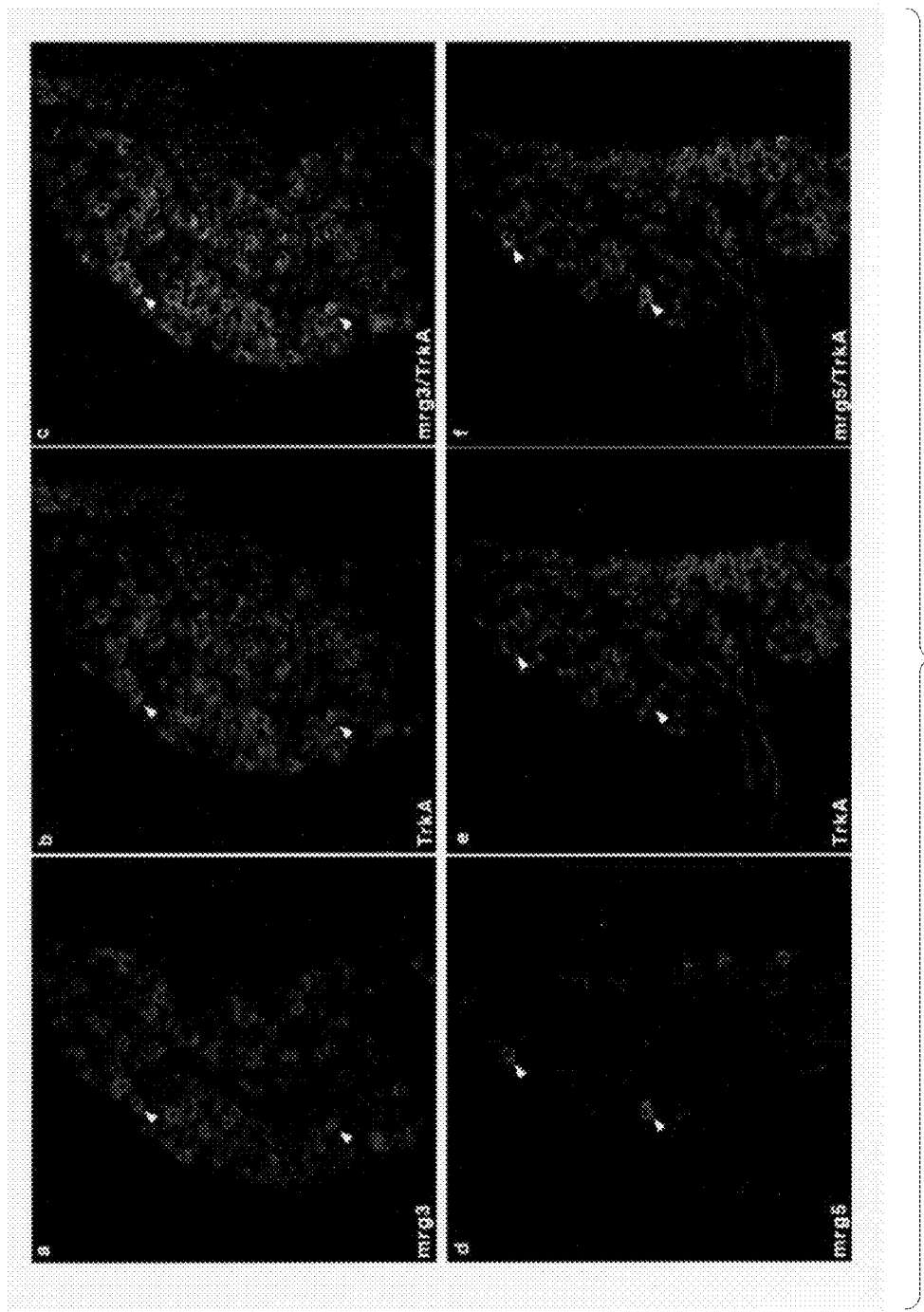

FIG. 2C shows that mrgs and VR1 define two different populations of nociceptive neurons in DRG. The combination of in situ hybridizations with either mrg3 or mrg5 fluorescein-labeled antisense RNA probes and anti-VR1 antibody immunostaining demonstrated that neither mrg3 (a-c) nor mrg5 (d-f) were expressed by VR1-positive neurons. In the merged images (c,f), there are no colocalizations of VR1 with either mrg3 or mrg5. The white arrowheads are pointed to mrgs-expressing but VR1-negative nociceptive neurons.

Figure 2D:
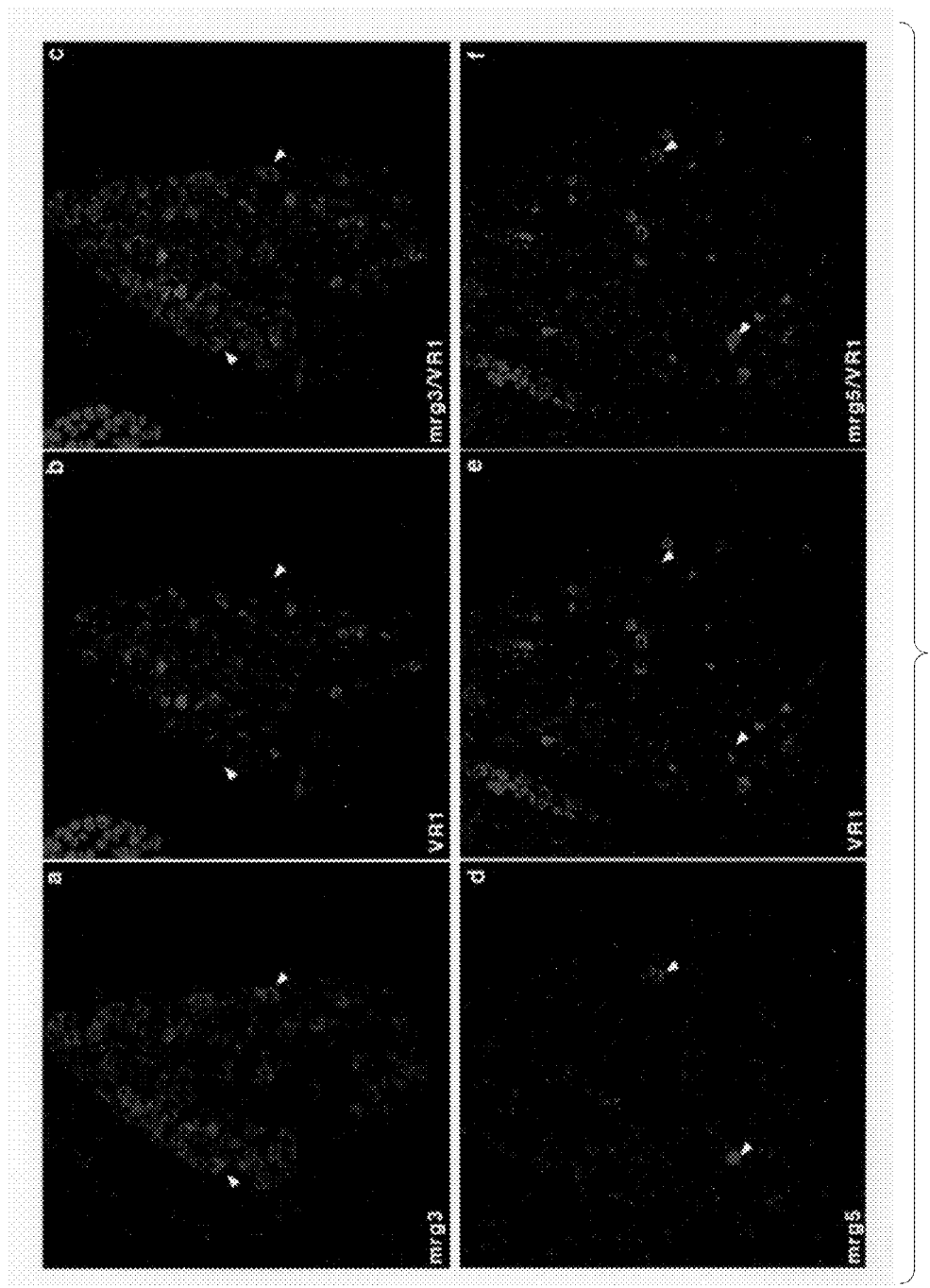
Figure 2E:
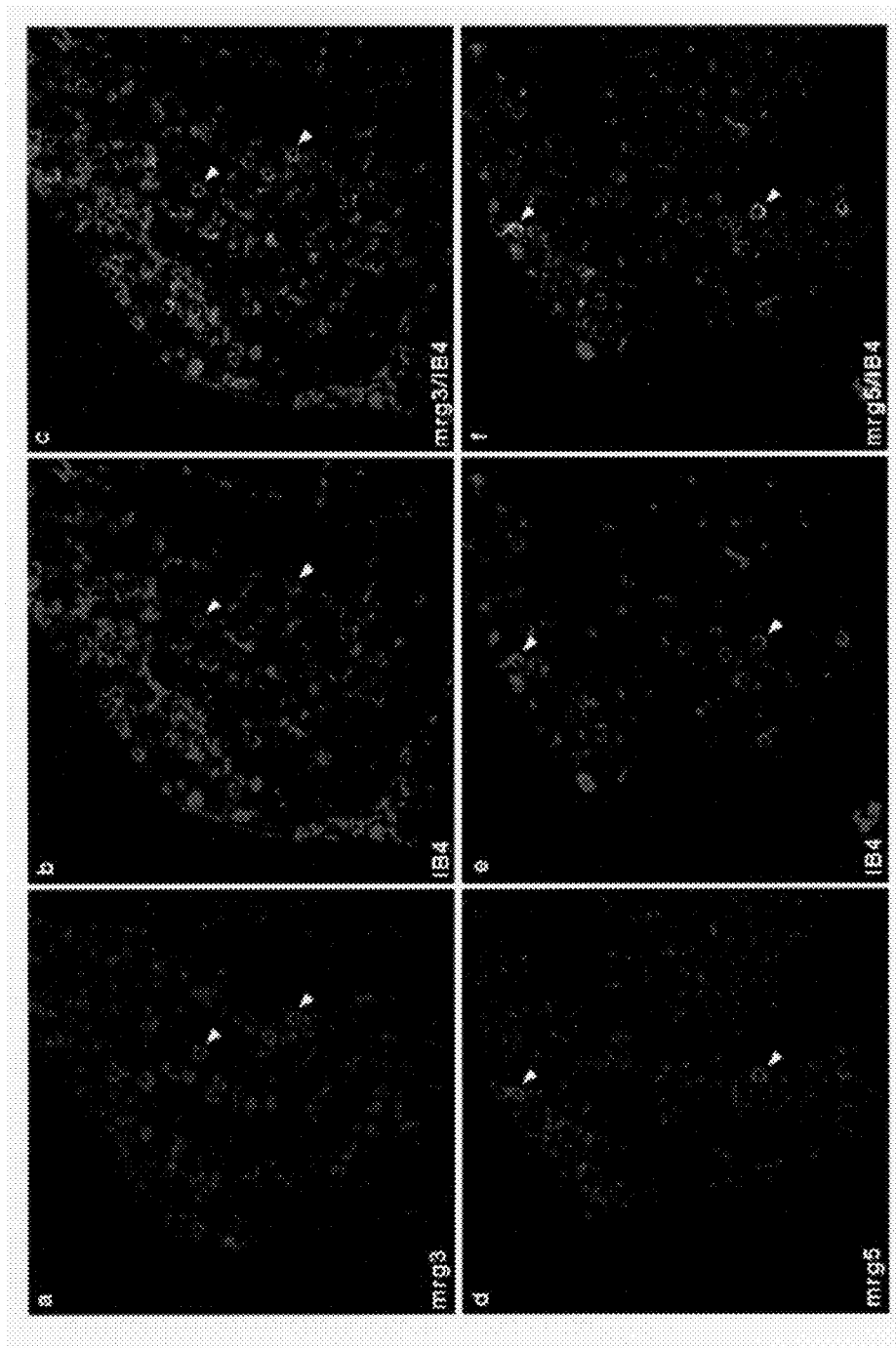

FIG. 2D shows that mrgs are expressed by IB4$^+$ nociceptive neurons. Double labeling technique was used to colocalize IB4 (b,e) and mrgs (a,d) in DRG neurons. The expressions of mrg3 and mrg5 were visualized by in situ hybridization as described before. The same DRG sections were subsequently undergone through FITC-conjugated lectin IB4 binding. In the merged images (c,f), there are extensive overlappings between mrgs and IB4 stainings (yellow neurons indicated by arrowheads).

Figure 3A:
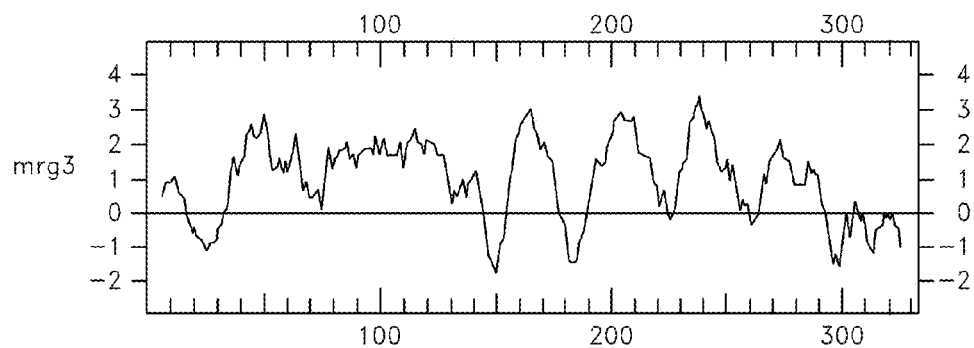
Figure 3B:
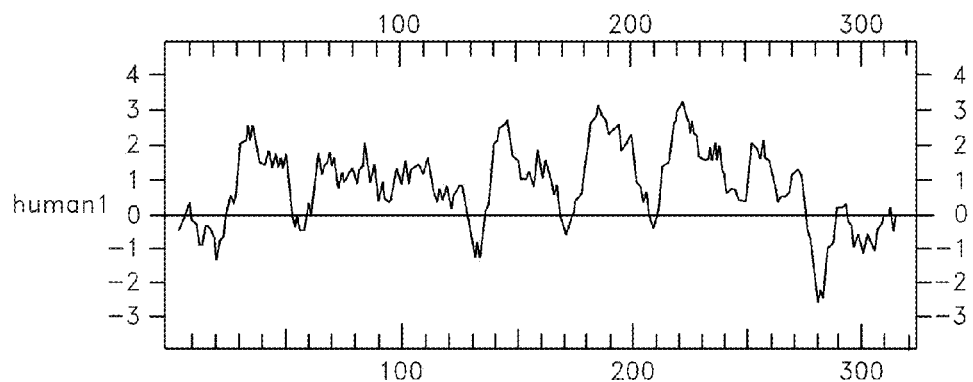
Figure 3C:
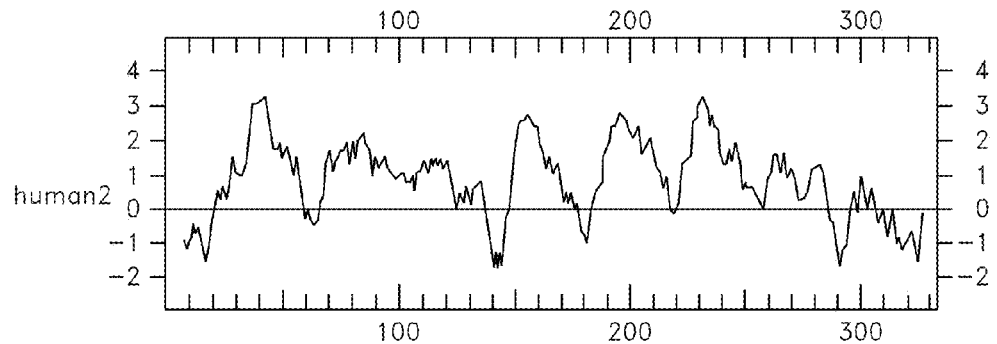

FIG. 3 compares the hydrophobicity plots predicting the transmembrane regions of the amino acid sequence of (A) mrg3 (SEQ ID NO: 2); (B) human1 gene (SEQ ID NO: 15); and (C) human2 gene (SEQ ID NO: 17). More positive values indicate hydrophobicity.

Figure 4A:
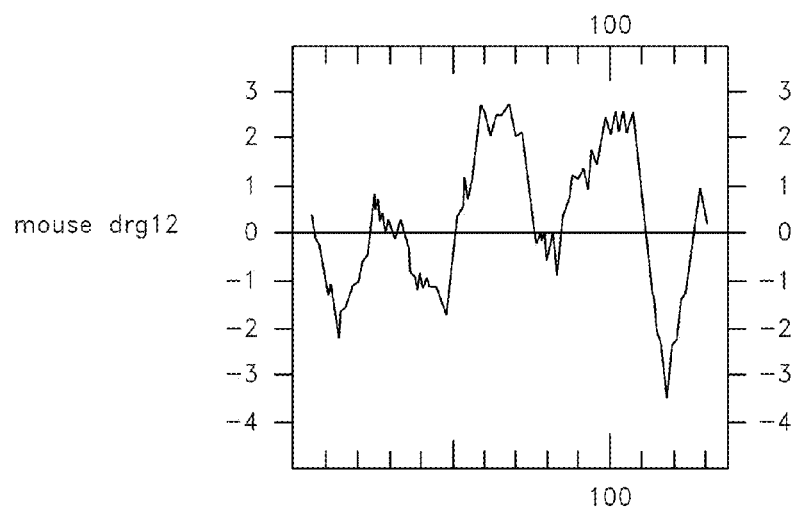
Figure 4B:
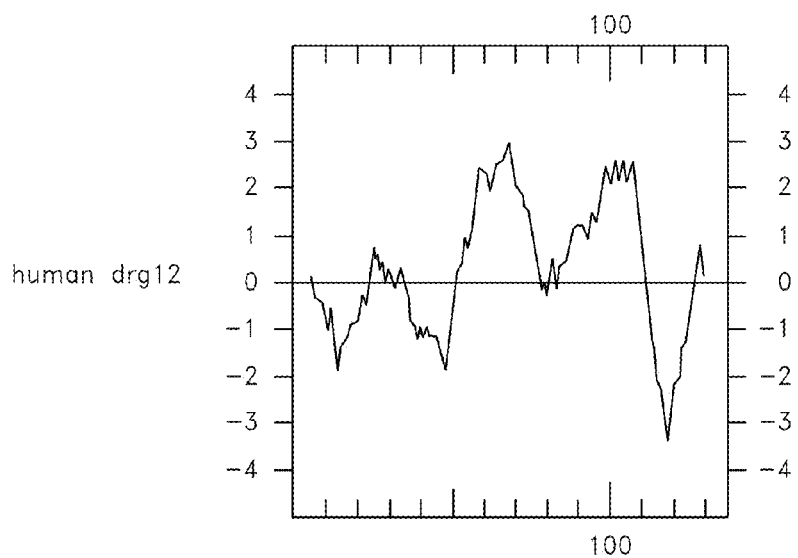

FIG. 4 compares the hydrophobicity plots predicting the transmembrane regions of the amino acid sequence of (A) mouse drg12 (SEQ ID NO: 14); (B) human drg12 (SEQ ID NO: 19)

Figure 5:
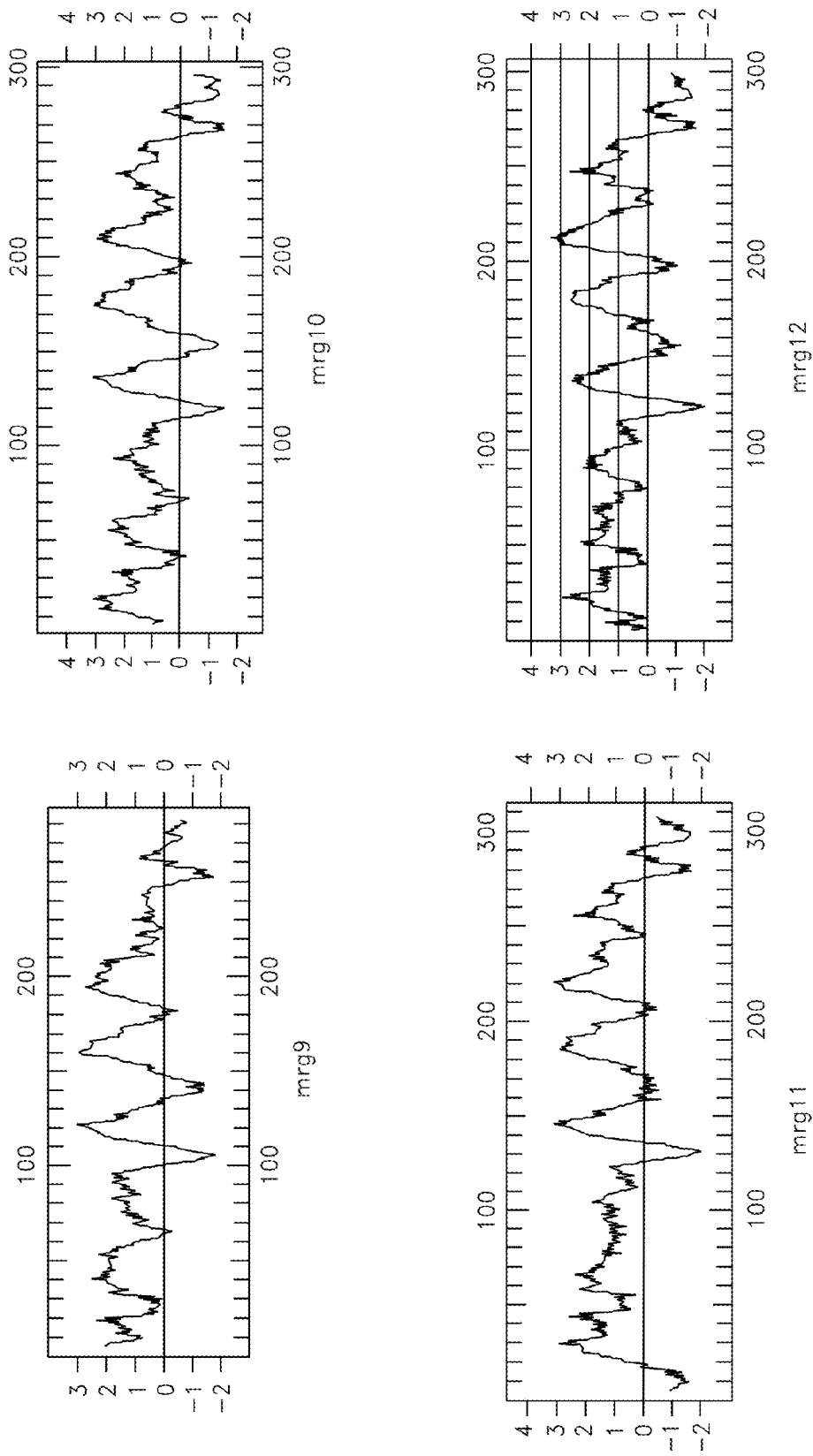

FIG. 5 compares the hydrophobicity plots predicting the transmembrane regions of the amino acid sequence of mrg9 (SEQ ID NO: 21); mrg10 (SEQ ID NO: 23); mrg11 (SEQ ID NO: 25) and mrg12 (SEQ ID NO: 27).

Figure 6A:
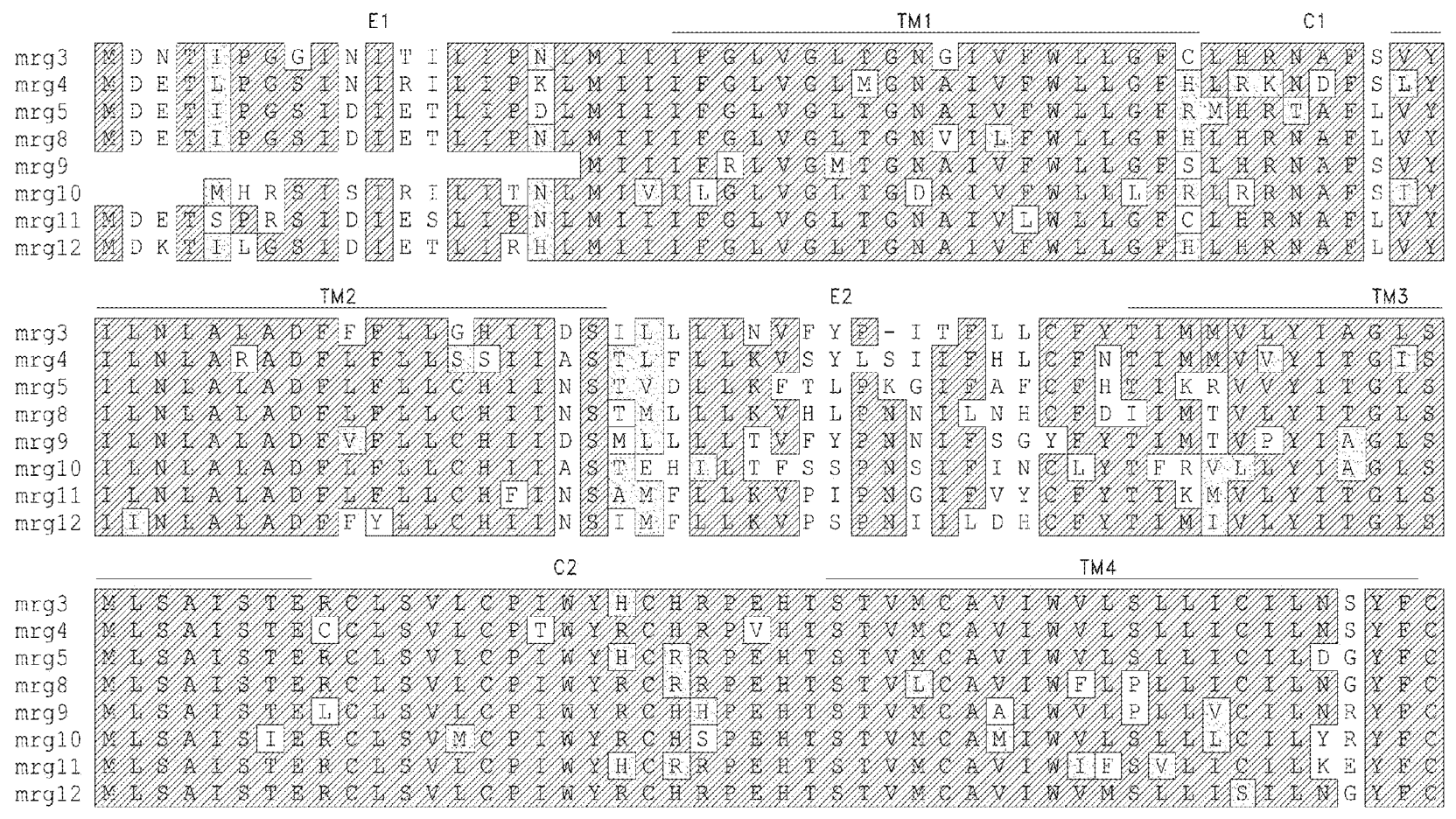
Figure 6B:
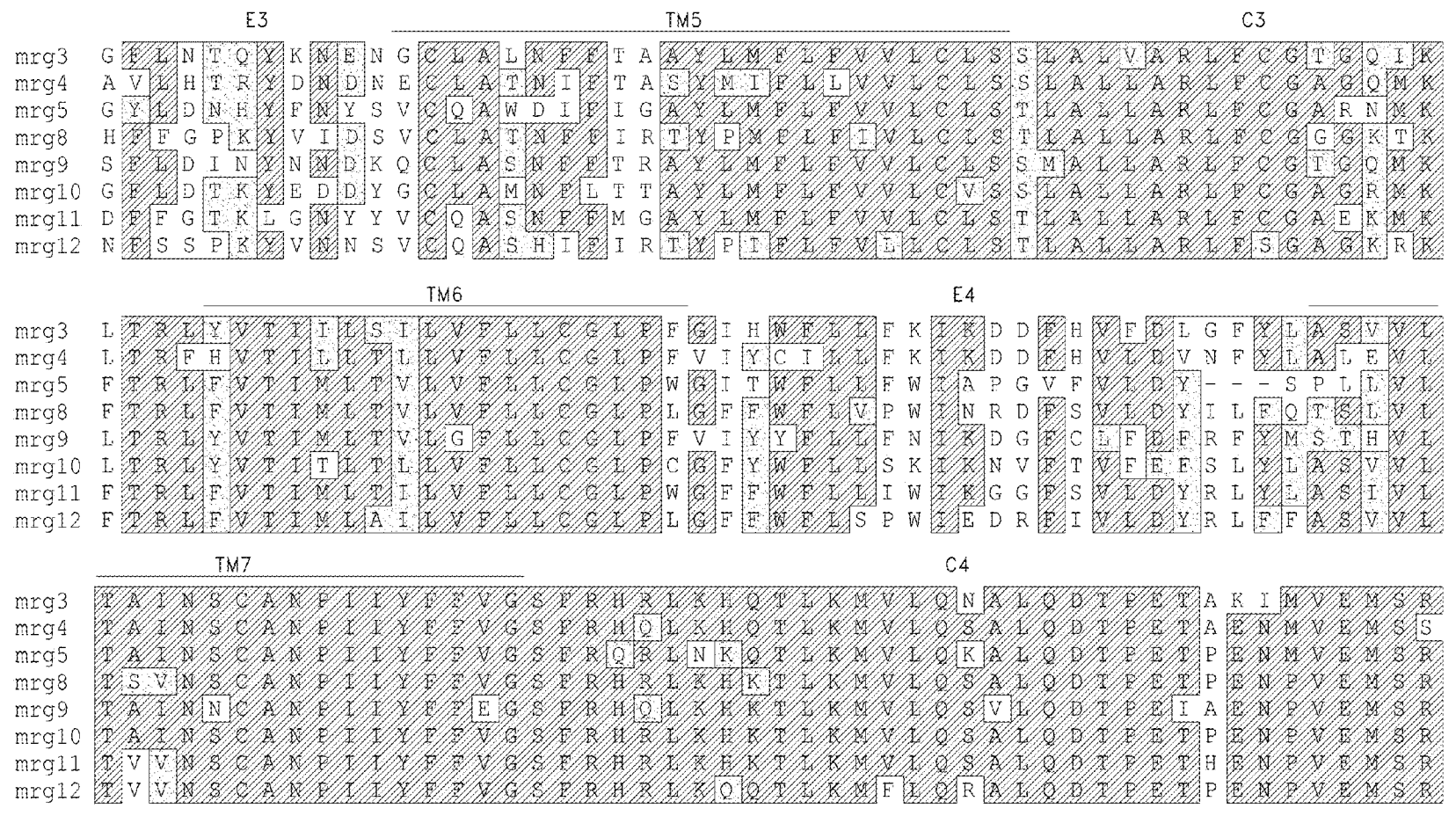
Figure 6D:
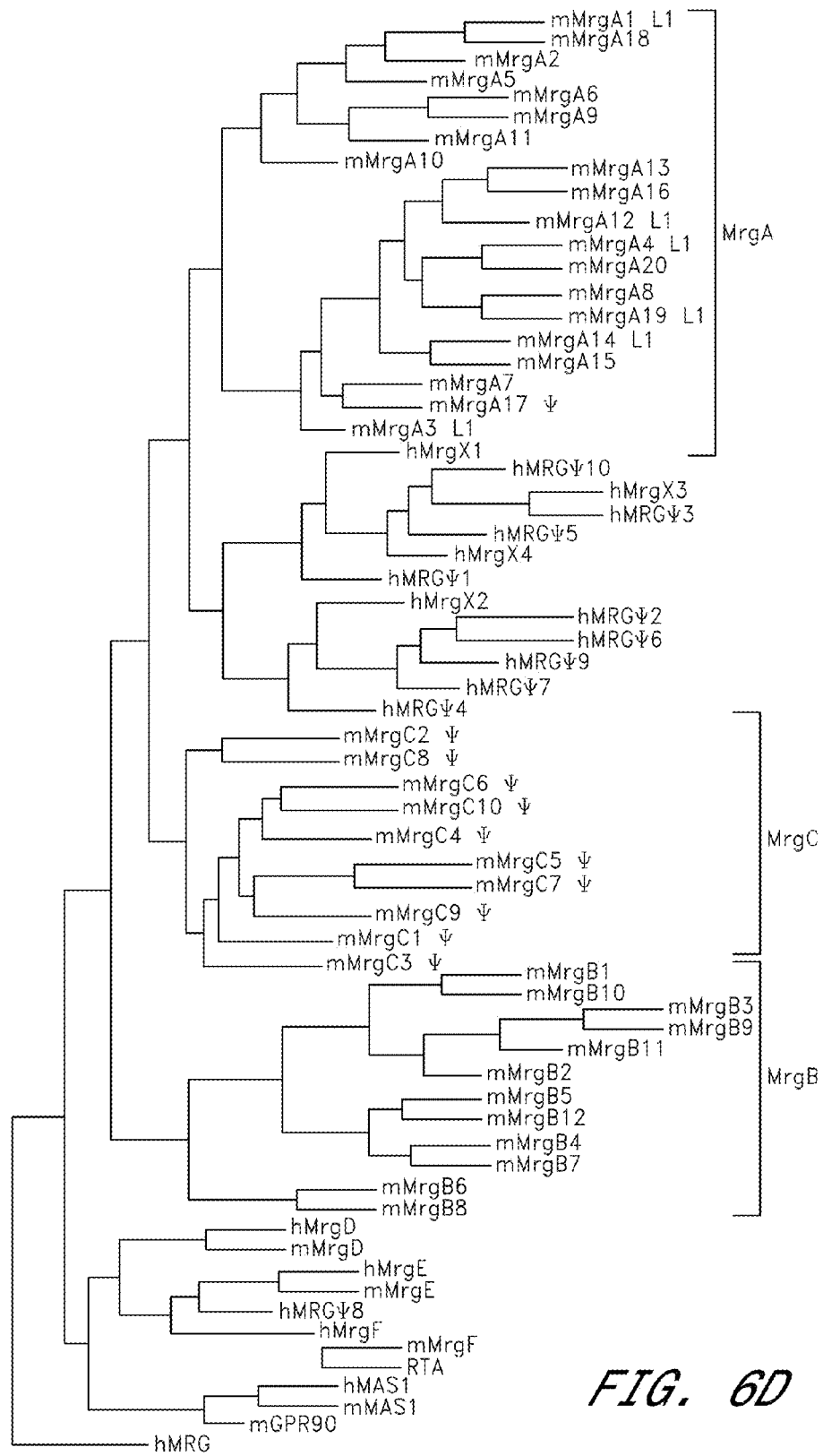

FIG. 6A is an alignment of the amino acid sequences of MRGA1-A8 deduced from nucleotide sequences of cDNA and BAC clones from strain C57BL/6J mice. MRGA1-A8 are depicted as mrg3 (MrgA1, SEQ ID NO: 2), mrg4 (MrgA2, SEQ ID NO: 4), mrg5 (MrgA3, SEQ ID NO: 6), mrg8 (MrgA4, SEQ ID NO: 12), mrg9 (MrgA5, SEQ ID NO: 21), mrg10 (MrgA6, SEQ ID NO: 23), mrg11 (MrgA7, SEQ ID NO: 25), and mrg12 (MrgA8, SEQ ID NO: 27). The predicted locations of the transmembrane (TM1-TM7), extracellular (E1-E4), and cytoplasmic (C1-C4) domains are indicated above the aligned sequences.

FIG. 6B depicts a phylogenetic analysis of MRG family members identified from database searches. The protein sequences of all MRGs were aligned using CLUSTALW (Thompson et al. *Nucleic Acids Res* 22: 4673-80 (1994)). The dendrogram was generated with the PHYLUP software package using the Neighbor-Joining method and 1,000 bootstrap trials. The horizontal length of the branches is proportional to the number of amino acid changes. Vertical distances are arbitrary. Mouse (m)Mrg genes with retrotransposon sequences ~650 nt 3' of their stop codon are highlighted (L1). All genes that are predicted to encode pseudogenes are indicated with the psi (Ψ) symbol.

FIG. 6C shows the chromosomal organization of one mouse Mrg cluster deduced from analysis of overlapping BAC clones. The cluster contains four intact ORFs and three pseudogenes.

Figure 7:
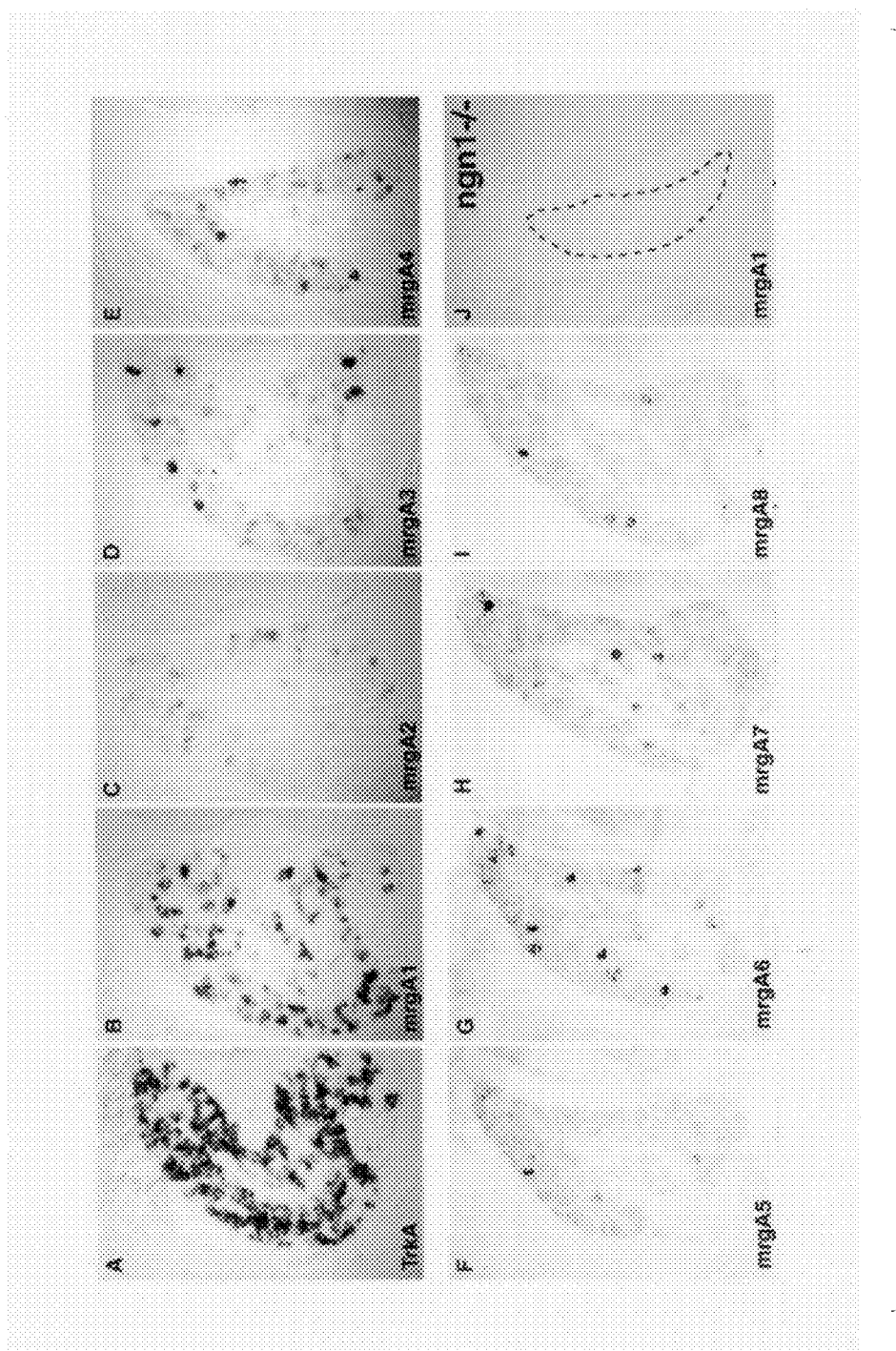

FIG. 7A shows the distribution of nociceptive sensory neurons in a postnatal day 0 (P0) DRG as revealed by expression of the NGF receptor trkA. This population is selectively eliminated in Ngn1$^{-/-}$ mutants (Ma et al. *Genes & Dev.* 13: 1717-1728 (1999)).

FIG. 7B shows in situ hybridization with cRNA probes detecting MrgA1. MrgA1 is expressed in a pattern similar to that of trkA$^+$ neurons on an adjacent section shown in FIG. 7A.

FIG. 7C-I shows in situ hybridization with cRNA probes detecting MrgA2-MrgA8.

FIG. 7J shows that MrgA1 expression is eliminated in Ngn1$^{-/-}$ mice, as is expression of other MrgA genes (not shown). Remaining DRG neurons are present in the area delimited by the dotted line, and can be visualized by expression of generic neuronal markers.

Figure 8:
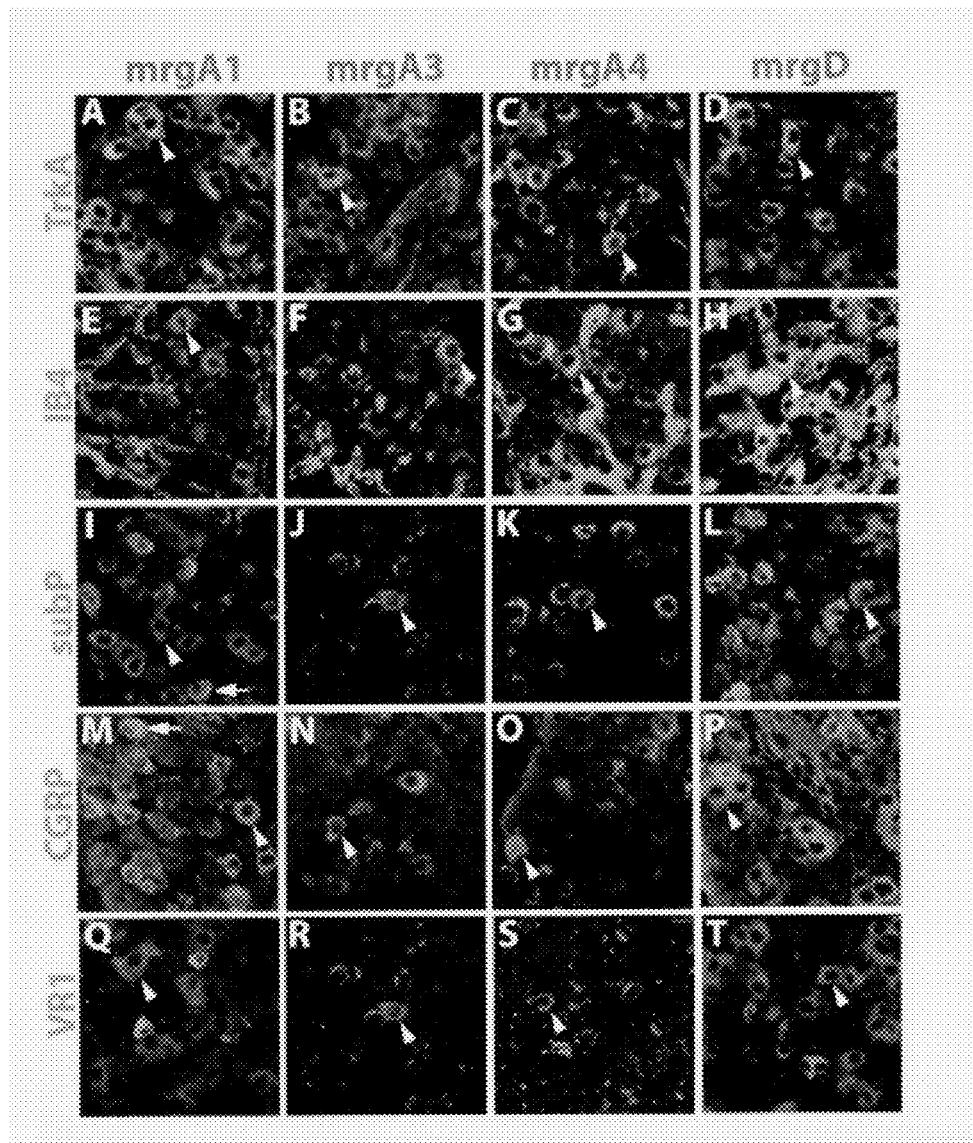

FIG. 8 shows that expression of MrgAs is restricted to non-peptidergic nociceptors that project to inner lamina II. Shown are confocal microscopic images of in situ hybridizations using the Mrg probes indicated, combined with fluorescent antibody detection of trkA (A-D), substance P (I-L), CGRP (M-P), VR1 (Q-T) or staining with fluorescent isolectin IB4 (IB4; E-H). MrgA$^+$ or MrgD$^+$ cells co-express trkA and IB4 (A-H, arrowheads), but most do not express subP, CGRP or VR1 (I-T, arrowheads; arrows in I, M indicate a minor subset of MrgA1$^+$ neurons that co-express SubP and CGRP).

Figure 9:
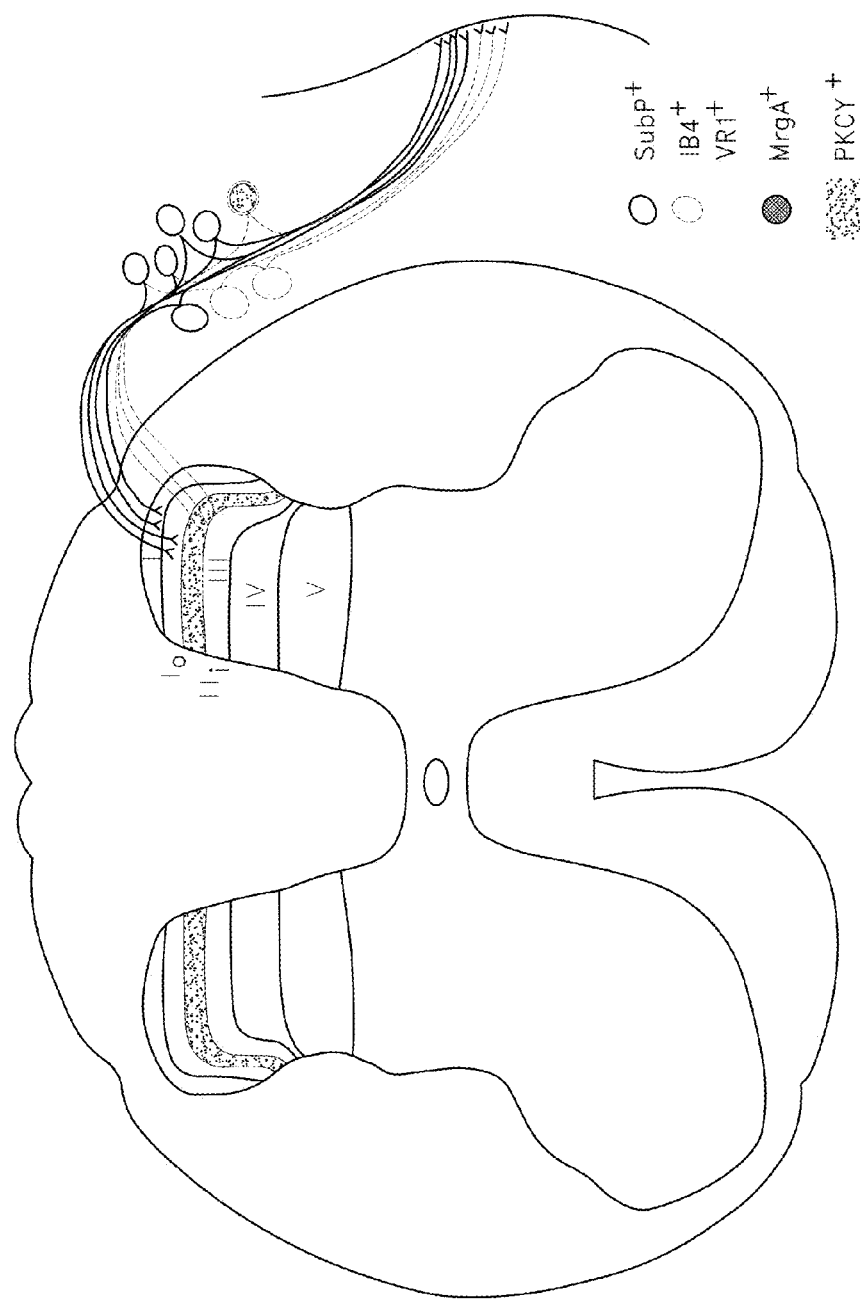

FIG. 9 is a schematic illustration of the restriction of MrgA (and MrgD) expression to non-peptidergic, IB4$^+$, VR1$^-$ sensory neurons that project to lamina IIi (Snider and McMahon *Neuron* 20: 629-32 (1998)). Post-synaptic neurons in lamina IIi express PKCγ.

Figure 10:
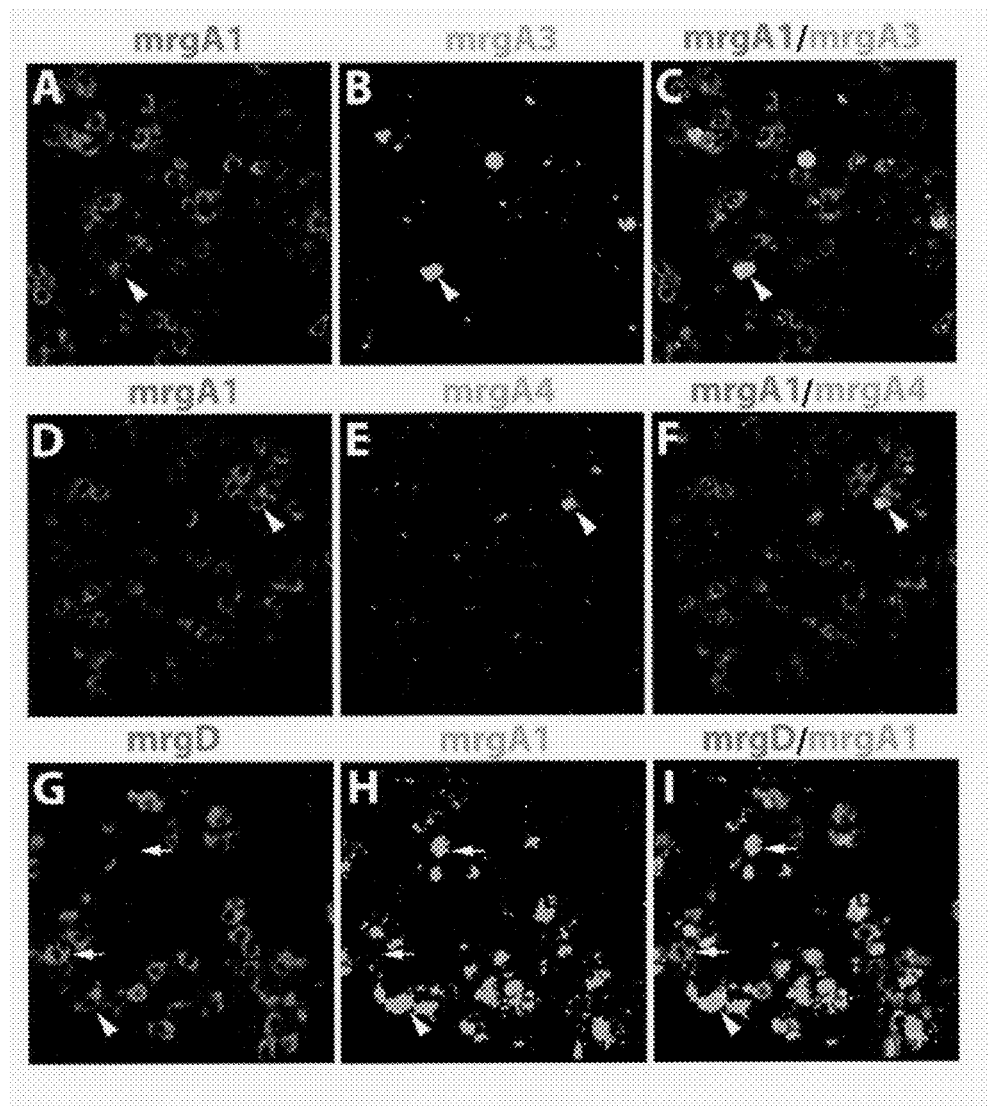

FIG. 10 shows that individual sensory neurons co-express multiple MrgAs. (A-C) double label in situ hybridization with MrgA1 (A) and A3 (B). (D-F) double labeling with MrgA1 (D) and MrgA4 (E). In both cases, cells expressing MrgA3 or A4 are a subset of those expressing MrgA1 (C, F, arrowheads). Arrows in (F) indicate intranuclear dots of MrgA4 expression which may represent sites of transcription. (G-I) Double label in situ with MrgA1 and MrgD. Some overlap overlap between the two populations is seen (I, arrowhead), while most cells express one receptor but not the other (I, arrows). Approximately 15% of cells expressing either MrgA1 or MrgD co-express both genes. Vertical bars to the right of panels (C, F, I) represent a z-series viewed along the y-axis, horizontal bars below the panels a z-series viewed along the x-axis. (J, K) comparison of in situ hybridization signals obtained using a single MrgA probe (J) and a mixture of 7 MrgA probes (K). Approximately 1% of neurons were labeled by the MrgA4 probe, while ~4.5% were labeled by the mixed probe. The sum of the percentage of neurons labeled by the individual MrgA2-8 probes is ~6.6%, suggesting that there is partial overlap within this population. (L) Venn diagram illustrating combinations of gene expression revealed by in situ analysis. The drawing is a conservative estimate of the number of subsets, since we do not yet know, for example, whether MrgAs2-8 partially overlap with MrgD. The sizes of the circles are not proportional.

Figure 11:
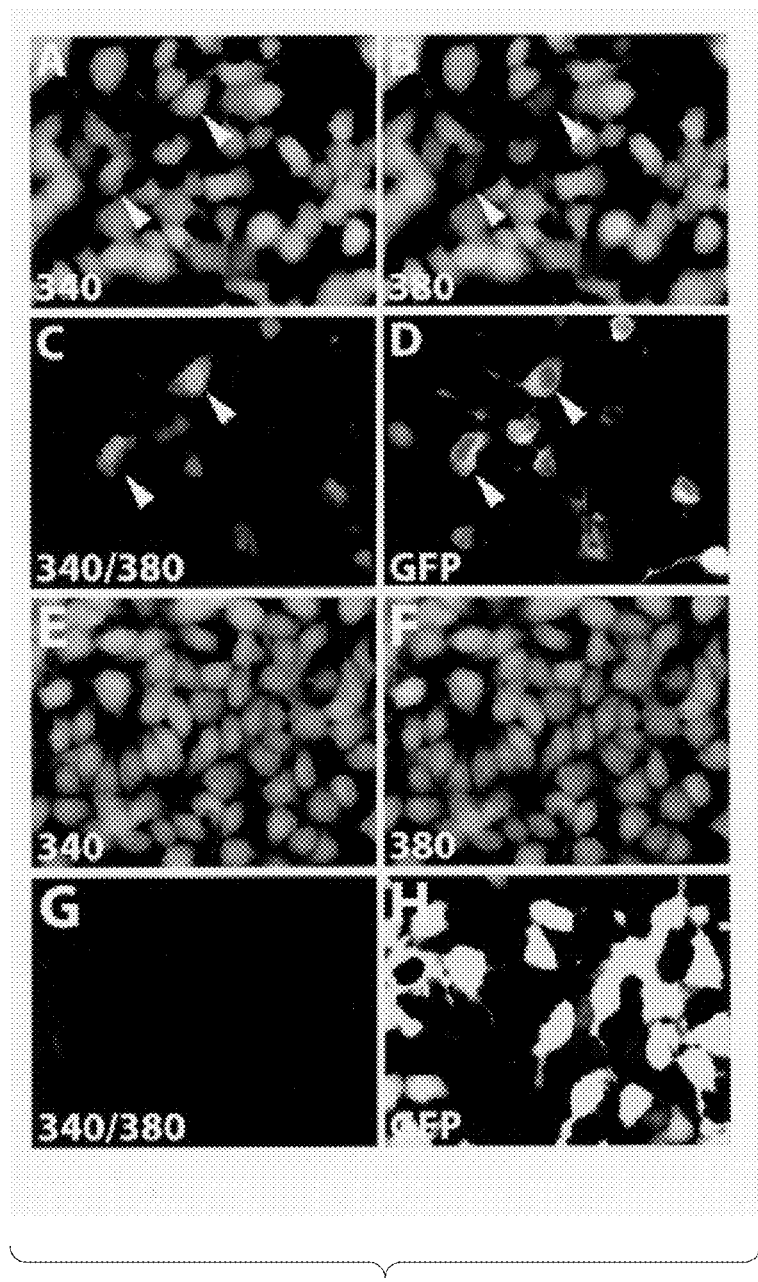

FIG. 11 shows elevated intracellular free $Ca^{++}$ elicited by FLRF in HEK cells expressing MRGA1. (A, B) and (E, F) illustrate Fura-2 fluorescence at 340 nm (A, E) and 380 nm (B, F) in HEK-$G\alpha_{15}$ cells expressing an MRGA1-GFP fusion protein (A-D) or GFP alone (E-H). The images were taken 2 minutes after the addition of 1 µM of FLRFamide. The perinuclear, punctate distribution of MRGA1-GFP revealed by intrinsic GFP fluorescence (D, arrowheads) is characteristic of the ER-Golgi network, indicating membrane integration and intracellular transport of the receptors. In contrast, the control GFP protein is cytoplasmic (H). The intracellular $Ca^{2+}$ ($[Ca^{2+}]_i$) release was determined from the FURA-2 340 nM/380 nM emission ratio (C, G). Note that MRGA1-expressing cells (but not surrounding untransfected cells) show an elevated ratio of Fura-2 fluorescence at 340/380 nm (C, arrowheads), indicating an increase in $[Ca^{2+}]_i$. In contrast, no such elevation is observed in control GFP-expressing cells (G). The elevated 340/380 fluorescence seen in MRGA1-expressing cells was dependent on the addition of ligand (not shown).

Figure 12A:
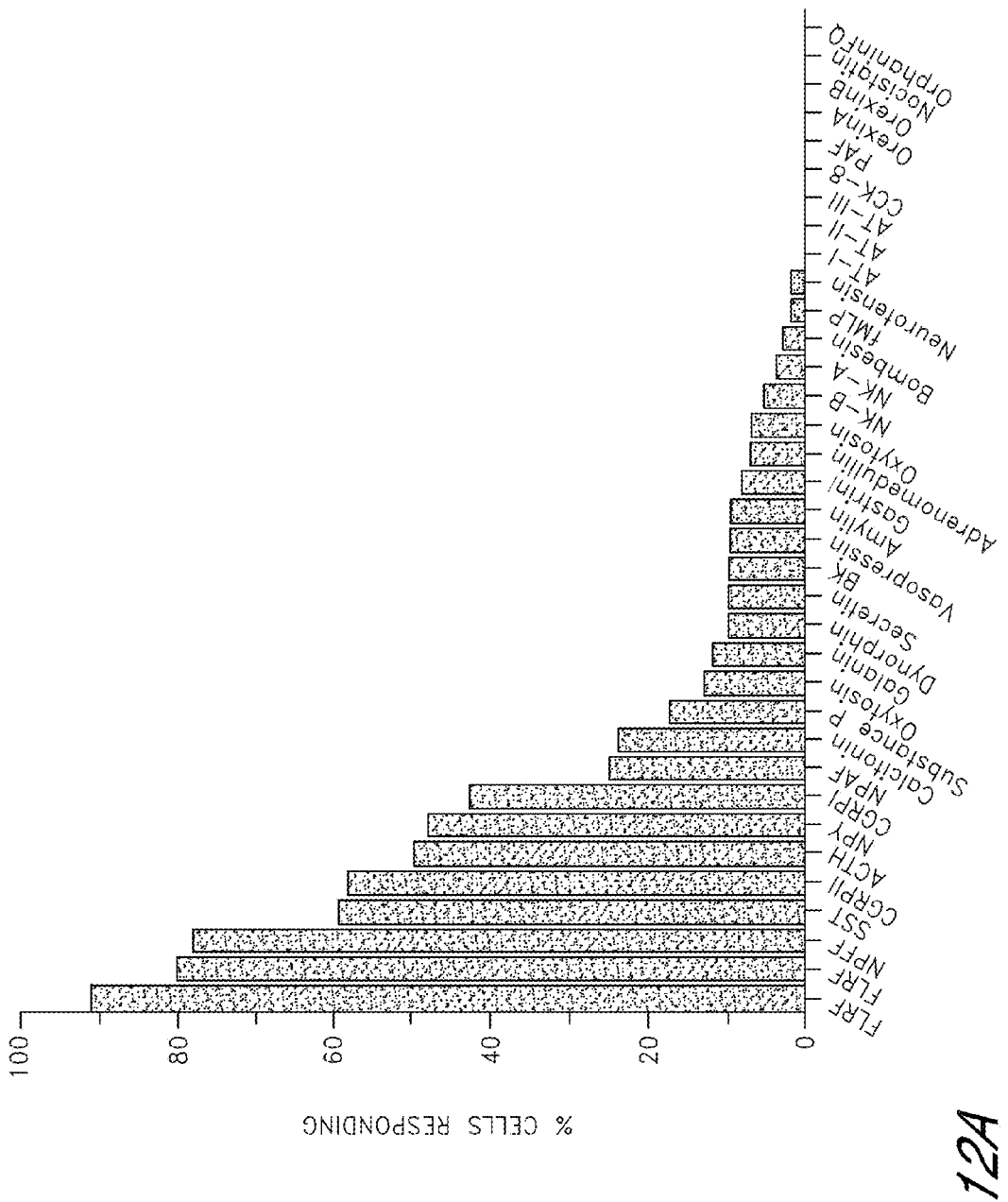

FIG. 12A shows activation of MRGA receptors expressed in heterologous cells by neuropeptide ligands. HEK-$G\alpha_{15}$ cells (Offermanns and Simon. *J Biol Chem* 270: 15175-80 (1995)) expressing MRGA1 were tested with the indicated ligands at a concentration of 1 µM. The data indicate the mean percentages of GFP-positive (i.e., transfected) cells showing calcium responses. None of the agonists indicated showed any responses through endogenous receptors in untransfected cells. Note that the RFamide neuropeptides FMRF, FLRF and NPFF, as well as NPY, ACTH, CGRP-I and -II and somatostatin (SST) produced the strongest responses.

Figure 12C:
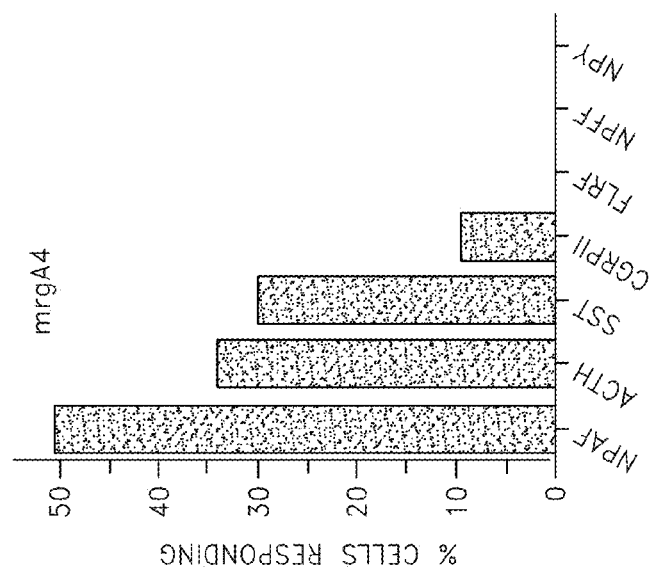
Figure 12B:
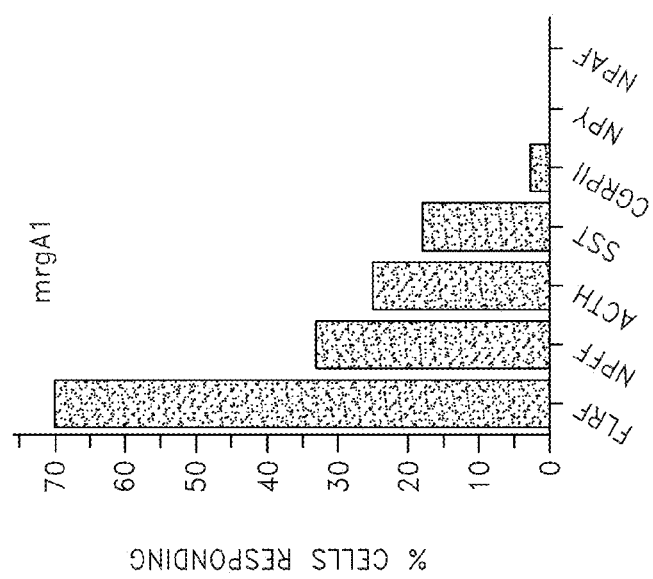

FIG. 12B shows the ligand selectivity of MRGA1 expressed in HEK cells lacking $G\alpha_{15}$. The cells were exposed to ligands at a concentration of 1 µM as in (A).

Figures 12D, 12E, 12F:
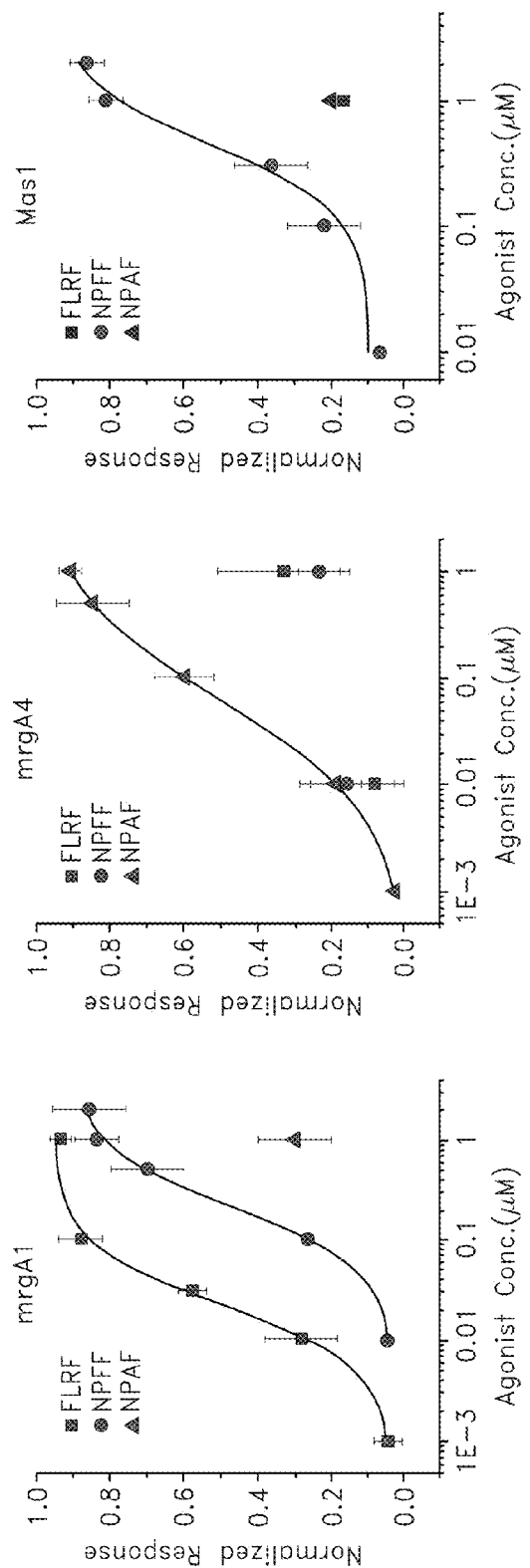

FIG. 12C shows the ligand selectivity of MRGA4. The data presented in FIGS. 12B and 12C indicate that the responses to the most effective ligands do not depend on the presence of $G\alpha_{15}$. Note that MRGA1-expressing cells respond to FLRF and NPFF but not to NPAF, while conversely MRGA4-expressing cells respond to NPAF but not NPFF or FLRF FIG. 12D shows dose-response curves for MRGA1 expressed in HEK-$G\alpha_{15}$ cells to selected RFamide neuropeptides. Each data point represents the mean±S.E.M. of at least 3 independent determinations; at least 20 GFP$^+$ cells were analyzed for each determination. Responses at each ligand concentration were normalized to the maximal response subsequently shown by the same cells to a 5 µM concentration of FLRF. MRGA1 (D) shows highest sensitivity to FLRF (squares, $EC_{50} \approx 20$ nM) and lower sensitivity to NPFF (circles, $EC_{50} \approx 200$ nM).

FIG. 12E shows dose-response curves for MRGA4 expressed in HEK-$G\alpha_{15}$ cells to selected RFamide neuropeptides. Each data point represents the mean±S.E.M. of at least 3 independent determinations; at least 20 GFP$^+$ cells were analyzed for each determination. Responses at each ligand concentration were normalized to the maximal response subsequently shown by the same cells to a 5 µM concentration of NPAF. MRGA4 is preferentially activated by NPAF (triangles, $EC_{50} \approx 60$ nM).

FIG. 12F shows dose-response curves for MAS1 expressed in HEK-$G\alpha_{15}$ cells to selected RFamide neuropeptides. Each data point represents the mean±S.E.M. of at least 3 independent determinations; at least 20 GFP$^+$ cells were analyzed for each determination. Responses at each ligand concentration were normalized to the maximal response subsequently shown by the same cells to a 5 µM concentration of NPFF. MAS1, like MRGA1, is activated by NPFF with similar efficacy ($EC_{50} \approx 400$ nM), but is not as well activated by FLRF (squares).

Figure 13:
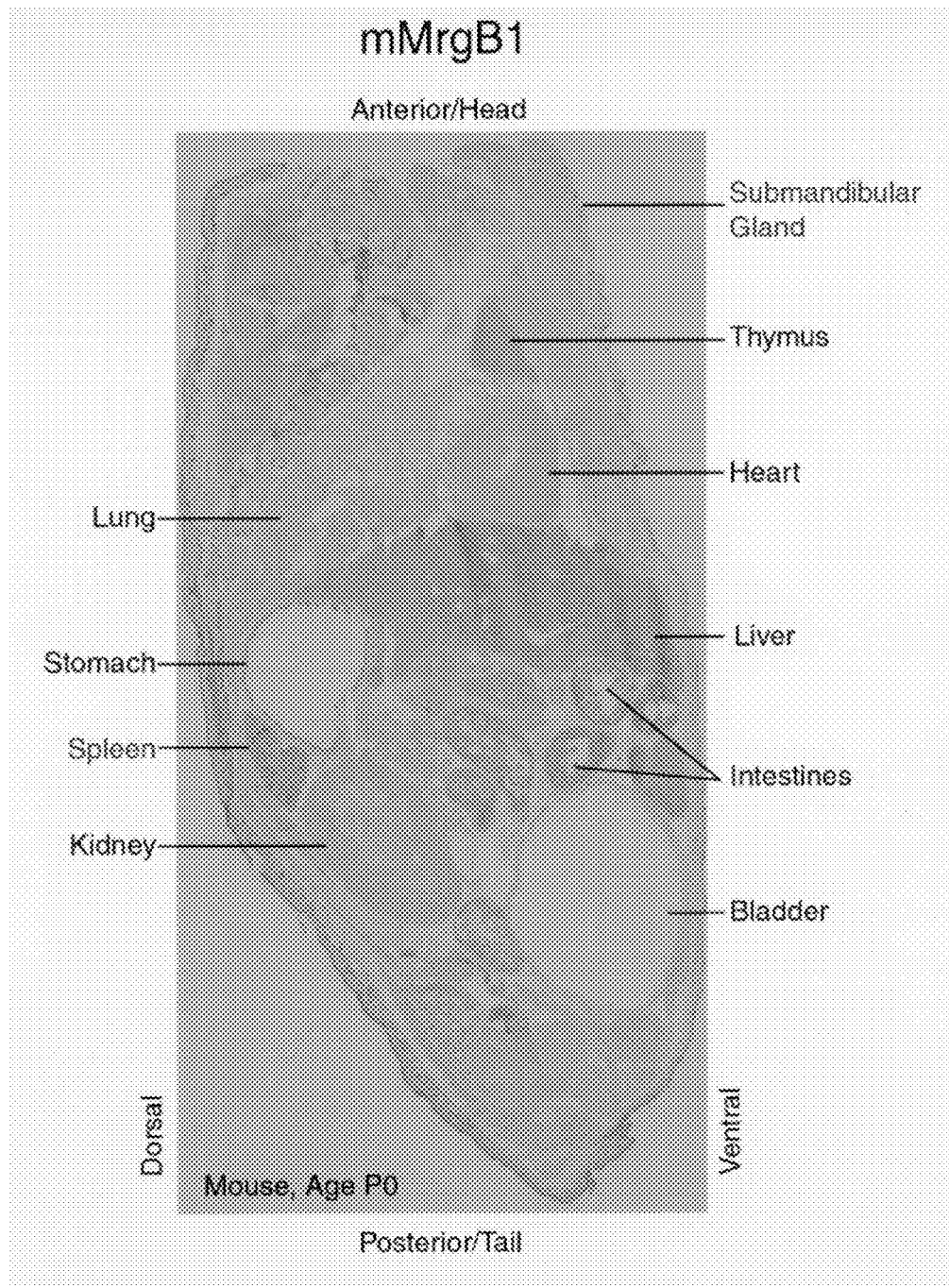

FIG. 13 depicts the expression pattern of mMrgB1 in a sagital section of a newborn mouse. The staining pattern indicates that the mMrgB1 gene is expressed in the scattered cells in the epidermal layer of the skin, in the spleen and in the submandibular gland.

Figure 14:
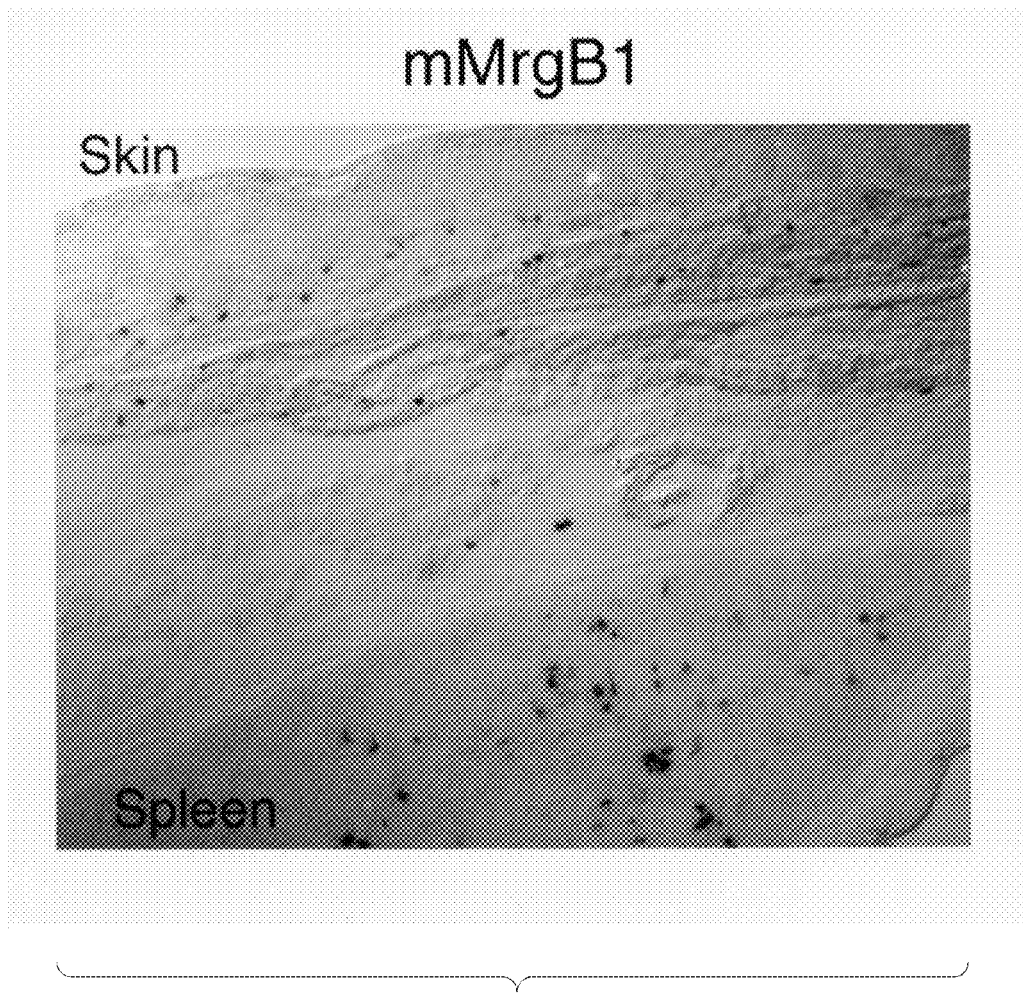

FIG. 14 is a higher magnification of the mMrgB1 expression in the spleen and skin depicted in FIG. 13.

Figure 15:
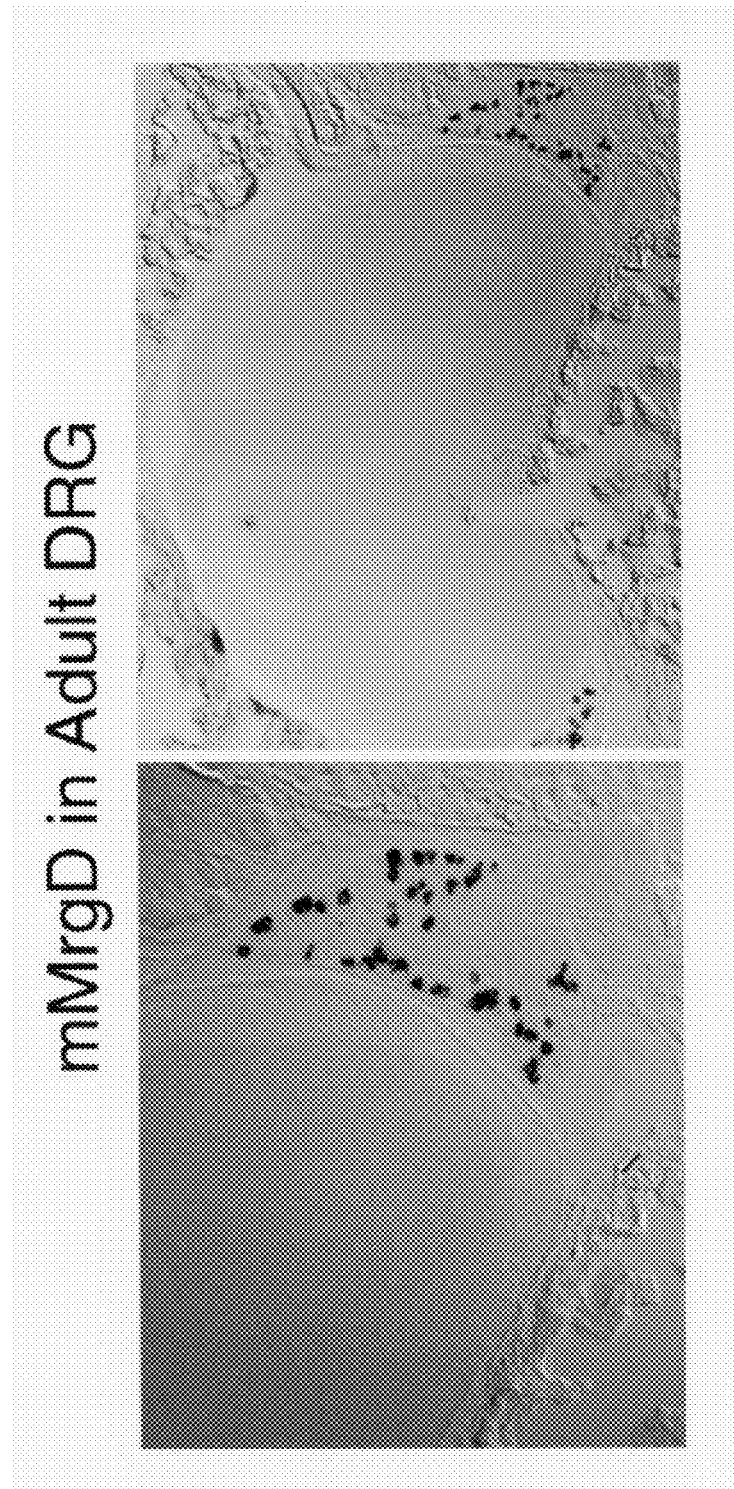

FIG. 15 shows the expression of mMrgD in adult dorsal root ganglia.

DETAILED DESCRIPTION OF THE PREFERRED EMBODIMENT

I. General Description

As described above, the present invention is based on the discovery of new genes that are expressed in the DRG of normal mice but not in Ngn1 null mutant mice. One of the novel gene families isolated from the screen encodes a receptor protein with 7 transmembrane segments, a characteristic of G protein-coupled receptors. This novel 7 transmembrane receptor is most closely related to the oncogene mas, and therefore was provisionally named mas-related gene-3 (mrg3). mrg3 is now known as MrgA1, and the terms are used interchangeably herein. Almost 50 members of the Mas-related gene (Mrg) family have been identified, many of which are specifically expressed in non-peptidergic nociceptors. Large families of G protein-coupled receptors are also expressed in other classes of sensory neurons, such as olfactory and gustatory neurons.

The murine Mrg family of GPCRs contains three major subfamilies (MrgA, B and C), each consisting of more than 10 highly duplicated genes, as well as several single-copy genes such as Mas1, Rta, MrgD and MrgE (FIG. 6B). The MrgA subfamily consists of at least twenty members in mice: MrgA1 (SEQ ID NO: 2); MrgA2 (SEQ ID NO: 4); MrgA3 (SEQ ID NO: 6); MrgA4 (SEQ ID NO: 11); MrgA5 (SEQ ID NO: 21); MrgA6 (SEQ ID NO: 23); MrgA7 (SEQ ID NO: 25); MrgA8 (SEQ ID NO: 27); MrgA9 (SEQ ID NO: 53); MrgA10 (SEQ ID NO: 55); MrgA11 (SEQ ID NO: 57); MrgA12 (SEQ ID NO: 59); MrgA13 (SEQ ID NO: 61); MrgA14 (SEQ ID NO: 63); MrgA15 (SEQ ID NO: 65); MrgA16 (SEQ ID NO: 67); MrgA17 (SEQ ID NO: 69); MrgA18 (SEQ ID NO: 71); MrgA19 (SEQ ID NO: 73); MrgA20 (SEQ ID NO: 75). Four human sequences that are most closes related to the MrgA subfamily have also been identified: MrgX1 (SEQ ID NO: 16); MrgX2 (SEQ ID NO: 18); MrgX3 (SEQ ID NO: 31); and MrgX4 (SEQ ID NO: 33).

The MrgB subfamily consists of at least twelve members in mice: MrgB1 (SEQ ID NO: 39); MrgB2 (SEQ ID NO: 41); MrgB3 (SEQ ID NO: 43); MrgB4 (SEQ ID NO: 45); MrgB5 (SEQ ID NO: 47); MrgB6 (SEQ ID NO: 77); MrgB7 (SEQ ID NO: 79); MrgB8 (SEQ ID NO: 81); MrgB9 (SEQ ID NO: 83); MrgB10 (SEQ ID NO: 85); MrgB11 (SEQ ID NO: 87); and MrgB12 (SEQ ID NO: 89).

Ten members of the MrgC subfamily have been identified in mice: MrgC1 (SEQ ID NO: 91); MrgC2 (SEQ ID NO: 93);

MrgC3 (SEQ ID NO: 95); MrgC4 (SEQ ID NO: 97); MrgC5 (SEQ ID NO: 99); MrgC6 (SEQ ID NO: 101); MrgC7 (SEQ ID NO: 103); MrgC8 (SEQ ID NO: 105); MrgC9 (SEQ ID NO: 107); and MrgC10 (SEQ ID NO: 109).

A single member of the MrgD subfamily has been identified in mice, mMrgD (SEQ ID NO: 49) and its ortholog identified in humans, hMrgD (SEQ ID NO: 35). Similarly, a single member of the MrgE subfamily has been identified in mice, mMrgE (SEQ ID NO: 51) and humans, hMrgE (SEQ ID NO: 37).

As is the case in other GPCR subfamilies, a number of the Mrgs appear to be pseudogenes, including all members of the MrgC subfamily. The presence of L1 retrotransposon elements near several Mrg genes raises the possibility that pseudogene expansion may have been driven by L1-mediated transduction (Goodier et al. *Hum Mol Genet* 9: 653-7 (2000)).

In contrast to the murine MrgA and B subfamilies, which together contain almost 40 intact coding sequences, only four intact human MrgX sequences were identified. The remaining 10 human Mrg sequences appear to be pseudogenes. Inclusion of other related receptors such as hMrgD and hMas1 brings the total number of intact human coding sequences in this family to nine (FIG. 6B).

Prior to the present invention, the primary nociceptive sensory neurons were thought not to specifically discriminate among different chemical stimuli, but rather to detect noxious stimuli of various modalities by virtue of broadly tuned receptors such as VR1 (Tominaga et al. *Neuron* 21: 531-43 (1998)). The expression of Mrgs reveals an unexpected degree of molecular diversification among nociceptive sensory neurons. Approximately 13-14% of sensory neurons express MrgA1, while 17-18% express MrgD and the overlap between these two populations is only 15%. The MrgA1$^+$ population seems to include most or all neurons expressing MrgA2-8. However, these latter MrgA genes are not all expressed in the same neurons. Thus the 8 MrgA genes and MrgD define at least 6 different neuronal subpopulations, and the remaining 16 MrgA genes add even greater diversity.

It is striking that both MrgA and D are expressed in IB4$^+$, VR1$^-$ sensory neurons. IB4$^+$ neurons are known to project to lamina IIi (Snider and McMahon *Neuron* 20: 629-32 (1998)), which has been implicated in chronic pain, such as that accompanying nerve injury (Malmberg et al. *Science* 278: 279-83 (1997)). VR1 is activated both by thermal stimuli and chemical stimuli such as capsaicin (Caterina et al. *Nature* 389: 816-824 (1997); Tominaga et al. *Neuron* 21: 531-43 (1998)), but VR1$^+$ neurons are dispensable for the detection of noxious mechanical stimuli (Caterina et al. *Science* 288: 306-13 (2000)). This indicates that one of the functions of MrgA$^+$ neurons is the detection of noxious mechanical stimuli accompanying neuropathic or inflammatory pain.

The existence of a family of putative G protein-coupled receptors specifically expressed in nociceptive sensory neurons suggests that these molecules are primary mediators or modulators of pain sensation. It is therefore of great interest to identify ligands, both endogenous and synthetic, that modulate the activity of these receptors, for the management of chronic intractable pain. Indeed, ligand screens in heterologous cell expression systems indicate that these receptors can interact with RF-amide neuropeptides of which the prototypic member is the molluscan cardioexcitatory peptide FMRF-amide (Price and Greenberg *Science* 197: 670-671 (1977)). Mammalian RF-amide peptides include NPFF and NPAF, which are derived from a common pro-peptide precursor expressed in neurons of laminae I and II of the dorsal spinal cord (Vilim et al. *Mol Pharmacol* 55: 804-11 (1999)). The expression of this neuropeptide FF precursor in the synaptic termination zone of Mrg-expressing sensory neurons, the ability of NPAF and NPFF to activate these receptors in functional assays, and the presence of binding sites for such peptides on primary sensory afferents in the dorsal horn (Gouarderes et al. *Synapse* 35: 45-52 (2000)), together indicate that these neuropeptides are ligands for Mrg receptors in vivo. As intrathecal injection of NPFF/NPAF peptides produces long-lasting antinociceptive effects in several chronic pain models (reviewed in Panula et al. *Brain Res* 848: 191-6 (1999)), including neuropathic pain (Xu et al. *Peptides* 20: 1071-7 (1999)), these data further indicate that Mrgs are directly involved in the modulation of pain.

One possibility for the extent of diversity among Mrgs expressed by murine nociceptors is that different Mrgs are expressed by sensory neurons that innervate different peripheral targets, such as gut, skin, hair follicles, blood vessels, bones and muscle. These targets may secrete different ligands for different Mrgs. Another possibility is that neurons expressing different Mrgs respond to a common modulator of peripheral nociceptor sensitivity, but with different affinities. Such a mechanism could, for example, provide a gradual restoration of normal sensitivities among the population of nociceptors during wound healing, as the concentration of such modulators gradually returned to baseline. Such a graded response might be coupled to, or even determine the activation thresholds of different subsets of nociceptors. Another novel gene family isolated in this screen, drg-12 encodes a protein with two putative transmembrane segments. Drg12 was identified from both mice (SEQ ID NO: 14) and in humans (SEQ ID NO: 29). In situ hybridization indicates that, like the mrg genes, this gene is also specifically expressed in a subset of DRG sensory neurons. As it is a membrane protein it may also be involved in signaling by these neurons. Although there are no obvious homologies between this protein and other known proteins, it is noteworthy that two purinergic receptors specifically expressed in nociceptive sensory neurons ($P_2X_2$ and $P_2X_3$) have a similar bipartite transmembrane topology. Therefore it is likely that the family drg-12 also encodes a receptor or ion channel involved in nociceptive sensory transduction or its modulation.

The proteins of the invention can serve as therapeutics and as a target for agents that modulate their expression or activity, for example in the treatment of chronic intractable pain and neuropathic pain. For example, agents may be identified which modulate biological processes associated with nociception such as the reception, transduction and transmission of pain signals.

II. Specific Embodiments

A. Definitions

Unless defined otherwise, technical and scientific terms used herein have the same meaning as commonly understood by one of ordinary skill in the art to which this invention belongs. See, e.g. Singleton et al., *Dictionary of Microbiology and Molecular Biology* 2nd ed., J. Wiley & Sons (New York, N.Y. 1994); Sambrook et al., *Molecular Cloning, A Laboratory Manual*, Cold Springs Harbor Press (Cold Springs Harbor, N.Y. 1989). For purposes of the present invention, the following terms are defined below.

As used herein, the "protein" or "polypeptide" refers, in part, to a protein that has the amino acid sequence depicted in SEQ ID NO: 2, 4, 6, 8, 10, 12, 14, 16, 18, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107 and 109. The terms also refer to naturally occurring allelic variants and proteins that have a slightly different amino acid sequence than those specifically recited above. Allelic variants, though possessing a slightly different amino acid sequence than those recited above, will still have the same or similar biological functions associated with the protein.

Identity or homology with respect to amino acid sequences is defined herein as the percentage of amino acid residues in the candidate sequence that are identical with the known peptides, after aligning the sequences and introducing gaps, if necessary, to achieve the maximum percent homology, and not considering any conservative substitutions as part of the sequence identity (see section B for the relevant parameters). Fusion proteins, or N-terminal, C-terminal or internal extensions, deletions, or insertions into the peptide sequence shall not be construed as affecting homology.

Proteins can be aligned using CLUSTALW (Thompson et al. *Nucleic Acids Res* 22:4673-80 (1994)) and homology or identity at the nucleotide or amino acid sequence level may be determined by BLAST (Basic Local Alignment Search Tool) analysis using the algorithm employed by the programs blastp, blastn, blastx, tblastn and tblastx (Karlin, et al. Proc. Natl. Acad. Sci. USA 87: 2264-2268 (1990) and Altschul, S. F. J. Mol. Evol. 36: 290-300 (1993), fully incorporated by reference) which are tailored for sequence similarity searching. The approach used by the BLAST program is to first consider similar segments between a query sequence and a database sequence, then to evaluate the statistical significance of all matches that are identified and finally to summarize only those matches which satisfy a preselected threshold of significance. For a discussion of basic issues in similarity searching of sequence databases, see Altschul et al. (Nature Genetics 6: 119-129 (1994)) which is fully incorporated by reference. The search parameters for histogram, descriptions, alignments, expect (i.e., the statistical significance threshold for reporting matches against database sequences), cutoff, matrix and filter are at the default settings. The default scoring matrix used by blastp, blastx, tblastn, and tblastx is the BLOSUM62 matrix (Henikoff, et al. Proc. Natl. Acad. Sci. USA 89: 10915-10919 (1992), fully incorporated by reference). For blastn, the scoring matrix is set by the ratios of M (i.e., the reward score for a pair of matching residues) to N (i.e., the penalty score for mismatching residues), wherein the default values for M and N are 5 and -4, respectively. Four blastn parameters were adjusted as follows: Q=10 (gap creation penalty); R=10 (gap extension penalty); wink=1 (generates word hits at every winkth position along the query); and gapw=16 (sets the window width within which gapped alignments are generated). The equivalent Blastp parameter settings were Q=9; R=2; wink=1; and gapw=32. A Bestfit comparison between sequences, available in the GCG package version 10.0, uses DNA parameters GAP=50 (gap creation penalty) and LEN=3 (gap extension penalty) and the equivalent settings in protein comparisons are GAP=8 and LEN=2.

"Variants" are biologically active polypeptides having an amino acid sequence which differs from the sequence of a native sequence polypeptide of the present invention, such as that shown in FIG. 1A for mrg3 (SEQ ID NO: 2), by virtue of an insertion, deletion, modification and/or substitution of one or more amino acid residues within the native sequence. Variants include peptide fragments of at least 5 amino acids, preferably at least 10 amino acids, more preferably at least 15 amino acids, even more preferably at least 20 amino acids that retain a biological activity of the corresponding native sequence polypeptide. Variants also include polypeptides wherein one or more amino acid residues are added at the N- or C-terminus of, or within, a native sequence. Further, variants also include polypeptides where a number of amino acid residues are deleted and optionally substituted by one or more different amino acid residues.

As used herein, a "conservative variant" refers to alterations in the amino acid sequence that do not adversely affect the biological functions of the protein. A substitution, insertion or deletion is said to adversely affect the protein when the altered sequence prevents or disrupts a biological function associated with the protein. For example, the overall charge, structure or hydrophobic/hydrophilic properties of the protein can be altered without adversely affecting a biological activity. Accordingly, the amino acid sequence can be altered, for example to render the peptide more hydrophobic or hydrophilic, without adversely affecting the biological activities of the protein.

As used herein, the "family of proteins" related to the amino acid sequences of SEQ ID NO: 2, 4, 6, 8, 10, 12, 14, 16, 18, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107 and 109 includes proteins that have been isolated from the dorsal root ganglia of organisms in addition to mice and humans. The methods used to identify and isolate other members of the family of proteins related to these proteins, such as the disclosed mouse and human proteins, are described below.

Unless indicated otherwise, the term "Mrg" when used herein refers to any one or more of the mammalian mas-related gene (Mrg) receptors (i.e. MrgA1-8, MrgB, MrgC, MrgD, MrgE, MrgX1-4 and any other members of the mas-related gene (Mrg) family now known or identified in the future), including native sequence mammalian, such as murine or human, Mrg receptors, Mrg receptor variants; Mrg receptor extracellular domain; and chimeric Mrg receptors (each of which is defined herein). The term specifically includes native sequence murine Mrg receptors of the MrgA family, such as SEQ ID NOs: 2, 4, 6 12, 21, 23, 25, 27, 53, 55, 57, 59, 61, 63, 65, 67, 69, 71, 73, and 75; native sequence murine Mrg receptors of the MrgB family, such as SEQ ID NOs: 39, 41, 43, 45, 47, 77, 79, 81, 83, 85, 87, and 89; native sequence murine Mrg receptors of the MrgC family, such as SEQ ID NOs: 91, 93, 95, 97, 99, 101, 103, 105, 107 and 109; native sequence murine Mrg receptors of the MrgD family, such as SEQ ID NO: 49; native sequence murine Mrg receptors of the MrgE family, such as SEQ ID NO: 51; their human homologues, and the native sequence human Mrg receptors termed "MrgX" of SEQ ID NOs: 16, 18, 31 and 33.

The terms "mas-related gene", "mrg" and "Mrg" are used interchangeably herein. Further, the terms mrg3, MrgA1 and mMrgA1 are used interchangeably, as are the terms mrg4, MrgA2 and mMrgA2, the terms mrg5, MrgA3 and mMrgA3, the terms mrg8, MrgA4 and mMrgA4, the terms mrg9, MrgA5 and mMrgA5, the terms mrg10, MrgA6 and mMrgA6, the terms mrg11, MrgA7 and mMrgA7, the terms mrg12, MrgA8 and mMrgA8, the terms human1, MrgX1 and hMrgX1, the terms human2, MrgX2 and hMrgX2, the terms human 4, MrgX3 and hMrgX3, and the terms human5, MrgX4 and hMrgX4. These terms all refer to native sequence Mrg proteins as described herein as well as functional derivatives, including amino acid sequence variants thereof.

A "native" or "native sequence" Mrg or drg-12 receptor has the amino acid sequence of a naturally occurring Mrg or drg-12 receptor in any mammalian species (including humans), irrespective of its mode of preparation. Accordingly, a native or native sequence Mrg or drg-12 receptor may be isolated from nature, produced by techniques of recombinant DNA technology, chemically synthesized, or produced by any combinations of these or similar methods. Native Mrg and drg-12 receptors specifically include polypeptides having the amino acid sequence of naturally occurring allelic variants, isoforms or spliced variants of these receptors, known in the art or hereinafter discovered.

Figure 1B:
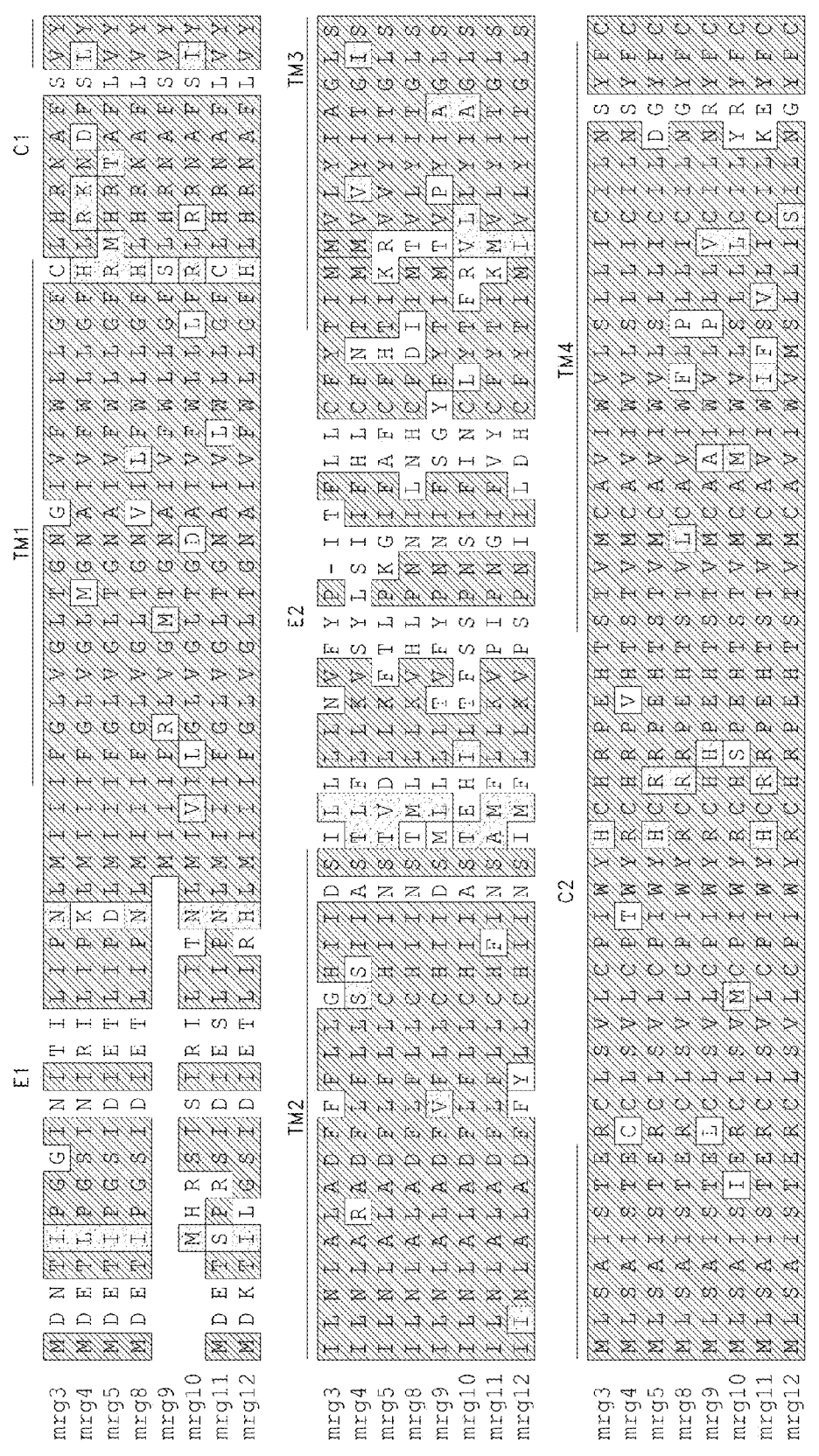
Figure 1C:
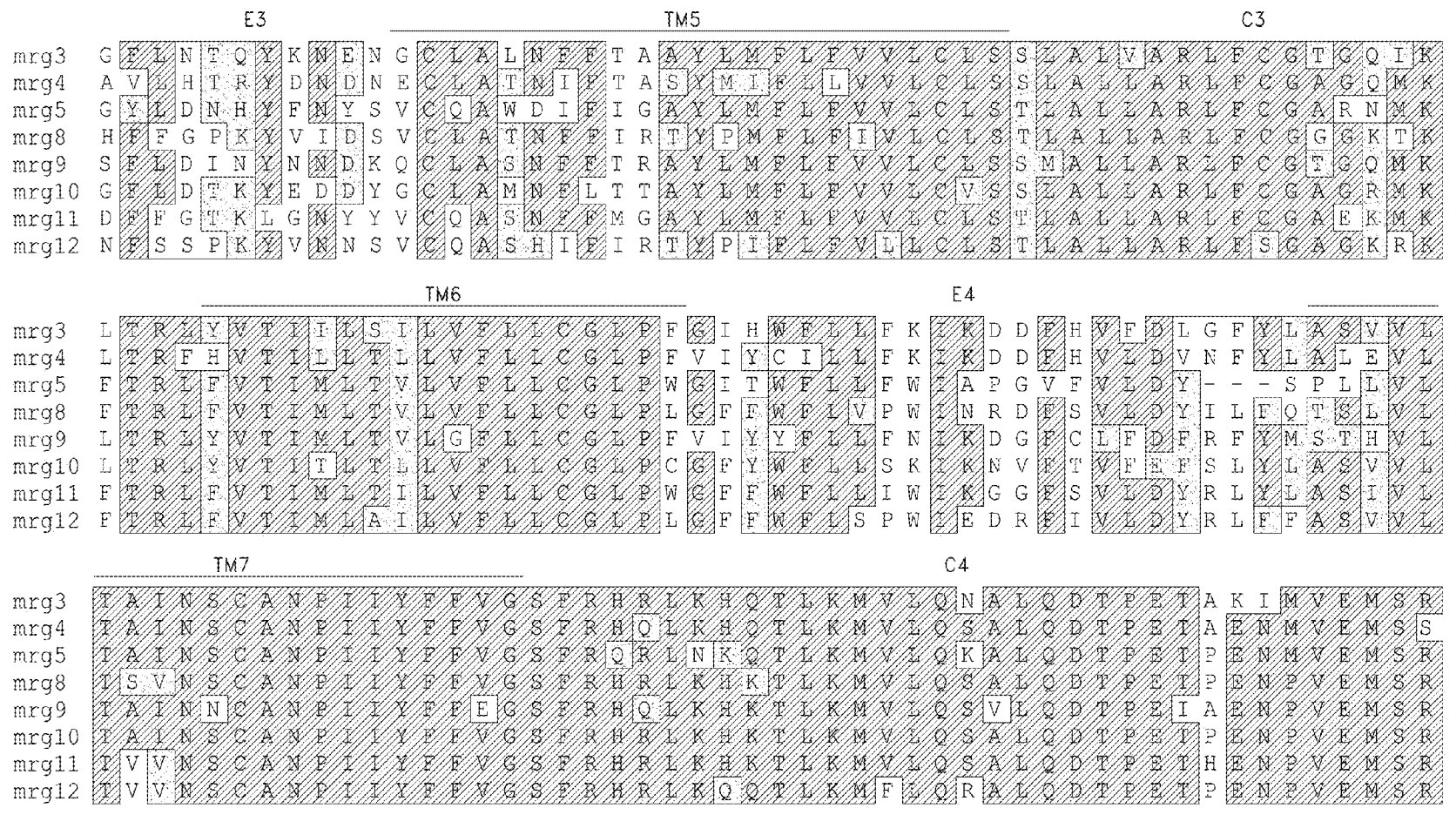

The "extracellular domain" (ECD) is a form of the Mrg or drg-12 receptor which is essentially free of the transmembrane and cytoplasmic domains, i.e., has less than 1% of such domains, preferably 0.5 to 0% of such domains, and more preferably 0.1 to 0% of such domains. Ordinarily, the ECD will have an amino acid sequence having at least about 60% amino acid sequence identity with the amino acid sequence of one or more of the ECDs of a native Mrg or drg-12 protein, for example as indicated in FIGS. 1B-D for mrg3 (E1, E2 etc. . . . ), preferably at least about 65%, more preferably at least about 75%, even more preferably at least about 80%, even more preferably at least about 90%, with increasing preference of 95%, to at least 99% amino acid sequence identity, and finally to 100% identity, and thus includes polypeptide variants as defined below.

The first predicted extracellular domain (ECD1) comprises approximately amino acids 1 to 21 for MrgA1, 1 to 21 for MrgA2, 1 to 21 for MrgA3, 1 to 21 for MrgA4, 1 to 3 for MrgA5, 1 to 17 for MrgA6, 1 to 21 for MrgA7 and 1 to 21 for MrgA8. The second predicted extracellular domain (ECD2) comprises approximately amino acids 70 to 87 for MrgA1, 70 to 88 for MrgA2, 70 to 88 for MrgA3, 70 to 88 for MrgA4, 52 to 70 for MrgA5, 66 to 84 for MrgA6, 70 to 88 for MrgA7 and 70 to 88 for MrgA8. The third predicted extracellular domain (ECD3) comprises approximately amino acids 149 to 160 for MrgA1, 150 to 161 for MrgA2, 150 to 161 for MrgA3, 150 to 161 for MrgA4, 132 to 144 for MrgA5, 146 to 157 for MrgA6, 150 to 161 for MrgA7 and 150 to 161 for MrgA8. The fourth predicted extracellular domain (ECD4) comprises approximately amino acids 222 to 2244 for MrgA1, 223 to 245 for MrgA2, 223 to 242 for MrgA3, 223 to 245 for MrgA4, 205 to 225 for MrgA5, 219 to 241 for MrgA6, 223 to 245 for MrgA7 and 223 to 245 for MrgA8.

The term "drg-12" when used herein refers to any one or more of the mammalian drg-12 receptors now known or identified in the future, including native sequence mammalian, such as murine or human, drg-12 receptors, drg-12 receptor variants; drg-12 receptor extracellular domain; and chimeric drg-12 receptors (each of which is defined herein). The term specifically includes native sequence murine drg-12 receptor, such as SEQ ID NO: 14, and any human homologues, such as human drg-12 (SEQ ID NO: 29).

As used herein, "nucleic acid" is defined as RNA or DNA that encodes a protein or peptide as defined above, is complementary to a nucleic acid sequence encoding such peptides, hybridizes to such a nucleic acid and remains stably bound to it under appropriate stringency conditions, exhibits at least about 50%, 60%, 70%, 75%, 85%, 90% or 95% nucleotide sequence identity across the open reading frame, or encodes a polypeptide sharing at least about 50%, 60%, 70% or 75% sequence identity, preferably at least about 80%, and more preferably at least about 85%, and even more preferably at least about 90 or 95% or more identity with the peptide sequences. Specifically contemplated are genomic DNA, cDNA, mRNA and antisense molecules, as well as nucleic acids based on alternative backbones or including alternative bases whether derived from natural sources or synthesized. Such hybridizing or complementary nucleic acids, however, are defined further as being novel and unobvious over any prior art nucleic acid including that which encodes, hybridizes under appropriate stringency conditions, or is complementary to nucleic acid encoding a protein according to the present invention.

As used herein, the terms nucleic acid, polynucleotide and nucleotide are interchangeable and refer to any nucleic acid, whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sultone linkages, and combinations of such linkages.

The terms nucleic acid, polynucleotide and nucleotide also specifically include nucleic acids composed of bases other than the five biologically occurring bases (adenine, guanine, thymine, cytosine and uracil). For example, a polynucleotide of the invention might contain at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyl-uracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5N-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine.

Furthermore, a polynucleotide used in the invention may comprise at least one modified sugar moiety selected from the group including but not limited to arabinose, 2-fluoroarabinose, xylulose, and hexose.

"Stringent conditions" are those that (1) employ low ionic strength and high temperature for washing, for example, 0.015 M NaCl/0.0015 M sodium citrate/0.1% SDS at 50° C., or (2) employ during hybridization a denaturing agent such as formamide, for example, 50% (vol/vol) formamide with 0.1% bovine serum albumin/0.1% Ficoll/0.1% polyvinylpyrolidone/50 mM sodium phosphate buffer at pH 6.5 with 750 mM NaCl, 75 mM sodium citrate at 42° C. Another example is use of 50% formamide, 5×SSC (0.75M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC and 0.1% SDS. A skilled artisan can readily determine and vary the stringency conditions appropriately to obtain a clear and detectable hybridization signal.

As used herein, a nucleic acid molecule is said to be "isolated" when the nucleic acid molecule is substantially separated from contaminant nucleic acid molecules encoding other polypeptides.

As used herein, a fragment of an encoding nucleic acid molecule refers to a small portion of the entire protein coding sequence. The size of the fragment will be determined by the intended use. For example, if the fragment is chosen so as to encode an active portion of the protein, the fragment will need to be large enough to encode the functional region(s) of the protein. For instance, fragments which encode peptides corresponding to predicted antigenic regions may be prepared (see FIGS. 3 and 4). If the fragment is to be used as a nucleic acid probe or PCR primer, then the fragment length is chosen so as to obtain a relatively small number of false positives during probing/priming (see the discussion in Section H).

Highly related gene homologs are polynucleotides encoding proteins that have at least about 60% amino acid sequence identity with the amino acid sequence of a naturally occurring native sequence polynucleotide of the invention, such as MrgA1 (SEQ ID NO: 2), preferably at least about 65%, 70%, 75%, 80%, with increasing preference of at least about 85% to at least about 99% amino acid sequence identity, in 1% increments.

The term "mammal" is defined as an individual belonging to the class Mammalia and includes, without limitation, humans, domestic and farm animals, and zoo, sports, or pet animals, such as sheep, dogs, horses, cats or cows. Preferably, the mammal herein is human.

"Functional derivatives" include amino acid sequence variants, and covalent derivatives of the native polypeptides as long as they retain a qualitative biological activity of the corresponding native polypeptide.

By "Mrg ligand" is meant a molecule which specifically binds to and preferably activates an Mrg receptor. Examples of Mrg ligands include, but are not limited to RF-amide neuropeptides, such as FMRF, FLRF, NPAF, NPFF, and RFRP-1 for MrgA receptors, such as MrgA1. The ability of a molecule to bind to Mrg can be determined, for example, by the ability of the putative ligand to bind to membrane fractions prepared from cells expressing Mrg.

Similarly, a drg-12 ligand is a molecule which specifically binds to and preferably activates a drg-12 receptor.

A "chimeric" molecule is a polypeptide comprising a full-length polypeptide of the present invention, a variant, or one or more domains of a polypeptide of the present invention fused or bonded to a heterologous polypeptide. The chimeric molecule will generally share at least one biological property in common with a naturally occurring native sequence polypeptide. An example of a chimeric molecule is one that is epitope tagged for purification purposes. Another chimeric molecule is an immunoadhesin.

The term "epitope-tagged" when used herein refers to a chimeric polypeptide comprising Mrg or drg-12 fused to a "tag polypeptide". The tag polypeptide has enough residues to provide an epitope against which an antibody can be made, yet is short enough such that it does not interfere with the biological activity of the Mrg or drg-12. The tag polypeptide preferably is fairly unique so that the antibody against it does not substantially cross-react with other epitopes. Suitable tag polypeptides generally have at least six amino acid residues and usually between about 8-50 amino acid residues (preferably between about 9-30 residues). Preferred are poly-histidine sequences, which bind nickel, allowing isolation of the tagged protein by Ni-NTA chromatography as described (See, e.g., Lindsay et al. *Neuron* 17:571-574 (1996)).

"Agonists" are molecules or compounds that stimulate one or more of the biological properties of a polypeptide of the present invention. These may include, but are not limited to, small organic and inorganic molecules, peptides, peptide mimetics and agonist antibodies.

The term "antagonist" is used in the broadest sense and refers to any molecule or compound that blocks, inhibits or neutralizes, either partially or fully, a biological activity mediated by a receptor of the present invention by preventing the binding of an agonist. Antagonists may include, but are not limited to, small organic and inorganic molecules, peptides, peptide mimetics and neutralizing antibodies.

The proteins of the present invention are preferably in isolated form. As used herein, a protein is said to be isolated when physical, mechanical or chemical methods are employed to remove the protein from cellular constituents that are normally associated with the protein. A skilled artisan can readily employ standard purification methods to obtain an isolated protein. In some instances, isolated proteins of the invention will have been separated or purified from many cellular constituents, but will still be associated with cellular membrane fragments or membrane constituents.

Thus, "isolated Mrg" and "isolated drg-12" means Mrg or drg-12 polypeptide, respectively, that has been purified from a protein source or has been prepared by recombinant or synthetic methods and purified. Purified Mrg or drg-12 is substantially free of other polypeptides or peptides. "Substantially free" here means less than about 5%, preferably less than about 2%, more preferably less than about 1%, even more preferably less than about 0.5%, most preferably less than about 0.1% contamination with other source proteins.

"Essentially pure" protein means a composition comprising at least about 90% by weight of the protein, based on total weight of the composition, preferably at least about 95% by weight, more preferably at least about 90% by weight, even more preferably at least about 95% by weight. "Essentially homogeneous" protein means a composition comprising at least about 99% by weight of protein, based on total weight of the composition.

"Biological property" is a biological or immunological activity, where biological activity refer to a biological function (either inhibitory or stimulatory) caused by a native sequence or variant polypeptide molecule herein, other than the ability to induce the production of an antibody against an epitope within such polypeptide, where the latter property is referred to as immunological activity. Biological properties specifically include the ability to bind a naturally occurring ligand of the receptor molecules herein, preferably specific binding, and even more preferably specific binding with high affinity.

"Antibodies" (Abs) and "immunoglobulins" (Igs) are glycoproteins having the same structural characteristics. While antibodies exhibit binding specificity to a specific antigen, immunoglobulins include both antibodies and other antibody-like molecules that lack antigen specificity. Polypeptides of the latter kind are, for example, produced at low levels by the lymph system and at increased levels by myelomas.

"Native antibodies" and "native immunoglobulins" are usually heterotetrameric glycoproteins, composed of two identical light (L) chains and two identical heavy (H) chains. Each light chain is linked to a heavy chain by one covalent disulfide bond. while The number of disulfide linkages varies among the heavy chains of different immunoglobulin isotypes. Each heavy and light chain also has regularly spaced intra-chain disulfide bridges. Each heavy chain has at one end a variable domain ($V_H$) followed by a number of constant domains. Each light chain has a variable domain at one end ($V_L$) and a constant domain at its other end. The constant domain of the light chain is aligned with the first constant domain of the heavy chain, and the light-chain variable domain is aligned with the variable domain of the heavy chain. Particular amino acid residues are believed to form an interface between the light- and heavy-chain variable domains.

The term "antibody" herein is used in the broadest sense and specifically covers human, non-human (e.g. murine) and humanized monoclonal antibodies (including full length monoclonal antibodies), polyclonal antibodies, multi-specific antibodies (e.g., bispecific antibodies), and antibody fragments so long as they exhibit the desired biological activity.

"Antibody fragments" comprise a portion of a full-length antibody, generally the antigen binding or variable domain thereof. Examples of antibody fragments include Fab, Fab', F(ab')$_2$, and Fv fragments; diabodies; linear antibodies; single-chain antibody molecules; and multi-specific antibodies formed from antibody fragments.

The term "monoclonal antibody" as used herein refers to an antibody obtained from a population of antibodies wherein the individual antibodies comprising the population are identical except for possible naturally occurring mutations that may be present in minor amounts. Monoclonal antibodies are highly specific and are directed against a single antigenic site. In addition, monoclonal antibodies may be made by any method known in the art. For example, the monoclonal antibodies to be used in accordance with the present invention may be made by the hybridoma method first described by Kohler et al., *Nature* 256:495 (1975), or may be made by recombinant DNA methods (see, e.g., U.S. Pat. No. 4,816, 567). The "monoclonal antibodies" may also be isolated from phage antibody libraries using the techniques described in Clackson et al., *Nature* 352:624-628 (1991) and Marks et al., *J. Mol. Biol.* 222:581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass. Fragments of chimeric antibodies are also included provided they exhibit the desired biological activity (U.S. Pat. No. 4,816,567; and Morrison et al., *Proc. Natl. Acad. Sci. USA* 81:6851-6855 (1984)).

"Humanized" forms of non-human (e.g., murine) antibodies are antibodies that contain minimal sequence derived from non-human immunoglobulin. Humanized antibodies are generally human immunoglobulins in which hypervariable region residues are replaced by hypervariable region residues from a non-human species such as mouse, rat, rabbit or non-human primate having the desired specificity, affinity, and capacity. Framework region (FR) residues of the human immunoglobulin may be replaced by corresponding non-human residues. In addition, humanized antibodies may comprise residues that are not found in either the recipient antibody or in the donor antibody. In general, the humanized antibody will comprise substantially all of at least one, and typically two, variable domains, in which all or substantially all of the hypervariable regions correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Reichmann et al., *Nature* 332:323-329 (1988); and Presta, *Curr. Op. Struct. Biol.* 2:593-596 (1992).

The term "epitope" is used to refer to binding sites for (monoclonal or polyclonal) antibodies on protein antigens.

By "agonist antibody" is meant an antibody which is a ligand for a receptor of the invention and thus, able to activate and/or stimulate one or more of the effector functions of native sequence Mrg or drg-12.

By "neutralizing antibody" is meant an antibody molecule as herein defined which is able to block or significantly reduce an effector function of a polypeptide of the invention. For example, a neutralizing antibody may inhibit or reduce Mrg or drg-12 activation by a known ligand.

The term "Mrg immunoadhesin" refers to a chimeric molecule that comprises at least a portion of an Mrg or drg-12 molecule (native or variant) and an immunoglobulin sequence. The immunoglobulin sequence preferably, but not necessarily, is an immunoglobulin constant domain. Immunoadhesins can possess many of the properties of human antibodies. Since immunoadhesins can be constructed from a human protein sequence with a desired specificity linked to an appropriate human immunoglobulin hinge and constant domain (Fc) sequence, the binding specificity of interest can be achieved using entirely human components. Such immunoadhesins are minimally immunogenic to the patient, and are safe for chronic or repeated use. If the two arms of the immunoadhesin structure have different specificities, the immunoadhesin is called a "bispecific immunoadhesin" by analogy to bispecific antibodies.

As used herein, "treatment" is a clinical intervention made in response to a disease, disorder or physiological condition manifested by a patient. The aim of treatment includes the alleviation or prevention of symptoms, slowing or stopping the progression or worsening of a disease, disorder, or condition and the remission of the disease, disorder or condition. "Treatment" refers to both therapeutic treatment and prophylactic or preventative measures. Those in need of treatment include those already affected by a disease or disorder or undesired physiological condition as well as those in which the disease or disorder or undesired physiological condition is to be prevented. Specifically, treatment may alleviate pain, including pain resulting from an existing condition or disorder, or to prevent pain in situations where pain is likely to be experienced.

In the methods of the present invention, the term "control" and grammatical variants thereof, are used to refer to the prevention, partial or complete inhibition, reduction, delay or slowing down of an unwanted event, such as the presence or onset of pain.

The term "effective amount" refers to an amount sufficient to effect beneficial or desirable clinical results. An effective amount of an agonist or antagonist is an amount that is effective to treat a disease, disorder or unwanted physiological condition.

"Pain" is a sensory experience perceived by nerve tissue distinct from sensations of touch, pressure, heat and cold. The range of pain sensations, as well as the variation of perception of pain by individuals, renders a precise definition of pain near impossible. In the context of the present invention, "pain" is used in the broadest possible sense and includes nociceptive pain, such as pain related to tissue damage and inflammation, pain related to noxious stimuli, acute pain, chronic pain, and neuropathic pain.

"Acute pain" is often short-lived with a specific cause and purpose; generally produces no persistent psychological reactions. Acute pain can occur during soft tissue injury, and with infection and inflammation. It can be modulated and removed by treating its cause and through combined strategies using analgesics to treat the pain and antibiotics to treat the infection.

"Chronic pain" is distinctly different from and more complex than acute pain. Chronic pain has no time limit, often has no apparent cause and serves no apparent biological purpose. Chronic pain can trigger multiple psychological problems that confound both patient and health care provider, leading to feelings of helplessness and hopelessness. The most common causes of chronic pain include low-back pain, headache, recurrent facial pain, pain associated with cancer and arthritis pain.

The pain is termed "neuropathic" when it is taken to represent neurologic dysfunction. "Neuropathic pain" has a complex and variable etiology. It is typically characterized by hyperalgesia (lowered pain threshold and enhanced pain perception) and by allodynia (pain from innocuous mechanical or thermal stimuli). Neuropathic pain is usually chronic and tends not to respond to the same drugs as "normal pain" (nociceptive pain), therefore, its treatment is much more difficult. Neuropathic pain may develop whenever nerves are damaged, by trauma, by disease such as diabetes, herpes zoster, or late-stage cancer, or by chemical injury (e.g., as an untoward consequence of agents including the false-nucleotide anti-HIV drugs). It may also develop after amputation (including mastectomy). Examples of neuropathic pain include monoradiculopathies, trigeminal neuralgia, postherpetic neuralgia, complex regional pain syndromes and the various peripheral neuropathies. This is in contrast with "normal pain" or "nociceptive pain," which includes normal postoperative pain, pain associated with trauma, and chronic pain of arthritis.

"Peripheral neuropathy" is a neurodegenerative disorder that affects the peripheral nerves, most often manifested as one or a combination of motor, sensory, sensorimotor, or autonomic dysfunction. Peripheral neuropathies may, for example, be characterized by the degeneration of peripheral sensory neurons, which may result from a disease or disorder such as diabetes (diabetic neuropathy), alcoholism and acquired immunodeficiency syndrome (AIDS), from therapy such as cytostatic drug therapy in cancer, or from genetic predisposition. Genetically acquired peripheral neuropathies include, for example, Krabbe's disease, Metachromatic leukodystrophy, and Charcot-Marie-Tooth (CMT) Disease. Peripheral neuropathies are often accompanied by pain.

"Pharmaceutically acceptable" carriers, excipients, or stabilizers are ones which are nontoxic to the cell or mammal being exposed thereto at the dosages and concentrations employed. Often the physiologically acceptable carrier is an aqueous pH buffered solution such as phosphate buffer or citrate buffer. The physiologically acceptable carrier may also comprise one or more of the following: antioxidants including ascorbic acid, low molecular weight (less than about 10 residues) polypeptides, proteins, such as serum albumin, gelatin, immunoglobulins; hydrophilic polymers such as polyvinylpyrrolidone, amino acids, carbohydrates including glucose, mannose, or dextrins, chelating agents such as EDTA, sugar alcohols such as mannitol or sorbitol, salt-forming counterions such as sodium, and nonionic surfactants such as Tween™, polyethylene glycol (PEG), and Pluronics™.

"Peptide mimetics" are molecules which serve as substitutes for peptides in interactions with the receptors of the present invention (Morgan et al., *Ann. Reports Med. Chem.* 24:243-252 (1989)). Peptide mimetics, as used herein, include synthetic structures that retain the structural and functional features of a peptide. Peptide mimetics may or may not contain amino acids and/or peptide bonds. The term, "peptide mimetics" also includes peptoids and oligopeptoids, which are peptides or oligomers of N-substituted amino acids (Simon et al., *Proc. Natl. Acad. Sci. USA* 89:9367-9371 (1972)). Further included as peptide mimetics are peptide libraries, which are collections of peptides designed to be of a given amino acid length and representing all conceivable sequences of amino acids corresponding thereto.

A. Proteins Expressed in Primary Sensory Neurons of Dorsal Root Ganglia

The present invention provides isolated mrg and drg-12 proteins, allelic variants of the proteins, and conservative amino acid substitutions of the proteins. Polypeptide sequences of several Mrg proteins of the present invention are provided in SEQ ID NOs: 2, 4, 6, 8, 10, 12, 16, 18, 21, 23, 25, 27, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107 and 109. Polypeptide sequences of several drg-12 proteins of the present invention are provided in SEQ ID NOs: 14, 19 and 29.

The proteins of the present invention further include insertion, deletion or conservative amino acid substitution variants of the sequences set forth in SEQ ID NOs: 2, 4, 6, 8, 10, 12, 14, 16, 18, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107 and 109.

Ordinarily, the variants, allelic variants, the conservative substitution variants, and the members of the protein family, including corresponding homologues in other species, will have an amino acid sequence having at least about 50%, or about 60% to 75% amino acid sequence identity with the sequences set forth in SEQ ID NOs: 2, 4, 6, 8, 10, 12, 14, 16, 18, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107 or 109, more preferably at least about 80%, even more preferably at least about 90%, and most preferably at least about 95% sequence identity with said sequences.

The proteins of the present invention include molecules having the amino acid sequence disclosed in SEQ ID NOs: 2, 4, 6, 8, 10, 12, 14, 16, 18, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107 and 109; fragments thereof having a consecutive sequence of at least about 3, 4, 5, 6, 10, 15, 20, 25, 30, 35 or more amino acid residues of the protein; amino acid sequence variants wherein one or more amino acid residues has been inserted N- or C-terminal to, or within, the disclosed coding sequence; and amino acid sequence variants of the disclosed sequence, or their fragments as defined above, that have been substituted by another residue. Such fragments, also referred to as peptides or polypeptides, may contain antigenic regions, functional regions of the protein identified as regions of the amino acid sequence which correspond to known protein domains, as well as regions of pronounced hydrophilicity. The regions are all easily identifiable by using commonly available protein sequence analysis software such as MACVECTOR™ (Oxford Molecular).

Contemplated variants further include those containing predetermined mutations by, e.g., homologous recombination, site-directed or PCR mutagenesis, and the corresponding proteins of other animal species, including but not limited to rabbit, rat, porcine, bovine, ovine, equine, human and non-human primate species, and the alleles or other naturally occurring variants of the family of proteins; and derivatives wherein the protein has been covalently modified by substitution, chemical, enzymatic, or other appropriate means with a moiety other than a naturally occurring amino acid (for example a detectable moiety such as an enzyme or radioisotope).

Protein domains such as a ligand binding domain, an extracellular domain, a transmembrane domain (e.g. comprising seven membrane spanning segments and cytosolic loops or two membrane spanning domains and cytosolic loops), the transmembrane domain and a cytoplasmic domain and an active site may all be found in the proteins or polypeptides of the invention. Such domains are useful for making chimeric proteins and for in vitro assays of the invention.

Variations in native sequence proteins of the present invention or in various domains identified therein, can be made, for example, using any techniques known in the art. Variation can be achieved, for example, by substitution of at least one amino acid with any other amino acid in one or more of the domains of the protein. A change in the amino acid sequence of a protein of the invention as compared with a native sequence protein may be produced by a substitution, deletion or insertion of one or more codons encoding the protein. A comparison of the sequence of the Mrg or drg-12 polypeptide to be changed with that of homologous known protein molecules may provide guidance as to which amino acid residues may be inserted, substituted or deleted without affecting a desired biological activity. In particular, it may be beneficial to minimize the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the full-length or mature native sequence.

Polypeptide fragments are also useful in the methods of the present invention. Such fragments may be truncated at the N-terminus or C-terminus, or may lack internal residues, for example, when compared with a full-length native protein. Certain fragments lack amino acid residues that are not essential for a desired biological activity of the Mrg or drg-12 polypeptide.

Mrg or drg-12 fragments may be prepared by any of a number of conventional techniques. Desired peptide fragments may be chemically synthesized or generated by enzymatic digestion, such as by treating the protein with an enzyme known to cleave proteins at sites defined by particular amino acid residues. Alternatively, the DNA encoding the protein may be digested with suitable restriction enzymes and the desired fragment isolated. Yet another suitable technique involves isolating and amplifying a DNA fragment encoding a desired polypeptide fragment, by polymerase chain reaction (PCR). Oligonucleotides that define the desired termini of the DNA fragment are employed at the 5' and 3' primers in the PCR. Preferably, Mrg or drg-12 polypeptide fragments share at least one biological and/or immunological activity with a native Mrg or drg-12 polypeptide, respectively.

In making amino acid sequence variants that retain the required biological properties of the corresponding native sequences, the hydropathic index of amino acids may be considered. For example, it is known that certain amino acids may be substituted for other amino acids having a similar hydropathic index or score without significant change in biological activity. Thus, isoleucine, which has a hydropathic index of +4.5, can generally be substituted for valine (+4.2) or leucine (+3.8), without significant impact on the biological activity of the polypeptide in which the substitution is made. Similarly, usually lysine (−3.9) can be substituted for arginine (−4.5), without the expectation of any significant change in the biological properties of the underlying polypeptide. Other considerations for choosing amino acid substitutions include the similarity of the side-chain substituents, for example, size, electrophilic character, charge in various amino acids. In general, alanine, glycine and serine; arginine and lysine; glutamate and aspartate; serine and threonine; and valine, leucine and isoleucine are interchangeable, without the expectation of any significant change in biological properties. Such substitutions are generally referred to as conservative amino acid substitutions, and are the preferred type of substitutions within the polypeptides of the present invention.

Non-conservative substitutions will entail exchanging a member of one class of amino acids for another class. Such substituted residues also may be introduced into the conservative substitution sites or, more preferably, into the remaining (non-conserved) sites.

The variations can be made using methods known in the art such as site-directed mutagenesis, alanine scanning mutagenesis, and PCR mutagenesis. Site-directed mutagenesis (Carter et al., *Nucl. Acids Res.*, 13:4331 (1986); Zoller et al., *Nucl. Acids Res.*, 10:6487 (1987)), cassette mutagenesis (Wells et al., *Gene*, 34:315 (1985)), restriction selection mutagenesis (Wells et al., *Philos. Trans. R. Soc. London Ser A*, 317:415 (1986)) or other known techniques can be performed on cloned DNA to produce the Mrg or drg-12 variant DNA.

Scanning amino acid analysis can be employed to identify one or more amino acids that can be replaced without a significant impact on biological activity. Among the preferred scanning amino acids are relatively small, neutral amino acids. Such amino acids include alanine, glycine, serine, and cysteine. Alanine is preferred because, in addition to being the most common amino acid, it eliminates the side-chain beyond the beta-carbon and is therefore less likely to alter the main-chain conformation of the variant (Cunningham and Wells, *Science*, 244: 1081-1085 (1989)). Further, alanine is frequently found in both buried and exposed positions (Creighton, *The Proteins*, (W. H. Freeman & Co., N.Y.); Chothia, *J. Mol. Biol.*, 150:1 (1976)). If alanine substitution does not yield adequate amounts of variation, an isoteric amino acid can be used.

As described below, members of the family of proteins can be used: 1) to identify agents which modulate at least one activity of the protein; 2) to identify binding partners for the protein, 3) as an antigen to raise polyclonal or monoclonal antibodies, 4) as a therapeutic target, 5) as diagnostic markers to specific populations of pain sensing neurons and 6) as targets for structure based ligand identification.

B. Nucleic Acid Molecules

The present invention further provides nucleic acid molecules that encode the mrg or drg-12 proteins having SEQ ID NO: 2, 4, 6, 8, 10, 12, 14, 16, 18, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107 or 109 and the related polypeptides herein described, preferably in isolated form. cDNAs encoding eight full-length variants of Mrg receptors (mMrgA1-8) are provided in FIG. 6A (SEQ ID NO: 1, 3, 5, 11, 20, 22, 24, 26).

Preferred molecules are those that hybridize under the above defined stringent conditions to the complement of SEQ ID NO: 1, 3, 5, 7, 9, 11, 13, 15, 17, 20, 22, 24, 26 or 28, 30, 32, 34, 36, 38, 40, 42, 44, 46, 48, 50, 52, 54, 56, 58, 60, 62, 64, 66, 68, 70, 7274, 76, 78, 80, 82, 84, 86, 88, 90, 92, 94, 96, 98, 100, 102, 104, 106 or 108 and which encode a functional peptide. Preferred hybridizing molecules are those that hybridize under the above conditions to the complement strand of the open reading frame or coding sequences of SEQ ID NO: 1, 3, 5, 7, 9, 11, 13, 15, 17, 20, 22, 24, 26 or 28, 30, 32, 34, 36, 38, 40, 42, 44, 46, 48, 50, 52, 54, 56, 58, 60, 62, 64, 66, 68, 70, 7274, 76, 78, 80, 82, 84, 86, 88, 90, 92, 94, 96, 98, 100, 102, 104, 106 or 108.

It is not intended that the methods of the present invention be limited by the source of the polynucleotide. The polynucleotide can be from a human or non-human mammal, derived from any recombinant source, synthesized in vitro or by chemical synthesis. The nucleotide may be DNA or RNA and may exist in a double-stranded, single-stranded or partially double-stranded form.

Nucleic acids useful in the present invention include, by way of example and not limitation, oligonucleotides such as antisense DNAs and/or RNAs; ribozymes; DNA for gene therapy; DNA and/or RNA chimeras; various structural forms of DNA including single-stranded DNA, double-stranded DNA, supercoiled DNA and/or triple-helix DNA; Z-DNA; and the like. The nucleic acids may be prepared by any conventional means typically used to prepare nucleic acids in large quantity. For example, DNAs and RNAs may be chemically synthesized using commercially available reagents and synthesizers by methods that are well-known in the art (see, e.g., Gait, 1985, *Oligonucleotide Synthesis: A Practical Approach*, IRL Press, Oxford, England).

Any mRNA transcript encoded by Mrg or drg-12 nucleic acid sequences may be used in the methods of the present invention, including in particular, mRNA transcripts resulting from alternative splicing or processing of mRNA precursors.

Nucleic acids having modified nucleoside linkages may also be used in the methods of the present invention. Modified nucleic acids may, for example, have greater resistance to degradation. Such nucleic acids may be synthesized using reagents and methods that are well known in the art. For example, methods for synthesizing nucleic acids containing phosphonate phosphorothioate, phosphorodithioate, phosphoramidate methoxyethyl phosphoramidate, formacetal, thioformacetal, diisopropylsilyl, acetamidate, carbamate, dimethylene-sulfide ($-CH_2-S-CH_2-$), dimethylene-sulfoxide ($-CH_2-SO-CH_2-$), dimethylene-sulfone ($-CH_2-SO_2-CH_2-$), 2'-O-alkyl, and 2'-deoxy-2'-fluoro phosphorothioate internucleoside linkages are well known in the art.

In some embodiments of the present invention, the nucleotide used is an α-anomeric nucleotide. An α-anomeric nucleotide forms specific double-stranded hybrids with complementary RNA in which, contrary to the usual β-units, the strands run parallel to each other (Gautier et al., 1987, Nucl. Acids Res. 15:6625-6641). The nucleotide may be a 2'-0-methylribonucleotide (Inoue et al., 1987, Nucl. Acids Res. 15:6131-6148), or a chimeric RNA-DNA analogue (Inoue et al., 1987, FEBS Lett. 215:327-330).

Means for purifying the nucleic acids of the present invention are well known in the art and the skilled artisan will be able to choose the most appropriate method of purification for the particular circumstances. Such a choice may be made, in part, based on the size of the DNA, the amount to be purified and the desired purity. For example, the nucleic acids can be purified by reverse phase or ion exchange HPLC, size exclusion chromatography or gel electrophoresis.

Isolated or purified polynucleotides having at least 10 nucleotides (i.e., a hybridizable portion) of an Mrg or drg-12 coding sequence or its complement may also be used in the methods of the present invention. In other embodiments, the polynucleotides contain at least 25 (continuous) nucleotides, 50 nucleotides, 100 nucleotides, 150 nucleotides, or 200 nucleotides of an Mrg coding sequence, or a full-length Mrg coding sequence. Nucleic acids can be single or double stranded. Additionally, the invention relates to polynucleotides that selectively hybridize to a complement of the foregoing coding sequences. In preferred embodiments, the polynucleotides contain at least 10, 25, 50, 100, 150 or 200 nucleotides or the entire length of an Mrg coding sequence.

Nucleotide sequences that encode a mutant of an Mrg protein, peptide fragments of Mrg, truncated forms of Mrg, and Mrg fusion proteins may also be useful in the methods of the present invention. Nucleotides encoding fusion proteins may include, but are not limited to, full length Mrg sequences, truncated forms of Mrg, or nucleotides encoding peptide fragments of Mrg fused to an unrelated protein or peptide, such as for example, a domain fused to an Ig Fc domain or fused to an enzyme such as a fluorescent protein or a luminescent protein which can be used as a marker.

Furthermore, polynucleotide variants that have been generated, at least in part, by some form of directed evolution, such as gene shuffling or recursive sequence recombination may be used in the methods of the present invention. For example, using such techniques novel sequences can be generated encoding proteins similar to Mrg or drg-12 but having altered functional or structural characteristics.

Highly related gene homologs of the Mrg encoding polynucleotide sequences described above may also be useful in the present invention. Highly related homologs can encode proteins sharing functional activities with Mrg proteins.

The present invention further provides fragments of the encoding nucleic acid molecule. Fragments of the encoding nucleic acid molecules of the present invention (i.e., synthetic oligonucleotides) that are used as probes or specific primers for the polymerase chain reaction (PCR), or to synthesize gene sequences encoding proteins of the invention, can easily be synthesized by chemical techniques, for example, the phosphotriester method of Matteucci, et al., (J. Am. Chem. Soc. 103:3185-3191, 1981) or using automated synthesis methods. In addition, larger DNA segments can readily be prepared by well known methods, such as synthesis of a group of oligonucleotides that define various modular segments of the gene, followed by ligation of oligonucleotides to build the complete modified gene.

The encoding nucleic acid molecules of the present invention may further be modified so as to contain a detectable label for diagnostic and probe purposes. A variety of such labels are known in the art and can readily be employed with the encoding molecules herein described. Suitable labels include, but are not limited to, biotin, radiolabeled nucleotides and the like. A skilled artisan can readily employ any such label to obtain labeled variants of the nucleic acid molecules of the invention.

Any nucleotide sequence which encodes the amino acid sequence of a protein of the invention can be used to generate recombinant molecules which direct the expression of the protein, as described in more detail below. In addition, the methods of the present invention may also utilize a fusion polynucleotide comprising an Mrg or drg-12 coding sequence and a second coding sequence for a heterologous protein.

C. Isolation of Other Related Nucleic Acid Molecules

As described above, the identification and characterization of a nucleic acid molecule encoding an mrg or drg-12 protein allows a skilled artisan to isolate nucleic acid molecules that encode other members of the same protein family in addition to the sequences herein described Essentially, a skilled artisan can readily use the amino acid sequence of SEQ ID NO: 2, 4, 6, 8, 10, 12, 14, 16, 18, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107 or 109 to generate antibody probes to screen expression libraries prepared from appropriate cells. Typically, polyclonal antiserum from mammals such as rabbits immunized with the purified protein (as described below) or monoclonal antibodies can be used to probe a mammalian cDNA or genomic expression library, such as a lambda gt11 library, to obtain the appropriate coding sequence for other members of the protein family. The cloned cDNA sequence can be expressed as a fusion protein, expressed directly using its own control sequences, or expressed by constructions using control sequences appropriate to the particular host used for expression of the protein.

Alternatively, a portion of the coding sequence herein described can be synthesized and used as a probe to retrieve DNA encoding a member of the Mrg protein family from cells derived from any mammalian organism, particularly cells believed to express Mrg proteins. Oligomers containing approximately 18-20 nucleotides (encoding about a 6-7 amino acid stretch) are prepared and used to screen genomic DNA or cDNA libraries to obtain hybridization under stringent conditions or conditions of sufficient stringency to eliminate an undue level of false positives. Oligonucleotides corresponding to either the 5' or 3' terminus of the coding sequence may be used to obtain longer nucleotide sequences.

It may be necessary to screen multiple cDNA libraries to obtain a full-length cDNA. In addition, it may be necessary to use a technique such as the RACE (Rapid Amplification of cDNA Ends) technique to obtain the complete 5' terminal coding region. RACE is a PCR-based strategy for amplifying the 5' end of incomplete cDNAs. To obtain the 5' end of the cDNA, PCR is carried out on 5'-RACE-Ready cDNA using an anchor primer and a 3' primer. A second PCR is then carried out using the anchored primer and a nested 3' primer. Once a full length cDNA sequence is obtained, it may be translated into amino acid sequence and examined for identifiable regions such as a continuous open reading frame flanked by translation initiation and termination sites, a potential signal sequence and finally overall structural similarity to the protein sequences disclosed herein.

Related nucleic acid molecules may also be retrieved by using pairs of oligonucleotide primers in a polymerase chain reaction (PCR) to selectively clone an encoding nucleic acid molecule. The oligonucleotide primers may be degenerate oligonucleotide primer pools designed on the basis of the protein coding sequences disclosed herein. The template for the reaction may be cDNA obtained by reverse transcription (RT) of mRNA prepared from, for example, human or non-human cell lines or tissues known or suspected to express an Mrg or drg-12 gene allele, such as DRG tissue. A PCR denature/anneal/extend cycle for using such PCR primers is well known in the art and can readily be adapted for use in isolating other encoding nucleic acid molecules.

The PCR product may be subcloned and sequenced to ensure that the amplified sequences represent the sequences of an Mrg or drg-12 coding sequence. The PCR fragment may then be used to isolate a full-length cDNA clone by a variety of methods. For example, the amplified fragment may be labeled and used to screen a cDNA library. Alternatively, the labeled fragment may be used to isolate genomic clones via the screening of a genomic library.

PCR technology may also be utilized to isolate full-length cDNA sequences. RNA may be isolated, from an appropriate cellular or tissue source, such as dorsal root ganglion (DRG) and an RT reaction may be carried out using an oligonucleotide primer specific for the most 5' end of the amplified fragment to prime first strand synthesis. The resulting RNA/DNA hybrid may then be "tailed" with guanines in a terminal transferase reaction, the hybrid may be digested with RNAase H, and second strand synthesis may then be primed with a poly-C primer. This allows isolation of cDNA sequences upstream of the amplified fragment.

Nucleic acid molecules encoding other members of the mrg and drg-12 families may also be identified in existing genomic or other sequence information using any available computational method, including but not limited to: PSI-BLAST (Altschul, et al. (1997) Nucleic Acids Res. 25:3389-3402); PHI-BLAST (Zhang, et al. (1998), Nucleic Acids Res. 26:3986-3990), 3D-PSSM (Kelly et al. *J. Mol. Biol.* 299(2): 499-520 (2000)); and other computational analysis methods (Shi et al. *Biochem. Biophys. Res. Commun.* 262(1):132-8 (1999) and Matsunami et. al. *Nature* 404(6778):601-4 (2000).

A cDNA clone of a mutant or allelic variant of an Mrg or drg-12 gene may also be isolated. A possible source of a mutant or variant protein is tissue known to express Mrg or drg-12, such as DRG tissue, obtained from an individual putatively carrying a mutant or variant form of Mrg or drg-12. Such an individual may be identified, for example, by a demonstration of increased or decreased responsiveness to painful stimuli. In one embodiment, a mutant or variant Mrg or drg-12 gene may be identified by PCR. The first cDNA strand may be synthesized by hybridizing an oligo-dT oligonucleotide to mRNA isolated from the tissue putatively carrying a variant and extending the new strand with reverse transcriptase. The second strand of the cDNA is then synthesized using an oligonucleotide that hybridizes specifically to the 5' end of the normal gene. Using these two primers, the product is then amplified via PCR, cloned into a suitable vector, and subjected to DNA sequence analysis through methods well known to those of skill in the art. By comparing the DNA sequence of the mutant Mrg allele to that of the normal Mrg allele, the mutation(s) responsible for any loss or alteration of function of the mutant Mrg gene product can be ascertained.

Alternatively, a genomic library can be constructed using DNA obtained from an individual suspected of or known to carry a mutant Mrg allele, or a cDNA library can be constructed using RNA from a tissue known, or suspected, to express a mutant Mrg allele. An unimpaired Mrg gene or any suitable fragment thereof may then be labeled and used as a probe to identify the corresponding mutant Mrg allele in such libraries. Clones containing the mutant Mrg gene sequences may then be purified and subjected to sequence analysis according to methods well known to those of skill in the art.

Additionally, an expression library can be constructed utilizing cDNA synthesized from, for example, RNA isolated from a tissue known, or suspected, to express a mutant Mrg allele in an individual suspected of carrying such a mutant allele. In this manner, gene products made by the putatively mutant tissue may be expressed and screened using standard antibody screening techniques in conjunction with antibodies raised against the normal Mrg gene product, as described, below.

D. Recombinant DNA Molecules Containing a Nucleic Acid Molecule

The present invention further provides recombinant DNA molecules (rDNAs) that contain a coding sequence. As used herein, a rDNA molecule is a DNA molecule that has been subjected to molecular manipulation in situ. Methods for generating rDNA molecules are well known in the art, for example, see Sambrook et al., Molecular Cloning: A Laboratory Manual, 2nd edition, 1989; Cold Spring Harbor Laboratory Press, Cold Spring Harbor, N.Y. In the preferred rDNA molecules, a coding DNA sequence is operably linked to expression control sequences and/or vector sequences.

Thus the present invention also contemplates DNA vectors that contain any of the Mrg or drg-12 coding sequences and/or their complements, optionally associated with a regulatory element that directs the expression of the coding sequences.

The choice of vector and/or expression control sequences to which one of the protein family encoding sequences of the present invention is operably linked depends directly, as is well known in the art, on the functional properties desired, e.g., protein expression, and the host cell to be transformed. A vector contemplated by the present invention is at least capable of directing the replication or insertion into the host chromosome, and preferably also expression, of the structural gene included in the rDNA molecule.

Both cloning and expression vectors contain a nucleic acid sequence that enables the vector to replicate in one or more selected host cells. In cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells.

In addition to being capable of replication in at least one class of organism most expression vectors can be transfected into another organism for expression. For example, a vector is replicated in *E. coli* and then the same vector is transfected into yeast or mammalian cells for expression.

DNA may also be amplified by insertion into the host genome. For example, transfection of *Bacillus* with a vector comprising a DNA sequence complementary to a *Bacillus* genomic sequence results in homologous recombination with the genome and insertion of the DNA from the vector. One disadvantage to this type of system is that the recovery of genomic DNA encoding the protein of interest is more complex than that of an exogenously replicated vector because restriction enzyme digestion is required to excise the DNA.

Expression control elements that are used for regulating the expression of an operably linked protein encoding sequence are known in the art and include, but are not limited to, inducible promoters, constitutive promoters, secretion signals, and other regulatory elements. Preferably, the inducible promoter is readily controlled, such as being responsive to a nutrient in the host cell's medium.

In one embodiment, the vector containing a coding nucleic acid molecule will include a prokaryotic replicon, i.e., a DNA sequence having the ability to direct autonomous replication and maintenance of the recombinant DNA molecule extrachromosomally in a prokaryotic host cell, such as a bacterial host cell, transformed therewith. Such replicons are well known in the art. In addition, vectors that include a prokaryotic replicon may also include a gene whose expression confers a detectable marker such as a drug resistance. Typical bacterial drug resistance genes are those that confer resistance to ampicillin or tetracycline.

Vectors that include a prokaryotic replicon can further include a prokaryotic or bacteriophage promoter capable of directing the expression (transcription and translation) of the coding gene sequences in a bacterial host cell, such as *E. coli*. A promoter is an expression control element formed by a DNA sequence that permits binding of RNA polymerase and transcription to occur. Promoter sequences that are compatible with bacterial hosts are typically provided in plasmid vectors containing convenient restriction sites for insertion of a DNA segment of the present invention. Typical of such vector plasmids are pUC8, pUC9, pBR322 and pBR329 available from BioRad Laboratories, (Richmond, Calif.), pPL and pKK223 available from Pharmacia (Piscataway, N.J.).

Expression vectors compatible with eukaryotic cells, preferably those compatible with vertebrate cells, can also be used to form rDNA molecules that contain a coding sequence. Eukaryotic cell expression vectors are well known in the art and are available from several commercial sources. Typically, such vectors are provided containing convenient restriction sites for insertion of the desired DNA segment. Typical of such vectors are pSVL and pKSV-10 (Pharmacia), pBPV-1/pML2d (International Biotechnologies, Inc.), pTDT1 (ATCC, #31255), eukaryotic viral vectors such as adenoviral or retroviral vectors, and the like eukaryotic expression vectors.

Eukaryotic cell expression vectors used to construct the rDNA molecules of the present invention may further include a selectable marker that is effective in an eukaryotic cell, preferably a drug resistance selection marker. This gene encodes a factor necessary for the survival or growth of transformed host cells grown in a selective culture medium. Host cells not transformed with the vector containing the selection gene will not survive in the culture medium. Typical selection genes encode proteins that confer resistance to antibiotics or other toxins, e.g., ampicillin, neomycin, methotrexate, or tetracycline, complement auxotrophic deficiencies, or supply critical nutrients withheld from the media. A preferred drug resistance marker is the gene whose expression results in neomycin resistance, i.e., the neomycin phosphotransferase (neo) gene. (Southern et al., *J. Mol. Anal. Genet.* 1:327-341, 1982.) The selectable marker can optionally be present on a separate plasmid and introduced by co-transfection.

In one example of a selection system, mammalian cell transformants are placed under selection pressure such that only the transformants are able to survive by virtue of having taken up the vector(s). Selection pressure is imposed by progressively increasing the concentration of selection agent in the culture medium, thereby stimulating amplification of both the selection gene and the DNA that encodes the desired protein. Amplification is the process by which genes in greater demand for the production of a protein critical for growth are reiterated in tandem within the chromosomes of successive generations of recombinant cells. Increased quantities of the desired protein, such as Mrg, are synthesized from the amplified DNA. Examples of amplifiable genes include DHFR, thymidine kinase, metallothionein-I and -II, adenosine deaminase, and ornithine decarboxylase.

Thus in one embodiment Chinese hamster ovary (CHO) cells deficient in DHFR activity are prepared and propagated as described by Urlaub et al., *Proc. Natl. Acad. Sci. USA*, 77:4216 (1980). The CHO cells are then transformed with the DHFR selection gene and transformants are are identified by culturing in a culture medium that contains methotrexate (Mtx), a competitive antagonist of DHFR. The transformed cells are then exposed to increased levels of methotrexate. This leads to the synthesis of multiple copies of the DHFR gene, and, concomitantly, multiple copies of other DNA comprising the expression vectors, such as the DNA encoding the protein of interest, for example DNA encoding Mrg.

Alternatively, host cells can be transformed or co-transformed with DNA sequences encoding a protein of interest such as Mrg, wild-type DHFR protein, and another selectable marker such as aminoglycoside 3'-phosphotransferase (APH). The transformants can then be selected by growth in medium containing a selection agent for the selectable marker such as an aminoglycosidic antibiotic, e.g., kanamycin, neomycin, or G418.

As mentioned above, expression and cloning vectors usually contain a promoter that is recognized by the host organism and is operably linked to the nucleic acid encoding the protein of interest. Promoters are untranslated sequences located upstream (5') to the start codon of a structural gene (generally within about 100 to 1000 bp) and control the transcription and translation of the particular nucleic acid sequence, such as an Mrg nucleic acid sequence, to which they are operably linked. Promoters may be inducible or constitutive. Inducible promoters initiate increased levels of transcription from DNA under their control in response to some change in culture conditions, such as a change in temperature. Many different promoters are well known in the art, as are methods for operably linking the promoter to the DNA encoding the protein of interest. Both the native Mrg or drg-12 promoter sequence and many heterologous promoters may be used to direct amplification and/or expression of the Mrg or drg-12 DNA. However, heterologous promoters are preferred, as they generally permit greater transcription and higher yields of the desired protein as compared to the native promoter.

Promoters suitable for use with prokaryotic hosts include, for example, the β-lactamase and lactose promoter systems (Chang et al., *Nature,* 275:615 (1978); Goeddel et al., *Nature,* 281:544 (1979)). However, other bacterial promoters are well known in the art and are suitable. Promoters for use in bacterial systems also will contain a Shine-Delgarno (S.D.) sequence operably linked to the DNA encoding the protein of interest.

Promoter sequences that can be used in eukaryotic cells are also well known. Virtually all eukaryotic genes have an AT-rich region located approximately 25 to 30 bases upstream from the transcription initiation site. Another sequence found 70 to 80 bases upstream from the start of transcription of many genes is a CXCAAT region where X may be any nucleotide. At the 3' end of most eukaryotic genes is an AATAAA sequence that may be the signal for addition of the poly-A tail to the 3' end of the coding sequence. All of these sequences may be inserted into eukaryotic expression vectors.

Examples of suitable promoting sequences for use with yeast hosts include the promoters for 3-phosphoglycerate kinase (Hitzeman et al., *J. Biol. Chem.,* 255:2073 (1980)) or other glycolytic enzymes (Hess et al., *J. Adv. Enzyme Reg.,* 7:149 (1968); Holland, *Biochemistry,* 17:4900 (1978)).

Inducible promoters for use with yeast are also well known and include the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Mrg or drg-12 transcription from vectors in mammalian host cells may also be controlled by promoters obtained from the genomes of viruses such as polyoma virus, fowlpox virus, adenovirus, bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, and from the promoter normally associated with the native sequence, provided such promoters are compatible with the host cell systems.

Transcription may be increased by inserting an enhancer sequence into the vector. Enhancers are cis-acting elements of DNA, usually about 10 to 300 bp in length, that act on a promoter to increase its transcription. Many enhancer sequences are now known from mammalian genes (globin, elastase, albumin, α-fetoprotein, and insulin). Preferably an enhancer from a eukaryotic cell virus will be used. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the protein-encoding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. These sequences are often found in the 5' and, occasionally 3', untranslated regions of eukaryotic or viral DNAs or cDNAs and are well known in the art.

Plasmid vectors containing one or more of the components described above are readily constructed using standard techniques well known in the art.

For analysis to confirm correct sequences in plasmids constructed, the plasmid may be replicated in *E. coli,* purified, and analyzed by restriction endonuclease digestion, and/or sequenced by conventional methods.

Particularly useful in the preparation of proteins of the present invention are expression vectors that provide for transient expression in mammalian cells of DNA encoding Mrg or drg-12. Transient expression involves the use of an expression vector that is able to replicate efficiently in a host cell, such that the host cell accumulates many copies of the expression vector and, in turn, synthesizes high levels of a the polypeptide encoded by the expression vector. Sambrook et al., supra, pp. 16.17-16.22. Transient expression systems allow for the convenient positive identification of polypeptides encoded by cloned DNAs, as well as for the screening of such polypeptides for desired biological or physiological properties. Thus, transient expression systems are particularly useful in the invention for purposes of identifying biologically active analogs and variants of the polypeptides of the invention and for identifying agonists and antagonists thereof.

Other methods, vectors, and host cells suitable for adaptation to the synthesis of Mrg or drg-12 in recombinant vertebrate cell culture are well known in the art and are readily adapted to the specific circumstances.

E. Host Cells Containing an Exogenously Supplied Coding Nucleic Acid Molecule

The present invention further provides host cells transformed with a nucleic acid molecule that encodes a protein of the present invention. The host cell can be either prokaryotic or eukaryotic but is preferably eukaryotic.

Eukaryotic cells useful for expression of a protein of the invention are not limited, so long as the cell line is compatible with cell culture methods and compatible with the propagation of the expression vector and expression of the gene product. Such host cells are capable of complex processing and glycosylation activities. In principle, any higher eukaryotic cell culture is workable, whether from vertebrate or invertebrate culture. Preferred eukaryotic host cells include, but are not limited to, yeast, insect and mammalian cells, preferably vertebrate cells such as those from a mouse, rat, monkey or human cell line. Preferred eukaryotic host cells include Chinese hamster ovary (CHO) cells available from the ATCC as CCL61, NIH Swiss mouse embryo cells (NIH/3T3) available from the ATCC as CRL 1658, baby hamster kidney cells (BHK), HEK293 cells and the like eukaryotic tissue culture cell lines.

Propagation of vertebrate cells in culture is a routine procedure. See, e.g., *Tissue Culture,* Academic Press, Kruse and Patterson, editors (1973). Additional examples of useful mammalian host cell lines that can be readily cultured are monkey kidney CV1 line transformed by SV40 (COS-7, ATCC CRL 1651); mouse sertoli cells (TM4, Mather, *Biol. Reprod.*, 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); and mouse mammary tumor (MMT 060562, ATCC CCL51).

*Xenopus oocytes* may also be directly injected with RNA capable of expressing either the mrg or drg-12 proteins by standard procedures (see Tominaga et al. *Jpn J. Pharmacol.* 83(1):20-4 (2000); Tominaga et al. *Neuron* 21(3):531-43 (1998) and Bisogno et al. *Biochem, Biophys. Res. Commun.* 262(1):275-84 (1999)).

Examples of invertebrate cells that can be used as hosts include plant and insect cells. Numerous baculoviral strains and variants and corresponding permissive insect host cells are known in the art and may be utilized in the methods of the present invention. In addition, plant cell cultures are known and may be transfected, for example, by incubation with *Agrobacterium tumefaciens*, which has been manipulated to contain Mrg or drg-12 encoding DNA.

Any prokaryotic host can be used to express a rDNA molecule encoding a protein or a protein fragment of the invention. Suitable prokaryotes include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as *Bacilli* such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. The preferred prokaryotic host is *E. coli*. In addition, it is preferably that the host cell secrete minimal amounts of proteolytic enzymes.

In addition to prokaryotes, eukaryotic microbes such as filamentous fungi or yeast are suitable cloning or expression hosts for Mrg- or drg-12-encoding vectors. For example, *Saccharomyces cerevisiae* may be used. In addition a number of other genera, species, and strains are commonly available and useful herein, such as *Schizosaccharomyces pombe* (Beach et al. *Nature*, 290:140 (1981); EP 139,383); *Kluyveromyces* hosts (U.S. Pat. No. 4,943,529; Fleer et al., supra) such as, e.g., *K. lactis* (MW98-8C, CBS683, CBS4574; Louvencourt et al., *J. Bacteriol.*, 737 (1983)), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., supra), *K. thermotolerans*, and *K. marxianus; yarrowia* (EP 402,226); *Pichia pastoris* (EP 183, 070; Sreekrishna et al. *J. Basic Microbiol.*, 28:265-278 (1988)); *Candida; Trichoderma reesia* (EP 244,234); *Neurospora crassa* (Case et al. *Proc. Natl. Acad. Sci. USA*, 76:5259-5263 (1979)); *Schwanniomyces* such as *Schwanniomyces occidentalis* (EP 394,538); and filamentous fungi such as, e.g., *Neurospora, Penicillium, Tolypocladium* (WO 91/00357), and *Aspergillus* hosts such as *A. nidulans* (Ballance et al. *Biochem. Biophys. Res. Commun.*, 112:284-289 (1983); Tilburn et al., *Gene*, 26:205-221 (1983); Yelton et al. *Proc. Natl. Acad. Sci. USA*, 81:1470-1474 (1984)) and *A. niger* (Kelly et al. *EMBO J.*, 4:475-479 (1985)).

Transformation of appropriate cell hosts with a rDNA molecule of the present invention is accomplished by well known methods that typically depend on the type of vector used and host system employed. With regard to transformation of prokaryotic host cells, electroporation and salt treatment methods are typically employed, see, for example, Cohen et al. *Proc. Natl. Acad. Sci. USA* 69:2110, (1972); and Maniatis et al., Molecular Cloning, A Laboratory Manual, Cold Spring Harbor Laboratory, Cold Spring Harbor, N.Y. (1982). With regard to transformation of vertebrate cells with vectors containing rDNAs, electroporation, cationic lipid or salt treatment methods are typically employed, see, for example, Graham et al. *Virol.* 52:456, (1973); Wigler et al. *Proc. Natl. Acad. Sci. USA* 76:1373-76, (1979). The calcium phosphate precipitation method is preferred. However, other methods of for introducing DNA into cells may also be used, including nuclear microinjection and bacterial protoplast fusion.

For transient expression of recombinant channels, transformed host cells for the measurement of $Na^+$ current or intracellular $Na^+$ levels are typically prepared by co-transfecting constructs into cells such as HEK293 cells. with a fluorescent reporter plasmid (such as pGreen Lantern-1, Life Technologies) using the calcium-phosphate precipitation technique (Ukomadu et al. *Neuron* 8, 663-676 (1992)). After forty-eight hours, cells with green fluorescence are selected for recording (Dib-Hajj et al. *FEBS Lett.* 416, 11-14 (1997)). Similarly, for transient expression of Mrg receptors and measurement of intracellular $Ca^{2+}$ changes in response to receptor activation as described in Example 4, HEK cells can be co-transfected with Mrg expression constructs and a fluorescent reporter plasmid. HEK293 cells are typically grown in high glucose DMEM (Life Technologies) supplemented with 10% fetal calf serum (Life Technologies).

Prokaryotic cells used to produce polypeptides of this invention are cultured in suitable media as described generally in Sambrook et al., supra.

The mammalian host cells used to produce the polypeptides of this invention may be cultured in a variety of media, including but not limited to commercially available media such as Ham's F10 (Sigma), Minimal Essential Medium ((MEM), Sigma), RPMI-1640 (Sigma), and Dulbecco's Modified Eagle's Medium ((DMEM), Sigma). In addition, any of the media described in Ham et al. *Meth. Enz.*, 58:44 (1979), Barnes et al. *Anal. Biochem.* 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics, trace elements, and glucose or an equivalent energy source. Any other necessary supplements may also be included at appropriate concentrations as determined by the skilled practitioner. The culture conditions are those previously used with the host cell selected for expression, and will be apparent to the skilled artisan.

The host cells referred to in this disclosure encompass cells in culture as well as cells that are within a host animal.

Successfully transformed cells, i.e., cells that contain a rDNA molecule of the present invention, can be identified by well known techniques including the selection for a selectable marker. For example, cells resulting from the introduction of an rDNA of the present invention can be cloned to produce single colonies. Cells from those colonies can be harvested, lysed and their DNA content examined for the presence of the rDNA using a method such as that described by Southern, *J. Mol. Biol.* 98:503, (1975), or Berent et al., *Biotech.* 3:208, (1985) or the proteins produced from the cell assayed via an immunological method as described below.

Gene amplification and/or expression may be measured by any technique known in the art, including Southern blotting, Northern blotting to quantitate the transcription of mRNA (Thomas, *Proc. Natl. Acad. Sci. USA*, 77:5201-5205 (1980)), dot blotting (DNA analysis), or in situ hybridization, using an appropriately labeled probe, based on the sequences provided herein. Various labels may be employed, most commonly radioisotopes, particularly $^{32}$P. Immunological methods for measuring gene expression include immunohistochemical staining of tissue sections or cells in culture, as well as assaying protein levels in culture medium or body fluids. With immunohistochemical staining techniques, a cell sample is prepared by dehydration and fixation, followed by reaction with labeled antibodies specific for the gene product, where the labels are usually visually detectable, such as enzymatic labels, fluorescent labels, luminescent labels, and the like.

Antibodies useful for immunohistochemical staining and/or assay of sample fluids may be either monoclonal or polyclonal, and may be prepared as described herein.

F. Production of Recombinant Proteins Using an rDNA Molecule

The present invention further provides methods for producing a protein of the invention using nucleic acid molecules herein described. In general terms, the production of a recombinant form of a protein typically involves the following steps:

A nucleic acid molecule is first obtained that encodes a mrg or drg-12 protein of the invention, for example, nucleotides 115-1026 of SEQ ID NO: 1, nucleotides 115-1029 of SEQ ID NO: 1, nucleotides 137-1051 of SEQ ID NO: 3, nucleotides 137-1054 of SEQ ID NO: 3, nucleotides 165-1070 of SEQ ID NO: 5, nucleotides 165-1073 of SEQ ID NO: 5, nucleotides 1-450 of SEQ ID NO: 7, nucleotides 1-459 of SEQ ID NO: 9, nucleotides 1820-2734 of SEQ ID NO: 11, nucleotides 170-574 of SEQ ID NO: 13, nucleotides 170-577 of SEQ ID NO: 13, nucleotides 328-1293 of SEQ ID NO: 15, nucleotides 328-1296 of SEQ ID NO:15, nucleotides 171-1160 of SEQ ID NO: 17, nucleotides 171-1163 of SEQ ID NO:17, nucleotides 83-943 of SEQ ID NO: 20, nucleotides 83-946 of SEQ ID NO:20; nucleotides 16-918 of SEQ ID NO: 22, nucleotides 16-921 of SEQ ID NO: 22; nucleotides 106-1020 of SEQ ID NO: 24, nucleotides 106-1023 of SEQ ID NO: 24; nucleotides 45-959 of SEQ ID NO: 26, nucleotides 45-962 of SEQ ID NO: 26, nucleotides 1-405 of SEQ ID NO: 28 and nucleotides 1-408 of SEQ ID NO: 28. If the encoding sequence is uninterrupted by introns, as are these sequences, it is directly suitable for expression in any host.

The nucleic acid molecule is then preferably placed in operable linkage with suitable control sequences, as described above, to form an expression unit containing the protein open reading frame. The expression unit is used to transform a suitable host and the transformed host is cultured under conditions that allow the production of the recombinant protein. Optionally the recombinant protein is isolated from the medium or from the cells; recovery and purification of the protein may not be necessary in some instances where some impurities may be tolerated or when the recombinant cells are used, for instance, in high throughput assays.

Each of the foregoing steps can be done in a variety of ways. For example, the desired coding sequences may be obtained from genomic fragments and used directly in appropriate hosts. The construction of expression vectors that are operable in a variety of hosts is accomplished using appropriate replicons and control sequences, as set forth above. The control sequences, expression vectors, and transformation methods are dependent on the type of host cell used to express the gene and were discussed in detail earlier. Suitable restriction sites can, if not normally available, be added to the ends of the coding sequence so as to provide an excisable gene to insert into these vectors. A skilled artisan can readily adapt any host/expression system known in the art for use with the nucleic acid molecules of the invention to produce recombinant protein.

In one embodiment, Mrg or drg-12 may be produced by homologous recombination. Briefly, primary human cells containing an Mrg- or drg-12-encoding gene are transformed with a vector comprising an amplifiable gene (such as dihydrofolate reductase (DHFR)) and at least one flanking region of a length of at least about 150 bp that is homologous with a DNA sequence at the locus of the coding region of the Mrg or drg-12 gene. The amplifiable gene must be located such that it does not interfere with expression of the Mrg or drg-12 gene. Upon transformation the construct becomes homologously integrated into the genome of the primary cells to define an amplifiable region.

Transformed cells are then selected for by means of the amplifiable gene or another marker present in the construct. The presence of the marker gene establishes the presence and integration of the construct into the host genome. PCR, followed by sequencing or restriction fragment analysis. may be used to confirm that homologous recombination occurred.

The entire amplifiable region is then isolated from the identified primary cells and transformed into host cells. Clones are then selected that contain the amplifiable region, which is then amplified by treatment with an amplifying agent. Finally, the host cells are grown so as to express the gene and produce the desired protein.

The proteins of this invention may be produced recombinantly not only directly, but also as a fusion polypeptide with a heterologous polypeptide. In one embodiment the heterologous polypeptide may be a signal sequence. In general, the signal sequence may be a component of the vector, or it may be a part of the Mrg or drg-12 DNA that is inserted into the vector. The heterologous signal sequence selected preferably is one that is recognized and processed (i.e., cleaved by a signal peptidase) by the host cell. For expression in prokaryotic host cells the signal sequence may be a prokaryotic signal sequence selected, for example, from the group consisting of the alkaline phosphatase, penicillinase, lpp, and heat-stable enterotoxin II leaders. For yeast secretion the native signal sequence may be substituted by, e.g., the yeast invertase leader, α factor leader (including *Saccharomyces* and *Kluyveromyces* α-factor leaders, or acid phosphatase leader and the *C. albicans* glucoamylase leader). In mammalian cell expression any native signal sequence is satisfactory. Alternatively it may be substituted with a signal sequence from related proteins, as well as viral secretory leaders, for example, the herpes simplex gD signal. The DNA for such precursor regions is ligated in reading frame to DNA encoding the mature protein or a soluble variant thereof.

The heterologous polypeptide may also be a marker polypeptide that can be used, for example, to identify the location of expression of the fusion protein. The marker polypeptide may be any known in the art, such as a fluorescent protein. A prefered marker protein is green fluorescent protein (GFP).

G. Modifications of Mrg polypeptides

Covalent modifications of Mrg and drg-12 and their respective variants are included within the scope of this invention. In one embodiment, specific amino acid residues of a polypeptide of the invention are reacted with an organic derivatizing agent. Derivatization with bifunctional agents is useful, for instance, for crosslinking Mrg or Mrg fragments or derivatives to a water-insoluble support matrix or surface for use in methods for purifying anti-Mrg antibodies and identifying binding partners and ligands. In addition, Mrg or Mrg fragments may be crosslinked to each other to modulate binding specificity and effector function. Many crosslinking agents are known in the art and include, but are not limited to, 1,1-bis(diazoacetyl)-2-phenylethane, glutaraldehyde, N-hydroxysuccinimide esters, bifunctional maleimides such as bis-N-maleimido-1,8-octane and agents such as methyl-3-[(p-azidophenyl)dithio]propioimidate.

Other contemplated modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains (T. E. Creighton, *Proteins: Structure and Molecular Properties*, W. H. Freeman & Co., San Francisco, pp. 79-86 (1983)), acetylation of the N-terminal amine, and amidation of any C-terminal carboxyl group.

Modification of the glycosylation patterns of the polypeptides of the invention are also contemplated. Methods for altering the glycosylation pattern of polypeptides are well known in the art. For example, one or more of the carbohydrate moities found in native sequence Mrg or drg-12 may be removed chemically, enzymatically or by modifying the glycosylation site. Alternatively, additional gycosylation can be added, such as by manipulating the composition of the carbohydrate moities directly or by adding glycosylation sites not present in the native sequence Mrg or drg-12 by altering the amino acid sequence.

Another type of covalent modification of the polypeptides of the invention comprises linking the polypeptide or a fragment or derivative thereof to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337.

The polypeptides of the present invention may also be modified in a way to form a chimeric molecule comprising Mrg or drg-12 fused to another, heterologous polypeptide or amino acid sequence.

In one embodiment, such a chimeric molecule comprises a fusion of the Mrg or drg-12 with a tag polypeptide that provides an epitope to which an anti-tag antibody can selectively bind. The epitope tag is generally placed at the amino- or carboxyl-terminus of the polypeptide. The epitope tag allows for identification of the chimeric protein as well as purification of the chimeric protein by affinity purification using an anti-tag antibody or another type of affinity matrix that binds to the epitope tag. A number of tag polypeptides and their respective antibodies are well known in the art. Well known tags include poly-histidine (poly-his) or poly-histidine-glycine (poly-his-gly) tags; the flue HA tag polypeptide (Field et al., *Mol. Cell. Biol.*, 8:2159-2165 (1988)); the c-myc tag (Evan et al., *Molecular and Cellular Biology*, 5:3610-3616 (1985)); the Herpes Simplex virus glycoprotein D (gD) tag (Paborsky et al., *Protein Engineering*, 3(6):547-553 (1990)) and the Flag-peptide (Hopp et al., *BioTechnology*, 6:1204-1210 (1988)).

In another embodiment, the chimeric molecule comprises a fusion of Mrg or drg-12 with an immunoglobulin or a particular region of an immunoglobulin. To produce an immunoadhesin, the polypeptide of the invention or a fragment or specific domain(s) thereof could be fused to the Fc region of an IgG molecule. Typically the fusion is to an immunoglobulin heavy chain constant region sequence. Mrg- or drg-12-immunoglobulin chimeras for use in the present invention are normally prepared from nucleic acid encoding one or more extracellular domains, or fragments thereof, of an Mrg or drg-12 receptor fused C-terminally to nucleic acid encoding the N-terminus of an immunoglobulin constant domain sequence. N-terminal fusions are also possible.

While not required in the immunoadhesins of the present invention, an immunoglobulin light chain might be present either covalently linked to an Mrg- or drg-12-immunoglobulin heavy chain fusion polypeptide, or directly fused to Mrg or drg-12. In order to obtain covalent association, DNA encoding an immunoglobulin light chain may be coexpressed with the DNA encoding the Mrg- or drg-12-immunoglobulin heavy chain fusion protein. Upon secretion, the hybrid heavy chain and the light chain will be covalently associated to provide an immunoglobulin-like structure comprising two disulfide-linked immunoglobulin heavy chain-light chain pairs.

Bispecific immunoadhesins may also be made. Such immunoadhesins may combine an Mrg or drg-12 domain and a domain, such as the extracellular domain, from another receptor. Alternatively, the immunoadhesins herein might comprise portions of two different Mrg receptors, each fused to an immunoglobulin heavy chain constant domain sequence.

In yet another embodiment, the chimeric molecule of the present invention comprises a fusion of Mrg or drg-12 or a fragment or domain(s) thereof, with a heterologous receptor or fragment or domain(s) thereof. The heterologous receptor may be a related Mrg or drg-12 family member, or may be completely unrelated. The heterologous protein fused to the Mrg or drg-12 protein may be chosen to obtain a fusion protein with a desired ligand specificity or a desired affinity for a particular ligand or to obtain a fusion protein with a desired effector function.

H. Methods of Using mrgs or drgs as Molecular or Diagnostic Probes

The sequences and antibodies, proteins and peptides of the present invention may be used as molecular probes for the detection of cells or tissues related to or involved with sensory perception, especially perception of pain. Although many methods may be used to detect the nucleic acids or proteins of the invention in situ, preferred probes include antisense molecules and anti-mrg or anti-drg-12 antibodies.

Probes for the detection of the nucleic acids or proteins of the invention may find use in the identification of the involvement of Mrg or drg-12 proteins in particular disease states, such as glaucoma or chronic pain, or in enhanced or inhibited sensory perception. In particular, probes of the present invention may be useful in determining if Mrg or drg-12 expression is increased or decreased in patients demonstrating changes in sensory perception, such as in patients with allodynia, hyperalgesia or chronic pain, or patients with a disease or disorder, such as glaucoma. A determination of decreased expression or overexpression of a polypeptide of the invention may be useful in identifying a therapeutic approach to treating the disorder, such as by administering Mrg or drg-12 agonists or antagonists.

Determination of changes in Mrg or drg-12 expression levels in animal models of disease states, particularly pain, may also be useful in identifying the types of disorders that might be effectively treated by compounds that modify expression or activity.

Further, the probes of the invention, including antisense molecules and antibodies, may be used to detect the expression of mutant or variant forms of Mrg or drg-12 variants. The ability to detect such variants may be useful in identifying the role that the variants play in particular disease states and in the symptoms experienced by particular patients. Identification of the involvement of a variant of Mrg or drg-12 in a disease or disorder may suggest a therapeutic approach for treatment of the disease or disorder, such as gene therapy or the administration of agonists or antagonists known to bind the receptor variant.

In addition, probes of the invention may be used to determine the exact expression patterns of the various Mrg and drg-12 family members, including the relationship of one to another. For example, the microscopy images of in situ hybridization in FIG. 2 show the localization of antisense staining against a nucleotide of SEQ ID NO:2 ("mrg3") and of SEQ ID NO:4 ("mrg4") in transverse sections of dorsal root ganglia (DRG) from newborn wild type (WT) and Neurogenin1 null mutant (Ngn1$^{-/-}$) mice. White dashed lines outline the DRG and black dashed lines outline the spinal cord. Note that in the Ngn1$^{-/-}$ mutant, the size of the DRG is severely reduced due to the loss of nociceptive sensory neurons, identified using three other independent markers (trkA; VR-1 and SNS-TTXi (Ma et al., (1999)). mrg3 is expressed in a subset of DRG in WT mice (A) but is absent in the Ngn1$^{-/-}$ DRG (B). mrg4 is expressed in a smaller subset of DRG than that of mrg3 (C). It is also absent in the Ngn1$^{-/-}$ DRG (D). The loss of mrg-expressing neurons in the Ngn1$^{-/-}$ DRG indicates that these neurons are likely to be nociceptive.

Expression of mrgs in subsets of dorsal root ganglia (DRG) neurons are shown in FIG. 2A. Frozen transverse sections of DRG from wild-type (a-i) and ngn1$^{-/-}$ (j) mutant new born mice were annealed with antisense digoxigenin RNA probes, and hybridization was visualized with an alkaline phosphatase-conjugated antibody. Positive signals are shown as dark purple stainings. TrkA is expressed in a large portion of wild-type DRG neurons (a) but absent in ngn1$^{-/-}$ (data not shown). Each of the eight mrg genes (b-i) is expressed in a small subset of neurons in wild-type DRG in completely absent in ngn1$^{-/-}$ DRG (j and data not shown). Black dash line outlines the ngn1$^{-/-}$ mutant DRG.

In FIG. 2B, mrgs are expressed by TrkA$^+$ nociceptive neurons. Double labeling technique was used to colocalize TrkA (green; [b,e]) and mrgs (red; [a,d]) in DRG neurons. During the double labeling experiments frozen sections of wild-type DRG were undergone in situ hybridizations with either mrg3 (a-c) or mrg5 (d-f) fluorescein-labeled antisense RNA probes followed by anti-TrkA antibody immunostaining. The same two frames (a and b, d and e) were digitally superimposed to reveal the extent of colocalization (c, f). The colocalizations of TrkA with either mrg3 or mrg5 appear yellow in merged images (c, f, respectively). The white arrowheads indicate examples of double positive cells.

In FIG. 2C, mrgs and VR1 define two different populations of nociceptive neurons in DRG. The combination of in situ hybridizations (red) with either mrg3 or mrg5 fluorescein-labeled antisense RNA probes and anti-VR1 antibody immunostaining (green) demonstrated that neither mrg3 (a-c) nor mrg5 (d-f) were expressed by VR1-positive neurons. In the merged images (c,f), there are no colocalizations of VR1 with either mrg3 or mrg5. The white arrowheads are pointed to mrgs-expressing but VR1-negative nociceptive neurons.

In FIG. 2D mrgs are shown to be expressed by IB4$^+$ nociceptive neurons. Double labeling technique was used to colocalize IB4 (green; [b,e]) and mrgs (red; [a,d]) in DRG neurons. The expressions of mrg3 and mrg5 were visualized by in situ hybridization as described before. The same DRG sections were subsequently undergone through FITC-conjugated lectin IB4 binding. In the merged images (c,f), there are extensive overlappings between mrgs and IB4 stainings (yellow neurons indicated by arrowheads).

Information about the expression patterns of the receptors of the invention in normal tissue and tissue taken from animal models of disease or patients suffering from a disease or disorder will be useful in further defining the biological function of the receptors and in tailoring treatment regimens to the specific receptor or combination of receptors involved in a particular disease or disorder.

I. Methods to Identify Binding Partners

As discussed in more detail below, several peptides have been putatively identified as endogenous ligands for Mrg receptors. In particular the RF-amide peptides, including NPAF and NPFF, have been shown to efficiently stimulate several of the Mrg receptors. In order to identify additional new ligands for the Mrg receptors and ligands for drg-12, it is first necessary to indentify compounds that bind to these receptors. Thus, another embodiment of the present invention provides methods of isolating and identifying binding partners or ligands of proteins of the invention. Macromolecules that interact with Mrg are referred to, for purposes of this discussion, as "binding partners." While the discussion below is specificially directed to identifying binding partners for Mrg receptors, it is contemplated that the assays of the invention may be used to identify binding partners for drg-12 as well.

Receptor binding can be tested using Mrg receptors isolated from their native source or synthesized directly. However, Mrg receptors obtained by the recombinant methods described above are preferred.

The compounds which may be screened in accordance with the invention include, but are not limited to polypeptides, peptides, including but not limited to members of random peptide libraries; (see, e.g., Lam, K. S. et al., 1991, Nature 354:82-84; Houghten, R. et al., 1991, Nature 354:84-86) and combinatorial chemistry-derived molecular libraries made of D- and/or L-configuration amino acids, phosphopeptides (including, but not limited to members of random or partially degenerate, directed phosphopeptide libraries; see, e.g., Songyang, Z. et al., 1993, Cell 72:767-778), peptide mimetics, antibodies (including, but not limited to, polyclonal, monoclonal, humanized, anti-idiotypic, chimeric or single chain antibodies, FAb, F(abN)$_2$ and FAb expression library fragments, and epitope-binding fragments thereof), and small organic or inorganic molecules.

The ability of candidate or test compounds to bind Mrg receptors can be measured directly or indirectly, such as in competitive binding assays. In competitive binding experiments, the concentration of the test compound necessary to displace 50% of another compound bound to the receptor (IC$_{50}$) is used as a measure of binding affinity. In these experiments the other compound is a ligand known to bind to the Mrg receptor with high affinity, such as an RF-amide peptide.

A variety of assay formats may be employed, including biochemical screening assays, immunoassays, cell-based assays and protein-protein binding assays, all of which are well characterized in the art. In one embodiment the assay involves anchoring the test compound onto a solid phase, adding the non-immobilized component comprising the Mrg receptor, and detecting Mrg/test compound complexes anchored on the solid phase at the end of the reaction. In an alternative embodiment, the Mrg may be anchored onto a solid surface, and the test compound, which is not anchored. In both situations either the test compound or the Mrg receptor is labeled, either directly or indirectly, to allow for identification of complexes. For example, an Mrg-Ig immunoadhesin may be anchored to a solid support and contacted with one or more test compounds.

Microtiter plates are preferably utilized as the solid phase and the anchored component may be immobilized by non-covalent or covalent attachments. Non-covalent attachment may be accomplished by simply coating the solid surface with a solution of the protein and drying. Alternatively, an immobilized antibody, preferably a monoclonal antibody, specific for the protein to be immobilized may be used to anchor the protein to the solid surface.

Alternatively, a reaction can be conducted in a liquid phase, the reaction products separated from unreacted components, and complexes detected; e.g., using an immobilized antibody specific for either Mrg polypeptide, peptide or fusion protein or the test compound to anchor any complexes formed in solution, and a labeled antibody specific for the other component of the possible complex to detect anchored complexes.

In one embodiment of these methods, a protein of the invention or a fragment of a protein of the invention, for instance, an extracellular domain fragment, is mixed with one or more potential binding partners, or an extract or fraction of a cell, under conditions that allow the association of potential binding partners with the protein of the invention. After mixing, peptides, polypeptides, proteins or other molecules that have become associated with a protein of the invention are separated from the mixture. The binding partner that bound to the protein of the invention can then be removed, identified and further analyzed. To identify and isolate a binding partner, the entire Mrg protein, for instance a protein comprising the entire amino acid sequence of SEQ ID NOs: 2, 4, 6, 8, 10, 12, 16, 18, 21, 23, 25, 27, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107 or 109 can be used. Alternatively, a fragment of the Mrg polypeptide can be used.

As used herein, a cellular extract refers to a preparation or fraction which is made from a lysed or disrupted cell. The preferred source of cellular extracts will be cells derived from DRG. Alternatively, cellular extracts may be prepared from cells derived from any tissue, including normal human kidney tissue, or available cell lines, particularly kidney derived cell lines.

A variety of methods can be used to obtain an extract of a cell. Cells can be disrupted using either physical or chemical disruption methods. Examples of physical disruption methods include, but are not limited to, sonication and mechanical shearing. Examples of chemical lysis methods include, but are not limited to, detergent lysis and enzyme lysis. A skilled artisan can readily adapt methods for preparing cellular extracts in order to obtain extracts for use in the present methods.

Once an extract of a cell is prepared, the extract is mixed with the protein of the invention under conditions in which association of the protein with the binding partner can occur. Alternatively, one or more known compounds or molecules can be mixed with the protein of the invention. A variety of conditions can be used, the most preferred being conditions that closely resemble conditions found in the cytoplasm of a human cell. Features such as osmolarity, pH, temperature, and the concentration of cellular extract used, can be varied to optimize the association of the protein with the binding partner.

After mixing under appropriate conditions, the bound complex is separated from the mixture. A variety of techniques can be utilized to separate the mixture. For example, antibodies specific to a protein of the invention can be used to immunoprecipitate the binding partner complex. Alternatively, standard chemical separation techniques such as chromatography and density/sediment centrifugation can be used.

After removal of non-associated cellular constituents found in the extract, and/or unbound compounds or molecules, the binding partner can be dissociated from the complex using conventional methods. For example, dissociation can be accomplished by altering the salt concentration or pH of the mixture.

To aid in separating associated binding partner pairs from the mixed extract, the protein of the invention can be immobilized on a solid support. For example, the protein can be attached to a nitrocellulose matrix or acrylic beads. Attachment of the protein to a solid support aids in separating peptide/binding partner pairs from other constituents found in the extract. The identified binding partners can be either a single protein or a complex made up of two or more proteins or any other macromolecule.

Alternatively, binding partners may be identified using a Far-Western assay according to the procedures of Takayama et al. *Methods Mol. Biol.* 69:171-84 (1997) or Sauder et al. *J Gen. Virol.* 77(5): 991-6 or identified through the use of epitope tagged proteins or GST fusion proteins.

Binding partners may also be identified in whole cell binding assays that are well known in the art. In one embodiment, an Mrg receptor is expressed in cells in which it is not normally expressed, such as COS cells. The cells expressing Mrg are then contacted with a potential binding partner that has previously been labeled, preferably with radioactivity or a fluorescent marker. The cells are then washed to remove unbound material and the binding of the potential binding partner to the cells is assessed, for example by collecting the cells on a filter and counting radioactivity. The amount of binding of the potential binding partner to untransfected cells or mock transfected cells is subtracted as background.

This type of assay may be carried out in several alternative ways. For example, in one embodiment it is done using cell membrane fractions from cells transfected with an Mrg or known to express an Mrg, rather than whole cells. In another embodiment purified Mrg is refolded in lipids to produce membranes that are used in the assay.

Alternatively, the nucleic acid molecules of the invention can be used in cell based systems to detect protein-protein interactions (see WO99/55356). These systems have been used to identify other protein partner pairs and can readily be adapted to employ the nucleic acid molecules herein described.

Any method suitable for detecting protein-protein interactions may be employed for identifying proteins, including but not limited to soluble, transmembrane or intracellular proteins, that interact with Mrg receptors. Among the traditional methods which may be employed are co-immunoprecipitation, crosslinking and co-purification through gradients or chromatographic columns to identify proteins that interact with Mrg. For such assays, the Mrg component can be a full-length protein, a soluble derivative thereof, a peptide corresponding to a domain of interest, or a fusion protein containing some region of Mrg.

Methods may be employed which result in the simultaneous identification of genes that encode proteins capable of interacting with Mrg. These methods include, for example, probing expression libraries, using labeled Mrg or a variant thereof.

One method of detecting protein interactions in vivo that may be used to identify Mrg binding partners is the yeast two-hybrid system. This system is well known in the art and is commercially available from Clontech (Palo Alto, Calif.).

Briefly, two hybrid proteins are employed, one comprising the DNA-binding domain of a transcription activator protein fused to the Mrg receptor, or a polypeptide, peptide, or fusion protein therefrom, and the other comprising the transcription activator protein's activation domain fused to an unknown target protein. These proteins are expressed in a strain of the yeast *Saccharomyces cerevisiae* that contains a reporter gene (e.g., HBS or lacZ) whose regulatory region contains the transcription activator's binding site. While either hybrid protein alone cannot activate transcription of the reporter gene, interaction of the two hybrid proteins reconstitutes the functional activator protein and results in expression of the reporter gene, which is detected by an assay for the reporter gene product.

The target protein is preferably obtained from tissue or cells known to express the Mrg receptor, such as DRG cells. For example, a cDNA library prepared from DRG cells may be used.

Binding partners may also be identified by their ability to interfere with or disrupt the interaction of known ligands. Even if they do not activate Mrg receptors, binding partners that interfere with interactions with known ligands may be useful in regulating or augmenting Mrg activity in the body and/or controlling disorders associated with Mrg activity (or a deficiency thereof).

Compounds that interfere with the interaction between Mrg and a known ligand may be identified by preparing a reaction mixture containing Mrg, or some variant or fragment thereof, and a known binding partner, such as an RF-amide peptide, under conditions and for a time sufficient to allow the two to interact and bind, thus forming a complex. In order to test a compound for inhibitory activity, the reaction mixture is prepared in the presence and absence of the test compound. The test compound may be initially included in the reaction mixture, or may be added at a time subsequent to the addition of the Mrg and its binding partner. Control reaction mixtures are incubated without the test compound. The formation of any complexes between the Mrg and the binding partner is then detected. The formation of a complex in the control reaction, but not in the reaction mixture containing the test compound indicates that the compound interferes with the interaction of the Mrg and the known binding partner. Additionally, complex formation within reaction mixtures containing the test compound and normal Mrg protein may also be compared to complex formation within reaction mixtures containing the test compound and a mutant Mrg. This comparison may be important in those cases wherein it is desirable to identify compounds that specifically disrupt interactions of mutant, or mutated, Mrg but not the normal proteins.

The order of addition of reactants can be varied to obtain different information about the compounds being tested. For example, test compounds that interfere with the interaction by competition can be identified by conducting the binding reaction in the presence of the test substance. In this case the test compound is added to the reaction mixture prior to, or simultaneously with, Mrg and the known binding partner. Alternatively, test compounds that have the ability to disrupt preformed complexes can be identified by adding the test compound to the reaction mixture after complexes have been formed.

In an alternate embodiment of the invention, a preformed complex of Mrg and an interactive binding partner is prepared in which either the Mrg or its binding partners is labeled, but the signal generated by the label is quenched due to formation of the complex (see, e.g., U.S. Pat. No. 4,109,496 to Rubenstein which utilizes this approach for immunoassays). The addition of a test compound that competes with and displaces one of the species from the preformed complex results in the generation of a signal above background. In this way, test substances which disrupt the interaction can be identified. Whole cells expressing Mrg, membrane fractions prepared from cells expressing Mrg or membranes containing refolded Mrg may be used in the assays described above. However, these same asays can be employed using peptide fragments that correspond to the binding domains of Mrg and/or the interactive or binding partner (in cases where the binding partner is a protein), in place of one or both of the full length proteins. Any number of methods routinely practiced in the art can be used to identify and isolate the binding sites. These methods include, but are not limited to, mutagenesis of the gene encoding an Mrg protein and screening for disruption of binding of a known ligand.

The compounds identified can be useful, for example, in modulating the activity of wild type and/or mutant Mrg; can be useful in elaborating the biological function of Mrg receptors; can be utilized in screens for identifying compounds that disrupt normal Mrg receptor interactions or may themselves disrupt or activate such interactions; and can be useful therapeutically.

J. Methods to Identify Agents that Modulate the Expression of a Nucleic Acid.

Another embodiment of the present invention provides methods for identifying agents that modulate the expression of a nucleic acid encoding a mrg or drg-12 protein of the invention or another protein involved in an mrg or drg-12 mediated pathway. These agents may be, but are not limited to, peptides, peptide mimetics, and small organic molecules that are able to gain entry into an appropriate cell (e.g., in the DRG) and affect the expression of a gene. Agents that modulate the expression of Mrg or drg-12 or a protein in an mrg mediated pathway may be useful therapeutically, for example to increase or decrease sensory perception, such as the perception of pain, to treat glaucoma, or to increase or decrease wound healing.

Such assays may utilize any available means of monitoring for changes in the expression level of the nucleic acids of the invention. As used herein, an agent is said to modulate the expression of a nucleic acid of the invention, for instance a nucleic acid encoding the protein having the sequence of SEQ ID NOs: 2, 4, 6, 8, 10, 12, 14, 16, 18, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107 or 109 if it is capable of up- or down-regulating expression of the gene or mRNA levels nucleic acid in a cell.

In one assay format, cell lines that contain reporter gene fusions between the open reading frames and/or the 5' or 3' regulatory sequences of a gene of the invention and any assayable fusion partner may be prepared. Numerous assayable fusion partners are known and readily available including the firefly luciferase gene and the gene encoding chloramphenicol acetyltransferase (Alam et al. *Anal. Biochem.* 188: 245-254 (1990)). Cell lines containing the reporter gene fusions are then exposed to the agent to be tested under appropriate conditions and time. Differential expression of the reporter gene between samples exposed to the agent and control samples identifies agents which modulate the expression of a nucleic acid encoding a mrg or drg-12 protein.

Additional assay formats may be used to monitor the ability of the agent to modulate the expression of a nucleic acid encoding a mrg or drg-12 protein of the invention. For instance, mRNA expression may be monitored directly by hybridization to the nucleic acids of the invention. Cell lines are exposed to the agent to be tested under appropriate conditions and time and total RNA or mRNA is isolated by standard procedures such those disclosed in Sambrook et al. (*Molecular Cloning: A Laboratory Manual*, 2nd Ed. Cold Spring Harbor Laboratory Press, 1989).

Probes to detect differences in RNA expression levels between cells exposed to the agent and control cells may be prepared from the nucleic acids of the invention. It is preferable, but not necessary, to design probes which hybridize only with target nucleic acids under conditions of high stringency. Only highly complementary nucleic acid hybrids form under conditions of high stringency. Accordingly, the stringency of the assay conditions determines the amount of complementarity which should exist between two nucleic acid strands in order to form a hybrid. Stringency should be chosen to maximize the difference in stability between the probe:target hybrid and potential probe:non-target hybrids.

Probes may be designed from the nucleic acids of the invention through methods known in the art. For instance, the G+C content of the probe and the probe length can affect probe binding to its target sequence. Methods to optimize probe specificity are commonly available in Sambrook et al. (*Molecular Cloning: A Laboratory Manual*, 2nd Ed. Cold Spring Harbor Laboratory Press, NY, 1989) or Ausubel et al. (*Current Protocols in Molecular Biology*, Greene Publishing Co., NY, 1995).

Hybridization conditions are modified using known methods, such as those described by Sambrook et al. and Ausubel et al., as required for each probe. Hybridization of total cellular RNA or RNA enriched for polyA RNA can be accomplished in any available format. For instance, total cellular RNA or RNA enriched for polyA RNA can be affixed to a solid support and the solid support exposed to at least one probe comprising at least one, or part of one of the sequences of the invention under conditions in which the probe will specifically hybridize. Alternatively, nucleic acid fragments comprising at least one, or part of one of the sequences of the invention can be affixed to a solid support, such as a silicon chip or porous glass wafer. The wafer can then be exposed to total cellular RNA or polyA RNA from a sample under conditions in which the affixed sequences will specifically hybridize. Such wafers and hybridization methods are widely available, for example, those disclosed by Beattie (WO 95/11755). By examining for the ability of a given probe to specifically hybridize to an RNA sample from an untreated cell population and from a cell population exposed to the agent, agents which up or down regulate the expression of a nucleic acid encoding a mrg or drg-12 are identified.

Hybridization for qualitative and quantitative analysis of mRNAs may also be carried out by using a RNase Protection Assay (i.e., RPA, see Ma et al. Methods 10: 273-238 (1996)). Briefly, an expression vehicle comprising cDNA encoding the gene product and a phage specific DNA dependent RNA polymerase promoter (e.g., T7, T3 or SP6 RNA polymerase) is linearized at the 3' end of the cDNA molecule, downstream from the phage promoter, wherein such a linearized molecule is subsequently used as a template for synthesis of a labeled antisense transcript of the cDNA by in vitro transcription. The labeled transcript is then hybridized to a mixture of isolated RNA (i.e., total or fractionated mRNA) by incubation at 45° C. overnight in a buffer comprising 80% formamide, 40 mM Pipes, pH 6.4, 0.4 M NaCl and 1 mM EDTA. The resulting hybrids are then digested in a buffer comprising 40 µg/ml ribonuclease A and 2 µg/ml ribonuclease. After deactivation and extraction of extraneous proteins, the samples are loaded onto urea/polyacrylamide gels for analysis.

In another assay format, products, cells or cell lines are first be identified which express mrg or drg-12 gene products physiologically. Cells and/or cell lines so identified would be expected to comprise the necessary cellular machinery such that the fidelity of modulation of the transcriptional apparatus is maintained with regard to exogenous contact of agent with appropriate surface transduction mechanisms and/or the cytosolic cascades. Such cells or cell lines are then transduced or transfected with an expression vehicle (e.g., a plasmid or viral vector) construct comprising an operable non-translated 5' or 3'-promoter containing end of the structural gene encoding the instant gene products fused to one or more antigenic fragments, which are peculiar to the instant gene products, wherein said fragments are under the transcriptional control of said promoter and are expressed as polypeptides whose molecular weight can be distinguished from the naturally occurring polypeptides or may further comprise an immunologically distinct tag. Such a process is well known in the art.

Cells or cell lines transduced or transfected as outlined above are then contacted with agents under appropriate conditions; for example, the agent comprises a pharmaceutically acceptable excipient and is contacted with cells comprised in an aqueous physiological buffer such as phosphate buffered saline (PBS) at physiological pH, Eagles balanced salt solution (BSS) at physiological pH, PBS or BSS comprising serum or conditioned media comprising PBS or BSS and/or serum incubated at 37° C. Said conditions may be modulated as deemed necessary by one of skill in the art. Subsequent to contacting the cells with the agent, said cells will be disrupted and the polypeptides of the lysate are fractionated such that a polypeptide fraction is pooled and contacted with an antibody to be further processed by immunological assay (e.g., ELISA, immunoprecipitation or Western blot). The pool of proteins isolated from the "agent-contacted" sample will be compared with a control sample where only the excipient is contacted with the cells and an increase or decrease in the immunologically generated signal from the "agent-contacted" sample compared to the control will be used to distinguish the effectiveness of the agent.

The probes described above for identifying differential expression of Mrg mRNA in response to applied agents can also be used to identify differential expression of Mrg mRNA in populations of mammals, for example populations with differing levels of sensory perception. Methods for identifying differential expression of genes are well known in the art. In one embodiment, mRNA is prepared from tissue or cells taken from patients exhibiting altered sensory perception, such as patients experiencing neuropathic pain, or suffering from a disease or disorder in which the Mrg receptor may play a role, such as glaucoma, and Mrg expression levels are quantified using the probes described above. The Mrg expression levels may then be compared to those in other populations to determine the role that Mrg expression is playing in the alteration of sensory perception and to determine whether treatment aimed at increasing or decreasing Mrg expression levels would be appropriate.

K. Methods to Identify Agents that Modulate Protein Levels or at Least One Activity of the Proteins of DRG Primary Sensory Neurons.

Another embodiment of the present invention provides methods for identifying agents or conditions that modulate protein levels and/or at least one activity of a mrg or drg-12 protein of the invention, including agonists and antagonists. Such methods or assays may utilize any means of monitoring or detecting the desired activity.

In one format, the relative amounts of a protein of the invention between a cell population that has been exposed to the agent to be tested compared to an unexposed control cell population may be assayed. In this format, probes such as specific antibodies are used to monitor the differential expression of the protein in the different cell populations. Cell lines or populations are exposed to the agent to be tested under appropriate conditions and time. Cellular lysates may be prepared from the exposed cell line or population and a control, unexposed cell line or population. The cellular lysates are then analyzed with the probe.

In another embodiment, animals known to express Mrg or drg-12 receptors are subjected to a particular environmental stimulus and any change produced in Mrg or drg-12 protein expression by exposure to the stimulus is measured. Transgenic animals, such as transgenic mice, produced to express a particular Mrg in a particular location may be used. The environmental stimulus is not limited and may be, for example, exposure to stressful conditions, or exposure to noxious or painful stimuli. Differences in Mrg receptor expression levels in response to environmental stimuli may provide insight into the biological role of Mrgs and possible treatments for diseases or disorders related to the stimuli used.

Antibody probes are prepared by immunizing suitable mammalian hosts in appropriate immunization protocols using the peptides, polypeptides or proteins of the invention if they are of sufficient length, or, if desired, or if required to enhance immunogenicity, conjugated to suitable carriers. Methods for preparing immunogenic conjugates with carriers such as BSA, KLH, or other carrier proteins are well known in the art. In some circumstances, direct conjugation using, for example, carbodiimide reagents may be effective; in other instances linking reagents such as those supplied by Pierce Chemical Co. (Rockford, Ill.), may be desirable to provide accessibility to the hapten. The hapten peptides can be extended at either the amino or carboxy terminus with a cysteine residue or interspersed with cysteine residues, for example, to facilitate linking to a carrier. Administration of the immunogens is conducted generally by injection over a suitable time period and with use of suitable adjuvants, as is generally understood in the art. During the immunization schedule, titers of antibodies are taken to determine adequacy of antibody formation.

While the polyclonal antisera produced in this way may be satisfactory for some applications, for pharmaceutical compositions, use of monoclonal preparations is preferred. Immortalized cell lines which secrete the desired monoclonal antibodies may be prepared using the standard method of Kohler and Milstein *Nature* 256:495-497 (1975)) or modifications which effect immortalization of lymphocytes or spleen cells, as is generally known. The immortalized cell lines secreting the desired antibodies are screened by immunoassay in which the antigen is the peptide hapten, polypeptide or protein. When the appropriate immortalized cell culture secreting the desired antibody is identified, the cells can be cultured either in vitro or by production in ascites fluid.

The desired monoclonal antibodies are then recovered from the culture supernatant or from the ascites supernatant. Fragments of the monoclonals or the polyclonal antisera which contain the immunologically significant portion can be used as antagonists, as well as the intact antibodies. Use of immunologically reactive fragments, such as the Fab, Fab', of $F(ab')_2$ fragments is often preferable, especially in a therapeutic context, as these fragments are generally less immunogenic than the whole immunoglobulin.

The antibodies or fragments may also be produced, using current technology, by recombinant means. Antibody regions that bind specifically to the desired regions of the protein can also be produced in the context of chimeras with multiple species origin, such as humanized antibodies as discussed in more detail below.

1. Identification of Agonists and Antagonists

The present invention provides for assays to identify compounds that serve as agonists or antagonists of one or more of the biological properties of Mrg and/or drg-12. Mrg agonists and antagonists may be useful in the prevention and treatment of problems associated with sensory perception, particularly nociception. Mrg agonists and antagonists may alter sensory perception, particularly the perception of pain. For example, compounds identified as Mrg receptor agonists may be used to stimulate Mrg receptor activation and thus may be effective in treating mammals suffering from pain by reducing the perception of pain. Compounds that are identified as Mrg receptor antagonists may be used, for example, to decrease the effector functions of Mrg receptors. This may be useful in cases where the Mrg receptors contain a mutation that produces increased responsiveness, or in cases of Mrg receptor overexpression. For instance, Mrg receptor antagonists may be useful in increasing the sensitivity of mammals to pain where appropriate, such as in diseases involving decreased sensory responsiveness, like some forms of diabetes.

Assays for identifying agonists or antagonsts may be done in vitro or in vivo, by monitoring the response of a cell following binding of the ligand to the receptor. An agonist will produce a cellular response, while an antagonist will have no effect on cellular response but will be capable of preventing cellular response to a known agonist.

a. Small Molecules

Small molecules may have the ability to act as Mrg agonists or antagonists and thus may be screened for an effect on a biological activity of Mrg. Small molecules preferably have a molecular weight of less than 10 kD, more preferably less than 5 kD and even more preferably less than 2 kD. Such small molecules may include naturally occurring small molecules, synthetic organic or inorganic compounds, peptides and peptide mimetics. However, small molecules in the present invention are not limited to these forms. Extensive libraries of small molecules are commercially available and a wide variety of assays are well known in the art to screen these molecules for the desired activity.

Candidate Mrg agonist and antagonist small molecules are preferably first identified in an assay that allows for the rapid identification of potential agonists and antagonists. An example of such an assay is a binding assay wherein the ability of the candidate molecule to bind to the Mrg receptor is measured, such as those described above. In another example, the ability of candidate molecules to interfere with the binding of a known ligand, for example FMRFamide to MrgA1, is measured. Candidate molecules that are identified by their ability to bind to Mrg proteins or interfere with the binding of known ligands are then tested for their ability to stimulate one or more biological activities.

The activity of the proteins of the invention may be monitored in cells expressing the mrg and/or drg-12 proteins of the invention by assaying for physiological changes in the cells upon exposure to the agent or agents to be tested. Such physiological changes include but are not limited to the flow of current across the membrane of the cell.

In one embodiment the protein is expressed in a cell that is capable of producing a second messenger response and that does not normally express Mrg or drg-12. The cell is then contacted with the compound of interest and changes in the second messenger response are measured. Methods to monitor or assay these changes are readily available. For instance, the mrg genes of the invention may be expressed in cells expressing Gα15, a G protein α subunit that links receptor activation to increases in intracellular calcium [$Ca^{2+}$] which can be monitored at the single cell level using the FURA-2 calcium indicator dye as disclosed in Chandrashekar et al. *Cell* 100:703-711, (2000). This assay is described in more detail in Example 5.

Similar assays may also be used to identify inhibitors or antagonists of Mrg or drg-12 activation. For example, cells expressing Mrg or drg-12 and capable of producing a quantifiable response to receptor activation are contacted with a known Mrg or drg-12 activator and the compound to be tested. In one embodiment, HEK cells expressing Gα15 and MrgA1 are contacted with FMRFamide and the compound to be tested. The cellular response is measured, in this case increase in [$Ca^{2+}$]. A decreased response compared to the known activator by itself indicates that the compound acts as an inhibitor of activation.

While such assays may be formatted in any manner, particularly preferred formats are those that allow high-throughput screening (HTP). In HTP assays of the invention, it is possible to screen thousands of different modulators or ligands in a single day. For instance, each well of a microtiter plate can be used to run a separate assay, for instance an assay based on the ability of the test compounds to modulate receptor activation derived increases in intracellular calcium as described above.

Agents that are assayed in the above method can be randomly selected or rationally selected or designed. As used herein, an agent is said to be randomly selected when the agent is chosen randomly without considering the specific sequences involved in the association of the a protein of the invention alone or with its associated substrates, binding partners, etc. An example of randomly selected agents is the use a chemical library or a peptide combinatorial library, or a growth broth of an organism.

As used herein, an agent is said to be rationally selected or designed when the agent is chosen on a nonrandom basis which takes into account the sequence of the target site and/or its conformation in connection with the agent's action. Sites of interest might be peptides within the membrane spanning regions, cytoplasmic and extracellular peptide loops between these transmembrane regions, or selected sequences within the N-terminal extracellular domain or C-terminal intracellular domain. Agents can be rationally selected or rationally designed by utilizing the peptide sequences that make up these sites.

The agents of the present invention can be, as examples, peptides, small molecules, vitamin derivatives, as well as carbohydrates. Dominant negative proteins, DNAs encoding these proteins, antibodies to these proteins, peptide fragments of these proteins or mimics of these proteins may be introduced into cells to affect function. "Mimic" used herein refers to the modification of a region or several regions of a peptide molecule to provide a structure chemically different from the parent peptide but topographically and functionally similar to the parent peptide (see Grant G A. in: Meyers (ed.) Molecular Biology and Biotechnology (New York, VCH Publishers, 1995), pp. 659-664). A skilled artisan can readily recognize that there is no limit as to the structural nature of the agents of the present invention.

The peptide agents of the invention can be prepared using standard solid phase (or solution phase) peptide synthesis methods, as is known in the art. In addition, the DNA encoding these peptides may be synthesized using commercially available oligonucleotide synthesis instrumentation and produced recombinantly using standard recombinant production systems. The production using solid phase peptide synthesis is necessitated if non-gene-encoded amino acids are to be included.

b. Antibodies

Another class of agents of the present invention are antibodies immunoreactive with critical positions of proteins of the invention. These antibodies may be human or non-human, polyclonal or monoclonal and may serve as agonist antibodies or neutralizing antibodies. They include amino acid sequence variants, glycosylation variants and fragments of antibodies. Antibody agents are obtained by immunization of suitable mammalian subjects with peptides, containing as antigenic regions, those portions of the protein intended to be targeted by the antibodies. General techniques for the production of such antibodies and the selection of agonist or neutralizing antibodies are well known in the art.

The antibodies of the present invention can be polyclonal antibodies, monoclonal antibodies, chimeric antibodies, humanized antibodies, human antibodies, heteroconjugate antibodies, or antibody fragments. In addition, the antibodies can be made by any method known in the art, including recombinant methods.

Mrg agonist and neutralizing antibodies may be preliminarily identified based on their ability to bind the Mrg receptor. For example, Western blot techniques well known in the art may be used to screen a variety of antibodies for their ability to bind Mrg. Mrg agonist and neutralizing antibodies are then identified from the group of candidate antibodies based on their biological activity. In one embodiment, Mrg agonist antibodies are identified by their ability to induce activation of a second messenger system in cells expressing the Mrg protein and comprising a second messenger system. For example, HEK cells overexpressing Gα15 and transfected with mrg may be contacted with a potential Mrg agonist antibody. An increase in intracellular calcium, measured as described in Example 5, would indicate that the antibody is an agonist antibody.

Identification of a neutralizing antibody involves contacting a cell expressing Mrg with a known Mrg ligand, such as an RF-amide peptide, and the candidate antibody and observing the effect of the antibody on Mrg activation. In one embodiment, Mrg receptors expressed in HEK cells overexpressing Gα15 are contacted with an Mrg ligand such as FMRFamide and the candidate neutralizing antibody. A decrease in responsiveness to the ligand, measured as described in Example 5, would indicate that the antibody is a neutralizing antibody.

c. Other Antagonists

The Mrg or drg-12 antagonists are not limited to Mrg or drg-12 ligands. Other antagonists include variants of a native Mrg or drg-12 receptor that retains the ability to bind an endogenous ligand but is not able to mediate a biological response. Soluble receptors and immunoadhesins that bind Mrg or drg-12 ligands may also be antagonists, as may antibodies that specifically bind a ligand near its binding site and prevent its interaction with the native receptor. These antagonists may be identified in the assays described above.

d. Computer Modeling

Computer modeling and searching technologies permit identification of compounds, or the improvement of already identified compounds, that can modulate Mrg receptor expression or activity. Once an agonist or antagonist is identified, the active sites or regions, such as ligand binding sites, are determined. The active site can be identified using methods known in the art including, for example, by determining the effect of various amino acid substitutions or deletions on ligand binding or from study of complexes of the relevant compound or composition with its natural ligand, such as with X-ray crystallography.

Next, the three dimensional geometric structure of the active site is determined such as by X-ray crystallography, NMR, chemical crosslinking or other methods known in the art. Computer modeling can be utilized to make predictions about the structure where the experimental results are not clear. Examples of molecular modeling systems are the CHARMm and QUANTA programs (Polygen Corporation, Waltham, Mass.). Once a predicted structure is determined, candidate modulating compounds can be identified by searching databases containing compounds along with information on their molecular structure in an effort to find compounds that have structures capable of interacting with the active site. The compounds found from this search are potential modulators of the activity of the proteins of the present invention and can be tested in the assays described above.

The agonistic or antagonistic activity of test compounds identified in cell based assays as described above can be further elucidated in assays using animals, for example transgenic animals that overexpress Mrg receptors as described in more detail below. In one embodiment, the effect of administration of potential Mrg antagonists or agonists on the responsiveness of such transgenic animals to sensory stimuli, such as noxious or painful stimuli, is measured. The therapeutic utility of such compounds may be confirmed by testing in these types of experiments or in animal models of particular disorders, for example animal models of neuropathic pain.

L. Uses for Agents that Modulate at Least One Activity of the Proteins.

As provided in the Examples, the mrg or drg-12 proteins and nucleic acids of the invention, are expressed in the primary nociceptive sensory neurons of DRG. In addition the Mrg receptors are expressed in specialized skin cells that play a role in wound repair. Further, proteins homologous to Mrg receptors are expressed in the trabecular meshwork of the eye and a role for them has been suggested in the regulation of pressure in the eye (Gonzalez et al. Invest. Ophth. Vis. Sci. 41: 3678-3693 (2000)). Thus, the present invention further provides compositions containing one or more agents that modulate expression or at least one activity of a protein of the invention. For example, the invention provides ligands that directly activate Mrg receptors.

Agents that modulate, up-or-down-regulate the expression of the protein or agents such as agonists or antagonists of at least one activity of the protein may be used to modulate biological and pathologic processes associated with the protein's function and activity. Several agents that activate the Mrg receptors are identified in the examples, including the RF-amide peptides. Thus the present invention provides methods to treat impaired sensory perception, such as pain, including neuropathic pain, as well as to promote wound healing, to restore normal sensitivity following injury and to treat ocular conditions, particularly those associated with pressure, such as glaucoma.

As described in the Figures and Examples, expression of a protein of the invention may be associated with biological processes of nociception, which may also be considered pathological processes. As used herein, an agent is said to modulate a biological or pathological process when the agent alters the degree, severity or nature of the process. For instance, the neuronal transmission of pain signals may be prevented or modulated by the administration of agents which up-regulate down-regulate or modulate in some way the expression or at least one activity of a protein of the invention.

The pain that may be treated by the proteins of the present invention and agonists and antagonists thereof, is not limited in any way and includes pain associated with a disease or disorder, pain associated with tissue damage, pain associated with inflammation, pain associated with noxious stimuli of any kind, and neuropathic pain, including pain associated with peripheral neuropathies, as well as pain without an identifiable source. The pain may be subjective and does not have to be associated with an objectively quantifiable behavior or response.

In addition to treating pain, the compounds and methods of the present invention may be useful for increasing or decreasing sensory responses. It may be useful to increase responsiveness to stimuli, including noxious stimuli and painful stimuli, in some disease states that are characterized by a decreased responsiveness to stimuli, for example in diabetes.

Certain conditions, such as chronic disease states associated with pain and peripheral neuropathies and particularly conditions resulting from a defective Mrg gene, can benefit from an increase in the responsiveness to Mrg receptor ligands. Thus these condition may be treated by increasing the number of functional Mrg receptors in cells of patients suffering from such conditions. This could be increasing the expression of Mrg receptor in cells through gene therapy using Mrg-encoding nucleic acid. This includes both gene therapy where a lasting effect is achieved by a single treatment, and gene therapy where the increased expression is transient. Selective expression of Mrg in appropriate cells may be achieved by using Mrg genes controlled by tissue specific or inducible promoters or by producing localized infection with replication defective viruses carrying a recombinant Mrg gene, or by any other method known in the art.

In a further embodiment, patients that suffer from an excess of Mrg, hypersensitivity to Mrg ligands or excessive activation of Mrg may be treated by administering an effective amount of anti-sense RNA or anti-sense oligodeoxyribonucleotides corresponding to the Mrg gene coding region, thereby decreasing expression of Mrg.

As used herein, a subject to be treated can be any mammal, so long as the mammal is in need of modulation of a pathological or biological process mediated by a protein of the invention. For example, the subject may be experiencing pain or may be anticipating a painful event, such as surgery. The invention is particularly useful in the treatment of human subjects.

In the therapeutic methods of the present invention the patient is administered an effective amount of a composition of the present invention, such as an Mrg protein, peptide fragment, Mrg variant, Mrg agonist, Mrg antagonist, or anti-Mrg antibody of the invention.

The agents of the present invention can be provided alone, or in combination with other agents that modulate a particular biological or pathological process. For example, an agent of the present invention can be administered in combination with other known drugs or may be combined with analgesic drugs or non-analgesic drugs used during the treatment of pain that occurs in the presence or absence of one or more other pathological processes. As used herein, two or more agents are said to be administered in combination when the two agents are administered simultaneously or are administered independently in a fashion such that the agents will act at the same time.

The agents of the present invention are administered to a mammal, preferably to a human patient, in accord with known methods. Thus the agents of the present invention can be administered via parenteral, subcutaneous, intravenous, intramuscular, intraperitoneal, intracerebrospinal, intra-articular, intrasynovial, intrathecal, transdermal, topical, inhalation or buccal routes. They may be administered continuously by infusion or by bolus injection. Generally, where the disorder permits the agents should be delivered in a site-specific manner. Alternatively, or concurrently, administration may be by the oral route. The dosage administered will be dependent upon the age, health, and weight of the recipient, kind of concurrent treatment, if any, frequency of treatment, and the nature of the effect desired.

The toxicity and therapeutic efficacy of agents of the present invention can be determined by standard pharmaceutical procedures in cell cultures or experimental animals. While agents that exhibit toxic side effects can be used, care should be taken to design a delivery system that targets such compounds to the desired site of action in order to reduce side effects.

While individual needs vary, determination of optimal ranges of effective amounts of each component is within the skill of the art. For the prevention or treatment of disease, the appropriate dosage of agent will depend on the type of disease to be treated, the severity and course of the disease, whether the agent is administered for preventive or therapeutic purposes, previous therapy, the patient's clinical history and response to the agent, and the discretion of the attending physician. Therapeutic agents are suitably administered to the patient at one time or over a series of treatments. Typical dosages comprise 0.1 to 100 µg/kg body wt. The preferred dosages comprise 0.1 to 10 µg/kg body wt. The most preferred dosages comprise 0.1 to 1 µg/kg body wt. For repeated administrations over several days or longer, depending on the condition, the treatment is sustained until a desired suppression of disease symptoms occurs. The progress of this therapy is easily monitored by conventional techniques and assays.

In addition to the pharmacologically active agent, the compositions of the present invention may contain suitable pharmaceutically acceptable carriers comprising excipients and auxiliaries that facilitate processing of the active compounds into preparations which can be used pharmaceutically for delivery to the site of action. Suitable formulations for parenteral administration include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, and/or dextran. Optionally, the suspension may also contain stabilizers. Liposomes can also be used to encapsulate the agent for delivery into the cell. The agent can also be prepared as a sustained-release formulation, including semipermeable matrices of solid hydrophobic polymers containing the protein. The sustained release preparation may take the form of a gel, film or capsule.

The pharmaceutical formulation for systemic administration according to the invention may be formulated for enteral, parenteral or topical administration. Indeed, all three types of formulations may be used simultaneously to achieve systemic administration of the active ingredient.

Suitable formulations for oral administration include hard or soft gelatin capsules, pills, tablets, including coated tablets, elixirs, suspensions, syrups or inhalations and controlled release forms thereof.

In practicing the methods of this invention, the compounds of this invention may be used alone or in combination with other therapeutic or diagnostic agents. In certain preferred embodiments, the compounds of this invention may be co-administered along with other compounds typically prescribed for these conditions according to generally accepted medical practice. The compounds of this invention can be utilized in vivo, ordinarily in mammals, such as humans, sheep, horses, cattle, pigs, dogs, cats, rats and mice, or in vitro. When used in vivo, the compounds must be sterile. This is readily accomplished by filtration through sterile filtration membranes.

a. Articles of Manufacture

In another embodiment of the invention, an article of manufacture containing materials useful for the treatment of the disorders described above is provided. The article of manufacture comprises a container and a label or package insert(s) on or associated with the container. Suitable containers include, for example, bottles, vials, syringes, etc. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). At least one active agent in the composition is an Mrg agonist. The label or package insert indicates that the composition is used for treating the condition of choice, such as to treat impaired sensory perception, for example to reduce neuropathic pain. In one embodiment, the label or package inserts indicates that the composition comprising the Mrg agonist can be used to treat pain, glaucoma or to accelerate wound healing.

M. Transgenic Animals

Transgenic animals containing mutant, knock-out or modified genes corresponding to the mrg and/or drg-12 sequences are also included in the invention. Transgenic animals are genetically modified animals into which recombinant, exogenous or cloned genetic material has been experimentally transferred. Such genetic material is often referred to as a "transgene". The nucleic acid sequence of the transgene, in this case a form of SEQ ID NOS: 1, 3, 5, 7, 9, 11, 13, 15, 17, 20, 22, 24, 26 or 28, 30, 32, 34, 36, 38, 40, 42, 44, 46, 48, 50, 52, 54, 56, 58, 60, 62, 64, 66, 68, 70, 7274, 76, 78, 80, 82, 84, 86, 88, 90, 92, 94, 96, 98, 100, 102, 104, 106 or 108 may be integrated either at a locus of a genome where that particular nucleic acid sequence is not otherwise normally found or at the normal locus for the transgene. In addition the transgene may encode a non-functional variant. The transgene may consist of nucleic acid sequences derived from the genome of the same species or of a different species than the species of the target animal.

The term "germ cell line transgenic animal" refers to a transgenic animal in which the genetic alteration or genetic information was introduced into a germ line cell, thereby conferring the ability of the transgenic animal to transfer the genetic information to offspring. If such offspring in fact possess some or all of that alteration or genetic information, then they too are transgenic animals.

The alteration or genetic information may be foreign to the species of animal to which the recipient belongs, foreign only to the particular individual recipient, or may be genetic information already possessed by the recipient. In the last case, the altered or introduced gene may be expressed differently than the native gene.

Transgenic animals can be produced by a variety of different methods including transfection, electroporation, microinjection, gene targeting in embryonic stem cells and recombinant viral and retroviral infection (see, e.g., U.S. Pat. No. 4,736,866; U.S. Pat. No. 5,602,307; Mullins et al. *Hypertension* 22(4):630-633 (1993); Brenin et al. *Surg. Oncol.* 6(2)99-

110 (1997); Tuan (ed.), *Recombinant Gene Expression Protocols, Methods in Molecular Biology No. 62*, Humana Press (1997)).

A number of recombinant or transgenic mice have been produced, including those which express an activated oncogene sequence (U.S. Pat. No. 4,736,866); express simian SV40 T-antigen (U.S. Pat. No. 5,728,915); lack the expression of interferon regulatory factor 1 (IRF-1) (U.S. Pat. No. 5,731,490); exhibit dopaminergic dysfunction (U.S. Pat. No. 5,723,719); express at least one human gene which participates in blood pressure control (U.S. Pat. No. 5,731,489); display greater similarity to the conditions existing in naturally occurring Alzheimer's disease (U.S. Pat. No. 5,720, 936); have a reduced capacity to mediate cellular adhesion (U.S. Pat. No. 5,602,307); possess a bovine growth hormone gene (Clutter et al. *Genetics* 143(4):1753-1760 (1996)); or, are capable of generating a fully human antibody response (McCarthy *The Lancet* 349(9049):405 (1997)).

While mice and rats remain the animals of choice for most transgenic experimentation, in some instances it is preferable or even necessary to use alternative animal species. Transgenic procedures have been successfully utilized in a variety of non-murine animals, including sheep, goats, pigs, dogs, cats, monkeys, chimpanzees, hamsters, rabbits, cows and guinea pigs (see, e.g., Kim et al. *Mol. Reprod. Dev.* 46(4): 515-526 (1997); Houdebine *Reprod. Nutr. Dev.* 35(6):609-617 (1995); Petters *Reprod. Fertil. Dev.* 6(5):643-645 (1994); Schnieke et al. *Science* 278(5346):2130-2133 (1997); and Amoah J. Animal *Science* 75(2):578-585 (1997)).

The method of introduction of nucleic acid fragments into recombination competent mammalian cells can be by any method that favors co-transformation of multiple nucleic acid molecules. Detailed procedures for producing transgenic animals are readily available to one skilled in the art, including the disclosures in U.S. Pat. No. 5,489,743 and U.S. Pat. No. 5,602,307.

It is contemplated that mice lacking a particular Mrg or drg-12 gene, or in which expression of a particular Mrg or drg-12 has been increased or decreased will be used in an assay for determining how Mrgs influence behavior, including sensory responses, particularly responses to painful stimuli. In particular, transgenic mice will be used to determine if Mrg mediates the response to a particular type of noxious stimuli, such as mechanical, thermal or chemical. Thus in one embodiment transgenic mice lacking native Mrg receptors, or in which Mrg receptor expression levels have been modified, will be tested to determine their sensitivity to pressure, temperature, and other noxious stimuli. Assays for determining sensitivity to stimuli are well known in the art. These include, but are not limited to, assays that measure responsiveness to mechanical pain (von Frey hairs or tail pinch), thermal pain (latency to lick or jump in the hot plate assay), chemical pain (latency to lick when a noxious substance such as capsaicin or formalin is injected in the paw), visceral pain (abdominal stretching in response to intraperitoneal injection of acetic acid) and neuropathic pain. For example, mice in which one or more Mrgs have been deleted will be tested for their responsiveness to a variety of painful stimuli of varying intensity. By determining the sensory responses that are mediated by the Mrg receptors, therapeutic agents known to stimulate or inhibit Mrg receptors can be chosen for the treatment of disease states known to involve these types of responses. In addition, therapeutics specifically aimed at treating disorders involving these responses can be developed by targeting the Mrg receptors.

In one embodiment, transgenic mice expressing one or more human Mrg proteins are produced. The expression pattern of the human Mrg protein may then be determined and the effect of the expression of the human Mrg protein on various sensory modalities may be investigated. Further, the efficacy of potential therapeutic agents may be investigated in these mice.

In addition, the effects of changes in the expression levels of specific Mrg proteins can be investigated in animal models of disease states. By identifying the effect of increasing or decreasing Mrg receptor levels and activation, therapeutic regimens useful in treating the diseases can be developed. In one embodiment, mice in which Mrg receptor expression levels have been increased or decreased are tested in models of neuropathic pain.

Further, mice in which Mrg expression levels have been manipulated may be tested for their ability to respond to compounds known to modulate responsiveness to pain, such as analgesics. In this way the role of Mrg in the sensation of pain may be further elucidated. For example, a lack of response to a known analgesic in the transgenic mice lacking Mrg would indicate that the Mrg receptors play a role in mediating the action of the analgesic.

Another preferred transgenic mouse is one in which the Mrg gene is modified to express a marker or tracer such as green fluorescent protein (GFP). By examining the expression pattern of the marker or tracer, the exact location and projection of Mrg containing neurons and other cells can be mapped. This information will be compared to the location and projection of neurons and other cells whose involvement in specific disease states has previously been identified. In this way additional therapeutic uses for the compounds of the present invention may be realized.

N. Diagnostic Methods

As described in the Examples, the genes and proteins of the invention may be used to diagnose or monitor the presence or absence of sensory neurons and of biological or pathological activity in sensory neurons. For instance, expression of the genes or proteins of the invention may be used to differentiate between normal and abnormal sensory neuronal activities associated with acute pain, chronic intractable pain, or allodynia. Expression levels can also be used to differentiate between various stages or the severity of neuronal abnormalities. One means of diagnosing pathological states of sensory neurons involved in pain transmission using the nucleic acid molecules or proteins of the invention involves obtaining tissue from living subjects. These subjects may be non-human animal models of pain.

The use of molecular biological tools has become routine in forensic technology. For example, nucleic acid probes may be used to determine the expression of a nucleic acid molecule comprising all or at least part of the sequences of the invention in forensic/pathology specimens. Further, nucleic acid assays may be carried out by any means of conducting a transcriptional profiling analysis. In addition to nucleic acid analysis, forensic methods of the invention may target the proteins of the invention to determine up or down regulation of the genes (Shiverick et al., *Biochim Biophys Acta* 393(1): 124-33 (1975)).

Methods of the invention may involve treatment of tissues with collagenases or other proteases to make the tissue amenable to cell lysis (Semenov et al., *Biull Eksp Biol Med* 104(7): 113-6 (1987)). Further, it is possible to obtain biopsy samples from different regions of the kidney or other tissues for analysis.

Assays to detect nucleic acid or protein molecules of the invention may be in any available format. Typical assays for nucleic acid molecules include hybridization or PCR based formats. Typical assays for the detection of proteins, polypeptides or peptides of the invention include the use of antibody probes in any available format such as in situ binding assays, etc. See Harlow et al., Antibodies: A Laboratory Manual, Cold Spring Harbor Laboratory, 1988 and Section G. In preferred embodiments, assays are carried-out with appropriate controls.

The above methods may also be used in other diagnostic protocols, including protocols and methods to detect disease states in other tissues or organs.

O. Methods of Identifying Other Genes Expressed in Primary Nociceptive Sensory Neurons.

As described in the Examples, the mrg and drg-12 genes of the invention have been identified RNA using a suppression-PCR-based method (Clontech) to enrich for genes expressed in the DRG of wild type but not Ngn1 mutant mice. This general method may be used to identify and isolate other DRG specific genes by producing transgenic mice that do not express other genes required for the development or presence of the nociceptive subset of DRG neurons. For instance, TrkA$^{-/-}$ mice may be used in the methods of the invention to isolate other genes associated with nociceptive DRG neurons (see Lindsay *Philos. Trans R. Soc. Lond. B. Biol. Sci.* 351 (1338): 365-73 (1996) and Walsh et al. *J. Neurosci.* 19(10): 4155-68).

Without further description, it is believed that one of ordinary skill in the art can, using the preceding description and the following illustrative examples, make and utilize the compounds of the present invention and practice the claimed methods. The following working examples therefore, specifically point out preferred embodiments of the present invention, and are not to be construed as limiting in any way the remainder of the disclosure.

EXAMPLES

Example 1

Positive Selection-Based Differential Hybridization Between Wild Type and Ngn1$^{-/-}$ DRG to Identify Candidate Genes Involved in Nociception Previous studies have shown that Neurogenin1 (Ngn1), a bHLH transcription factor (Ma et al. *Cell* 87: 43-52 (1996)), is required for cell fate determination of nociceptive sensory neurons in dorsal root ganglia (DRG) (Ma et al. *Genes & Dev.* 13: 1717-1728 (1999)). In Ngn1$^{-/-}$ mutant mouse embryos most if not all trkA$^+$ neurons, which include the nociceptive subclass, fail to be generated. This mutant phenotype was exploited to isolate genes specifically expressed in such neurons, by subtracting cDNAs from neonatal wild-type and Ngn1$^{-/-}$ DRG. Genes expressed in the former but not the latter cDNA population are specific to trkA$^+$ nociceptive neurons.

Total RNA was isolated from the dorsal root ganglia (DRG) of newborn wild type or Ngn1$^{-/-}$ mice (see Ma et al. Genes Develop. 13:1717-1728 (1999), Fode et al. Neuron 20:483-494 (1998) and Ma et al. Neuron 20:469-482 (1998)). A suppression-PCR-based method (Clontech) was then used to enrich for genes expressed in wild type but not Ngn1 mutant DRG. Briefly, cDNA was synthesized from the RNA using Superscript reverse transcriptase (Gibco) with oligo dT primers, and was amplified with the Smart PCR Amplification Kit (Clontech). The amplified wild-type and Ngn1$^{-/-}$ DRG cDNAs were used as tester and driver, respectively, in the PCR-Select subtractive hybridization protocol (Clontech). Differential screening by dot blot analysis identified several clones, which were enriched in cDNA from wild-type DRG compared to that from Ngn1$^{-/-}$ DRG. These clones were analyzed further by nucleotide sequencing and in situ hybridization.

Approximately 1,600 positives were identified in the primary screen, and of these 142 were sequenced. Fifty of these represented known genes, and 92 represented new genes (see Table 2). Among the known genes were several signaling molecules specifically expressed in nociceptive sensory neurons. These included VR-1, calcitonin gene-related peptide (CGRP), the tetrodotoxin-insensitive sodium channel (SNS-TTXi) and diacylglycerol kinase. Among the new genes were several encoding proteins with structural features characteristic of ion channels or receptors, which were revealed by in situ hybridization to be specifically expressed in a subset of DRG sensory neurons. These molecules are described in more detail in Examples 2 and 3.

TABLE 2

Summary of results of the differential hybridization screening for genes involved in pain sensation.

| # of times isolated from the screen | Name |
|---|---|
| A. Known genes: | |
| 13 | NaN |
| 9 | Diacylglycerol kinase |
| 7 | Synaptophysin IIa |
| 5 | Vanilloid receptor1 |
| 3 | GluR5-2c |
| 2 | CGRP |
| 2 | CLIM1 |
| 1 | SNS-TTXi |
| 1 | Alpha N-catenin I |
| 1 | Brain Na channel III |
| 1 | NICA6 |
| 1 | Secretogranin |
| B. Novel genes: | |
| 2 | Mrg3 (a novel G-protein-coupled receptor) |
| 2 | DRG12 |

Note:
Previous studies have shown that the genes with bolded letters are expressed specifically in nociceptors.

Example 2

A Novel Family of Putative G Protein-Coupled Receptors Specifically Expressed in Nociceptive Sensory Neurons Among the novel genes isolated from the screen were two independent clones encoding a receptor protein with 7 transmembrane segments (SEQ ID NO: 1), a characteristic of G protein-coupled receptors. The novel 7 transmembrane receptor isolated is most closely related to the oncogene mas, and therefore has been named mas-related gene-3 (mrg3). mrg3 is also known as mas-related gene A1, or MrgA1. A complete coding sequence for mrg3 has been deduced from the genomic DNA sequence (FIGS. 1B-D and SEQ ID NO: 2). MrgA1 shows significant homology (35% identity) to MAS1 (Young et al. *Cell* 45: 711-9 (1986)). It also shares significant homology (30-35% identity) with two other mammalian GPCRs, called Mas-related gene 1 (MRG1) (Monnot et al. *Mol Endocrinol* 5: 1477-87 (1991)) and rat thoracic aorta (RTA) (Ross et al. *Proc Natl Acad Sci USA* 87: 3052-6 (1990)).

Such G protein-coupled receptors are expressed in other classes of sensory neurons, such as olfactory and gustatory neurons, but molecules in this class had not previously been described in DRG sensory neurons, with the exception of the Protease-Activated Receptors (PARs).

Further screening of mouse DRG cDNA library and mouse genomic library by using mrg3 DNA as a probe has identified nine additional closely related genes named mrg4 (MrgA2), mrg5 (MrgA3), mrg6, mrg7, mrg8 (MrgA4), mrg9 (MrgA5), mrg10 (MrgA6), mrg11 (MrgA7), and mrg12 (MrgA8). Among them, mrg4, 5 and mrg 8-12 contain full-length open reading frames (see FIGS. 1A-1D). Two human homologues were found by searching databases using the blast program. The protein alignment of the eight mrg genes, mrg3-8 and human1-2, suggested that they define a novel G protein-coupled receptor gene family (FIGS. 1A-1D).

In particular MrgA1-4 were isolated from a P0 mouse DRG cDNA library and clones containing the entire ORFs of MRGsA5-8 were isolated from a mouse genomic BAC library arrayed on filters (Incyte Genomics). FIG. 6A shows an alignment of the polypeptide sequence of MrgA1-8 and indicates the transmembrane domains as well as the cytoplasmic and extracellular loops. In addition, other mouse MrgAs, as well as other human Mrg sequences, were identified by searching the Celera mouse and human (Venter et al. *Science* 291: 1304-51 (2001)) genomic databases, using the TBLASTN program with MrgA1 as the query. Table 3 shows that the MrgA genes are highly homologous to each other. This high degree of homology combined with the presence of certain characteristic conserved residues indicates that they define a novel subfamily of the MAS family of GPCRs.

To identify additional members of the mouse Mrg family, TBLASTN searches were run against the Celera mouse fragment database (indexed Jan. 7, 2001; 18,251,375 fragments) using MRGA1 and MRGA4 protein sequences as queries. These searches identified 299 unique mouse genomic DNA fragments. The sequences of these fragments were downloaded and assembled into contigs with GELMERGE (GCG Wisconsin Package) under stringent conditions (90% identity, 20 nt minimum overlap). GELMERGE was run again (80% identity, 20 nt minimum overlap) to reduce the dataset further. The consensus nucleotide sequence from each contig was then queried against the Celera mouse fragment database with BLASTN to identify additional sequences for assembly (final n=536 fragments). The consensus sequences from the final assembly were placed into a FASTA formatted database. This database was then searched with TFASTY using MRGA1 as query to identify the potential coding regions from each consensus sequence, regardless of whether the error-prone genomic sequence introduced stop codons or frameshifts into the proteins (Pearson, W. R. (1999). Flexible similarity searching with the FASTA3 program package. In Bioinformatics Methods and Protocols, S. Misener and S. A. Krawetz, eds. (Totowa, N.J.: Humana Press), pp. 185-219). The protein sequences from these searches were then combined into a single FASTA formatted file for phylogenetic analysis.

Using this analysis, 16 additional members of the murine MrgA subfamily were identified (FIG. 6B). In addition to this subfamily, two closely related Mrg subfamilies called MrgB and MrgC, were also discovered (FIG. 6B). To confirm the existence of an ORF in the mouse MrgB genes, high-fidelity PCR was used to amplify mMrgB1-5, mMrgD, and mMrgE from C57B1/6 mouse genomic DNA. Several independent clones were sequenced and confirmed the ORF predictions. The presence of numerous stop codons and frame shifts in the assembled Celera sequence indicated that the mMrgC genes are pseudogenes.

The MrgB subfamily contains 14 genes, whereas MrgC has 12 members. The percent sequence identity within each of these subfamilies is greater than 50% (Table 3). Strikingly, all 12 MrgC members appear to be pseudogenes (FIG. 1B, "Ψ"), as they contain multiple premature stop codons, frameshift mutations or both. Together, therefore, the MrgA and MrgB subfamilies comprise 36 intact ORFs.

TABLE 3

Similarity and identity between murine MRG subfamilies

|  | mMRGA1 | mMRGA2 | mMRGA3 | mMRGB1 | mMRGB2 | mMRGB3 | mMRGC1 | mMRGC2 | mMRGC3 |
|---|---|---|---|---|---|---|---|---|---|
| mMRGA1 | — | 77.9 | 73.1 | 48.1 | 46.3 | 43.6 | 44.9 | 46.7 | 47.8 |
| mMRGA2 | 87.5 | — | 71.8 | 42.4 | 45.4 | 42.7 | 41.5 | 44.5 | 43.5 |
| mMRGA3 | 85.1 | 83.1 | — | 47.9 | 46.8 | 44.2 | 46.0 | 49.8 | 46.6 |
| mMRGB1 | 72.1 | 66.8 | 70.2 | — | 57.6 | 50.0 | 42.9 | 47.1 | 45.3 |
| mMRGB2 | 68.7 | 67.7 | 69.4 | 72.7 | — | 53.5 | 41.8 | 44.4 | 43.1 |
| mMRGB3 | 65.2 | 65.7 | 64.6 | 69.5 | 73.5 | — | 37.0 | 38.8 | 36.4 |
| mMRGC1 | 69.5 | 65.2 | 70.9 | 64.4 | 67.0 | 63.3 | — | 76.0 | 79.1 |
| mMRGC2 | 69.8 | 72.5 | 74.2 | 69.4 | 70.8 | 65.7 | 81.4 | — | 78.8 |
| mMRGC3 | 70.9 | 67.2 | 71.0 | 66.2 | 69.5 | 64.6 | 86.1 | 86.3 | — |

Percent identity (top-right, bold) and percent similarity (bottom-left) between the protein sequences are indicated. "hMRG" indicates a human MRG amino acid sequence; "mMRG" indicates a murine MRG sequence. "hMRGX" is used to indicate a human homolog of mMRGA and mMRGB sequences (FIG. 1B). Values were derived from global alignments using the GAP program in the GCG package.

Searches of the Celera (Venter et al. *Science* 291: 1304-51 (2001)) and public (Consortium. *Nature* 409: 860-921 (2001)) genomic sequence databases, using both BLAST (Altschul et al. *Journal of Molecular Biology* 215: 403-410 (1990)) and Hidden Markov Models (HMMs (Eddy. *Bioinformatics* 14, 755-63 (1998)), revealed 4 closely related (~50% identity) full-length human genes, and at least 10 human pseudogenes. Briefly, TBLASTN searches were run against the Celera human genome database (Venter et al. *Science* 291: 1304-51 (2001)) using the mMrgA1 protein sequence as the query. The genomic sequences that were identified in this search were downloaded, placed into a FASTA formatted database and searched with TFASTY to identify a non-redundant set of proteins. With the exception of hMrgX3, hMrgE, and hMrgΨ8, all human Mrgs were independently identified from a similar analysis of the public human genome sequence (Consortium. *Nature* 409: 860-921 (2001)). Human MrgX1-4 sequences were independently verified from PCR-amplified products derived from human BAC clones containing the genes.

Although the human genes appear to be more similar to the murine MrgA subfamily than the MrgB subfamily in the phylogenetic tree (FIG. 6B, hMrgX1-4), in the absence of clear orthologous pairs we currently refer to them as hMrgX genes. In addition to the MrgA, B and C subfamilies, a number of additional Mas1-related orphan GPCRs were identified by this search, including those we refer to as Mrgs D-F (FIG. 6B). Several of these sequences, such as MrgD, have clear human orthologs (FIG. 6B, hMrgD). At the protein level hMrgD and mMrgD are 58% identical and 73% similar, while at the nucleotide level they are 73% identical. All together, we identified almost 45 murine and 9 human intact coding sequences belonging to this family.

TABLE 4

Similarity and identity between human and murine MRGs

|  | hMRGX2 | hMRGE | mMRGA1 | mMRGB4 | mMRGB1 | mMRGD | mMRGE |
|---|---|---|---|---|---|---|---|
| hMRGX2 | — | 40.2 | 55.6 | 50.1 | 53.4 | 40.5 | 38.8 |
| hMRGE | 62.8 | — | 36.6 | 32.8 | 32.8 | 33.9 | 76.5 |
| mMRGA1 | 74.8 | 57.7 | — | 48.1 | 48.1 | 37.1 | 39.7 |
| mMRGB4 | 71.0 | 58.0 | 70.4 | — | 54.5 | 34.8 | 36.6 |
| mMRGB1 | 73.5 | 60.5 | 72.1 | 74.1 | — | 36.5 | 33.8 |
| mMRGD | 61.1 | 57.6 | 59.5 | 64.2 | 61.3 | — | 35.1 |
| mMRGE | 59.0 | 84.0 | 62.5 | 63.7 | 59.1 | 59.3 | — |

Percent identity (top-right, bold) and percent similarity (bottom-left) between the protein sequences are indicated. "hMRG" indicates a human MRG amino acid sequence; "mMRG" indicates a murine MRG sequence. "hMRGX" is used to indicate a human homolog of mMRGA and mMRGB sequences (FIG. 1B). Values were derived from global alignments using the GAP program in the GCG package.

MRG receptors have short (3-21 amino acid) N-termini with no apparent signal peptide, which are predicted to be located extracellularly. The transmembrane domains and intracellular domains are highly conserved suggesting that the receptors have a shared function. The most divergent regions of MRGA-family receptors appear localized to the extracellular loops (FIG. 6A), suggesting that these receptors recognize different ligands, or the same ligand but with different affinities. Interestingly, we identified 12 single nucleotide polymorphisms in the MrgA1 coding sequence between murine strains C57BL/6J and 129SvJ. These 12 changes resulted in 6 amino acid substitutions, all of which were either conservative, or which substituted residues expressed at the same position by other family members.

A large mouse genomic contig was built by analyzing overlapping BAC clones containing MrgA sequences (FIG. 6C). There are 7 MrgA genes, including 3 pseudogenes, residing in this contig. Such clustering is a common feature of GPCR-encoding gene families (Xie et al. *Mamm Genome* 11: 1070-8 (2000)). Strikingly, all of the human Mrg genes (with the exception of Mas1 and Mrg1) are located on chromosome 11, which also contains 50% of all human olfactory receptors genes. All of the MrgA genes in the murine BAC contig (FIG. 6C) encode intact ORFs with N-terminal methionines, like many other GPCR-encoding genes. Using the Celera mouse genome database, sequences flanking each MrgA coding region were obtained and analyzed. This analysis revealed that at least six MrgA genes have L1 retrotransposon sequences located ~650 bp downstream of their coding sequences (FIG. 6B, indicated by "L1").

All of the eight full-length mas-related genes, mrg3-5 and mrg8-12, are enriched in nociceptive sensory neurons as indicated by their expression in a subset of DRG sensory neurons which are eliminated in ngn1$^{-/-}$ mutant DRG (FIGS. 2 and 2A).

Example 3

A Novel Two-Transmembrane Segment Protein Specifically Expressed in Nociceptive Sensory Neurons Another novel gene isolated in this screen, drg12 (SEQ ID NO: 13), encodes a protein with two putative transmembrane segments (SEQ ID NO: 14). In situ hybridization indicates that, like the mrg genes, this gene is also specifically expressed in a subset of DRG sensory neurons. Although there are no obvious homologies between this protein and other sequences in the database, it is noteworthy that two purinergic receptors specifically expressed in nociceptive sensory neurons ($P_2X_2$ and $P_2X_3$) have a similar bipartite transmembrane topology. Therefore it is likely that drg12 also encodes a receptor or ion channel involved in nociceptive sensory transduction or its modulation. The hydrophobicity of a homologous region of a drg12 human sequence (SEQ ID NO: 19) is compared with the hydrophobicity of mouse drg12 in FIG. 4.

Example 4 mrg and drg-12 Genes are Specifically Expressed in Nociceptive Sensory Neurons

The prediction of function for mrg-family and drg-12 genes is based on their structure and expression pattern, taken together with the identification of ligands as described below. To determine whether Mrg proteins are expressed in DRG neurons, in situ hybridization using dioxygenin-labeled riboprobes was performed. Briefly, tissue was obtained from P0 mouse pups and fixed in 4% paraformaldehyde overnight at 4° C., cryoprotected in 30% sucrose overnight and embedded in OCT. Tissue sections were cut transversely on a cryostat at 18 μm. Non-isotopic in situ hybridization on frozen sections was performed as previously described using cRNA probes (Ma et al. *Cell* 87: 43-52 (1996); Perez et al. *Development* 126: 1715-1728 (1999)). Eight MrgAs, 5 MrgBs and MrgD were used as probes. At least 10 DRGs were analyzed to count the number of neurons positive for each probe.

Mrg and drg12 genes, including all eight MrgAs (MrgA1-8), are expressed in subsets of small-diameter sensory neurons in the dorsal root ganglia (DRG) of the mouse (FIG. 7B-I). Importantly, the expression of all eight MrgAs was virtually absent in the DRGs of Ngn1$^{-/-}$ animals (FIG. 7J), consistent with the design of the substractive hybridization screen. Among the eight MrgA clones examined, MrgA1 has the widest expression within sensory neurons in DRGs (13.5%). Other MrgAs are only expressed in several cells per DRG section (ranging from 0.2-1.5% of DRG neurons). This differential abundance may explain why only MrgA1 was isolated in the original screen. No obvious differences in the expression patterns of MrgA1-8 were noticed in DRGs from different axial levels. This expression is highly specific, in that expression of these genes has thus far not been detected in any other tissue of the body or in any other region of the nervous system thus far examined.

Like the MrgA genes, MrgD was also specifically expressed in a subset of DRG sensory neurons (see below, FIG. 15). In contrast, MrgB1-5 were not detectably expressed in DRGs. However, mMrgB1 expression has been observed in scattered cells in the epidermal layer of skin in newborn mice, as well as in the spleen and the submandibular gland (FIGS. 13 and 14). These cells appear to be immune cells that play a role in wound repair. mMrgB2 also shows this expression pattern. In contrast, mMrgB3, mMrgB4 and mMrgB5 do not appear to be expressed in any of these tissues.

Using Northern blot analysis, human MrgD was found to be expressed in human dorsal root gangli neurons. A Northern blot containing 20 μg total RNA from human DRG neurons was hybridized with a human MrgD probe and a transcript of 4.4 kb was detected. Further analysis indicated that human MrgD is not expressed in human brain, heart, skeletal muscle, thymus, colon, spleen, kidney, liver, small intestine, placenta, lung or peripheral blood leukocytes. Thus, like mMrgD, human MrgD shows highly restricted expression in pain sensing neurons. In addition, the data indicate that the mouse and human MrgD are functional orthologs.

These results indicate that Mrg and drg12 genes are expressed in primary sensory neurons. However, DRG contain different classes of neurons subserving different types of sensation: e.g., heat, pain, touch and body position. Independent identification is provided by the fact that the neurons that express the mrg-family and drg12 genes are largely or completely eliminated in Ngn1$^{-/-}$ DRG (FIG. 2), because the Ngn1 mutation is independently known to largely or completely eliminate the nociceptive (noxious stimuli-sensing) subset of DRG neurons, identified by expression of the independent markers trkA, VR-1 and SNS-TTXi (Ma et. al. *Genes & Dev.* 13: 1717-1728 (1999)). The loss of mrg- and drg12-expressing neurons in Ngn1$^{-/-}$ mutant DRG therefore indicates that these genes are very likely expressed in nociceptive sensory neurons. Although small numbers of sensory neurons of other classes (trkB$^+$ and trkC$^+$) are eliminated in the Ngn1$^{-/-}$ mutant as well, mrg and drg12 genes are unlikely to be expressed in these classes of sensory neurons, because if they were then the majority of mrg- and drg12-expressing sensory neurons would be predicted to be spared in the Ngn1$^{-/-}$ mutant, and that is not the case.

The lack of expression of MrgAs in DRGs from Ngn1$^{-/-}$ mice is consistent with the idea that they are expressed in cutaneous sensory neurons. Furthermore, the distribution of MrgA1$^+$ cells was similar to that of neurons expressing trkA, a marker of nociceptive sensory neurons (McMahon et al. *Neuron* 12: 1161-71 (1994); Snider and Silos-Santiago *Philos Trans R Soc Lond B Biol Sci* 351: 395-403 (1996)) (FIG. 7A, B). To directly determine whether MrgA genes are expressed in trkA$^+$ cells, in situ hybridization was performed for MrgA1, A3 and A4 in conjunction with immunolabeling using anti-trkA antibodies, on neonatal DRG. Fluorescein-UTP-labeled cRNA probes were detected with alkaline phosphatase-(AP-) conjugated anti-fluorescein antibody (1:2000, Roche) and developed with Fast Red (Roche) to generate a red fluorescent signal. After the fluorescent in situ hybridization was performed, sections were incubated in primary antibodies against TrkA (1:5000, gift from Dr. Louis Reichardt), VR1 (1:5000, gift from Dr. D. Julius), CGRP (1:500, Chemicon), or SubstanceP (1:1000, Diasorin). All antibodies were diluted in 1×PBS containing 1% normal goat serum and 0.1% TritonX-100. Primary antibody incubations were carried out overnight at 4° C. Secondary antibodies used were goat-anti-rabbit-IgG conjugated to Alexa 488 (1:250, Molecular Probes). For double-labeling with *Griffonia simplicifolia* IB4 lectin, sections were incubated with 12.5 μg/ml FITC-conjugated IB4 lectin (Sigma) following in situ hybridization.

Double labeling experiment using mrgs antisense RNA probes with anti-trkA antibodies confirmed that mrgs, specifically MrgAs, are co-expressed by trkA+ nociceptive neurons in DRG (see FIG. 7B and FIG. 8A-C). Similar results were obtained for MrgD (FIG. 8D). Taken together, these data indicate that MrgAs and MrgD are specifically expressed by nociceptive sensory neurons in DRG.

Further experiments were carried out to determine whether Mrgs are expressed in particular subsets of nociceptors. Additional double labeling experiments using mrgs antisense RNA probes with anit-VR1 and isolectin B4 (IB4)-labeling, as described above, have shown that mrgs are preferentially expressed by IB4+ nociceptive neurons but not VR1-expressing nociceptive neurons (FIGS. 2C and 2D). In particular, combined fluorescent labeling for IB4 together with in situ hybridization with MrgA1, A3, A4 and MrgD probes clearly showed that these receptors are expressed by IB4$^+$ neurons (FIG. 8E-H), and may be restricted to this subset. This result indicates that these Mrgs are expressed by non-peptidergic nociceptive neurons that project to lamina IIi (Snider and McMahon *Neuron* 20: 629-32 (1998)). Consistent with this assignment, the majority (90%) of MrgA1$^+$, and all MrgA3$^+$, A4$^+$ and MrgD$^+$ cells, lack substance P expression (FIG. 8I-L). Similarly, the majority (70%) of MrgA1$^+$, and all MrgA3$^+$, A4$^+$ and MrgD$^+$ cells, do not express CGRP (FIG. 8M-P), another neuropeptide expressed by C-fiber nociceptors. Previous studies had shown that IB4+ nociceptive neurons were involved in neuropathic pain resulting from nerve injury (Malmberg, A. B. et al. *Science* 278: 279-83 (1997)). Neuropathic pain including postherpetic neuralgia, reflex sympathetic dystrophy, and phantom limb pain is the most difficult pain to be managed. Mrgs may play essential roles in mediating neuropathic pain and may provide alternative solutions to manage neuropathic pain.

Recent studies have provided evidence for the existence of two neurochemically and functionally distinct subpopulations of IB4$^+$ nociceptors: those that express the vanilloid receptor VR1 (Caterina et al. *Science* 288: 306-13 (1997)), and those that do not (Michael and Priestley *J Neurosci* 19: 1844-54 (1999); Stucky and Lewin *J Neurosci* 19: 6497-505 (1999)). Strikingly, in situ hybridization with MrgA or D probes combined with anti-VR1 antibody immunostaining indicated that the MrgA1, A3, A4 and D-expressing cell population was mutually exclusive with VR1$^+$ cells (FIG. 8Q-T). In summary, these expression data demonstrate that MrgA and D genes are expressed in the subclass of nonpeptidergic cutaneous sensory neurons that are IB4$^+$ and VR1$^-$ (FIG. 9).

MrgA1 is Co-Expressed with Other MrgA Genes

MrgA1 is more broadly expressed than are the other MrgA genes (FIG. 2), suggesting MrgA1 and MrgA2-8 are expressed by different or overlapping subsets of nociceptors. Double-label in situ hybridization studies using probes labeled with digoxigenin and fluorescein indicated that most or all neurons expressing MrgA3 or MrgA4 co-express MrgA1 (FIG. 10A-F). Interestingly, the fluorescent in situ hybridization signals for MrgA3 and A4 using tyramide amplification often appeared as dots within nuclei that were circumscribed by the cytoplasmic expression of MrgA1 mRNA, detected by Fast Red (FIG. 10F). Such dots were not observed using the less-sensitive Fast Red detection method, and were only observed in the nuclei of MrgA1+ cells. Similar intranuclear dots have previously been observed in studies of pheromone receptor gene expression, and have been suggested to represent sites of transcription (Pantages and Dulac *Neuron* 28: 835-845 (2000)). The results for MrgA1, 3 and 4 indicate that those neurons that express the rarer MrgA genes (MrgA2-8) are a subset of those that express MrgA1.

To address the question of whether MrgsA2-A8 are expressed in the same or in different neurons, the number of neurons labeled by single probes was compared to that labeled by a mixture of all 7 probes (Buck and Axel *Cell* 65: 175-187 (1991)). Approximately 3-fold more neurons (4.5% vs. 1%) were labeled by the mixed probe than by an individual probe to MrgA4 (FIG. 10J, K), indicating that these genes are not all co-expressed in the same population of neurons. However, the percentage of neurons labeled by the mixed probe (4.5%) was less than the sum of the percentage of neurons labeled by each of the 7 individual probes (6.6%), indicating that there is some overlap in the expression of MrgA2-A8. In addition, higher signal intensity was observed in individual neurons using the mixed probe, than using a single probe.

Double-labeling experiments with MrgA1 and MrgD probes were also performed. These proteins share only 60% sequence similarity, as shown in FIG. 6B and Table 3. The results of these experiments indicated only partial overlap between neurons expressing these two receptors (FIG. 10G-I). Approximately 15% (118/786) of neurons expressing either MrgA1 or MrgD co-expressed both genes. Thirty-four percent (118/344) of MrgA1+ cells co-expressed MrgD, while 26.7% (118/442) of MrgD+ cells co-expressed MrgA1.

Taken together, these data indicate the existence of at least three distinct subpopulations of IB4+, VR1− sensory neurons: MrgA1+MrgD+; MrgA1+MrgD− and MrgA1− MrgD+. The MrgA1+ subset is further subdivided into different subsets expressing one or more of the MrgsA2-A8.

Mrg-Family Genes Encode Putative G-Protein Coupled Receptors (GPCRs).

Hydrophobicity plots of the encoded amino acid sequences of the mrg-family genes predicts membrane proteins with 7 transmembrane segments. Such a structure is characteristic of receptors that signal through "G-proteins." G proteins are a family of cytoplasmic molecules that activate or inhibit enzymes involved in the generation or degradation of "second messenger" molecules, such as cyclic nucleotides (cAMP, cGMP), $IP_3$ and intracellular free calcium ($Ca^{++}$). Such second messenger molecules then activate or inhibit other molecules involved in intercellular signaling, such as ion channels and other receptors.

G protein-coupled receptors (GPCRs) constitute one of the largest super-families of membrane receptors, and contain many subfamilies of receptors specific for different ligands. These ligands include neurotransmitters and neuropeptides manufactured by the body (e.g., noradrenaline, adrenaline, dopamine; and substance P, somatostatin, respectively), as well as sensory molecules present in the external world (odorants, tastants).

Although the mrg-family genes are highly homologous, the most divergent regions were the extracellular domains (see FIG. 6A). The variability of the extracellular domains of mrg family suggests that they may recognize different ligands.

The fact that the mrg-family genes encode GPCRs, and are specifically expressed in nociceptive sensory neurons, suggest that these receptors are involved, directly or indirectly, in the sensation or modulation of pain, heat or other noxious stimuli. Therefore the mrg-encoded receptors are useful as targets for identifying drugs that effect the sensation or modulation of pain, heat or other noxious stimuli. The nature of the most useful type of drug (agonistic or antagonistic) will reflect the nature of the normal influence of these receptors on the sensation of such noxious stimuli. For example, if mrg-encoded receptors normally act negatively, to inhibit or suppress pain, then agonistic drugs would provide useful therapeutics; conversely, if the receptors normally act positively, to promote or enhance pain, then antagonistic drugs would provide useful therapeutics. There might even be certain clinical settings in which it would be useful to enhance sensitivity to noxious stimuli, for example in peripheral sensory neuropathies associated with diabetes.

The nature of the influence of mrg-encoded GPCRs on pain sensation may be revealed by the phenotypic consequences of targeted mutation of these genes in mice. For example, if such mice displayed enhanced sensitivity to noxious stimuli, then it could be concluded that the receptors normally function to inhibit or suppress pain responses, and vice-versa. Alternatively, high-throughput screens may be used to identify small molecules that bind tightly to the mrg-encoded receptors. Such molecules would be expected to fall into two categories: agonists and antagonists. Agonists would be identified by their ability to activate intracellular second messenger pathways in a receptor-dependent manner, while antagonists would inhibit them. Testing of such drugs in animal models of pain sensitivity will then reveal further information concerning the function of the GPCRs: for example, if the molecules behave as receptor antagonists in vitro, and they suppress sensitivity or responsiveness to noxious stimuli in vivo, then it may be concluded that the receptor normally functions to promote or enhance pain sensation. Conversely, if receptor agonists suppress, while antagonists enhance, pain sensation in vivo, then it may be concluded that the receptor normally functions to suppress or inhibit pain sensation.

drg12 Encodes a Putative Transmembrane Signaling Molecule

Hydrophobicity plots of the encoded amino acid sequence of the drg12 gene predicts a membrane protein with 2 transmembrane segments. The membrane localization of this protein has been verified by immuno-staining of cultured cells transfected with an epitope-tagged version of the polypeptide. Although the DRG12 amino acid sequence has no homology to known families of proteins, its bipartite transmembrane structure strongly suggests that it is involved in some aspect of intercellular signaling, for example as a receptor, ion channel or modulator of another receptor or ion channel. This prediction is supported by the precedent that two known receptors with a similar bipartite transmembrane topology, the purinergic $P_2X_2$ and $P_2X_3$ receptors, are like DRG12, specifically expressed in nociceptive sensory neurons.

Based on this structural data, and its specific expression in nociceptive sensory neurons, it is probable that DRG12 is involved, directly or indirectly, in the sensation or modulation of noxious stimuli. Accordingly, the drg12-encoded protein is a useful target for the development of novel therapeutics for the treatment of pain.

Example 5

Mrg Proteins are Receptors for Neuropeptides

As discussed above, the structure of the proteins encoded by Mrg genes indicates that they function as receptors. To identify ligands for the Mrg receptors, selected MrgA genes were tested in a calcium release assay. MrgA genes, including MrgA1 and MrgA4, were cloned into a eukaryotic expression vector and transfected into human embryonic kidney (HEK) 293 cells. HEK-293 cells were obtained from the ATCC and cultured in DMEM supplemented with 10% fetal bovine serum. An HEK293-G$\alpha_{15}$ cell line stably expressing G$\alpha_{15}$ was provided by Aurora Biosciences Corporation and grown on Matrigel™ (growth factor reduced Matrigel, Becton Dickinson, diluted 1:200 with serum-free DMEM)-coated flasks and maintained at 37° C. in DMEM (GibcoBRL) supplemented with 10% heat-inactivated fetal bovine serum, 2 mM L-glutamine, 0.1 mM non-essential amino acids, 1 mM sodium pyruvate, 25 mM HEPES and 3 µg/ml blasticidin-S. For transfection, cells were seeded on Matrigel-coated 35 mm glass-bottom dishes (Bioptech Inc., Butler, Pa.). After 16-24 hr, cells were transfected using FuGENE 6 (Roche). Transfection efficiencies were estimated by visualization of GFP fused to the C-terminus of MrgA1 and A4, and were typically >60%. Fusing GFP to the C-termini of the MrgA coding sequences additionally allowed for visual confirmation of the intracellular distribution of the receptors and their membrane integration in the transfected cells (FIG. 11D).

To increase the sensitivity of the calcium release assay, in some experiments the MRGA-GFP fusion proteins were expressed in HEK 293 cells modified to express G$\alpha_{15}$, which couples GPCRs to a signal transduction pathway leading to the release of intracellular free Ca$^{2+}$ (Offermann and Simon *J Biol Chem* 270: 15175-80 (1995)). This calcium release can be monitored ratiometrically using Fura-2 as a fluorescent indicator dye (Tsien et al. *Cell Calcium* 6: 145-57 (1985)) (FIG. 11A-C). This heterologous expression system has been previously used to identify ligands for taste receptors (Chandrashekar et al. *Cell* 100: 703-11 (2000)).

Because MRGAs exhibit the highest sequence similarity to peptide hormone receptors, approximately 45 candidate peptides were screened for their ability to activate MRGA1, using the intracellular Ca$^{2+}$-release assay. Briefly, transfected cells were washed once in Hank's balanced salt solution with 11 mM D-glucose and 10 mM HEPES, pH 7.4 (assay buffer) and loaded with 2 µM Fura-2 AM (Molecular Probes) at room temperature for 90 min, with rotation. Loaded cells were washed twice with assay buffer and placed on a micro-perfusion chamber (Bioptech). The chamber was mounted on top of a Olympus IMT2 inverted microscope, and imaged with an Olympus DPlanApo 40× oil immersion objective lens. Samples were illuminated by a 75W xenon bulb, and a computer-controlled filter changer (Lambda-10; Shutter Instruments) was used to switch the excitation wavelength. A cooled CCD camera (Photometric) was used in detecting fluorescence. GFP-positive cells within a field were identified using an excitation wavelength of 400 nm, a dichroic 505 nm long-pass filter and an emitter bandpass of 535 nm (Chroma Technology). In the same field, calcium measurements were performed at an excitation wavelength of 340 nm and 380 nm, and an emission wavelength of 510 nm. Agonists were diluted in assay buffer and solution changes accomplished by micro-perfusion pump (Bioptech). Fura-2 fluorescence signals (340 nm, 380 nm and the 340/380 ratio) originating from GFP-positive cells were continuously monitored at 0.4- or 1-second intervals and collected using Axon Imaging Workbench 4.0 software (Axon). Instrument calibration was carried out with standard calcium solutions (Molecular probes) in glass bottom dishes (MatTek Corp.).

At a concentration of 1 µM, numerous neuropeptides produced some level of activation of MrgA1-expressing cells (FIG. 12A). These included ACTH, CGRP-I and -II, NPY and somatostatin (SST). Nevertheless, many other peptide hormones did not activate MRGA1, including angiotensins I-III and neurokinins A and B, alpha-MSH and gamma2-MSH (FIG. 12A and data not shown). MrgA1 was only very weakly activated by ecosanoid ligands such as Prostaglandin-E1 and Arachidonic Acid (data not shown).

The most efficient responses in MrgA1-expressing HEK cells were elicited by RFamide peptides, including FLRF and the molluscan cardioactive neuropeptide FMRFamide (Price and Greenberg *Science* 197: 670-671 (1977)) (Phe-Met-Arg-Phe-amide) (FIG. 11C, 12A). Two mammalian RFamide peptides, NPAF and NPFF, which are cleaved from a common pro-peptide precursor (Vilim et al. *Mol Pharmacol* 55: 804-11 (1999)) were then tested. The response of MrgA1-expressing cells to NPFF at 1 µM was similar to that seen with FMRFamide, while that to NPAF was significantly lower (FIG. 12A). MrgA1 was also weakly activated by two other RFamide ligands, $\gamma_1$-MSH and schistoFLRF (data not shown).

In order to examine further the specificity of activation of MrgA1 and A4, the top candidate ligands emerging from the initial screen were tested on these same receptors expressed in HEK cells lacking G$\alpha_{15}$. MrgA1 and A4 expressed in this system retained responses to RFamide peptides (FIG. 12B, C), demonstrating that the intracellular Ca$^{2+}$ release responses seen in the initial screen are not dependent on the presence of exogenous G$\alpha_{15}$. This indicates that MrgAs act in HEK cells via Gq or Gi. The response of MrgA1-expressing HEK cells to NPFF was lower than that to FLRF (FIG. 12B), and there was no response to NPAF. Conversely, MrgA4-expressing cells responded to NPAF, but not to NPFF or FLRF (FIG. 12C). In both cases, the response to NPY seen in G$\alpha_{15}$-expressing cells (FIG. 11A) was lost completely, while those to CGRP-II and ACTH were considerably diminished.

In order to determine the lowest concentrations of RFamide ligands capable of activating MrgA1 and A4, dose-response experiments were carried out in HEK cells expressing G$\alpha_{15}$, which afforded greater sensitivity (FIG. 12D, E). These experiments indicated that MrgA1 could be activated by FLRF at nanomolar concentrations (FIG. 12D; EC$_{50}$≈20 nM), and by NPFF at about an order of magnitude higher concentration (FIG. 12D; EC$_{50}$≈200 nM), whereas NPAF was much less effective. In contrast, MrgA4 was well activated by NPAF (FIG. 12E; EC$_{50}$≈60 nM), and much more weakly activated by FLRF and NPFF. Neither receptor showed strong activation in response to RFRP-1, -2 or -3, a series of RFamide ligands produced from a different precursor (Hinuma et al. *Nat Cell Biol* 2: 703-8 (2000)). These data confirm that MrgA1 and MrgA4 display different selectivities towards different RFamide ligands in this system. By contrast, these receptors responded similarly to ACTH (EC$_{50}$~60- and 200 nM for MrgA1 and A4, respectively; data not shown).

Finally, given the sequence similarity between MRGA receptors and MAS1, the responsiveness of cells expressing exogenous Mas1 to NPFF, NPAF and FLRF was tested. MAS1 showed a profile distinct from both MrgA1 and MrgA4 (FIG. 12F): like MrgA1, it was activated by NPFF at a similar concentration of the peptide (EC$_{50}$≈400 nM), but unlike MrgA1 it was poorly activated by FLRF. In contrast to MrgA4, MAS1 did not respond well to NPAF. No response was detected in MAS1-expressing cells upon exposure to Angiotensins I and II, ligands which have been previously reported to activate this receptor (Jackson, T. R., et al. *Nature* 335: 437-40 (1988)). Nor did MAS1 respond to ACTH. Thus, MAS1, MrgA1 and MrgA4 expressed in this heterologous system are all activated by RFamide family ligands, but with differing ligand-sensitivities and -selectivities (Table 4).

TABLE 4

Selectivity of activation of Mas-related
GPCRs by RF-amide ligands in HEK cells

| receptor | A. Ligand | | |
|---|---|---|---|
| | FLRF | NPFF | NPAF |
| MRGA1 | +++ | ++ | +/− |
| MRGA4 | +/− | +/− | +++ |
| MAS1 | +/− | ++ | +/− |

Figure 6E:
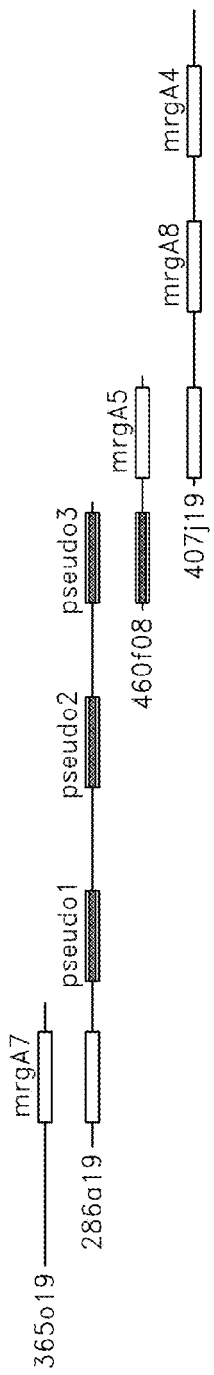

Relative efficacy of activation of the indicated receptors by the indicated ligands is shown. For quantification, see FIG. 6. "+++" indicates 10 nM<$EC_{50}$<100 nM; "++" indicates 100 nM<$EC_{50}$<500 nM; "+/−" indicates weak response seen at 1 µM. For details see FIG. 6.

A novel family consisting of close to 50 MAS1 related g-protein coupled receptors has been identified. The specific expression of several classes of these receptors in a subset of nociceptive sensory neurons indicates that these receptors play a role in the sensation or modulation of pain. Consistently, these receptors have been shown to be activated by RFamide neuropeptides, which are known to mediate analgesia. As a result, these receptors provide a novel target for anti-nociceptive drugs.

Although the present invention has been described in detail with reference to examples above, it is understood that various modifications can be made without departing from the spirit of the invention. Accordingly, the invention is limited only by the following claims. All cited patents, patent applications and publications referred to in this application are herein incorporated by reference in their entirety.

What is claimed is:

1. A method for identifying a compound useful in altering sensory perception in a mammal comprising the steps of: a) expressing a polypeptide comprising the amino acid sequence of SEQ ID NO: 35 in a host cell capable of producing a second messenger response; b) contacting the host cell with one or more test compounds; c) measuring the second messenger response in the host cell; and d) identifying compounds that increase the measured second messenger response as compounds that are useful in altering sensory perception in a mammal.

2. The method of claim 1 wherein said host cell is a eukaryotic cell.

3. The method of claim 2 wherein the eukaryotic cell is a hamster embryonic kidney (HEK) cell.

4. The method of claim 3 wherein said HEK cell expresses $G\alpha_{15}$.

5. The method of claim 1 wherein measuring a second messenger response comprises measuring a change in intercellular calcium concentration.

6. The method of claim 5 wherein said change in intercellular calcium concentration is measured with FURA-2 calcium indicator dye.

7. The method of claim 1 wherein measuring a second messenger response comprises measuring the flow of current across the membrane of the cell.

8. The method of claim 1 wherein said sensory perception is the perception of pain.

9. A method for identifying a compound useful in treating impaired sensory perception in a mammal comprising the steps of: a) expressing a polypeptide comprising the amino acid sequence of SEQ ID NO: 35 in a host cell capable of producing a second messenger response; b) contacting the host cell with an RFamide peptide; c) contacting the host cell with one or more test compounds; d) measuring the second messenger response in the host cell; and e) identifying compounds that alter the measured second messenger response to the RFamide peptide as compounds that are useful in treating impaired sensory perception in a mammal.

10. The method of claim 9 wherein the impaired sensory perception is pain.

* * * * *

SEQUENCE LISTING

```
<160> NUMBER OF SEQ ID NOS: 109

<210> SEQ ID NO 1
<211> LENGTH: 1088
<212> TYPE: DNA
<213> ORGANISM: Mus Musculus
<220> FEATURE:
<221> NAME/KEY: CDS
<222> LOCATION: (115)...(1026)

<400> SEQUENCE: 1
acagaagcca gagagctaca tccagcaaga ggaatggggg aaagcagcac ctgtgcaggg      60
tttctagccc taaacacatc ggcctcgcca acagcaccca caacaactaa tcca atg     117
                                                              Met
                                                              1 gac aat acc atc cct gga ggt atc aac atc acg att ctg atc cca aac     165
Asp Asn Thr Ile Pro Gly Gly Ile Asn Ile Thr Ile Leu Ile Pro Asn
            5                  10                  15 ttg atg atc atc atc ttc gga ctg gtc ggg ctg aca gga aat ggc att     213
Leu Met Ile Ile Ile Phe Gly Leu Val Gly Leu Thr Gly Asn Gly Ile
         20                  25                  30 gtg ttc tgg ctc ctg ggc ttc tgt ttg cac agg aac gcc ttc tca gtc     261
Val Phe Trp Leu Leu Gly Phe Cys Leu His Arg Asn Ala Phe Ser Val
     35                  40                  45 tac atc cta aac tta gct cta gct gac ttc ttc ttc cta ggt cac         309
Tyr Ile Leu Asn Leu Ala Leu Ala Asp Phe Phe Phe Leu Leu Gly His
 50                  55                  60                  65 atc ata gat tcc ata ctg ctt ctt ctc aat gtt ttc tac cca att acc     357
Ile Ile Asp Ser Ile Leu Leu Leu Leu Asn Val Phe Tyr Pro Ile Thr
             70                  75                  80 ttt ctc ttg tgc ttt tac acg atc atg atg gtt ctc tat atc gca ggc     405
Phe Leu Leu Cys Phe Tyr Thr Ile Met Met Val Leu Tyr Ile Ala Gly
         85                  90                  95 ctg agc atg ctc agt gcc atc agc act gag cgc tgc ctg tct gta ctg     453
Leu Ser Met Leu Ser Ala Ile Ser Thr Glu Arg Cys Leu Ser Val Leu
    100                 105                 110 tgc ccc atc tgg tat cac tgt cac cgc cca gaa cac aca tca act gtc     501
Cys Pro Ile Trp Tyr His Cys His Arg Pro Glu His Thr Ser Thr Val
115                 120                 125 atg tgt gct gtc atc tgg gtc ctg tcc ctg ttg atc tgc att ctg aat     549
Met Cys Ala Val Ile Trp Val Leu Ser Leu Leu Ile Cys Ile Leu Asn
130                 135                 140                 145 agt tat ttc tgc ggt ttc tta aat acc caa tat aaa aat gaa aat ggg     597
Ser Tyr Phe Cys Gly Phe Leu Asn Thr Gln Tyr Lys Asn Glu Asn Gly
            150                 155                 160
```

```
tgt ctg gca ttg aac ttc ttt act gct gca tac ctg atg ttt ttg ttt    645
Cys Leu Ala Leu Asn Phe Phe Thr Ala Ala Tyr Leu Met Phe Leu Phe
            165                 170                 175 gtg gtc ctc tgt ctg tcc agc ctg gct ctg gtg gcc agg ttg ttc tgt    693
Val Val Leu Cys Leu Ser Ser Leu Ala Leu Val Ala Arg Leu Phe Cys
        180                 185                 190 ggt act ggg cag ata aag ctt acc aga ttg tat gta acc att att ctg    741
Gly Thr Gly Gln Ile Lys Leu Thr Arg Leu Tyr Val Thr Ile Ile Leu
    195                 200                 205 agc att ttg gtt ttt ctc ctt tgc gga ttg ccc ttt ggc atc cac tgg    789
Ser Ile Leu Val Phe Leu Leu Cys Gly Leu Pro Phe Gly Ile His Trp
210                 215                 220                 225 ttt ctg tta ttc aag att aag gat gat ttt cat gta ttt gat ctt gga    837
Phe Leu Leu Phe Lys Ile Lys Asp Asp Phe His Val Phe Asp Leu Gly
                230                 235                 240 ttt tat ctg gca tca gtt gtc ctg act gct att aat agc tgt gcc aac    885
Phe Tyr Leu Ala Ser Val Val Leu Thr Ala Ile Asn Ser Cys Ala Asn
            245                 250                 255 ccc atc att tac ttc ttc gtg gga tcc ttc agg cat cgg ttg aag cac    933
Pro Ile Ile Tyr Phe Phe Val Gly Ser Phe Arg His Arg Leu Lys His
        260                 265                 270 cag acc ctc aaa atg gtt ctc cag aat gca ctg caa gac act cct gag    981
Gln Thr Leu Lys Met Val Leu Gln Asn Ala Leu Gln Asp Thr Pro Glu
    275                 280                 285 aca gcc aaa atc atg gtg gag atg tca aga agc aaa tca gag cca       1026
Thr Ala Lys Ile Met Val Glu Met Ser Arg Ser Lys Ser Glu Pro
290                 295                 300 tgatgaagag cctttgcctg cccttagaa gtggctttgg ggtgagcatt gccctgctgc   1086
ac                                                                 1088

<210> SEQ ID NO 2
<211> LENGTH: 304
<212> TYPE: PRT
<213> ORGANISM: Mus Musculus

<400> SEQUENCE: 2

Met Asp Asn Thr Ile Pro Gly Gly Ile Asn Ile Thr Ile Leu Ile Pro
1               5                   10                  15

Asn Leu Met Ile Ile Phe Gly Leu Val Gly Leu Thr Gly Asn Gly
            20                  25                  30

Ile Val Phe Trp Leu Leu Gly Phe Cys Leu His Arg Asn Ala Phe Ser
        35                  40                  45

Val Tyr Ile Leu Asn Leu Ala Leu Ala Asp Phe Phe Phe Leu Leu Gly
    50                  55                  60

His Ile Ile Asp Ser Ile Leu Leu Leu Leu Asn Val Phe Tyr Pro Ile
65                  70                  75                  80

Thr Phe Leu Leu Cys Phe Tyr Thr Ile Met Met Val Leu Tyr Ile Ala
                85                  90                  95

Gly Leu Ser Met Leu Ser Ala Ile Ser Thr Glu Arg Cys Leu Ser Val
            100                 105                 110

Leu Cys Pro Ile Trp Tyr His Cys His Arg Pro Glu His Thr Ser Thr
        115                 120                 125

Val Met Cys Ala Val Ile Trp Val Leu Ser Leu Leu Ile Cys Ile Leu
    130                 135                 140

Asn Ser Tyr Phe Cys Gly Phe Leu Asn Thr Gln Tyr Lys Asn Glu Asn
145                 150                 155                 160
```

```
Gly Cys Leu Ala Leu Asn Phe Phe Thr Ala Ala Tyr Leu Met Phe Leu
            165                 170                 175

Phe Val Val Leu Cys Leu Ser Ser Leu Ala Leu Val Ala Arg Leu Phe
        180                 185                 190

Cys Gly Thr Gly Gln Ile Lys Leu Thr Arg Leu Tyr Val Thr Ile Ile
    195                 200                 205

Leu Ser Ile Leu Val Phe Leu Leu Cys Gly Leu Pro Phe Gly Ile His
210                 215                 220

Trp Phe Leu Leu Phe Lys Ile Lys Asp Asp Phe His Val Phe Asp Leu
225                 230                 235                 240

Gly Phe Tyr Leu Ala Ser Val Val Leu Thr Ala Ile Asn Ser Cys Ala
            245                 250                 255

Asn Pro Ile Ile Tyr Phe Phe Val Gly Ser Phe Arg His Arg Leu Lys
        260                 265                 270

His Gln Thr Leu Lys Met Val Leu Gln Asn Ala Leu Gln Asp Thr Pro
    275                 280                 285

Glu Thr Ala Lys Ile Met Val Glu Met Ser Arg Ser Lys Ser Glu Pro
290                 295                 300

<210> SEQ ID NO 3
<211> LENGTH: 1234
<212> TYPE: DNA
<213> ORGANISM: Mus musculus
<220> FEATURE:
<221> NAME/KEY: CDS
<222> LOCATION: (137)...(1051)

<400> SEQUENCE: 3
tctgtagtga ctgtatcttt ccttctacac aagccagtga gctacatcca acaagaggat        60
tggggaaagc aatggtgaag catttcttgc ctttaagacc tcagcctcac caacagcacc       120
agtgacaaca aatcca atg gac gaa acc ctc cct gga agt atc aac att agg       172
               Met Asp Glu Thr Leu Pro Gly Ser Ile Asn Ile Arg
                 1               5                  10 att ctg atc cca aaa ttg atg atc atc atc ttc gga ctg gtc gga ctg       220
Ile Leu Ile Pro Lys Leu Met Ile Ile Ile Phe Gly Leu Val Gly Leu
         15                  20                  25 atg gga aac gcc att gtg ttc tgg ctc ctg ggc ttc cac ttg cgc aag       268
Met Gly Asn Ala Ile Val Phe Trp Leu Leu Gly Phe His Leu Arg Lys
 30                  35                  40 aat gac ttc tca ctc tac atc cta aac ttg gcc cgg gct gac ttc ctt       316
Asn Asp Phe Ser Leu Tyr Ile Leu Asn Leu Ala Arg Ala Asp Phe Leu
 45                  50                  55                  60 ttc ctc ctc agt agt atc ata gct tcc acc ctg ttt ctt ctc aaa gtt       364
Phe Leu Leu Ser Ser Ile Ile Ala Ser Thr Leu Phe Leu Leu Lys Val
             65                  70                  75 tcc tac ctc agc atc atc ttt cac ttg tgc ttt aac acc att atg atg       412
Ser Tyr Leu Ser Ile Ile Phe His Leu Cys Phe Asn Thr Ile Met Met
         80                  85                  90 gtt gtc tac atc aca ggg ata agc atg ctc agt gcc atc agc act gag       460
Val Val Tyr Ile Thr Gly Ile Ser Met Leu Ser Ala Ile Ser Thr Glu
     95                 100                 105 tgc tgc ctg tct gtc ctg tgc ccc acc tgg tat cgc tgc cac cgt cca       508
Cys Cys Leu Ser Val Leu Cys Pro Thr Trp Tyr Arg Cys His Arg Pro
110                 115                 120 gta cat aca tca act gtc atg tgt gct gtg atc tgg gtc cta tcc ctg       556
Val His Thr Ser Thr Val Met Cys Ala Val Ile Trp Val Leu Ser Leu
125                 130                 135                 140
```

```
ttg atc tgc att ctg aat agc tat ttc tgt gct gtc tta cat acc aga        604
Leu Ile Cys Ile Leu Asn Ser Tyr Phe Cys Ala Val Leu His Thr Arg
            145                 150                 155 tat gat aat gac aat gag tgt ctg gca act aac atc ttt acc gcc tcg        652
Tyr Asp Asn Asp Asn Glu Cys Leu Ala Thr Asn Ile Phe Thr Ala Ser
        160                 165                 170 tac atg ata ttt ttg ctt gtg gtc ctc tgt ctg tcc agc ctg gct ctg        700
Tyr Met Ile Phe Leu Leu Val Val Leu Cys Leu Ser Ser Leu Ala Leu
    175                 180                 185 ctg gcc agg ttg ttc tgt ggc gct ggg cag atg aag ctt acc aga ttt        748
Leu Ala Arg Leu Phe Cys Gly Ala Gly Gln Met Lys Leu Thr Arg Phe
190                 195                 200 cat gtg acc atc ttg ctg acc ctt ttg gtt ttt ctc ctc tgc ggg ttg        796
His Val Thr Ile Leu Leu Thr Leu Leu Val Phe Leu Leu Cys Gly Leu
205                 210                 215                 220 ccc ttt gtc atc tac tgc atc ctg tta ttc aag att aag gat gat ttc        844
Pro Phe Val Ile Tyr Cys Ile Leu Leu Phe Lys Ile Lys Asp Asp Phe
            225                 230                 235 cat gta tta gat gtt aat ttt tat cta gca tta gaa gtc ctg act gct        892
His Val Leu Asp Val Asn Phe Tyr Leu Ala Leu Glu Val Leu Thr Ala
        240                 245                 250 att aac agc tgt gcc aac ccc atc atc tac ttc ttc gtg ggc tct ttc        940
Ile Asn Ser Cys Ala Asn Pro Ile Ile Tyr Phe Phe Val Gly Ser Phe
    255                 260                 265 aga cat cag ttg aag cac cag acc ctc aaa atg gtt ctc cag agt gca        988
Arg His Gln Leu Lys His Gln Thr Leu Lys Met Val Leu Gln Ser Ala
270                 275                 280 ctg cag gac act cct gag aca gct gaa aac atg gta gag atg tca agt       1036
Leu Gln Asp Thr Pro Glu Thr Ala Glu Asn Met Val Glu Met Ser Ser
285                 290                 295                 300 aac aaa gca gag cct tgatgaagag cctctacctg gacctcagag gtggctttgg       1091
Asn Lys Ala Glu Pro
                305 agtgagcact gccctgctgc acttgaccac tgtccactct tctctcagct tactgatttg       1151 acatgcctca gtggtccacc aacaacttca acatctctcc actaacttag tttttctacc       1211 cctcctgaat aaaagcatta atc                                                1234

<210> SEQ ID NO 4
<211> LENGTH: 305
<212> TYPE: PRT
<213> ORGANISM: Mus musculus

<400> SEQUENCE: 4

Met Asp Glu Thr Leu Pro Gly Ser Ile Asn Ile Arg Ile Leu Ile Pro
1               5                   10                  15

Lys Leu Met Ile Ile Phe Gly Leu Val Gly Leu Met Gly Asn Ala
            20                  25                  30

Ile Val Phe Trp Leu Leu Gly Phe His Leu Arg Lys Asn Asp Phe Ser
        35                  40                  45

Leu Tyr Ile Leu Asn Leu Ala Arg Ala Asp Phe Phe Leu Leu Ser
    50                  55                  60

Ser Ile Ile Ala Ser Thr Leu Phe Leu Leu Lys Val Ser Tyr Leu Ser
65                  70                  75                  80

Ile Ile Phe His Leu Cys Phe Asn Thr Ile Met Met Val Val Tyr Ile
                85                  90                  95

Thr Gly Ile Ser Met Leu Ser Ala Ile Ser Thr Glu Cys Cys Leu Ser
            100                 105                 110
```

-continued

```
Val Leu Cys Pro Thr Trp Tyr Arg Cys His Arg Pro Val His Thr Ser
        115                 120                 125
Thr Val Met Cys Ala Val Ile Trp Val Leu Ser Leu Leu Ile Cys Ile
    130                 135                 140
Leu Asn Ser Tyr Phe Cys Ala Val Leu His Thr Arg Tyr Asp Asn Asp
145                 150                 155                 160
Asn Glu Cys Leu Ala Thr Asn Ile Phe Thr Ala Ser Tyr Met Ile Phe
                165                 170                 175
Leu Leu Val Val Leu Cys Leu Ser Leu Ala Leu Leu Ala Arg Leu
            180                 185                 190
Phe Cys Gly Ala Gly Gln Met Lys Leu Thr Arg Phe His Val Thr Ile
        195                 200                 205
Leu Leu Thr Leu Leu Val Phe Leu Leu Cys Gly Leu Pro Phe Val Ile
    210                 215                 220
Tyr Cys Ile Leu Leu Phe Lys Ile Lys Asp Asp Phe His Val Leu Asp
225                 230                 235                 240
Val Asn Phe Tyr Leu Ala Leu Glu Val Leu Thr Ala Ile Asn Ser Cys
                245                 250                 255
Ala Asn Pro Ile Ile Tyr Phe Phe Val Gly Ser Phe Arg His Gln Leu
            260                 265                 270
Lys His Gln Thr Leu Lys Met Val Leu Gln Ser Ala Leu Gln Asp Thr
        275                 280                 285
Pro Glu Thr Ala Glu Asn Met Val Glu Met Ser Ser Asn Lys Ala Glu
    290                 295                 300
Pro
305
```

<210> SEQ ID NO 5
<211> LENGTH: 1312
<212> TYPE: DNA
<213> ORGANISM: Mus musculus
<220> FEATURE:
<221> NAME/KEY: CDS
<222> LOCATION: (165)...(1070)

<400> SEQUENCE: 5

```
cgcggccgcg tcgacaagaa atattctgta gtgactgtat ccttccttct acacaagcca      60
gcaagctaca tccagcaaga ggaatgggag aaagcaacac cagtgcaggg tttctggccc     120
gaaacacctc agcctcgaca tgacacccca caacaacaaa ttca atg aac gaa acc     176
                                                  Met Asn Glu Thr
                                                   1 atc cct gga agt att gac atc gag acc ctg atc cca gac ttg atg atc     224
Ile Pro Gly Ser Ile Asp Ile Glu Thr Leu Ile Pro Asp Leu Met Ile
 5                   10                  15                  20 atc atc ttc gga ctg gtc ggg ctg aca gga aat gcg att gtg ttc tgg     272
Ile Ile Phe Gly Leu Val Gly Leu Thr Gly Asn Ala Ile Val Phe Trp
             25                  30                  35 ctc ctt ggc ttc cgc atg cac agg act gcc ttc tta gtc tac atc cta     320
Leu Leu Gly Phe Arg Met His Arg Thr Ala Phe Leu Val Tyr Ile Leu
         40                  45                  50 aac ttg gcc ctg gct gac ttc ctc ttc ctt ctc tgt cac atc ata aat     368
Asn Leu Ala Leu Ala Asp Phe Leu Phe Leu Leu Cys His Ile Ile Asn
     55                  60                  65 tcc aca gtg gat ctt ctc aag ttt acc cta ccc aaa gga att ttt gcc     416
Ser Thr Val Asp Leu Leu Lys Phe Thr Leu Pro Lys Gly Ile Phe Ala
 70                  75                  80 ttt tgt ttt cac act atc aaa agg gtt ctc tat atc aca ggc ctg agc     464
```

```
                Phe Cys Phe His Thr Ile Lys Arg Val Leu Tyr Ile Thr Gly Leu Ser
                 85                  90                  95                 100 atg ctc agt gcc atc agc act gag cgc tgc ctg tct gtc ctg tgc ccc             512
Met Leu Ser Ala Ile Ser Thr Glu Arg Cys Leu Ser Val Leu Cys Pro
                    105                 110                 115 atc tgg tat cac tgc cgc cgc cca gaa cac aca tca act gtc atg tgt             560
Ile Trp Tyr His Cys Arg Arg Pro Glu His Thr Ser Thr Val Met Cys
            120                 125                 130 gct gtg atc tgg gtc ctg tcc ctg ttg atc tgc att ctg gat ggt tat             608
Ala Val Ile Trp Val Leu Ser Leu Leu Ile Cys Ile Leu Asp Gly Tyr
        135                 140                 145 ttc tgc ggt tac tta gat aac cat tat ttc aat tac tct gtg tgt cag             656
Phe Cys Gly Tyr Leu Asp Asn His Tyr Phe Asn Tyr Ser Val Cys Gln
    150                 155                 160 gca tgg gac atc ttt atc gga gca tac ctg atg ttt ttg ttt gta gtc             704
Ala Trp Asp Ile Phe Ile Gly Ala Tyr Leu Met Phe Leu Phe Val Val
165                 170                 175                 180 ctc tgt ctg tcc acc ctg gct cta ctg gcc agg ttg ttc tgt ggt gct             752
Leu Cys Leu Ser Thr Leu Ala Leu Leu Ala Arg Leu Phe Cys Gly Ala
                185                 190                 195 agg aat atg aaa ttt acc aga tta ttc gtg acc atc atg ctg acc gtt             800
Arg Asn Met Lys Phe Thr Arg Leu Phe Val Thr Ile Met Leu Thr Val
            200                 205                 210 ttg gtt ttt ctt ctc tgt ggg ttg ccc tgg ggc atc acc tgg ttc ctg             848
Leu Val Phe Leu Leu Cys Gly Leu Pro Trp Gly Ile Thr Trp Phe Leu
        215                 220                 225 tta ttc tgg att gca cct ggt gtg ttt gta cta gat tat agc cct ctt             896
Leu Phe Trp Ile Ala Pro Gly Val Phe Val Leu Asp Tyr Ser Pro Leu
    230                 235                 240 ctg gtc cta act gct att aac agc tgt gcc aac ccc att att tac ttc             944
Leu Val Leu Thr Ala Ile Asn Ser Cys Ala Asn Pro Ile Ile Tyr Phe
245                 250                 255                 260 ttc gtg ggc tcc ttc agg caa cgg ttg aat aaa cag acc ctc aaa atg             992
Phe Val Gly Ser Phe Arg Gln Arg Leu Asn Lys Gln Thr Leu Lys Met
                265                 270                 275 gtt ctc cag aaa gcc ctg cag gac act cct gag aca cct gaa aac atg            1040
Val Leu Gln Lys Ala Leu Gln Asp Thr Pro Glu Thr Pro Glu Asn Met
            280                 285                 290 gtg gag atg tca aga aac aaa gca gag ccg tgatgaagag cctctgccta             1090
Val Glu Met Ser Arg Asn Lys Ala Glu Pro
        295                 300 gacttcagag gtggatttgg agtgagcact gccctgctgc acttgaccac tgtccactct          1150
cctctcagct tactgacttg acatgcctca ctggtccacc aacaccttcc aaagctctcc          1210
actgacttag tatttatacc tctcccaaac aatagcatta ttcaaaaact ataatttctg          1270
catccttctt tacattaata aaattcccat actaagttca aa                             1312

<210> SEQ ID NO 6
<211> LENGTH: 302
<212> TYPE: PRT
<213> ORGANISM: Mus musculus

<400> SEQUENCE: 6

Met Asn Glu Thr Ile Pro Gly Ser Ile Asp Ile Glu Thr Leu Ile Pro
 1               5                  10                  15

Asp Leu Met Ile Ile Ile Phe Gly Leu Val Gly Leu Thr Gly Asn Ala
                20                  25                  30

Ile Val Phe Trp Leu Leu Gly Phe Arg Met His Arg Thr Ala Phe Leu
            35                  40                  45
```

Val Tyr Ile Leu Asn Leu Ala Leu Ala Asp Phe Leu Phe Leu Leu Cys
 50                  55                  60

His Ile Ile Asn Ser Thr Val Asp Leu Leu Lys Phe Thr Leu Pro Lys
 65                  70                  75                  80

Gly Ile Phe Ala Phe Cys Phe His Thr Ile Lys Arg Val Leu Tyr Ile
                 85                  90                  95

Thr Gly Leu Ser Met Leu Ser Ala Ile Ser Thr Glu Arg Cys Leu Ser
             100                 105                 110

Val Leu Cys Pro Ile Trp Tyr His Cys Arg Arg Pro Glu His Thr Ser
         115                 120                 125

Thr Val Met Cys Ala Val Ile Trp Val Leu Ser Leu Ile Cys Ile
130                 135                 140

Leu Asp Gly Tyr Phe Cys Gly Tyr Leu Asp Asn His Tyr Phe Asn Tyr
145                 150                 155                 160

Ser Val Cys Gln Ala Trp Asp Ile Phe Ile Gly Ala Tyr Leu Met Phe
                 165                 170                 175

Leu Phe Val Val Leu Cys Leu Ser Thr Leu Ala Leu Leu Ala Arg Leu
             180                 185                 190

Phe Cys Gly Ala Arg Asn Met Lys Phe Thr Arg Leu Phe Val Thr Ile
         195                 200                 205

Met Leu Thr Val Leu Val Phe Leu Leu Cys Gly Leu Pro Trp Gly Ile
210                 215                 220

Thr Trp Phe Leu Leu Phe Trp Ile Ala Pro Gly Val Phe Val Leu Asp
225                 230                 235                 240

Tyr Ser Pro Leu Leu Val Leu Thr Ala Ile Asn Ser Cys Ala Asn Pro
                 245                 250                 255

Ile Ile Tyr Phe Phe Val Gly Ser Phe Arg Gln Arg Leu Asn Lys Gln
             260                 265                 270

Thr Leu Lys Met Val Leu Gln Lys Ala Leu Gln Asp Thr Pro Glu Thr
         275                 280                 285

Pro Glu Asn Met Val Glu Met Ser Arg Asn Lys Ala Glu Pro
    290                 295                 300

<210> SEQ ID NO 7
<211> LENGTH: 450
<212> TYPE: DNA
<213> ORGANISM: Mus musculus
<220> FEATURE:
<221> NAME/KEY: CDS
<222> LOCATION: (1)...(450)

<400> SEQUENCE: 7 ctg tgc cgg atc tgg tat cac tgc cgc cgc cca gaa cac aca tca act     48
Leu Cys Arg Ile Trp Tyr His Cys Arg Arg Pro Glu His Thr Ser Thr
 1               5                  10                  15 gtc atg tgt gct gtc atc tgg gtc ctg tcc ctg ttg atc tgc att ctg     96
Val Met Cys Ala Val Ile Trp Val Leu Ser Leu Leu Ile Cys Ile Leu
             20                  25                  30 aat agt tat ttc tgc ggt ttc tta aat acc caa tat aaa aat gaa aat    144
Asn Ser Tyr Phe Cys Gly Phe Leu Asn Thr Gln Tyr Lys Asn Glu Asn
         35                  40                  45 ggg tgt ctg gca ttg agc ttc ttt act gct gca tac ctg atg ttt ttg    192
Gly Cys Leu Ala Leu Ser Phe Phe Thr Ala Ala Tyr Leu Met Phe Leu
     50                  55                  60 ttt gtg gtc ctc tgt ctg tcc agc ctg gct ctg gtg gcc agg ttg ttc    240
Phe Val Val Leu Cys Leu Ser Ser Leu Ala Leu Val Ala Arg Leu Phe
 65                  70                  75                  80

```
tgt ggt gct agg aat atg aaa ttt acc aga tta ttc gtg acc atc atg    288
Cys Gly Ala Arg Asn Met Lys Phe Thr Arg Leu Phe Val Thr Ile Met
                85                  90                  95 ctg acc gtt ttg gtt ttt ctt ctc tgt ggg ttg ccc tgg ggc atc acc    336
Leu Thr Val Leu Val Phe Leu Leu Cys Gly Leu Pro Trp Gly Ile Thr
            100                 105                 110 tgg ttc ctg tta ttc tgg att gca cct ggt gtg ttt gta cta gat tat    384
Trp Phe Leu Leu Phe Trp Ile Ala Pro Gly Val Phe Val Leu Asp Tyr
        115                 120                 125 agc cct ctt ctg gtc cta act gct att aac agc tgt gcc aac ccc att    432
Ser Pro Leu Leu Val Leu Thr Ala Ile Asn Ser Cys Ala Asn Pro Ile
    130                 135                 140 att tac ttc ttc gtc ggc                                            450
Ile Tyr Phe Phe Val Gly
145                 150

<210> SEQ ID NO 8
<211> LENGTH: 150
<212> TYPE: PRT
<213> ORGANISM: Mus musculus

<400> SEQUENCE: 8

Leu Cys Arg Ile Trp Tyr His Cys Arg Arg Pro Glu His Thr Ser Thr
1               5                   10                  15

Val Met Cys Ala Val Ile Trp Val Leu Ser Leu Leu Ile Cys Ile Leu
            20                  25                  30

Asn Ser Tyr Phe Cys Gly Phe Leu Asn Thr Gln Tyr Lys Asn Glu Asn
        35                  40                  45

Gly Cys Leu Ala Leu Ser Phe Phe Thr Ala Ala Tyr Leu Met Phe Leu
    50                  55                  60

Phe Val Val Leu Cys Leu Ser Ser Leu Ala Leu Val Ala Arg Leu Phe
65                  70                  75                  80

Cys Gly Ala Arg Asn Met Lys Phe Thr Arg Leu Phe Val Thr Ile Met
                85                  90                  95

Leu Thr Val Leu Val Phe Leu Leu Cys Gly Leu Pro Trp Gly Ile Thr
            100                 105                 110

Trp Phe Leu Leu Phe Trp Ile Ala Pro Gly Val Phe Val Leu Asp Tyr
        115                 120                 125

Ser Pro Leu Leu Val Leu Thr Ala Ile Asn Ser Cys Ala Asn Pro Ile
    130                 135                 140

Ile Tyr Phe Phe Val Gly
145                 150

<210> SEQ ID NO 9
<211> LENGTH: 459
<212> TYPE: DNA
<213> ORGANISM: Mus musculus
<220> FEATURE:
<221> NAME/KEY: CDS
<222> LOCATION: (1)...(459)

<400> SEQUENCE: 9 ctg tgc ccg acg tgg tat cgc tgc cac cgt cca gta cat aca tca act    48
Leu Cys Pro Thr Trp Tyr Arg Cys His Arg Pro Val His Thr Ser Thr
1               5                   10                  15 gtc atg tgt gct gtg atc tgg gtc cta tcc ctg ttg atc tgc att ctg    96
Val Met Cys Ala Val Ile Trp Val Leu Ser Leu Leu Ile Cys Ile Leu
            20                  25                  30 aat agc tat ttc tgt gct gtc tta cat acc aga tat gat aat gac aat   144
```

```
Asn Ser Tyr Phe Cys Ala Val Leu His Thr Arg Tyr Asp Asn Asp Asn
         35                  40                  45 gag tgt ctg gca act aac atc ttt acc gcc tcg tac atg ata ttt ttg    192
Glu Cys Leu Ala Thr Asn Ile Phe Thr Ala Ser Tyr Met Ile Phe Leu
 50                  55                  60 ctt gtg gtc ctc tgt ctg tcc agc ctg gct ctg gcc agg ttg ttc        240
Leu Val Val Leu Cys Leu Ser Ser Leu Ala Leu Ala Arg Leu Phe
 65                  70                  75                  80 tgt ggc gct ggg cag atg aag ctt acc aga ttt cat gtg acc atc ttg    288
Cys Gly Ala Gly Gln Met Lys Leu Thr Arg Phe His Val Thr Ile Leu
                 85                  90                  95 ctg acc ctt ttg gtt ttt ctc ctc tgc ggg ttg ccc ttt gtc atc tac    336
Leu Thr Leu Leu Val Phe Leu Leu Cys Gly Leu Pro Phe Val Ile Tyr
            100                 105                 110 tgc atc ctg tta ttc aag att aag gat gat ttc cat gta tta gat gtt    384
Cys Ile Leu Leu Phe Lys Ile Lys Asp Asp Phe His Val Leu Asp Val
        115                 120                 125 aat ctt tat cta gca tta gaa gtc ctg act gct att aac agc tgt gcc    432
Asn Leu Tyr Leu Ala Leu Glu Val Leu Thr Ala Ile Asn Ser Cys Ala
130                 135                 140 aac ccc atc atc tac ttc ttc gtc gga                                459
Asn Pro Ile Ile Tyr Phe Phe Val Gly
145                 150

<210> SEQ ID NO 10
<211> LENGTH: 153
<212> TYPE: PRT
<213> ORGANISM: Mus musculus

<400> SEQUENCE: 10

Leu Cys Pro Thr Trp Tyr Arg Cys His Arg Pro Val His Thr Ser Thr
 1               5                  10                  15

Val Met Cys Ala Val Ile Trp Val Leu Ser Leu Leu Ile Cys Ile Leu
             20                  25                  30

Asn Ser Tyr Phe Cys Ala Val Leu His Thr Arg Tyr Asp Asn Asp Asn
         35                  40                  45

Glu Cys Leu Ala Thr Asn Ile Phe Thr Ala Ser Tyr Met Ile Phe Leu
 50                  55                  60

Leu Val Val Leu Cys Leu Ser Ser Leu Ala Leu Ala Arg Leu Phe
 65                  70                  75                  80

Cys Gly Ala Gly Gln Met Lys Leu Thr Arg Phe His Val Thr Ile Leu
                 85                  90                  95

Leu Thr Leu Leu Val Phe Leu Leu Cys Gly Leu Pro Phe Val Ile Tyr
            100                 105                 110

Cys Ile Leu Leu Phe Lys Ile Lys Asp Asp Phe His Val Leu Asp Val
        115                 120                 125

Asn Leu Tyr Leu Ala Leu Glu Val Leu Thr Ala Ile Asn Ser Cys Ala
130                 135                 140

Asn Pro Ile Ile Tyr Phe Phe Val Gly
145                 150

<210> SEQ ID NO 11
<211> LENGTH: 2853
<212> TYPE: DNA
<213> ORGANISM: Mus musculus
<220> FEATURE:
<221> NAME/KEY: CDS
<222> LOCATION: (1820)...(2734)

<400> SEQUENCE: 11
```

```
caaggattct acaaacccaa gtatgcaagt caacaatcta aatataattt gttccttttg      60
aagttagtgg ttcaatataa cagacaaata catcatgccc tgaaattagc tttgaacaat     120
gctaagccca taatgggaag taaaagattt gcttggttcc cactttcttc cttttctatt     180
ccgtttggac catagtggct agtgtctctt acaagatcac aagaaggagg ctctgcattt     240
atttctgagt gcctgtctgc atcctccttt ggcctggagg tcctctatga atcctgaag      300 taagaaagaa atgttccaga ctctgatttt tcttcctaga ccaatgctat tcccttccat     360
gttgccaaca acttctcatc actctttctg tactttcttt tagctgggtg gtttcttaat     420
ctacagtatt gactgtcatg tcaaagttgg gtatttttg gctttagata tttcttctct      480
ggcttttctc ccatccacac ataatcaaaa cactgaggtg atgacactaa gggactgctc     540
aaaggaaaag ggtgggttcc tgggctttgg ggttattaat aatttgcctg tcctctgcca     600
gcctctatca actcccctaa aacacaaaaa taattgttcc tagcaggcaa gcacgacctg     660
acaattaatt aatgatcata aaaagtgcat tataaacatc tgaaaacctc ataataaaac     720
tcaacacctt atacagtgag tatgttgtgg ggtctgcata aatccaacaa aactccaatg     780
gagtggtact cagctattaa aaatgaggaa ttcacgaaat tcttagccaa atgattagaa     840
gtagaaaata tgatcctgag tgagaaaaga acaggcttgg tatgtactca ctgataagtg     900
gatactagcc caaaagctgc aaataatcag gataaaattc acagaccaca tgaacctcaa     960
taagaaggaa gaccaaagta tgggcgtttc ggtccttctt agaaggagaa caaaatactc    1020
ccaagagcaa atatggagat aaagtgtaga acaggcacta aaggaaaagt cacccagaga    1080
atgttccacc tggggattca tcccatatac agttaccaaa cccagacact cttatggatg    1140
ccaaggagtg aatgctgaca tagctgtttc ctaagaggcc atgccagaca cttacaaata    1200
cagaggccca agttagcaac caaccattag actgagcaca gggttcctaa tagaggagtc    1260
agagaaagga ctgagggagt tgaagggggtt tgcatcccca taagaaaaac aacaacatga    1320
accaacaaga cactctcccc accaaccccc tgaactccta gggactaagc catcaacaaa    1380
agagtacaca tggctccaga tgcatatgtt gcagaggatg ccatatcat gcattgatgg      1440 aagaggtcct tgaacctatg aaggttctat tgatgcccca gtgtaaggga atcgagggca    1500
gagaggtgga agtgggtgtg tgggttgagc aacaccctca cagaagcagg gggagggagg    1560
atgagatggg ggtttccagg aagggggggaa gcaggaaagg ggataacatt ttaaatttaa    1620
atatagaaaa tatccaatac aaaacatttt gaacaaacaa caaaaaactc acaaaaacaa    1680
caacaacaaa aaaagaaat taaaagttgt gttcatagtg aaggcctcat ttcttctttg      1740
tgttcccagc aacaccagtg cagggttcct ggccctaaac acctcagcct cggcaatggc    1800
acccacaaca acaaatccaa atg aac gaa acc atc cct gga agt att gac atc    1852
                       Met Asn Glu Thr Ile Pro Gly Ser Ile Asp Ile
                       1               5                   10 gag acc ctg atc cca aac ttg atg atc atc atc ttc gga ctg gtc ggg    1900
Glu Thr Leu Ile Pro Asn Leu Met Ile Ile Ile Phe Gly Leu Val Gly
          15                  20                  25 ctg aca gga aat gtc att ttg ttt tgg ctc ctg ggc ttc cac ttg cac    1948
Leu Thr Gly Asn Val Ile Leu Phe Trp Leu Leu Gly Phe His Leu His
          30                  35                  40 agg aat gcc ttc tta gtc tac atc cta aac ttg gcc ctg gct gac ttc    1996
Arg Asn Ala Phe Leu Val Tyr Ile Leu Asn Leu Ala Leu Ala Asp Phe
          45                  50                  55 ctc ttc ctt ctc tgt cac atc ata aat tcc aca atg ctt ctt ctc aag    2044
Leu Phe Leu Leu Cys His Ile Ile Asn Ser Thr Met Leu Leu Leu Lys
```

|  |  |  |  |  |  |  |  |  |  |  |  |  |  |  |  |
|---|---|---|---|---|---|---|---|---|---|---|---|---|---|---|---|
| | | 60 | | | | 65 | | | | 70 | | | | 75 | |

```
gtt cac cta ccc aac aat att ttg aac cat tgc ttt gac atc atc atg      2092
Val His Leu Pro Asn Asn Ile Leu Asn His Cys Phe Asp Ile Ile Met
                 80                  85                  90 aca gtt ctc tac atc aca ggc ctg agc atg ctc agt gcc atc agc act      2140
Thr Val Leu Tyr Ile Thr Gly Leu Ser Met Leu Ser Ala Ile Ser Thr
             95                 100                 105 gag cgc tgc ctg tct gtc ctg tgc ccc atc tgg tat cgg tgc cgc cgc      2188
Glu Arg Cys Leu Ser Val Leu Cys Pro Ile Trp Tyr Arg Cys Arg Arg
         110                 115                 120 cca gaa cac aca tca act gtc ctg tgt gct gtg atc tgg ttc ctg ccc      2236
Pro Glu His Thr Ser Thr Val Leu Cys Ala Val Ile Trp Phe Leu Pro
     125                 130                 135 ctg ttg atc tgc att ctg aat gga tat ttc tgt cat ttc ttt ggt ccc      2284
Leu Leu Ile Cys Ile Leu Asn Gly Tyr Phe Cys His Phe Phe Gly Pro
140                 145                 150                 155 aaa tat gta att gac tct gtg tgt ctg gca acg aac ttc ttt atc aga      2332
Lys Tyr Val Ile Asp Ser Val Cys Leu Ala Thr Asn Phe Phe Ile Arg
                 160                 165                 170 aca tac ccg atg ttt ttg ttt ata gtc ctc tgt ctg tcc acc ctg gct      2380
Thr Tyr Pro Met Phe Leu Phe Ile Val Leu Cys Leu Ser Thr Leu Ala
             175                 180                 185 ctg ctg gcc agg ttg ttc tgt ggt ggt ggg aag acg aaa ttt acc aga      2428
Leu Leu Ala Arg Leu Phe Cys Gly Gly Gly Lys Thr Lys Phe Thr Arg
         190                 195                 200 tta ttc gtg acc atc atg ctg acc gtt ttg gtt ttt ctt ctc tgt ggg      2476
Leu Phe Val Thr Ile Met Leu Thr Val Leu Val Phe Leu Leu Cys Gly
     205                 210                 215 ttg ccc ctg ggc ttc ttc tgg ttt ctg gtg ccg tgg att aac cgt gat      2524
Leu Pro Leu Gly Phe Phe Trp Phe Leu Val Pro Trp Ile Asn Arg Asp
220                 225                 230                 235 ttc agt gta cta gat tat ata ctt ttt cag aca tca ctt gtc cta act      2572
Phe Ser Val Leu Asp Tyr Ile Leu Phe Gln Thr Ser Leu Val Leu Thr
                 240                 245                 250 tct gtt aac agc tgt gcc aac ccc atc att tac ttc ttt gtg ggc tcc      2620
Ser Val Asn Ser Cys Ala Asn Pro Ile Ile Tyr Phe Phe Val Gly Ser
             255                 260                 265 ttc agg cat cgg ttg aag cac aag acc ctc aaa atg gtt ctc cag agt      2668
Phe Arg His Arg Leu Lys His Lys Thr Leu Lys Met Val Leu Gln Ser
         270                 275                 280 gca ttg cag gac act cct gag aca cct gaa aac atg gtg gag atg tca      2716
Ala Leu Gln Asp Thr Pro Glu Thr Pro Glu Asn Met Val Glu Met Ser
     285                 290                 295 aga agc aaa gca gag ccg tgatgaagag cctctacctg gacctcagag             2764
Arg Ser Lys Ala Glu Pro
300                 305 gtggctttgg attgagcact gccctgctgc acttgaccac tgtccactct cctctcagct    2824
tactgacttt ggatgcctca gtggtccaa                                      2853

<210> SEQ ID NO 12
<211> LENGTH: 305
<212> TYPE: PRT
<213> ORGANISM: Mus musculus

<400> SEQUENCE: 12

Met Asn Glu Thr Ile Pro Gly Ser Ile Asp Ile Glu Thr Leu Ile Pro
1               5                   10                  15

Asn Leu Met Ile Ile Ile Phe Gly Leu Val Gly Leu Thr Gly Asn Val
            20                  25                  30
```

```
Ile Leu Phe Trp Leu Leu Gly Phe His Leu His Arg Asn Ala Phe Leu
             35                  40                  45
Val Tyr Ile Leu Asn Leu Ala Leu Ala Asp Phe Phe Leu Leu Cys
     50                  55                  60
His Ile Ile Asn Ser Thr Met Leu Leu Lys Val His Leu Pro Asn
 65                  70                  75                  80
Asn Ile Leu Asn His Cys Phe Asp Ile Ile Met Thr Val Leu Tyr Ile
                 85                  90                  95
Thr Gly Leu Ser Met Leu Ser Ala Ile Ser Thr Glu Arg Cys Leu Ser
            100                 105                 110
Val Leu Cys Pro Ile Trp Tyr Arg Cys Arg Arg Pro Glu His Thr Ser
            115                 120                 125
Thr Val Leu Cys Ala Val Ile Trp Phe Leu Pro Leu Leu Ile Cys Ile
        130                 135                 140
Leu Asn Gly Tyr Phe Cys His Phe Phe Gly Pro Lys Tyr Val Ile Asp
145                 150                 155                 160
Ser Val Cys Leu Ala Thr Asn Phe Phe Ile Arg Thr Tyr Pro Met Phe
                165                 170                 175
Leu Phe Ile Val Leu Cys Leu Ser Thr Leu Ala Leu Leu Ala Arg Leu
            180                 185                 190
Phe Cys Gly Gly Gly Lys Thr Lys Phe Thr Arg Leu Phe Val Thr Ile
        195                 200                 205
Met Leu Thr Val Leu Val Phe Leu Leu Cys Gly Leu Pro Leu Gly Phe
    210                 215                 220
Phe Trp Phe Leu Val Pro Trp Ile Asn Arg Asp Phe Ser Val Leu Asp
225                 230                 235                 240
Tyr Ile Leu Phe Gln Thr Ser Leu Val Leu Thr Ser Val Asn Ser Cys
                245                 250                 255
Ala Asn Pro Ile Ile Tyr Phe Phe Val Gly Ser Phe Arg His Arg Leu
            260                 265                 270
Lys His Lys Thr Leu Lys Met Val Leu Gln Ser Ala Leu Gln Asp Thr
        275                 280                 285
Pro Glu Thr Pro Glu Asn Met Val Glu Met Ser Arg Ser Lys Ala Glu
    290                 295                 300
Pro
305

<210> SEQ ID NO 13
<211> LENGTH: 3391
<212> TYPE: DNA
<213> ORGANISM: Mus musculus
<220> FEATURE:
<221> NAME/KEY: CDS
<222> LOCATION: (170)...(574)

<400> SEQUENCE: 13
ccgaaaacca acaaaataga accgcgggtg cctttctcca gctgggatga aggacttgag     60
cagaaactca ttgccagctt cctccctacg cgagagccga ctgagtccca ggtcccagt    120 cttccccgg gacgttgtgc acggtgccca ttcttgagca gccacaaca atg gag gtg    178
                                                    Met Glu Val
                                                      1 ctc ccc aag gcc ctg gag gta gac gag agg tct cca gag tcc aag gac    226
Leu Pro Lys Ala Leu Glu Val Asp Glu Arg Ser Pro Glu Ser Lys Asp
  5                  10                  15 ctg ctg ccc agc cag aca gcc agc tcc ctg tgc atc agt tcc aga agt    274
```

| | | |
|---|---|---|
| Leu Leu Pro Ser Gln Thr Ala Ser Ser Leu Cys Ile Ser Arg Ser<br>20                        25                         30                     35 | |

```
gag tct gtc tgg acc acc aca ccc aaa agc aac tgg gaa atc tac cac    322
Glu Ser Val Trp Thr Thr Thr Pro Lys Ser Asn Trp Glu Ile Tyr His
            40                  45                  50 aag ccc atc atc atc atg tca gtg gga gct gcc att ctg ctc ttt ggc    370
Lys Pro Ile Ile Ile Met Ser Val Gly Ala Ala Ile Leu Leu Phe Gly
                55                  60                  65 gtg gcc atc acc tgt gtg gcc tac atc ttg gaa gag aag cat aaa gtt    418
Val Ala Ile Thr Cys Val Ala Tyr Ile Leu Glu Glu Lys His Lys Val
        70                  75                  80 gtg caa gtg ctc agg atg ata ggg cct gcc ttc ctg tcc ctg gga ctc    466
Val Gln Val Leu Arg Met Ile Gly Pro Ala Phe Leu Ser Leu Gly Leu
    85                  90                  95 atg atg ctg gtg tgt ggg ctg gtg tgg gtc ccc ata atc aaa aag aag    514
Met Met Leu Val Cys Gly Leu Val Trp Val Pro Ile Ile Lys Lys Lys
100                 105                 110                 115 cag aag caa agg cag aag tcc aac ttc ttc caa agc ctc aag ttc ttc    562
Gln Lys Gln Arg Gln Lys Ser Asn Phe Phe Gln Ser Leu Lys Phe Phe
                120                 125                 130 ctc ctg aac cgc tgatgactgg ttgtccagaa gatctgctaa ccaataagca        614
Leu Leu Asn Arg
            135 gcctcctacc ttctcttcgg gtaccacaaa gttgatccag gcaaaccctc ctcttggccc    674
tgtggacagg atagagctca gggcttcacc ctcatacaac ctagcagcat tgctgactga    734
gtctcacctg gtttccatag ctgtggatgc tgtgccttg gatactttca ttaccctcat    794
ccctggcacc tgcattcagc catcagccat cccattctct ctgccaaggg caatgtgtgc    854
atgctaggaa attctttggg ggttgactac attcccaagg agaacttgta tgttacggtt    914
gtgtgcctga tcttagattc ccatctacat ccttctggaa ccaaaagtga ccaagcagat    974
aaggctgact tcagtcccat tgggtttgac agccttggct ccctccttgg atgggacatt   1034
gactaacatt acaagagaaa ggatatgtct catgtatcac acattccaaa atctggacag   1094
tgatggggct gggggtgagg gaaacactgt ctagagtaaa ccattcctct gggagtaatc   1154
tggaacttat acagtgaagg aagttagctc ctaaatatat gatattggca caagaggcaa   1214
tatgcaggct aagaggtatc aacacttccc cttgatcctc caatgcgctt cttgcagaat   1274
gcctttatat tagcaattag ccaagaacaa atgctctttg ttctaacttc cttccccacc   1334
acatctctgc gtctacacag ctccagaaca gaaggacggg aggccacaga tgtgacctgt   1394
aagatcatct ccttctcctg tcaatcaaga cctaacctga aattgaatgc catgtccgac   1454
tcacgctgca tggggtttta gagataggtt cactggaaaa aaggaaatct cagcctccct   1514
cctccctgtt cctccctacc aaacaagcaa gtatttattg agtttccttc tctaggccta   1574
cgttgggaac agccagaccc agtctctgat gtcatcttat ttccaaaagt gaaagaggga   1634
aaaacatggc caagccaact ggcaatactc catactgagt tcttagggtg gccatgggaa   1694
cacatggatc taacaaatgt acaggaagat agatttctgg agaccatgtt cacccct tct   1754
gaatatgaag gggaaggaag tgtttggaat gagcaagatg tgcaaggtag tcagcaactg   1814
ccttgcatgt ggagaagcta aggggaaaga gacagggtgg ggttaggatt ccgcatagct   1874
cccggatgct attccatcct ctcttgccta cttcccccct gcttcccagg tacct taca   1934
tccagctact ccttggtaca ctgcaggctt ctggggtcaa tagggactgg gaggggcatc   1994
tccagagggc ctaacaagta gatataaccc aagaggtaag taccctcaaa acttcattat   2054
```

```
agtcaccaag acacctttag gcaaaagacc gggcacctat aagaaatttc caaagctgtt   2114
ccaggcaagg ccaggccaga gagcagagga aggtacctag tagcaaagtg aatgacaaga   2174
gctgcattgg ttcaggttga ctcttcatcc ttaacctttg gcatttggg aacactatgg    2234
caaacaacct ccaacaggtc tccagatatc tcaaccattc acagtacttc tataggcagt   2294
tagaatccac cacctttgtt cctgttgcat tgtgggacat tcctcggagg aagtatttgt   2354
tttgtggaat caacacacac acacacacgc acagagagag agagagagag agagagagag   2414
agagagagag agagagagag agagaaagaa agagaaagaa agaaagaaag agaaagagac   2474
tgactcccta actaaaaagt cagagtttgg gaagcctgtg gcctttcaaa gctcacttaa   2534
gaatatcatg ttcctcatta agactcacat catcgagccc aggccctgca gtccacccat   2594
tccctgaata caggcagctc aggaccaacc ctggggttgt tgaaatactg cctagtgctt   2654
ccacgaatgt ctaatgcctc catgacaggg cttcagacc actcctttct cctgacatgg    2714
aaggacagcc ctggggtgga gcctctcaat cttctgtgcc ttcatgaaag gaacacaca    2774
gatgagctca cagccagctc acttggaatc cgcacccat gcacctcatt gtcctgagag     2834
ctcattgtct gggcacagct gtgggaagac ctttgcagat ctcactttca gtatgtctc    2894
aacagaaggg agtttgggga taatcacgat gccaggaaat cttcaagttc tagacatctt   2954
tcatagccac atcagtacct gttccccaac ccctgcccct caaggtaagt acttagcaaa   3014
caaaatcaaa gagcctttga gaaaatatcc caaatactgg ttaactcccc cggccttgca   3074
ccaaactccc cacaaaagtg atagtcagga agtgagcaga gtcacaccca acatcttgga   3134
aaattttgcc aaagaccatt gcctcatgaa aactggggtg gggataacct gtgagtgcag   3194
ccgggttgga tgccgtgtct ctgcaacaaa gcattctggg tagtgatttc agtcatctca   3254
gaagacaaga gcaacatcca cagcaccatc ccaccggact gtattacggg cttctgtcgc   3314
tcttctgttt tggagaattt aatctaaccc aacgcctaat ggaatcaatg tcgtattgaa   3374
ctgtattctg tttaaaa                                                  3391
```

<210> SEQ ID NO 14
<211> LENGTH: 135
<212> TYPE: PRT
<213> ORGANISM: Mus musculus

<400> SEQUENCE: 14

```
Met Glu Val Leu Pro Lys Ala Leu Glu Val Asp Glu Arg Ser Pro Glu
  1               5                  10                  15

Ser Lys Asp Leu Leu Pro Ser Gln Thr Ala Ser Ser Leu Cys Ile Ser
             20                  25                  30

Ser Arg Ser Glu Ser Val Trp Thr Thr Thr Pro Lys Ser Asn Trp Glu
         35                  40                  45

Ile Tyr His Lys Pro Ile Ile Ile Met Ser Val Gly Ala Ala Ile Leu
     50                  55                  60

Leu Phe Gly Val Ala Ile Thr Cys Val Ala Tyr Ile Leu Glu Glu Lys
 65                  70                  75                  80

His Lys Val Val Gln Val Leu Arg Met Ile Gly Pro Ala Phe Leu Ser
                 85                  90                  95

Leu Gly Leu Met Met Leu Val Cys Gly Leu Val Trp Val Pro Ile Ile
            100                 105                 110

Lys Lys Lys Gln Lys Gln Arg Gln Lys Ser Asn Phe Phe Gln Ser Leu
        115                 120                 125

Lys Phe Phe Leu Leu Asn Arg
    130                 135
```

<210> SEQ ID NO 15
<211> LENGTH: 2040
<212> TYPE: DNA
<213> ORGANISM: Homo sapiens
<220> FEATURE:
<221> NAME/KEY: CDS
<222> LOCATION: (328)...(1293)

<400> SEQUENCE: 15

```
gcccaggata gagtaatcat cgggtccaca gccctggcta gatgagtggg ggtgttttga    60
tcctaatgtt attcccatgt tagcacagaa cttgtgtggc agtagagaga ggtcaggctt   120
cagagtcagc aagaactgga tttcaaactg gatttgagga ccccaccctt ttgataggtg   180
acttattctc tgtgagtctc tgatctgccc tctttaaatg aggaagtaaa tcccacatgg   240
cagggtggtg gggagaatca gagatcatac agctggtgat cacaactggt ttctgtttcc   300
agggtcacca gactagggtt tctgagc atg gat cca acc atc tca acc ttg gac   354
                               Met Asp Pro Thr Ile Ser Thr Leu Asp
                                 1               5 aca gaa ctg aca cca atc aac gga act gag gag act ctt tgc tac aag    402
Thr Glu Leu Thr Pro Ile Asn Gly Thr Glu Glu Thr Leu Cys Tyr Lys
 10              15                  20                  25 cag acc ttg agc ctc acg gtg ctg acg tgc atc gtt tcc ctt gtc ggg    450
Gln Thr Leu Ser Leu Thr Val Leu Thr Cys Ile Val Ser Leu Val Gly
             30                  35                  40 ctg aca gga aac gca gtt gtg ctc tgg ctc ctg ggc tgc cgc atg cgc    498
Leu Thr Gly Asn Ala Val Val Leu Trp Leu Leu Gly Cys Arg Met Arg
         45                  50                  55 agg aac gcc ttc tcc atc tac atc ctc aac ttg gcc gca gca gac ttc    546
Arg Asn Ala Phe Ser Ile Tyr Ile Leu Asn Leu Ala Ala Ala Asp Phe
     60                  65                  70 ctc ttc ctc agc ggc cgc ctt ata tat tcc ctg tta agc ttc atc agt    594
Leu Phe Leu Ser Gly Arg Leu Ile Tyr Ser Leu Leu Ser Phe Ile Ser
 75                  80                  85 atc ccc cat acc atc tct aaa atc ctc tat cct gtg atg atg ttt tcc    642
Ile Pro His Thr Ile Ser Lys Ile Leu Tyr Pro Val Met Met Phe Ser
 90                  95                 100                 105 tac ttt gca ggc ctg agc ttt ctg agt gcc gtg agc acc gag cgc tgc    690
Tyr Phe Ala Gly Leu Ser Phe Leu Ser Ala Val Ser Thr Glu Arg Cys
                110                 115                 120 ctg tcc gtc ctg tgg ccc atc tgg tac cgc tgc cac cgc ccc aca cac    738
Leu Ser Val Leu Trp Pro Ile Trp Tyr Arg Cys His Arg Pro Thr His
            125                 130                 135 ctg tca gcg gtg gtg tgt gtc ctg ctc tgg gcc ctg tcc ctg ctg cgg    786
Leu Ser Ala Val Val Cys Val Leu Leu Trp Ala Leu Ser Leu Leu Arg
        140                 145                 150 agc atc ctg gag tgg atg tta tgt ggc ttc ctg ttc agt ggt gct gat    834
Ser Ile Leu Glu Trp Met Leu Cys Gly Phe Leu Phe Ser Gly Ala Asp
    155                 160                 165 tct gct tgg tgt caa aca tca gat ttc atc aca gtc gcg tgg ctg att    882
Ser Ala Trp Cys Gln Thr Ser Asp Phe Ile Thr Val Ala Trp Leu Ile
170                 175                 180                 185 ttt tta tgt gtg gtt ctc tgt ggg tcc agc ctg tcc ctg ctg atc agg    930
Phe Leu Cys Val Val Leu Cys Gly Ser Ser Leu Val Leu Leu Ile Arg
                190                 195                 200 att ctc tgt gga tcc cgg aag ata ccg ctg acc agg ctg tac gtg acc    978
Ile Leu Cys Gly Ser Arg Lys Ile Pro Leu Thr Arg Leu Tyr Val Thr
            205                 210                 215
```

| | | |
|---|---|---|
| atc ctg ctc aca gta ctg gtc ttc ctc ctc tgt ggc ctg ccc ttt ggc<br>Ile Leu Leu Thr Val Leu Val Phe Leu Leu Cys Gly Leu Pro Phe Gly<br>220                       225                   230 | | 1026 |
| att cag ttt ttc cta ttt tta tgg atc cac gtg gac agg gaa gtc tta<br>Ile Gln Phe Phe Leu Phe Leu Trp Ile His Val Asp Arg Glu Val Leu<br>235                       240                   245 | | 1074 |
| ttt tgt cat gtt cat cta gtt tct att ttc ctg tcc gct ctt aac agc<br>Phe Cys His Val His Leu Val Ser Ile Phe Leu Ser Ala Leu Asn Ser<br>250                       255                   260                   265 | | 1122 |
| agt gcc aac ccc atc att tac ttc ttc gtg ggc tcc ttt agg cag cgt<br>Ser Ala Asn Pro Ile Ile Tyr Phe Phe Val Gly Ser Phe Arg Gln Arg<br>                   270                   275                   280 | | 1170 |
| caa aat agg cag aac ctg aag ctg gtt ctc cag agg gct ctg cag gac<br>Gln Asn Arg Gln Asn Leu Lys Leu Val Leu Gln Arg Ala Leu Gln Asp<br>285                       290                   295 | | 1218 |
| gcg tct gag gtg gat gaa ggt gga ggg cag ctt cct gag gaa atc ctg<br>Ala Ser Glu Val Asp Glu Gly Gly Gly Gln Leu Pro Glu Glu Ile Leu<br>               300                   305                   310 | | 1266 |
| gag ctg tcg gga agc aga ttg gag cag tgaggaagag cctctgccct<br>Glu Leu Ser Gly Ser Arg Leu Glu Gln<br>315                     320 | | 1313 |
| gtcagacagg actttgagag caacactgcc ctgccaccct tgacaattat atgcgttttt | | 1373 |
| cttagccttc tgcctcagaa atgtctcagt ggttcctcaa ggtcttcaaa tagatgttta | | 1433 |
| tctaacctga cagttgcggt tttcacccat ggaaagcatt agtctgacag tacaatgttt | | 1493 |
| agattctcct tgatattacc aacacatttt ccctgttatc tcacactgaa tctttcctac | | 1553 |
| agaacacttt ttctgcaatt ttctttgtaa taaaggagt tcctgtacaa acccctaaaa | | 1613 |
| cactctttat acttctttcc tacctgatag catcaaaaag gaagattcct tattaatctc | | 1673 |
| tcagactatg ttcccctgaa aatcatgttc ccttctatga ctggaggcat tactgcagtt | | 1733 |
| agaagctcga ttcttaataa gtgagttctg ctatctctac attccattga attctcagat | | 1793 |
| acagagcaaa ataatgtcct tagagacaga ctctctcttc ataaaaacac tctcacctat | | 1853 |
| tggtttata aaaagtcttc ccctgtcatt tgttcacagc atggtgatat gttggccttg | | 1913 |
| gtttctagta aagacaactg tggcccctic cccttgagaa cttttaagtg cttatttagc | | 1973 |
| tcttcctgga ctaatggacc agtgaggagc ccataaatgt gccccagttc tattttggcc | | 2033 |
| attggaa | | 2040 |

<210> SEQ ID NO 16
<211> LENGTH: 322
<212> TYPE: PRT
<213> ORGANISM: Homo sapiens

<400> SEQUENCE: 16

Met Asp Pro Thr Ile Ser Thr Leu Asp Thr Glu Leu Thr Pro Ile Asn
1               5                   10                 15

Gly Thr Glu Glu Thr Leu Cys Tyr Lys Gln Thr Leu Ser Leu Thr Val
               20                   25                   30

Leu Thr Cys Ile Val Ser Leu Val Gly Leu Thr Gly Asn Ala Val Val
                   35                   40               45

Leu Trp Leu Leu Gly Cys Arg Met Arg Arg Asn Ala Phe Ser Ile Tyr
50                       55                   60

Ile Leu Asn Leu Ala Ala Ala Asp Phe Leu Phe Leu Ser Gly Arg Leu
65                     70                   75                   80

Ile Tyr Ser Leu Leu Ser Phe Ile Ser Ile Pro His Thr Ile Ser Lys
               85                   90                   95

```
Ile Leu Tyr Pro Val Met Met Phe Ser Tyr Phe Ala Gly Leu Ser Phe
                100                 105                 110

Leu Ser Ala Val Ser Thr Glu Arg Cys Leu Ser Val Leu Trp Pro Ile
            115                 120                 125

Trp Tyr Arg Cys His Arg Pro Thr His Leu Ser Ala Val Val Cys Val
        130                 135                 140

Leu Leu Trp Ala Leu Ser Leu Leu Arg Ser Ile Leu Glu Trp Met Leu
145                 150                 155                 160

Cys Gly Phe Leu Phe Ser Gly Ala Asp Ser Ala Trp Cys Gln Thr Ser
                165                 170                 175

Asp Phe Ile Thr Val Ala Trp Leu Ile Phe Leu Cys Val Val Leu Cys
            180                 185                 190

Gly Ser Ser Leu Val Leu Leu Ile Arg Ile Leu Cys Gly Ser Arg Lys
        195                 200                 205

Ile Pro Leu Thr Arg Leu Tyr Val Thr Ile Leu Leu Thr Val Leu Val
210                 215                 220

Phe Leu Leu Cys Gly Leu Pro Phe Gly Ile Gln Phe Phe Leu Phe Leu
225                 230                 235                 240

Trp Ile His Val Asp Arg Glu Val Leu Phe Cys His Val His Leu Val
                245                 250                 255

Ser Ile Phe Leu Ser Ala Leu Asn Ser Ser Ala Asn Pro Ile Ile Tyr
            260                 265                 270

Phe Phe Val Gly Ser Phe Arg Gln Arg Gln Asn Arg Gln Asn Leu Lys
        275                 280                 285

Leu Val Leu Gln Arg Ala Leu Gln Asp Ala Ser Glu Val Asp Glu Gly
290                 295                 300

Gly Gly Gln Leu Pro Glu Glu Ile Leu Glu Leu Ser Gly Ser Arg Leu
305                 310                 315                 320

Glu Gln

<210> SEQ ID NO 17
<211> LENGTH: 1300
<212> TYPE: DNA
<213> ORGANISM: Homo sapiens
<220> FEATURE:
<221> NAME/KEY: CDS
<222> LOCATION: (171)...(1160)

<400> SEQUENCE: 17
tccctggccc ttaataaatg acttaatctc ttcaagcctc tgatttcctc tcctgtaaaa       60
caggggcggt aattaccaca taacaggctg gtcatgaaaa tcagtgaaca tgcagcaggt      120
gctcaagtct tgttttttgtt tccaggggca ccagtggagg ttttctgagc atg gat       176
                                                        Met Asp
                                                         1 cca acc acc ccg gcc tgg gga aca gaa agt aca aca gtg aat gga aat      224
Pro Thr Thr Pro Ala Trp Gly Thr Glu Ser Thr Thr Val Asn Gly Asn
        5                  10                  15 gac caa gcc ctt ctt ctg ctt tgt ggc aag gag acc ctg atc ccg gtc      272
Asp Gln Ala Leu Leu Leu Leu Cys Gly Lys Glu Thr Leu Ile Pro Val
     20                  25                  30 ttc ctg atc ctt ttc att gcc ctg gtc ggg ctg gta gga aac ggg ttt      320
Phe Leu Ile Leu Phe Ile Ala Leu Val Gly Leu Val Gly Asn Gly Phe
 35                  40                  45                  50 gtg ctc tgg ctc ctg ggc ttc cgc atg cgc agg aac gcc ttc tct gtc      368
Val Leu Trp Leu Leu Gly Phe Arg Met Arg Arg Asn Ala Phe Ser Val
                 55                  60                  65
```

```
tac gtc ctc agc ctg gcc ggg gcc gac ttc ctc ttc ctc tgc ttc cag      416
Tyr Val Leu Ser Leu Ala Gly Ala Asp Phe Leu Phe Leu Cys Phe Gln
             70                  75                  80 att ata aat tgc ctg gtg tac ctc agt aac ttc ttc tgt tcc atc tcc      464
Ile Ile Asn Cys Leu Val Tyr Leu Ser Asn Phe Phe Cys Ser Ile Ser
         85                  90                  95 atc aat ttc cct agc ttc ttc acc act gtg atg acc tgt gcc tac ctt      512
Ile Asn Phe Pro Ser Phe Phe Thr Thr Val Met Thr Cys Ala Tyr Leu
100                 105                 110 gca ggc ctg agc atg ctg agc acc gtc agc acc gag cgc tgc ctg tcc      560
Ala Gly Leu Ser Met Leu Ser Thr Val Ser Thr Glu Arg Cys Leu Ser
115                 120                 125                 130 gtc ctg tgg ccc atc tgg tat cgc tgc cgc cgc ccc aga cac ctg tca      608
Val Leu Trp Pro Ile Trp Tyr Arg Cys Arg Arg Pro Arg His Leu Ser
             135                 140                 145 gcg gtc gtg tgt gtc ctg ctc tgg gcc ctg tcc cta ctg ctg agc atc      656
Ala Val Val Cys Val Leu Leu Trp Ala Leu Ser Leu Leu Leu Ser Ile
         150                 155                 160 ttg gaa ggg aag ttc tgt ggc ttc tta ttt agt gat ggt gac tct ggt      704
Leu Glu Gly Lys Phe Cys Gly Phe Leu Phe Ser Asp Gly Asp Ser Gly
    165                 170                 175 tgg tgt cag aca ttt gat ttc atc act gca gcg tgg ctg att ttt tta      752
Trp Cys Gln Thr Phe Asp Phe Ile Thr Ala Ala Trp Leu Ile Phe Leu
180                 185                 190 ttc atg gtt ctc tgt ggg tcc agt ctg gcc ctg ctg gtc agg atc ctc      800
Phe Met Val Leu Cys Gly Ser Ser Leu Ala Leu Leu Val Arg Ile Leu
195                 200                 205                 210 tgt ggc tcc agg ggt ctg cca ctg acc agg ctg tac ctg acc atc ctg      848
Cys Gly Ser Arg Gly Leu Pro Leu Thr Arg Leu Tyr Leu Thr Ile Leu
             215                 220                 225 ctc aca gtg ctg gtg ttc ctc ctc tgc ggc ctg ccc ttt ggc att cag      896
Leu Thr Val Leu Val Phe Leu Leu Cys Gly Leu Pro Phe Gly Ile Gln
         230                 235                 240 tgg ttc cta ata tta tgg atc tgg aag gat tct gat gtc tta ttt tgt      944
Trp Phe Leu Ile Leu Trp Ile Trp Lys Asp Ser Asp Val Leu Phe Cys
    245                 250                 255 cat att cat cca gtt tca gtt gtc ctg tca tct ctt aac agc agt gcc      992
His Ile His Pro Val Ser Val Val Leu Ser Ser Leu Asn Ser Ser Ala
260                 265                 270 aac ccc atc att tac ttc ttc gtg ggc tct ttt agg aag cag tgg cgg     1040
Asn Pro Ile Ile Tyr Phe Phe Val Gly Ser Phe Arg Lys Gln Trp Arg
275                 280                 285                 290 ctg cag cag ccg atc ctc aag ctg gct ctc cag agg gct ctg cag gac     1088
Leu Gln Gln Pro Ile Leu Lys Leu Ala Leu Gln Arg Ala Leu Gln Asp
             295                 300                 305 att gct gag gtg gat cac agt gaa gga tgc ttc cgt cag ggc acc ccg     1136
Ile Ala Glu Val Asp His Ser Glu Gly Cys Phe Arg Gln Gly Thr Pro
         310                 315                 320 gag atg tcg aga agc agt ctg gtg tagagatgga cagcctctac ttccatcaga   1190
Glu Met Ser Arg Ser Ser Leu Val
    325                 330 tatatgtggc tttgagaggc aactttgccc ctgtctgtct gatttgctga actttctcag  1250
tcctgatttt aaaacagtta agagagtcct tgtgaggatt aagtgagaca             1300

<210> SEQ ID NO 18
<211> LENGTH: 330
<212> TYPE: PRT
<213> ORGANISM: Homo sapiens
```

-continued

<400> SEQUENCE: 18

Met Asp Pro Thr Thr Pro Ala Trp Gly Thr Glu Ser Thr Thr Val Asn
1               5                   10                  15

Gly Asn Asp Gln Ala Leu Leu Leu Cys Gly Lys Glu Thr Leu Ile
            20                  25                  30

Pro Val Phe Leu Ile Leu Phe Ile Ala Leu Val Gly Leu Val Gly Asn
        35                  40                  45

Gly Phe Val Leu Trp Leu Leu Gly Phe Arg Met Arg Arg Asn Ala Phe
    50                  55                  60

Ser Val Tyr Val Leu Ser Leu Ala Gly Ala Asp Phe Leu Phe Leu Cys
65                  70                  75                  80

Phe Gln Ile Ile Asn Cys Leu Val Tyr Leu Ser Asn Phe Phe Cys Ser
                85                  90                  95

Ile Ser Ile Asn Phe Pro Ser Phe Phe Thr Thr Val Met Thr Cys Ala
            100                 105                 110

Tyr Leu Ala Gly Leu Ser Met Leu Ser Thr Val Ser Thr Glu Arg Cys
        115                 120                 125

Leu Ser Val Leu Trp Pro Ile Trp Tyr Arg Cys Arg Arg Pro Arg His
    130                 135                 140

Leu Ser Ala Val Val Cys Val Leu Leu Trp Ala Leu Ser Leu Leu Leu
145                 150                 155                 160

Ser Ile Leu Glu Gly Lys Phe Cys Gly Phe Leu Phe Ser Asp Gly Asp
                165                 170                 175

Ser Gly Trp Cys Gln Thr Phe Asp Phe Ile Thr Ala Ala Trp Leu Ile
            180                 185                 190

Phe Leu Phe Met Val Leu Cys Gly Ser Ser Leu Ala Leu Leu Val Arg
        195                 200                 205

Ile Leu Cys Gly Ser Arg Gly Leu Pro Leu Thr Arg Leu Tyr Leu Thr
    210                 215                 220

Ile Leu Leu Thr Val Leu Val Phe Leu Leu Cys Gly Leu Pro Phe Gly
225                 230                 235                 240

Ile Gln Trp Phe Leu Ile Leu Trp Ile Trp Lys Asp Ser Asp Val Leu
                245                 250                 255

Phe Cys His Ile His Pro Val Ser Val Val Leu Ser Ser Leu Asn Ser
            260                 265                 270

Ser Ala Asn Pro Ile Ile Tyr Phe Phe Val Gly Ser Phe Arg Lys Gln
        275                 280                 285

Trp Arg Leu Gln Gln Pro Ile Leu Lys Leu Ala Leu Gln Arg Ala Leu
    290                 295                 300

Gln Asp Ile Ala Glu Val Asp His Ser Glu Gly Cys Phe Arg Gln Gly
305                 310                 315                 320

Thr Pro Glu Met Ser Arg Ser Ser Leu Val
                325                 330

<210> SEQ ID NO 19
<211> LENGTH: 135
<212> TYPE: PRT
<213> ORGANISM: Homo sapiens

<400> SEQUENCE: 19

Met Glu Thr Leu Pro Lys Val Leu Glu Val Asp Glu Lys Ser Pro Glu
1               5                   10                  15

Ala Lys Asp Leu Leu Pro Ser Gln Thr Ala Ser Ser Leu Cys Ile Ser
            20                  25                  30

```
Ser Arg Ser Glu Ser Val Trp Thr Thr Pro Arg Ser Asn Trp Glu
    35                  40                  45

Ile Tyr Arg Lys Pro Ile Val Ile Met Ser Val Gly Gly Ala Ile Leu
 50                  55                  60

Leu Phe Gly Val Val Ile Thr Cys Leu Ala Tyr Thr Leu Lys Leu Ser
 65                  70                  75                  80

Asp Lys Ser Leu Ser Ile Leu Lys Met Val Gly Pro Gly Phe Leu Ser
                 85                  90                  95

Leu Gly Leu Met Met Leu Val Cys Gly Leu Val Trp Val Pro Ile Ile
            100                 105                 110

Lys Lys Lys Gln Lys His Arg Gln Lys Ser Asn Phe Leu Arg Ser Leu
        115                 120                 125

Lys Ser Phe Phe Leu Thr Arg
    130                 135

<210> SEQ ID NO 20
<211> LENGTH: 970
<212> TYPE: DNA
<213> ORGANISM: Mus musculus
<220> FEATURE:
<221> NAME/KEY: CDS
<222> LOCATION: (83)...(943)

<400> SEQUENCE: 20
gtgtcaccaa cagcacccac aacaaatcca atggacaaac ctctttggaa gtatggacat      60
ctggattctg acccgaaact ag atg atc atc ata ttc aga ctg gtt ggg atg     112
                         Met Ile Ile Ile Phe Arg Leu Val Gly Met
                           1               5                  10 aca gga aat gcc att gtg ttc tgg ctc ctg ggc ttc agc ttg cac agg     160
Thr Gly Asn Ala Ile Val Phe Trp Leu Leu Gly Phe Ser Leu His Arg
             15                  20                  25 aat gcc ttc tca gtc tac att tta aac ttg gcc ctt gct gac ttc gtc     208
Asn Ala Phe Ser Val Tyr Ile Leu Asn Leu Ala Leu Ala Asp Phe Val
         30                  35                  40 ttc ctc ctc tgt cac atc ata gat tcc atg ctg ctt ctc act gtt         256
Phe Leu Leu Cys His Ile Ile Asp Ser Met Leu Leu Leu Thr Val
     45                  50                  55 ttc tac ccc aac aat atc ttt tct ggg tac ttt tac acc atc atg acg     304
Phe Tyr Pro Asn Asn Ile Phe Ser Gly Tyr Phe Tyr Thr Ile Met Thr
 60                  65                  70 gtt ccc tac atc gca ggc ctg agc atg ctc agt gcc atc agc act gag     352
Val Pro Tyr Ile Ala Gly Leu Ser Met Leu Ser Ala Ile Ser Thr Glu
 75                  80                  85                  90 ctc tgc ctg tct gtc ctg tgc ccc atc tgg tat cgc tgc cac cac cca     400
Leu Cys Leu Ser Val Leu Cys Pro Ile Trp Tyr Arg Cys His His Pro
             95                 100                 105 gaa cac aca tca act gtc atg tgt gct gcg ata tgg gtc ctg ccc ctg     448
Glu His Thr Ser Thr Val Met Cys Ala Ala Ile Trp Val Leu Pro Leu
        110                 115                 120 ttg gtc tgc att ctg aat agg tat ttc tgc agt ttc tta gat atc aat     496
Leu Val Cys Ile Leu Asn Arg Tyr Phe Cys Ser Phe Leu Asp Ile Asn
    125                 130                 135 tat aac aat gac aaa cag tgt ctg gca tca aac ttc ttt act aga gca     544
Tyr Asn Asn Asp Lys Gln Cys Leu Ala Ser Asn Phe Phe Thr Arg Ala
140                 145                 150 tac ctg atg ttt ttg ttt gtg gtc ctt tgt ctg tcc agc atg gct ctg     592
Tyr Leu Met Phe Leu Phe Val Val Leu Cys Leu Ser Ser Met Ala Leu
155                 160                 165                 170 ctg gcc agg ttg ttc tgt ggc act ggg cag atg aag ctt acc aga ttg     640
```

```
Leu Ala Arg Leu Phe Cys Gly Thr Gly Gln Met Lys Leu Thr Arg Leu
            175                 180                 185 tac gtg acc atc atg ctg act gtt ttg ggt ttt ctc ctc tgt ggg ttg      688
Tyr Val Thr Ile Met Leu Thr Val Leu Gly Phe Leu Leu Cys Gly Leu
            190                 195                 200 ccc ttt gtc atc tac tac ttc ctg tta ttc aat att aag gat ggt ttt      736
Pro Phe Val Ile Tyr Tyr Phe Leu Leu Phe Asn Ile Lys Asp Gly Phe
            205                 210                 215 tgt tta ttt gat ttt aga ttt tat atg tca aca cat gtc ctg act gct      784
Cys Leu Phe Asp Phe Arg Phe Tyr Met Ser Thr His Val Leu Thr Ala
        220                 225                 230 att aac aac tgt gcc aac ccc ata att tac ttt ttc gag ggc tcc ttc      832
Ile Asn Asn Cys Ala Asn Pro Ile Ile Tyr Phe Phe Glu Gly Ser Phe
235                 240                 245                 250 agg cat cag ttg aag cac cag acc ctc aaa atg gtt ctc cag agt gta      880
Arg His Gln Leu Lys His Gln Thr Leu Lys Met Val Leu Gln Ser Val
                255                 260                 265 ctg cag gac act cct gag ata gct gaa aat atg gtg gag atg tca aga      928
Leu Gln Asp Thr Pro Glu Ile Ala Glu Asn Met Val Glu Met Ser Arg
            270                 275                 280 aac ata cca aag cca tgatgaaaag cctttgcctg gacctca                    970
Asn Ile Pro Lys Pro
            285

<210> SEQ ID NO 21
<211> LENGTH: 287
<212> TYPE: PRT
<213> ORGANISM: Mus musculus

<400> SEQUENCE: 21

Met Ile Ile Ile Phe Arg Leu Val Gly Met Thr Gly Asn Ala Ile Val
 1               5                  10                  15

Phe Trp Leu Leu Gly Phe Ser Leu His Arg Asn Ala Phe Ser Val Tyr
            20                  25                  30

Ile Leu Asn Leu Ala Leu Ala Asp Phe Val Phe Leu Leu Cys His Ile
        35                  40                  45

Ile Asp Ser Met Leu Leu Leu Thr Val Phe Tyr Pro Asn Asn Ile
 50                  55                  60

Phe Ser Gly Tyr Phe Tyr Thr Ile Met Thr Val Pro Tyr Ile Ala Gly
65                  70                  75                  80

Leu Ser Met Leu Ser Ala Ile Ser Thr Glu Leu Cys Leu Ser Val Leu
                85                  90                  95

Cys Pro Ile Trp Tyr Arg Cys His His Pro Glu His Thr Ser Thr Val
            100                 105                 110

Met Cys Ala Ala Ile Trp Val Leu Pro Leu Leu Val Cys Ile Leu Asn
        115                 120                 125

Arg Tyr Phe Cys Ser Phe Leu Asp Ile Asn Tyr Asn Asn Asp Lys Gln
130                 135                 140

Cys Leu Ala Ser Asn Phe Phe Thr Arg Ala Tyr Leu Met Phe Leu Phe
145                 150                 155                 160

Val Val Leu Cys Leu Ser Ser Met Ala Leu Leu Ala Arg Leu Phe Cys
                165                 170                 175

Gly Thr Gly Gln Met Lys Leu Thr Arg Leu Tyr Val Thr Ile Met Leu
            180                 185                 190

Thr Val Leu Gly Phe Leu Leu Cys Gly Leu Pro Phe Val Ile Tyr Tyr
        195                 200                 205

Phe Leu Leu Phe Asn Ile Lys Asp Gly Phe Cys Leu Phe Asp Phe Arg
```

```
                    210                 215                 220
Phe Tyr Met Ser Thr His Val Leu Thr Ala Ile Asn Asn Cys Ala Asn
225                 230                 235                 240

Pro Ile Ile Tyr Phe Phe Glu Gly Ser Phe Arg His Gln Leu Lys His
                245                 250                 255

Gln Thr Leu Lys Met Val Leu Gln Ser Val Leu Gln Asp Thr Pro Glu
            260                 265                 270

Ile Ala Glu Asn Met Val Glu Met Ser Arg Asn Ile Pro Lys Pro
        275                 280                 285

<210> SEQ ID NO 22
<211> LENGTH: 1024
<212> TYPE: DNA
<213> ORGANISM: Mus musculus
<220> FEATURE:
<221> NAME/KEY: CDS
<222> LOCATION: (16)...(918)

<400> SEQUENCE: 22
ccagtgcacg aaacc atg cat aga agt atc agc atc agg att ctg ata aca      51
              Met His Arg Ser Ile Ser Ile Arg Ile Leu Ile Thr
                1               5                   10 aac ttg atg atc gtc atc ctc gga cta gtc ggg cta aca gga aac gcc      99
Asn Leu Met Ile Val Ile Leu Gly Leu Val Gly Leu Thr Gly Asn Ala
        15                  20                  25 att gtg ttc tgg ctc ctg ctc ttc cgc ttg cgc agg aac gcc ttc tca     147
Ile Val Phe Trp Leu Leu Leu Phe Arg Leu Arg Arg Asn Ala Phe Ser
    30                  35                  40 atc tac atc cta aac ttg gcc ctg gct gac ttc ctc ttc ctc ctc tgc     195
Ile Tyr Ile Leu Asn Leu Ala Leu Ala Asp Phe Leu Phe Leu Leu Cys
45                  50                  55                  60 cac atc ata gct tcc aca gag cat att ctc acg ttt tcc tcc ccc aac     243
His Ile Ile Ala Ser Thr Glu His Ile Leu Thr Phe Ser Ser Pro Asn
                65                  70                  75 agt atc ttt atc aat tgc ctt tac acc ttc agg gtg ctt ctc tac atc     291
Ser Ile Phe Ile Asn Cys Leu Tyr Thr Phe Arg Val Leu Leu Tyr Ile
            80                  85                  90 gca ggc ctg agc atg ctc agt gcc atc agc att gag cgc tgc ctg tct     339
Ala Gly Leu Ser Met Leu Ser Ala Ile Ser Ile Glu Arg Cys Leu Ser
        95                  100                 105 gtc atg tgc ccc atc tgg tat cgc tgc cac agc cca gaa cac aca tca     387
Val Met Cys Pro Ile Trp Tyr Arg Cys His Ser Pro Glu His Thr Ser
    110                 115                 120 act gtc atg tgt gct atg atc tgg gtc ctg tct cta ttg ctc tgc att     435
Thr Val Met Cys Ala Met Ile Trp Val Leu Ser Leu Leu Leu Cys Ile
125                 130                 135                 140 ctg tat agg tat ttc tgc ggc ttc ttg gat acc aaa tat gaa gat gac     483
Leu Tyr Arg Tyr Phe Cys Gly Phe Leu Asp Thr Lys Tyr Glu Asp Asp
                145                 150                 155 tat ggg tgt cta gca atg aac ttc ctt act acc gca tac ctg atg ttt     531
Tyr Gly Cys Leu Ala Met Asn Phe Leu Thr Thr Ala Tyr Leu Met Phe
            160                 165                 170 ttg ttt gta gtc ctc tgt gtg tcc agc ctg gct ctg ctg gcc agg ttg     579
Leu Phe Val Val Leu Cys Val Ser Ser Leu Ala Leu Leu Ala Arg Leu
        175                 180                 185 ttc tgt ggc gct gga cgg atg aag ctt acc aga tta tac gtg acc atc     627
Phe Cys Gly Ala Gly Arg Met Lys Leu Thr Arg Leu Tyr Val Thr Ile
    190                 195                 200 acg ctg acc ctt ttg gtt ttt ctc ctc tgc ggg ttg ccc tgt ggc ttc     675
Thr Leu Thr Leu Leu Val Phe Leu Leu Cys Gly Leu Pro Cys Gly Phe
```

```
                205                 210                 215                 220
tac tgg ttc ctg tta tcc aaa att aag aat gtt ttt act gta ttt gaa         723
Tyr Trp Phe Leu Leu Ser Lys Ile Lys Asn Val Phe Thr Val Phe Glu
                    225                 230                 235 ttt agt ctt tat ctg gca tca gtt gtc ctg act gct att aac agc tgt         771
Phe Ser Leu Tyr Leu Ala Ser Val Val Leu Thr Ala Ile Asn Ser Cys
                240                 245                 250 gcc aac ccc atc att tac ttc ttt gtg ggc tca ttc agg cat cgg ttg         819
Ala Asn Pro Ile Ile Tyr Phe Phe Val Gly Ser Phe Arg His Arg Leu
                    255                 260                 265 aag cac cag acc ctc aaa atg gtt ctc cag agt gca ctg cag gac act         867
Lys His Gln Thr Leu Lys Met Val Leu Gln Ser Ala Leu Gln Asp Thr
                270                 275                 280 cct gag aca cct gaa aac atg gtg gag atg tca aga aac aaa gca gag         915
Pro Glu Thr Pro Glu Asn Met Val Glu Met Ser Arg Asn Lys Ala Glu
285                 290                 295                 300 ctg tgatgaagag cctctgcccg gacctcagag gtggctttgg agtgagcact              968
Leu
gccctgctgc acttggccac tgtccactct cctctcagct tactcacttg gcatgc          1024

<210> SEQ ID NO 23
<211> LENGTH: 301
<212> TYPE: PRT
<213> ORGANISM: Mus musculus

<400> SEQUENCE: 23

Met His Arg Ser Ile Ser Ile Arg Ile Leu Ile Thr Asn Leu Met Ile
1               5                   10                  15

Val Ile Leu Gly Leu Val Gly Leu Thr Gly Asn Ala Ile Val Phe Trp
                20                  25                  30

Leu Leu Leu Phe Arg Leu Arg Arg Asn Ala Phe Ser Ile Tyr Ile Leu
            35                  40                  45

Asn Leu Ala Leu Ala Asp Phe Leu Phe Leu Leu Cys His Ile Ile Ala
        50                  55                  60

Ser Thr Glu His Ile Leu Thr Phe Ser Ser Pro Asn Ser Ile Phe Ile
65                  70                  75                  80

Asn Cys Leu Tyr Thr Phe Arg Val Leu Leu Tyr Ile Ala Gly Leu Ser
                85                  90                  95

Met Leu Ser Ala Ile Ser Ile Glu Arg Cys Leu Ser Val Met Cys Pro
            100                 105                 110

Ile Trp Tyr Arg Cys His Ser Pro Glu His Thr Ser Thr Val Met Cys
        115                 120                 125

Ala Met Ile Trp Val Leu Ser Leu Leu Leu Cys Ile Leu Tyr Arg Tyr
    130                 135                 140

Phe Cys Gly Phe Leu Asp Thr Lys Tyr Glu Asp Asp Tyr Gly Cys Leu
145                 150                 155                 160

Ala Met Asn Phe Leu Thr Thr Ala Tyr Leu Met Phe Leu Phe Val Val
                165                 170                 175

Leu Cys Val Ser Ser Leu Ala Leu Leu Ala Arg Leu Phe Cys Gly Ala
            180                 185                 190

Gly Arg Met Lys Leu Thr Arg Leu Tyr Val Thr Ile Thr Leu Thr Leu
        195                 200                 205

Leu Val Phe Leu Leu Cys Gly Leu Pro Cys Gly Phe Tyr Trp Phe Leu
    210                 215                 220

Leu Ser Lys Ile Lys Asn Val Phe Thr Val Phe Glu Phe Ser Leu Tyr
225                 230                 235                 240
```

-continued

```
Leu Ala Ser Val Val Leu Thr Ala Ile Asn Ser Cys Ala Asn Pro Ile
            245                 250                 255

Ile Tyr Phe Phe Val Gly Ser Phe Arg His Arg Leu Lys His Gln Thr
        260                 265                 270

Leu Lys Met Val Leu Gln Ser Ala Leu Gln Asp Thr Pro Glu Thr Pro
    275                 280                 285

Glu Asn Met Val Glu Met Ser Arg Asn Lys Ala Glu Leu
290                 295                 300

<210> SEQ ID NO 24
<211> LENGTH: 1045
<212> TYPE: DNA
<213> ORGANISM: Mus musculus
<220> FEATURE:
<221> NAME/KEY: CDS
<222> LOCATION: (106)...(1020)

<400> SEQUENCE: 24
tttgtgttca tagtgaatga ctaatttctt ctttgtgttc ccagtgcaga gtttctggcc    60
ctaaacacct cagcctcagc aatgtcaccc acgacaacaa gtcca atg gac gaa acc   117
                                                Met Asp Glu Thr
                                                  1 agc cct aga agt att gac atc gag tca ctg atc cca aac ttg atg atc   165
Ser Pro Arg Ser Ile Asp Ile Glu Ser Leu Ile Pro Asn Leu Met Ile
  5                  10                  15                  20 atc atc ttt gga ctg gtt ggg ctg aca gga aat gcc att gtg ctc tgg   213
Ile Ile Phe Gly Leu Val Gly Leu Thr Gly Asn Ala Ile Val Leu Trp
                 25                  30                  35 ctc ctg ggc ttc tgc ttg cac agg aat gcc ttc tta gtc tac atc cta   261
Leu Leu Gly Phe Cys Leu His Arg Asn Ala Phe Leu Val Tyr Ile Leu
             40                  45                  50 aac ttg gcc ctg gct gac ttc ctc ttc ctc tgt cac ttc ata aat       309
Asn Leu Ala Leu Ala Asp Phe Leu Phe Leu Cys His Phe Ile Asn
         55                  60                  65 tca gca atg ttt ctt ctc aag gtt cct ata ccc aac ggt atc ttt gtc   357
Ser Ala Met Phe Leu Leu Lys Val Pro Ile Pro Asn Gly Ile Phe Val
     70                  75                  80 tat tgc ttt tac acc atc aaa atg gtt ctc tac atc aca ggc tga agc   405
Tyr Cys Phe Tyr Thr Ile Lys Met Val Leu Tyr Ile Thr Gly Leu Ser
 85                  90                  95                 100 atg ctc agt gcc atc agc act gag cgc tgc ctt tct gtc ctg tgc ccc   453
Met Leu Ser Ala Ile Ser Thr Glu Arg Cys Leu Ser Val Leu Cys Pro
                105                 110                 115 atc tgg tat cac tgc cgc cgc cca gaa cac aca tca act gtc atg tgt   501
Ile Trp Tyr His Cys Arg Arg Pro Glu His Thr Ser Thr Val Met Cys
            120                 125                 130 gct gtg att tgg atc ttt tcc gtg ttg atc tgc att ctg aaa gaa tat   549
Ala Val Ile Trp Ile Phe Ser Val Leu Ile Cys Ile Leu Lys Glu Tyr
        135                 140                 145 ttc tgt gat ttc ttt ggt acc aaa ttg gga aat tac tat gtg tgt cag   597
Phe Cys Asp Phe Phe Gly Thr Lys Leu Gly Asn Tyr Tyr Val Cys Gln
    150                 155                 160 gca tcc aac ttc ttt atg gga gca tac cta atg ttt ttg ttt gta gtc   645
Ala Ser Asn Phe Phe Met Gly Ala Tyr Leu Met Phe Leu Phe Val Val
165                 170                 175                 180 ctc tgt ctg tcc acc ctg gct ctg ctg gcc agg ttg ttc tgt ggt gct   693
Leu Cys Leu Ser Thr Leu Ala Leu Leu Ala Arg Leu Phe Cys Gly Ala
                185                 190                 195 gag aag atg aaa ttt acc aga tta ttc gtg acc atc atg ctg acc att   741
Glu Lys Met Lys Phe Thr Arg Leu Phe Val Thr Ile Met Leu Thr Ile
```

```
              200                 205                 210
ttg gtt ttt ctc ctc tgt ggg ttg cca tgg ggc ttc ttc tgg ttc ctg      789
Leu Val Phe Leu Leu Cys Gly Leu Pro Trp Gly Phe Phe Trp Phe Leu
            215                 220                 225 tta atc tgg att aag ggt ggt ttt agt gta cta gat tat aga ctt tat      837
Leu Ile Trp Ile Lys Gly Gly Phe Ser Val Leu Asp Tyr Arg Leu Tyr
230                 235                 240 ttg gca tca att gtc cta act gtt gtt aac agc tgt gcc aac ccc atc      885
Leu Ala Ser Ile Val Leu Thr Val Val Asn Ser Cys Ala Asn Pro Ile
245                 250                 255                 260 att tac ttc ttc gtg gga tca ttc agg cat cgg ttg aag cac cag acc      933
Ile Tyr Phe Phe Val Gly Ser Phe Arg His Arg Leu Lys His Gln Thr
                265                 270                 275 ctc aaa atg gtt ctc cag agt gca ctg cag gac act cct gag aca cat      981
Leu Lys Met Val Leu Gln Ser Ala Leu Gln Asp Thr Pro Glu Thr His
            280                 285                 290 gaa aac atg gtg gag atg tca aga atc aaa gca gag cag tgatgaagag      1030
Glu Asn Met Val Glu Met Ser Arg Ile Lys Ala Glu Gln
            295                 300                 305 cctctgcctg gacct                                                    1045

<210> SEQ ID NO 25
<211> LENGTH: 305
<212> TYPE: PRT
<213> ORGANISM: Mus musculus

<400> SEQUENCE: 25

Met Asp Glu Thr Ser Pro Arg Ser Ile Asp Ile Glu Ser Leu Ile Pro
1               5                   10                  15

Asn Leu Met Ile Ile Ile Phe Gly Leu Val Gly Leu Thr Gly Asn Ala
            20                  25                  30

Ile Val Leu Trp Leu Leu Gly Phe Cys Leu His Arg Asn Ala Phe Leu
        35                  40                  45

Val Tyr Ile Leu Asn Leu Ala Leu Ala Asp Phe Leu Phe Leu Leu Cys
    50                  55                  60

His Phe Ile Asn Ser Ala Met Phe Leu Leu Lys Val Pro Ile Pro Asn
65                  70                  75                  80

Gly Ile Phe Val Tyr Cys Phe Tyr Thr Ile Lys Met Val Leu Tyr Ile
                85                  90                  95

Thr Gly Leu Ser Met Leu Ser Ala Ile Ser Thr Glu Arg Cys Leu Ser
            100                 105                 110

Val Leu Cys Pro Ile Trp Tyr His Cys Arg Arg Pro Glu His Thr Ser
        115                 120                 125

Thr Val Met Cys Ala Val Ile Trp Ile Phe Ser Val Leu Ile Cys Ile
    130                 135                 140

Leu Lys Glu Tyr Phe Cys Asp Phe Phe Gly Thr Lys Leu Gly Asn Tyr
145                 150                 155                 160

Tyr Val Cys Gln Ala Ser Asn Phe Phe Met Gly Ala Tyr Leu Met Phe
                165                 170                 175

Leu Phe Val Val Leu Cys Leu Ser Thr Leu Ala Leu Leu Ala Arg Leu
            180                 185                 190

Phe Cys Gly Ala Glu Lys Met Lys Phe Thr Arg Leu Phe Val Thr Ile
        195                 200                 205

Met Leu Thr Ile Leu Val Phe Leu Leu Cys Gly Leu Pro Trp Gly Phe
    210                 215                 220

Phe Trp Phe Leu Leu Ile Trp Ile Lys Gly Gly Phe Ser Val Leu Asp
```

```
225                 230                 235                 240
Tyr Arg Leu Tyr Leu Ala Ser Ile Val Leu Thr Val Asn Ser Cys
                245                 250                 255

Ala Asn Pro Ile Ile Tyr Phe Phe Val Gly Ser Phe Arg His Arg Leu
                260                 265                 270

Lys His Gln Thr Leu Lys Met Val Leu Gln Ser Ala Leu Gln Asp Thr
                275                 280                 285

Pro Glu Thr His Glu Asn Met Val Glu Met Ser Arg Ile Lys Ala Glu
                290                 295                 300

Gln
305

<210> SEQ ID NO 26
<211> LENGTH: 980
<212> TYPE: DNA
<213> ORGANISM: Mus musculus
<220> FEATURE:
<221> NAME/KEY: CDS
<222> LOCATION: (45)...(959)

<400> SEQUENCE: 26
tagacacctc agcatatgca atggcaccca cgaccacaaa tcca atg gac aaa acc      56
                                                 Met Asp Lys Thr
                                                  1 atc ctt gga agt att gac atc gag acc ctg atc cga cat ttg atg atc     104
Ile Leu Gly Ser Ile Asp Ile Glu Thr Leu Ile Arg His Leu Met Ile
 5                  10                  15                  20 atc atc ttc gga ctg gtc ggg ctg aca gga aat gcc att gtg ttc tgg     152
Ile Ile Phe Gly Leu Val Gly Leu Thr Gly Asn Ala Ile Val Phe Trp
                25                  30                  35 ctc ctg ggc ttc cac ttg cac agg aat gcc ttc tta gtc tac atc ata     200
Leu Leu Gly Phe His Leu His Arg Asn Ala Phe Leu Val Tyr Ile Ile
            40                  45                  50 aac ttg gcc ctg gct gac ttc ttc tat ctg ctc tgt cac atc ata aat     248
Asn Leu Ala Leu Ala Asp Phe Phe Tyr Leu Leu Cys His Ile Ile Asn
        55                  60                  65 tcc ata atg ttt ctt ctc aag gtt ccc tca ccc aac att atc ttg gac     296
Ser Ile Met Phe Leu Leu Lys Val Pro Ser Pro Asn Ile Ile Leu Asp
    70                  75                  80 cat tgc ttt tac acc atc atg ata gtt ctc tac atc aca ggc ctg agc     344
His Cys Phe Tyr Thr Ile Met Ile Val Leu Tyr Ile Thr Gly Leu Ser
85                  90                  95                 100 atg ctc agc gcc atc agc act gag cgc tgc ctg tct gtc ctg tgc ccc     392
Met Leu Ser Ala Ile Ser Thr Glu Arg Cys Leu Ser Val Leu Cys Pro
                105                 110                 115 atc tgg tat cgc tgc cac cgt cca gaa cac aca tca act gtc atg tgt     440
Ile Trp Tyr Arg Cys His Arg Pro Glu His Thr Ser Thr Val Met Cys
            120                 125                 130 gct gtg atc tgg gta atg tcc ctg ttg atc tct att ctc aat gga tat     488
Ala Val Ile Trp Val Met Ser Leu Leu Ile Ser Ile Leu Asn Gly Tyr
        135                 140                 145 ttc tgt aat ttc tct agt ccc aaa tat gta aat aac tct gtg tgt cag     536
Phe Cys Asn Phe Ser Ser Pro Lys Tyr Val Asn Asn Ser Val Cys Gln
    150                 155                 160 gca tca cac atc ttt atc aga aca tac cca ata ttt ttg ttt gta ctc     584
Ala Ser His Ile Phe Ile Arg Thr Tyr Pro Ile Phe Leu Phe Val Leu
165                 170                 175                 180 ctc tgt ctg tcc acc ctt gct ctg ctg gcc agg ttg ttc tct ggt gct     632
Leu Cys Leu Ser Thr Leu Ala Leu Leu Ala Arg Leu Phe Ser Gly Ala
                185                 190                 195
```

```
ggg aag agg aaa ttt acc aga tta ttc gtg acc atc atg ctg gcc att      680
Gly Lys Arg Lys Phe Thr Arg Leu Phe Val Thr Ile Met Leu Ala Ile
            200                 205                 210 ttg gtt ttt ctt ctc tgt ggg tta ccc ctg ggc ttc ttc tgg ttt ctg      728
Leu Val Phe Leu Leu Cys Gly Leu Pro Leu Gly Phe Phe Trp Phe Leu
        215                 220                 225 tca ccc tgg att gag gat cgt ttc att gta cta gat tat aga ctt ttt      776
Ser Pro Trp Ile Glu Asp Arg Phe Ile Val Leu Asp Tyr Arg Leu Phe
    230                 235                 240 ttt gca tca gtt gtc cta act gtt gtt aac agc tgt gcc aac ccc atc      824
Phe Ala Ser Val Val Leu Thr Val Val Asn Ser Cys Ala Asn Pro Ile
245                 250                 255                 260 att tac ttc ttt gtg ggc tcc ttc agg cat cgg ttg aag caa cag acc      872
Ile Tyr Phe Phe Val Gly Ser Phe Arg His Arg Leu Lys Gln Gln Thr
                265                 270                 275 ctc aaa atg ttt ctc cag aga gca ctg cag gac acc cct gag aca cct      920
Leu Lys Met Phe Leu Gln Arg Ala Leu Gln Asp Thr Pro Glu Thr Pro
            280                 285                 290 gaa aac atg gtg gag atg tca aga agc aaa gca gag ccg tgatgaagag      969
Glu Asn Met Val Glu Met Ser Arg Ser Lys Ala Glu Pro
        295                 300                 305 cctcttccag g                                                          980

<210> SEQ ID NO 27
<211> LENGTH: 305
<212> TYPE: PRT
<213> ORGANISM: Mus musculus

<400> SEQUENCE: 27

Met Asp Lys Thr Ile Leu Gly Ser Ile Asp Ile Glu Thr Leu Ile Arg
 1               5                  10                  15

His Leu Met Ile Ile Phe Gly Leu Val Gly Leu Thr Gly Asn Ala
            20                  25                  30

Ile Val Phe Trp Leu Leu Gly Phe His Leu His Arg Asn Ala Phe Leu
        35                  40                  45

Val Tyr Ile Ile Asn Leu Ala Leu Ala Asp Phe Phe Tyr Leu Leu Cys
    50                  55                  60

His Ile Ile Asn Ser Ile Met Phe Leu Leu Lys Val Pro Ser Pro Asn
65                  70                  75                  80

Ile Ile Leu Asp His Cys Phe Tyr Thr Ile Met Ile Val Leu Tyr Ile
                85                  90                  95

Thr Gly Leu Ser Met Leu Ser Ala Ile Ser Thr Glu Arg Cys Leu Ser
            100                 105                 110

Val Leu Cys Pro Ile Trp Tyr Arg Cys His Arg Pro Glu His Thr Ser
        115                 120                 125

Thr Val Met Cys Ala Val Ile Trp Val Met Ser Leu Leu Ile Ser Ile
    130                 135                 140

Leu Asn Gly Tyr Phe Cys Asn Phe Ser Ser Pro Lys Tyr Val Asn Asn
145                 150                 155                 160

Ser Val Cys Gln Ala Ser His Ile Phe Ile Arg Thr Tyr Pro Ile Phe
                165                 170                 175

Leu Phe Val Leu Leu Cys Leu Ser Thr Leu Ala Leu Leu Ala Arg Leu
            180                 185                 190

Phe Ser Gly Ala Gly Lys Arg Lys Phe Thr Arg Leu Phe Val Thr Ile
        195                 200                 205

Met Leu Ala Ile Leu Val Phe Leu Leu Cys Gly Leu Pro Leu Gly Phe
```

```
                  210                 215                 220
Phe Trp Phe Leu Ser Pro Trp Ile Glu Asp Arg Phe Ile Val Leu Asp
225                 230                 235                 240

Tyr Arg Leu Phe Phe Ala Ser Val Val Leu Thr Val Val Asn Ser Cys
                245                 250                 255

Ala Asn Pro Ile Ile Tyr Phe Val Gly Ser Phe Arg His Arg Leu
                260                 265                 270

Lys Gln Gln Thr Leu Lys Met Phe Leu Gln Arg Ala Leu Gln Asp Thr
                275                 280                 285

Pro Glu Thr Pro Glu Asn Met Val Glu Met Ser Arg Ser Lys Ala Glu
    290                 295                 300

Pro
305

<210> SEQ ID NO 28
<211> LENGTH: 408
<212> TYPE: DNA
<213> ORGANISM: Homo sapiens
<220> FEATURE:
<221> NAME/KEY: CDS
<222> LOCATION: (1)...(405)

<400> SEQUENCE: 28 atg gag act ctc ccc aag gtt cta gag gtc gat gag aag tct cca gaa    48
Met Glu Thr Leu Pro Lys Val Leu Glu Val Asp Glu Lys Ser Pro Glu
1               5                   10                  15 gcc aag gac ctg ctg ccc agc cag acc gcc agc tcc ctg tgc atc agc    96
Ala Lys Asp Leu Leu Pro Ser Gln Thr Ala Ser Ser Leu Cys Ile Ser
                20                  25                  30 tcc agg agc gag tct gtc tgg acc acc acc ccc agg agt aac tgg gaa   144
Ser Arg Ser Glu Ser Val Trp Thr Thr Thr Pro Arg Ser Asn Trp Glu
            35                  40                  45 atc tac cgc aag ccc atc gtt atc atg tca gtg ggc ggt gcc atc ctg   192
Ile Tyr Arg Lys Pro Ile Val Ile Met Ser Val Gly Gly Ala Ile Leu
        50                  55                  60 ctt ttc ggc gtg gtc atc acc tgc ttg gcc tac acc ttg aag ctg agt   240
Leu Phe Gly Val Val Ile Thr Cys Leu Ala Tyr Thr Leu Lys Leu Ser
65                  70                  75                  80 gac aag agt ctc tcc atc ctc aaa atg gta ggg cct ggc ttc ctg tcc   288
Asp Lys Ser Leu Ser Ile Leu Lys Met Val Gly Pro Gly Phe Leu Ser
                85                  90                  95 ctg gga ctc atg atg ctg gtg tgc ggg ctg gtg tgg gtg ccc atc atc   336
Leu Gly Leu Met Met Leu Val Cys Gly Leu Val Trp Val Pro Ile Ile
                100                 105                 110 aaa aag aaa cag aag cac aga cag aag tcg aat ttc tta cgc agc ctc   384
Lys Lys Lys Gln Lys His Arg Gln Lys Ser Asn Phe Leu Arg Ser Leu
            115                 120                 125 aag tcc ttc ttc ctg act cgc tga                                   408
Lys Ser Phe Phe Leu Thr Arg
        130             135

<210> SEQ ID NO 29
<211> LENGTH: 135
<212> TYPE: PRT
<213> ORGANISM: Homo sapiens

<400> SEQUENCE: 29

Met Glu Thr Leu Pro Lys Val Leu Glu Val Asp Glu Lys Ser Pro Glu
1               5                   10                  15

Ala Lys Asp Leu Leu Pro Ser Gln Thr Ala Ser Ser Leu Cys Ile Ser
```

```
                    20                  25                  30
Ser Arg Ser Glu Ser Val Trp Thr Thr Thr Pro Arg Ser Asn Trp Glu
         35                  40                  45

Ile Tyr Arg Lys Pro Ile Val Ile Met Ser Val Gly Gly Ala Ile Leu
 50                  55                  60

Leu Phe Gly Val Val Ile Thr Cys Leu Ala Tyr Thr Leu Lys Leu Ser
 65                  70                  75                  80

Asp Lys Ser Leu Ser Ile Leu Lys Met Val Gly Pro Gly Phe Leu Ser
             85                  90                  95

Leu Gly Leu Met Met Leu Val Cys Gly Leu Val Trp Val Pro Ile Ile
             100                 105                 110

Lys Lys Lys Gln Lys His Arg Gln Lys Ser Asn Phe Leu Arg Ser Leu
         115                 120                 125

Lys Ser Phe Phe Leu Thr Arg
         130                 135

<210> SEQ ID NO 30
<211> LENGTH: 1400
<212> TYPE: DNA
<213> ORGANISM: Homo sapiens
<220> FEATURE:
<221> NAME/KEY: CDS
<222> LOCATION: (332)...(1297)

<400> SEQUENCE: 30
tcaggcccag gatagagtaa tcatcgggtc cacagcactg gctagatgag tgggggtgtt      60
ttgatcctaa tgttattccc atgttagcac agaacttgtg tggcagtaga gagaggtcag    120
gcttcagagt cagcaagaac tggatttcaa actggatttg aggaccccca ccttttgata    180
ggtgacttat tctctgtgag tctctgatct gccctcttta aatgaggaag taaatcccac    240
atggcagggt ggtggggaga atcagagatc atacagctgg tgatcacaac tggtttctgt    300
ttccagggtc accagactgg ggtttctgag c atg gat tca acc atc cca gtc      352
                                    Met Asp Ser Thr Ile Pro Val
                                     1               5 ttg ggt aca gaa ctg aca cca atc aac gga cgt gag gag act cct tgc    400
Leu Gly Thr Glu Leu Thr Pro Ile Asn Gly Arg Glu Glu Thr Pro Cys
         10                  15                  20 tac aag cag acc ctg agc ttc acg ggg ctg acg tgc atc gtt tcc ctt    448
Tyr Lys Gln Thr Leu Ser Phe Thr Gly Leu Thr Cys Ile Val Ser Leu
     25                  30                  35 gtc gcg ctg aca gga aac gcg gtt gtg ctc tgg ctc ctg ggc tgc cgc    496
Val Ala Leu Thr Gly Asn Ala Val Val Leu Trp Leu Leu Gly Cys Arg
 40                  45                  50                  55 atg cgc agg aac gct gtc tcc atc tac atc ctc aac ctg gtc gcg gcc    544
Met Arg Arg Asn Ala Val Ser Ile Tyr Ile Leu Asn Leu Val Ala Ala
             60                  65                  70 gac ttc ctc ttc ctt agc ggc cac att ata tgt tcg ccg tta cgc ctc    592
Asp Phe Leu Phe Leu Ser Gly His Ile Ile Cys Ser Pro Leu Arg Leu
         75                  80                  85 atc aat atc cgc cat ccc atc tcc aaa atc ctc agt cct gtg atg acc    640
Ile Asn Ile Arg His Pro Ile Ser Lys Ile Leu Ser Pro Val Met Thr
     90                  95                 100 ttt ccc tac ttt ata ggc cta agc atg ctg agc gcc atc agc acc gag    688
Phe Pro Tyr Phe Ile Gly Leu Ser Met Leu Ser Ala Ile Ser Thr Glu
105                 110                 115 cgc tgc ctg tcc atc ctg tgg ccc atc tgg tac cac tgc cgc cgc ccc    736
Arg Cys Leu Ser Ile Leu Trp Pro Ile Trp Tyr His Cys Arg Arg Pro
120                 125                 130                 135
```

```
aga tac ctg tca tcg gtc atg tgt gtc ctg ctc tgg gcc ctg tcc ctg      784
Arg Tyr Leu Ser Ser Val Met Cys Val Leu Leu Trp Ala Leu Ser Leu
            140                 145                 150 ctg cgg agt atc ctg gag tgg atg ttc tgt gac ttc ctg ttt agt ggt      832
Leu Arg Ser Ile Leu Glu Trp Met Phe Cys Asp Phe Leu Phe Ser Gly
            155                 160                 165 gct gat tct gtt tgg tgt gaa acg tca gat ttc att aca atc gcg tgg      880
Ala Asp Ser Val Trp Cys Glu Thr Ser Asp Phe Ile Thr Ile Ala Trp
        170                 175                 180 ctg gtt ttt tta tgt gtg gtt ctc tgt ggg tcc agc ctg gtc ctg ctg      928
Leu Val Phe Leu Cys Val Val Leu Cys Gly Ser Ser Leu Val Leu Leu
        185                 190                 195 gtc agg att ctc tgt gga tcc cgg aag atg ccg ctg acc agg ctg tac      976
Val Arg Ile Leu Cys Gly Ser Arg Lys Met Pro Leu Thr Arg Leu Tyr
200                 205                 210                 215 gtg acc atc ctc ctc aca gtg ctg gtc ttc ctc ctc tgt ggc ctg ccc     1024
Val Thr Ile Leu Leu Thr Val Leu Val Phe Leu Leu Cys Gly Leu Pro
                220                 225                 230 ttt ggc att cag tgg gcc ctg ttt tcc agg atc cac ctg gat tgg aaa     1072
Phe Gly Ile Gln Trp Ala Leu Phe Ser Arg Ile His Leu Asp Trp Lys
                235                 240                 245 gtc tta ttt tgt cat gtg cat cta gtt tcc att ttc ctg tcc gct ctt     1120
Val Leu Phe Cys His Val His Leu Val Ser Ile Phe Leu Ser Ala Leu
            250                 255                 260 aac agc agt gcc aac ccc atc att tac ttc ttc gtg ggc tcc ttt agg     1168
Asn Ser Ser Ala Asn Pro Ile Ile Tyr Phe Phe Val Gly Ser Phe Arg
            265                 270                 275 cag cgt caa aat agg cag aac ctg aag ctg gtt ctc cag agg gct ctg     1216
Gln Arg Gln Asn Arg Gln Asn Leu Lys Leu Val Leu Gln Arg Ala Leu
280                 285                 290                 295 cag gac acg cct gag gtg gat gaa ggt gga ggg tgg ctt cct cag gaa     1264
Gln Asp Thr Pro Glu Val Asp Glu Gly Gly Gly Trp Leu Pro Gln Glu
                300                 305                 310 acc ctg gag ctg tcg gga agc aga ttg gag cag tgaggaagaa cctctgccct   1317
Thr Leu Glu Leu Ser Gly Ser Arg Leu Glu Gln
            315                 320 gtcagacagg actttgagag caatgctgcc ctgccaccct tgacaattat atgcattttt   1377
cttagccttc tgcctcagaa atg                                           1400

<210> SEQ ID NO 31
<211> LENGTH: 322
<212> TYPE: PRT
<213> ORGANISM: Homo sapiens

<400> SEQUENCE: 31

Met Asp Ser Thr Ile Pro Val Leu Gly Thr Glu Leu Thr Pro Ile Asn
1               5                   10                  15

Gly Arg Glu Glu Thr Pro Cys Tyr Lys Gln Thr Leu Ser Phe Thr Gly
            20                  25                  30

Leu Thr Cys Ile Val Ser Leu Ala Leu Thr Gly Asn Ala Val Val
        35                  40                  45

Leu Trp Leu Leu Gly Cys Arg Met Arg Arg Asn Ala Val Ser Ile Tyr
    50                  55                  60

Ile Leu Asn Leu Val Ala Ala Asp Phe Leu Phe Leu Ser Gly His Ile
65                  70                  75                  80

Ile Cys Ser Pro Leu Arg Leu Ile Asn Ile Arg His Pro Ile Ser Lys
                85                  90                  95
```

```
Ile Leu Ser Pro Val Met Thr Phe Pro Tyr Phe Ile Gly Leu Ser Met
            100                 105                 110

Leu Ser Ala Ile Ser Thr Glu Arg Cys Leu Ser Ile Leu Trp Pro Ile
        115                 120                 125

Trp Tyr His Cys Arg Arg Pro Arg Tyr Leu Ser Val Met Cys Val
130                 135                 140

Leu Leu Trp Ala Leu Ser Leu Leu Arg Ser Ile Leu Glu Trp Met Phe
145                 150                 155                 160

Cys Asp Phe Leu Phe Ser Gly Ala Asp Ser Val Trp Cys Glu Thr Ser
                165                 170                 175

Asp Phe Ile Thr Ile Ala Trp Leu Val Phe Leu Cys Val Leu Cys
            180                 185                 190

Gly Ser Ser Leu Val Leu Val Arg Ile Leu Cys Gly Ser Arg Lys
        195                 200                 205

Met Pro Leu Thr Arg Leu Tyr Val Thr Ile Leu Leu Thr Val Leu Val
210                 215                 220

Phe Leu Leu Cys Gly Leu Pro Phe Gly Ile Gln Trp Ala Leu Phe Ser
225                 230                 235                 240

Arg Ile His Leu Asp Trp Lys Val Leu Phe Cys His Val His Leu Val
            245                 250                 255

Ser Ile Phe Leu Ser Ala Leu Asn Ser Ser Ala Asn Pro Ile Ile Tyr
            260                 265                 270

Phe Phe Val Gly Ser Phe Arg Gln Arg Gln Asn Arg Gln Asn Leu Lys
                275                 280                 285

Leu Val Leu Gln Arg Ala Leu Gln Asp Thr Pro Glu Val Asp Glu Gly
        290                 295                 300

Gly Gly Trp Leu Pro Gln Glu Thr Leu Glu Leu Ser Gly Ser Arg Leu
305                 310                 315                 320

Glu Gln

<210> SEQ ID NO 32
<211> LENGTH: 1604
<212> TYPE: DNA
<213> ORGANISM: Homo sapiens
<220> FEATURE:
<221> NAME/KEY: CDS
<222> LOCATION: (433)...(1398)

<400> SEQUENCE: 32
tgcatggtct tccttcctgt ccatggatga ccagtcctag tcacgagtgt gtcacaacca    60
cctctttgtg tatctgaatt cctccacctg aaagaaaatt tcagacccag gatagattaa   120
tcatcgggtc caaagccctg gccggatgag tgggggtgtt ttgatcctaa tgttattccc   180
atgtcagcac agaacttgtg tggcagtaga gagatgtcag gcttcagagt caacaagaac   240
tggatttcaa actggatttg aggaccccca cctttggtaa gtgacttatt atctgcgagc   300 ctctgttttct ctcttcttta aatgaggaca gtaaatccca tacggcaggg tggtggggag   360
aatcagagat gatacagctg gtgatcacat ctggtttgtg ttcccagggg caccagacta   420
gagtttctga gc atg gat cca acc gtc cca gtc ttc ggt aca aaa ctg aca   471
              Met Asp Pro Thr Val Pro Val Phe Gly Thr Lys Leu Thr
                1               5                   10 cca atc aac gga cgt gag gag act cct tgc tac aat cag acc ctg agc   519
Pro Ile Asn Gly Arg Glu Glu Thr Pro Cys Tyr Asn Gln Thr Leu Ser
     15                  20                  25 ttc acg gtg ctg acg tgc atc att tcc ctt gtc gga ctg aca gga aac   567
Phe Thr Val Leu Thr Cys Ile Ile Ser Leu Val Gly Leu Thr Gly Asn
```

```
              30                  35                  40                  45
gcg gta gtg ctc tgg ctc ctg ggc tac cgc atg cgc agg aac gct gtc       615
Ala Val Val Leu Trp Leu Leu Gly Tyr Arg Met Arg Arg Asn Ala Val
             50                  55                  60 tcc atc tac atc ctc aac ctg gcc gca gca gac ttc ctc ttc ctc agc       663
Ser Ile Tyr Ile Leu Asn Leu Ala Ala Ala Asp Phe Leu Phe Leu Ser
         65                  70                  75 ttc cag att ata cgt tcg cca tta cgc ctc atc aat atc agc cat ctc       711
Phe Gln Ile Ile Arg Ser Pro Leu Arg Leu Ile Asn Ile Ser His Leu
     80                  85                  90 atc cgc aaa atc ctc gtt tct gtg atg acc ttt ccc tac ttt aca ggc       759
Ile Arg Lys Ile Leu Val Ser Val Met Thr Phe Pro Tyr Phe Thr Gly
 95                 100                 105 ctg agt atg ctg agc gcc atc agc acc gag cgc tgc ctg tct gtt ctg       807
Leu Ser Met Leu Ser Ala Ile Ser Thr Glu Arg Cys Leu Ser Val Leu
110                 115                 120                 125 tgg ccc atc tgg tac cgc tgc cgc cgc cca aca cac ctg tca gcg gtc       855
Trp Pro Ile Trp Tyr Arg Cys Arg Arg Pro Thr His Leu Ser Ala Val
                130                 135                 140 gtg tgt gtc ctg ctc tgg ggc ctg tcc ctg ctg ttt agt atg ctg gag       903
Val Cys Val Leu Leu Trp Gly Leu Ser Leu Leu Phe Ser Met Leu Glu
            145                 150                 155 tgg agg ttc tgt gac ttc ctg ttt agt ggt gct gat tct agt tgg tgt       951
Trp Arg Phe Cys Asp Phe Leu Phe Ser Gly Ala Asp Ser Ser Trp Cys
        160                 165                 170 gaa acg tca gat ttc atc cca gtc gcg tgg ctg att ttt tta tgt gtg       999
Glu Thr Ser Asp Phe Ile Pro Val Ala Trp Leu Ile Phe Leu Cys Val
    175                 180                 185 gtt ctc tgt gtt tcc agc ctg gtc ctg ctg gtc agg atc ctc tgt gga       1047
Val Leu Cys Val Ser Ser Leu Val Leu Leu Val Arg Ile Leu Cys Gly
190                 195                 200                 205 tcc cgg aag atg ccg ctg acc agg ctg tac gtg acc atc ctg ctc aca       1095
Ser Arg Lys Met Pro Leu Thr Arg Leu Tyr Val Thr Ile Leu Leu Thr
                210                 215                 220 gtg ctg gtc ttc ctc ctc tgc ggc ctg ccc ttc ggc att ctg ggg gcc       1143
Val Leu Val Phe Leu Leu Cys Gly Leu Pro Phe Gly Ile Leu Gly Ala
            225                 230                 235 cta att tac agg atg cac ctg aat ttg gaa gtc tta tat tgt cat gtt       1191
Leu Ile Tyr Arg Met His Leu Asn Leu Glu Val Leu Tyr Cys His Val
        240                 245                 250 tat ctg gtt tgc atg tcc ctg tcc tct cta aac agt agt gcc aac ccc       1239
Tyr Leu Val Cys Met Ser Leu Ser Ser Leu Asn Ser Ser Ala Asn Pro
    255                 260                 265 atc att tac ttc ttc gtg ggc tcc ttt agg cag cgt caa aat agg cag       1287
Ile Ile Tyr Phe Phe Val Gly Ser Phe Arg Gln Arg Gln Asn Arg Gln
270                 275                 280                 285 aac ctg aag ctg gtt ctc cag agg gct ctg cag gac aag cct gag gtg       1335
Asn Leu Lys Leu Val Leu Gln Arg Ala Leu Gln Asp Lys Pro Glu Val
                290                 295                 300 gat aaa ggt gaa ggg cag ctt cct gag gaa agc ctg gag ctg tcg gga       1383
Asp Lys Gly Glu Gly Gln Leu Pro Glu Glu Ser Leu Glu Leu Ser Gly
            305                 310                 315 agc aga ttg ggg cca tgagggagag cctctgccct gtcagtcaga cgggactttg       1438
Ser Arg Leu Gly Pro
                320 agagcaacac tgtcctgcca cccttgacaa ttacatgcgt ttttcttagc gtttcgcctc     1498 agaaatgtct cagtggtaac tcaaggtctt caaataaatg tttatctaac ctgacagttg     1558 cagttttcac ccatggaaag cattagtctg acagtacaat gtttgg                    1604
```

<210> SEQ ID NO 33
<211> LENGTH: 322
<212> TYPE: PRT
<213> ORGANISM: Homo sapiens

<400> SEQUENCE: 33

```
Met Asp Pro Thr Val Pro Val Phe Gly Thr Lys Leu Thr Pro Ile Asn
 1               5                  10                  15

Gly Arg Glu Glu Thr Pro Cys Tyr Asn Gln Thr Leu Ser Phe Thr Val
            20                  25                  30

Leu Thr Cys Ile Ile Ser Leu Val Gly Leu Thr Gly Asn Ala Val Val
        35                  40                  45

Leu Trp Leu Leu Gly Tyr Arg Met Arg Arg Asn Ala Val Ser Ile Tyr
50                  55                  60

Ile Leu Asn Leu Ala Ala Ala Asp Phe Leu Phe Leu Ser Phe Gln Ile
65                  70                  75                  80

Ile Arg Ser Pro Leu Arg Leu Ile Asn Ile Ser His Leu Ile Arg Lys
                85                  90                  95

Ile Leu Val Ser Val Met Thr Phe Pro Tyr Phe Thr Gly Leu Ser Met
            100                 105                 110

Leu Ser Ala Ile Ser Thr Glu Arg Cys Leu Ser Val Leu Trp Pro Ile
        115                 120                 125

Trp Tyr Arg Cys Arg Arg Pro Thr His Leu Ser Ala Val Val Cys Val
130                 135                 140

Leu Leu Trp Gly Leu Ser Leu Leu Phe Ser Met Leu Glu Trp Arg Phe
145                 150                 155                 160

Cys Asp Phe Leu Phe Ser Gly Ala Asp Ser Ser Trp Cys Glu Thr Ser
                165                 170                 175

Asp Phe Ile Pro Val Ala Trp Leu Ile Phe Leu Cys Val Val Leu Cys
            180                 185                 190

Val Ser Ser Leu Val Leu Leu Val Arg Ile Leu Cys Gly Ser Arg Lys
        195                 200                 205

Met Pro Leu Thr Arg Leu Tyr Val Thr Ile Leu Leu Thr Val Leu Val
210                 215                 220

Phe Leu Leu Cys Gly Leu Pro Phe Gly Ile Leu Gly Ala Leu Ile Tyr
225                 230                 235                 240

Arg Met His Leu Asn Leu Glu Val Leu Tyr Cys His Val Tyr Leu Val
                245                 250                 255

Cys Met Ser Leu Ser Ser Leu Asn Ser Ser Ala Asn Pro Ile Ile Tyr
            260                 265                 270

Phe Phe Val Gly Ser Phe Arg Gln Arg Gln Asn Arg Gln Asn Leu Lys
        275                 280                 285

Leu Val Leu Gln Arg Ala Leu Gln Asp Lys Pro Glu Val Asp Lys Gly
290                 295                 300

Glu Gly Gln Leu Pro Glu Glu Ser Leu Glu Leu Ser Gly Ser Arg Leu
305                 310                 315                 320

Gly Pro
```

<210> SEQ ID NO 34
<211> LENGTH: 966
<212> TYPE: DNA
<213> ORGANISM: Homo sapiens

<400> SEQUENCE: 34

```
atgaaccaga ctttgaatag cagtgggacc gtggagtcag ccctaaacta ttccagaggg    60
agcacagtgc acacggccta cctggtgctg agctccctgg ccatgttcac ctgcctgtgc   120
gggatggcag gcaacagcat ggtgatctgg ctgctgggct tcgaatgca caggaacccc   180
ttctgcatct atatcctcaa cctggcggca gccgacctcc tcttcctctt cagcatggct   240
tccacgctca gcctggaaac ccagcccctg gtcaatacca ctgacaaggt ccacgagctg   300
atgaagagac tgatgtactt tgcctacaca gtgggcctga gctgctgac ggccatcagc   360
acccagcgct gtctctctgt cctcttccct atctggttca agtgtcaccg gcccaggcac   420
ctgtcagcct gggtgtgtgg cctgctgtgg acactctgtc cctgatgaa cgggttgacc   480
tcttccttct gcagcaagtt cttgaaattc aatgaagatc ggtgcttcag ggtggacatg   540
gtccaggccg ccctcatcat gggggtctta accccagtga tgactctgtc cagcctgacc   600
ctctttgtct gggtgcggag gagctcccag cagtggcggc ggcagcccac acggctgttc   660
gtggtggtcc tggcctctgt cctggtgttc ctcatctgtt ccctgcctct gagcatctac   720
tggtttgtgc tctactggtt gagcctgccg cccgagatgc aggtcctgtg cttcagcttg   780
tcacgcctct cctcgtccgt aagcagcagc gccaaccccg tcatctactt cctggtgggc   840
agccggagga gccacaggct gcccaccagg tccctgggga ctgtgctcca acaggcgctt   900
cgcgaggagc ccgagctgga aggtggggag acgccaccg tgggcaccaa tgagatgggg   960
gcttga                                                              966
```

<210> SEQ ID NO 35
<211> LENGTH: 321
<212> TYPE: PRT
<213> ORGANISM: Homo sapiens

<400> SEQUENCE: 35

```
Met Asn Gln Thr Leu Asn Ser Ser Gly Thr Val Glu Ser Ala Leu Asn
  1               5                  10                  15

Tyr Ser Arg Gly Ser Thr Val His Thr Ala Tyr Leu Val Leu Ser Ser
             20                  25                  30

Leu Ala Met Phe Thr Cys Leu Cys Gly Met Ala Gly Asn Ser Met Val
         35                  40                  45

Ile Trp Leu Leu Gly Phe Arg Met His Arg Asn Pro Phe Cys Ile Tyr
     50                  55                  60

Ile Leu Asn Leu Ala Ala Ala Asp Leu Leu Phe Leu Phe Ser Met Ala
 65                  70                  75                  80

Ser Thr Leu Ser Leu Glu Thr Gln Pro Leu Val Asn Thr Thr Asp Lys
                 85                  90                  95

Val His Glu Leu Met Lys Arg Leu Met Tyr Phe Ala Tyr Thr Val Gly
            100                 105                 110

Leu Ser Leu Leu Thr Ala Ile Ser Thr Gln Arg Cys Leu Ser Val Leu
        115                 120                 125

Phe Pro Ile Trp Phe Lys Cys His Arg Pro Arg His Leu Ser Ala Trp
    130                 135                 140

Val Cys Gly Leu Leu Trp Thr Leu Cys Leu Leu Met Asn Gly Leu Thr
145                 150                 155                 160

Ser Ser Phe Cys Ser Lys Phe Leu Lys Phe Asn Glu Asp Arg Cys Phe
                165                 170                 175

Arg Val Asp Met Val Gln Ala Ala Leu Ile Met Gly Val Leu Thr Pro
            180                 185                 190

Val Met Thr Leu Ser Ser Leu Thr Leu Phe Val Trp Val Arg Arg Ser
```

```
              195                 200                 205
Ser Gln Gln Trp Arg Arg Gln Pro Thr Arg Leu Phe Val Val Leu
210                 215                 220

Ala Ser Val Leu Val Phe Leu Ile Cys Ser Leu Pro Leu Ser Ile Tyr
225                 230                 235                 240

Trp Phe Val Leu Tyr Trp Leu Ser Leu Pro Glu Met Gln Val Leu
                245                 250                 255

Cys Phe Ser Leu Ser Arg Leu Ser Ser Val Ser Ser Ser Ala Asn
            260                 265                 270

Pro Val Ile Tyr Phe Leu Val Gly Ser Arg Arg Ser His Arg Leu Pro
        275                 280                 285

Thr Arg Ser Leu Gly Thr Val Leu Gln Gln Ala Leu Arg Glu Glu Pro
290                 295                 300

Glu Leu Glu Gly Gly Glu Thr Pro Thr Val Gly Thr Asn Glu Met Gly
305                 310                 315                 320

Ala

<210> SEQ ID NO 36
<211> LENGTH: 767
<212> TYPE: DNA
<213> ORGANISM: Homo sapiens
<220> FEATURE:
<221> NAME/KEY: CDS
<222> LOCATION: (2)...(716)

<400> SEQUENCE: 36 c cac atg gtg gcc atc gtc ccc gac ttg ctg caa ggc cgg ctg gac ttc      49
  His Met Val Ala Ile Val Pro Asp Leu Leu Gln Gly Arg Leu Asp Phe
   1               5                  10                  15 ccg ggc ttc gtg cag acc agc ctg gca acg ctg cgc ttc ttc tgc tac        97
Pro Gly Phe Val Gln Thr Ser Leu Ala Thr Leu Arg Phe Phe Cys Tyr
                 20                  25                  30 atc gtg ggc ctg agt ctc ctg gcg gcc gtc agc gtg gag cag tgc ctg       145
Ile Val Gly Leu Ser Leu Leu Ala Ala Val Ser Val Glu Gln Cys Leu
             35                  40                  45 gcc gcc ctc ttc cca gcc tgg tac tcg tgc cgc cgc cca cgc cac ctg       193
Ala Ala Leu Phe Pro Ala Trp Tyr Ser Cys Arg Arg Pro Arg His Leu
         50                  55                  60 acc acc tgt gtg tgc gcc ctc acc tgg gcc ctc tgc ctg ctg ctg cac       241
Thr Thr Cys Val Cys Ala Leu Thr Trp Ala Leu Cys Leu Leu Leu His
 65                  70                  75                  80 ctg ctc ctc agc agc gcc tgc acc cag ttc ttc ggg gag ccc agc cgc       289
Leu Leu Leu Ser Ser Ala Cys Thr Gln Phe Phe Gly Glu Pro Ser Arg
                 85                  90                  95 cac ttg tgc cgg acg ctg tgg ctg gtg gca gcg gtg ctg ctg gct ctg       337
His Leu Cys Arg Thr Leu Trp Leu Val Ala Ala Val Leu Leu Ala Leu
                100                 105                 110 ctg tgt tgc acc atg tgt ggg gcc agc ctt atg ctg ctg cgg gtg           385
Leu Cys Cys Thr Met Cys Gly Ala Ser Leu Met Leu Leu Arg Val
            115                 120                 125 gag cga ggc ccc cag cgg ccc cca ccc cgg ggc ttc cct ggg ctc atc       433
Glu Arg Gly Pro Gln Arg Pro Pro Pro Arg Gly Phe Pro Gly Leu Ile
        130                 135                 140 ctc ctc acc gtc ctc ctc ttc ctc ttc tgc ggc ctg ccc ttc ggc atc       481
Leu Leu Thr Val Leu Leu Phe Leu Phe Cys Gly Leu Pro Phe Gly Ile
145                 150                 155                 160 tac tgg ctg tcc cgg aac ctg ctc tgg tac atc ccc cac tac ttc tac       529
Tyr Trp Leu Ser Arg Asn Leu Leu Trp Tyr Ile Pro His Tyr Phe Tyr
                165                 170                 175
```

```
cac ttc agc ttc ctc atg gcc gcc gtg cac tgc gcg gcc aag ccc gtc        577
His Phe Ser Phe Leu Met Ala Ala Val His Cys Ala Ala Lys Pro Val
            180                 185                 190 gtc tac ttc tgc ctg ggc agt gcc cag ggc cgc agg ctg ccc ctc cgg        625
Val Tyr Phe Cys Leu Gly Ser Ala Gln Gly Arg Arg Leu Pro Leu Arg
            195                 200                 205 ctg gtc ctc cag cga gcg ctg gga gac gag gct gag ctg ggg gcc gtc        673
Leu Val Leu Gln Arg Ala Leu Gly Asp Glu Ala Glu Leu Gly Ala Val
    210                 215                 220 agg gag acc tcc cgc cgg ggc ctg gtg gac ata gca gcc tga g              716
Arg Glu Thr Ser Arg Arg Gly Leu Val Asp Ile Ala Ala  *
225             230                 235 ccctggggcc cccgacccca gctgcagccc ccgtgaggca agagggtgac t                767
```

<210> SEQ ID NO 37
<211> LENGTH: 237
<212> TYPE: PRT
<213> ORGANISM: Homo sapiens

<400> SEQUENCE: 37

```
His Met Val Ala Ile Val Pro Asp Leu Leu Gln Gly Arg Leu Asp Phe
 1               5                  10                  15

Pro Gly Phe Val Gln Thr Ser Leu Ala Thr Leu Arg Phe Phe Cys Tyr
            20                  25                  30

Ile Val Gly Leu Ser Leu Leu Ala Val Ser Val Glu Gln Cys Leu
            35                  40                  45

Ala Ala Leu Phe Pro Ala Trp Tyr Ser Cys Arg Arg Pro Arg His Leu
    50                  55                  60

Thr Thr Cys Val Cys Ala Leu Thr Trp Ala Leu Cys Leu Leu Leu His
65                  70                  75                  80

Leu Leu Leu Ser Ser Ala Cys Thr Gln Phe Phe Gly Glu Pro Ser Arg
                85                  90                  95

His Leu Cys Arg Thr Leu Trp Leu Val Ala Ala Val Leu Leu Ala Leu
            100                 105                 110

Leu Cys Cys Thr Met Cys Gly Ala Ser Leu Met Leu Leu Arg Val
            115                 120                 125

Glu Arg Gly Pro Gln Arg Pro Pro Arg Gly Phe Pro Gly Leu Ile
    130                 135                 140

Leu Leu Thr Val Leu Leu Phe Leu Phe Cys Gly Leu Pro Phe Gly Ile
145                 150                 155                 160

Tyr Trp Leu Ser Arg Asn Leu Leu Trp Tyr Ile Pro His Tyr Phe Tyr
                165                 170                 175

His Phe Ser Phe Leu Met Ala Ala Val His Cys Ala Ala Lys Pro Val
            180                 185                 190

Val Tyr Phe Cys Leu Gly Ser Ala Gln Gly Arg Arg Leu Pro Leu Arg
            195                 200                 205

Leu Val Leu Gln Arg Ala Leu Gly Asp Glu Ala Glu Leu Gly Ala Val
    210                 215                 220

Arg Glu Thr Ser Arg Arg Gly Leu Val Asp Ile Ala Ala
225                 230                 235
```

<210> SEQ ID NO 38
<211> LENGTH: 1361
<212> TYPE: DNA
<213> ORGANISM: Mus musculus
<220> FEATURE:
<221> NAME/KEY: CDS

<222> LOCATION: (48)...(1064)

<400> SEQUENCE: 38

```
tcttttttt ttttcattgc agaactgaga ttgcaccact cctgaaa atg gac tta      56
                                                    Met Asp Leu
                                                     1 gtc atc caa gac tgg acc att aat att aca gca ctg aaa gaa agc aat     104
Val Ile Gln Asp Trp Thr Ile Asn Ile Thr Ala Leu Lys Glu Ser Asn
     5                  10                  15 gac aat gga ata tca ttt tgt gaa gtt gtg tct cgt acc atg act ttt     152
Asp Asn Gly Ile Ser Phe Cys Glu Val Val Ser Arg Thr Met Thr Phe
 20                  25                  30                  35 ctt tcc ctc atc att gcc tta gtt ggg ctg gtt gga aat gcc aca gtg     200
Leu Ser Leu Ile Ile Ala Leu Val Gly Leu Val Gly Asn Ala Thr Val
                 40                  45                  50 tta tgg ttt ctg ggc ttc cag atg agc agg aat gcc ttc tct gtc tac     248
Leu Trp Phe Leu Gly Phe Gln Met Ser Arg Asn Ala Phe Ser Val Tyr
             55                  60                  65 atc ctc aac ctt gct ggt gct gac ttt gtc ttc atg tgc ttt caa att     296
Ile Leu Asn Leu Ala Gly Ala Asp Phe Val Phe Met Cys Phe Gln Ile
         70                  75                  80 gta cat tgt ttt tat att atc tta gac atc tac ttc atc ccc act aat     344
Val His Cys Phe Tyr Ile Ile Leu Asp Ile Tyr Phe Ile Pro Thr Asn
     85                  90                  95 ttt ttt tca tct tac act atg gtg tta aac att gct tac ctt agt ggt     392
Phe Phe Ser Ser Tyr Thr Met Val Leu Asn Ile Ala Tyr Leu Ser Gly
100                 105                 110                 115 ctg agc atc ctc act gtc att agc act gaa cgc ttc cta tct gtc atg     440
Leu Ser Ile Leu Thr Val Ile Ser Thr Glu Arg Phe Leu Ser Val Met
                 120                 125                 130 tgg ccc atc tgg tac cgc tgc caa cgc cca agg cac aca tca gct gtc     488
Trp Pro Ile Trp Tyr Arg Cys Gln Arg Pro Arg His Thr Ser Ala Val
             135                 140                 145 ata tgt act gtg ctt tgg gtc ttg tcc ctg gtg ttg agc ctc ctg gaa     536
Ile Cys Thr Val Leu Trp Val Leu Ser Leu Val Leu Ser Leu Leu Glu
         150                 155                 160 gga aag gaa tgt ggc ttc cta tat tac act agt ggc cct ggt ttg tgt     584
Gly Lys Glu Cys Gly Phe Leu Tyr Tyr Thr Ser Gly Pro Gly Leu Cys
165                 170                 175 aag aca ttt gat tta atc act act gca tgg tta att gtt tta ttt gtg     632
Lys Thr Phe Asp Leu Ile Thr Thr Ala Trp Leu Ile Val Leu Phe Val
180                 185                 190                 195 gtt ctc ttg gga tcc agt ctg gcc ttg gtg ctt acc atc ttc tgt ggc     680
Val Leu Leu Gly Ser Ser Leu Ala Leu Val Leu Thr Ile Phe Cys Gly
                 200                 205                 210 tta cac aag gtt cct gtg acc agg ttg tat gtg acc att gtg ttt aca     728
Leu His Lys Val Pro Val Thr Arg Leu Tyr Val Thr Ile Val Phe Thr
             215                 220                 225 gtg ctt gtc ttc ctg atc ttt ggt ctg ccc tat ggg atc tac tgg ttc     776
Val Leu Val Phe Leu Ile Phe Gly Leu Pro Tyr Gly Ile Tyr Trp Phe
         230                 235                 240 ctc tta gag tgg att agg gaa ttt cat gat aat aaa cct tgt ggt ttt     824
Leu Leu Glu Trp Ile Arg Glu Phe His Asp Asn Lys Pro Cys Gly Phe
245                 250                 255 cgt aac gtg aca ata ttt ctg tcc tgt att aac agc tgt gcc aac ccc     872
Arg Asn Val Thr Ile Phe Leu Ser Cys Ile Asn Ser Cys Ala Asn Pro
260                 265                 270                 275 atc att tac ttc ctt gtt ggc tcc att agg cac cat cgg ttt caa cgg     920
Ile Ile Tyr Phe Leu Val Gly Ser Ile Arg His His Arg Phe Gln Arg
                 280                 285                 290
```

```
aag act ctc aag ctt ctt ctg cag aga gcc atg caa gac tct cct gag    968
Lys Thr Leu Lys Leu Leu Leu Gln Arg Ala Met Gln Asp Ser Pro Glu
            295                 300                 305 gag gaa gaa tgt gga gag atg ggt tcc tca aga aga cct aga gaa ata   1016
Glu Glu Glu Cys Gly Glu Met Gly Ser Ser Arg Arg Pro Arg Glu Ile
        310                 315                 320 aaa act gtc tgg aag gga ctg aga gct gct ttg atc agg cat aaa tag   1064
Lys Thr Val Trp Lys Gly Leu Arg Ala Ala Leu Ile Arg His Lys  *
325                 330                 335 ctttgaagag aactatgttt ttatcacttt gtggcatttt cataatgttg tttagttgat   1124
gacccaaggt taactcagtt ggggaagtag tcaatgttgt agaagttgat tgatattgaa   1184
cttgttataa atactgagta cagtattttt gcagctatct tgctcagagc tttaccaact   1244
ccatttgatg ggactcctta taagctctat ggggtccagg agaggtgttg accacaattg   1304
acaaatccct cttcagaaga aaactcaaga aagtgcaatg aaaagttata tttctttt     1361

<210> SEQ ID NO 39
<211> LENGTH: 338
<212> TYPE: PRT
<213> ORGANISM: Mus musculus

<400> SEQUENCE: 39

Met Asp Leu Val Ile Gln Asp Trp Thr Ile Asn Ile Thr Ala Leu Lys
 1               5                  10                  15

Glu Ser Asn Asp Asn Gly Ile Ser Phe Cys Glu Val Val Ser Arg Thr
            20                  25                  30

Met Thr Phe Leu Ser Leu Ile Ile Ala Leu Val Gly Leu Val Gly Asn
        35                  40                  45

Ala Thr Val Leu Trp Phe Leu Gly Phe Gln Met Ser Arg Asn Ala Phe
    50                  55                  60

Ser Val Tyr Ile Leu Asn Leu Ala Gly Ala Asp Phe Val Phe Met Cys
65                  70                  75                  80

Phe Gln Ile Val His Cys Phe Tyr Ile Ile Leu Asp Ile Tyr Phe Ile
                85                  90                  95

Pro Thr Asn Phe Phe Ser Ser Tyr Thr Met Val Leu Asn Ile Ala Tyr
            100                 105                 110

Leu Ser Gly Leu Ser Ile Leu Thr Val Ile Ser Thr Glu Arg Phe Leu
        115                 120                 125

Ser Val Met Trp Pro Ile Trp Tyr Arg Cys Gln Arg Pro Arg His Thr
    130                 135                 140

Ser Ala Val Ile Cys Thr Val Leu Trp Val Leu Ser Leu Val Leu Ser
145                 150                 155                 160

Leu Leu Glu Gly Lys Glu Cys Gly Phe Leu Tyr Tyr Thr Ser Gly Pro
                165                 170                 175

Gly Leu Cys Lys Thr Phe Asp Leu Ile Thr Thr Ala Trp Leu Ile Val
            180                 185                 190

Leu Phe Val Val Leu Leu Gly Ser Ser Leu Ala Leu Val Leu Thr Ile
        195                 200                 205

Phe Cys Gly Leu His Lys Val Pro Val Thr Arg Leu Tyr Val Thr Ile
    210                 215                 220

Val Phe Thr Val Leu Val Phe Leu Ile Phe Gly Leu Pro Tyr Gly Ile
225                 230                 235                 240

Tyr Trp Phe Leu Leu Glu Trp Ile Arg Glu Phe His Asp Asn Lys Pro
                245                 250                 255
```

```
Cys Gly Phe Arg Asn Val Thr Ile Phe Leu Ser Cys Ile Asn Ser Cys
            260                 265                 270

Ala Asn Pro Ile Ile Tyr Phe Leu Val Gly Ser Ile Arg His His Arg
            275                 280                 285

Phe Gln Arg Lys Thr Leu Lys Leu Leu Leu Gln Arg Ala Met Gln Asp
            290                 295                 300

Ser Pro Glu Glu Glu Cys Gly Glu Met Gly Ser Ser Arg Arg Pro
305                 310                 315                 320

Arg Glu Ile Lys Thr Val Trp Lys Gly Leu Arg Ala Ala Leu Ile Arg
                325                 330                 335

His Lys

<210> SEQ ID NO 40
<211> LENGTH: 1278
<212> TYPE: DNA
<213> ORGANISM: Mus musculus

<400> SEQUENCE: 40
atttcctaat caagaatcta agcacctcag cctggaaaac gaacatcaca gtgctgaatg     60
gaagctacta catcgatact tcagtttgtg tcaccaggaa ccaagccatg attttgcttt    120
ccatcatcat ttccctggtt gggatgggac taaatgccat agtgctgtgg ttcctgggca    180
tccgtatgca cacgaatgcc ttcactgtct acattctcaa cctggctatg gctgactttc    240
tttacctgtg ctctcagttt gtaatttgtc ttcttattgc cttttatatc ttctactcaa    300
ttgacatcaa catcccttg gttctttatg ttgtgccaat atttgcttat ctttcaggtc    360
tgagcattct cagcaccatt agcattgagc gctgcttgtc tgtaatatgg cccatttggt    420
atcgctgtaa acgtccaaga cacacatcag ctatcacatg ttttgtgctt tgggttatgt    480
ccttattgtt gggtctcctg aagggaagg catgtggctt actgtttaat agctttgact    540
cttattggtg tgaaacattt gatgttatca ctaatatatg gtcagttgtt ttttttggtg    600
ttctctgtgg gtctagcctc accctgcttg tcaggatctt ctgtggctca cagcgaattc    660
ctatgaccag gctgtatgtg actattacac tcacagtctt ggtcttcctg atctttggtc    720 ttcccttgg gatctattgg atactctatc agtggattag caattttat tatgttgaaa    780 tttgtaattt ttatcttgag atactattcc tatcctgtgt taacagctgt atgaacccca    840
tcatttattt ccttgttggc tccattaggc accgaaggtc caggcggaag actctcaagc    900
tacttctgca gagagccatg caagacaccc tgaggagga acaaagtgga ataagagtt    960 cttcagaaca ccctgaagaa ctggaaactg ttcagagctg cagctgacaa ctgcttgatc    1020
agacaaaaat ggttttgatg gaaatacttt tccttatccg tgtggaccat ttttacaacc    1080
tttattcagt ttgttatctc atcttcaatt gtttaattag gacaataatt tttgtaaaag    1140
ttgagagaaa tgggtcttgt catactaata ctgaatgtag catttctgaa gctgtgttac    1200
ttagggattt accatctcct tttcatggga ctccttgtaa gtattctgtg gtagagaact    1260
tctcctattg ttgacaaa                                                  1278

<210> SEQ ID NO 41
<211> LENGTH: 338
<212> TYPE: PRT
<213> ORGANISM: Mus musculus

<400> SEQUENCE: 41

Met Ser Gly Asp Phe Leu Ile Lys Asn Leu Ser Thr Ser Ala Trp Lys
1               5                   10                  15
```

```
Thr Asn Ile Thr Val Leu Asn Gly Ser Tyr Tyr Ile Asp Thr Ser Val
         20                  25                  30
Cys Val Thr Arg Asn Gln Ala Met Ile Leu Ser Ile Ile Ile Ser
         35                  40                  45
Leu Val Gly Met Gly Leu Asn Ala Ile Val Leu Trp Phe Leu Gly Ile
 50                  55                  60
Arg Met His Thr Asn Ala Phe Thr Val Tyr Ile Leu Asn Leu Ala Met
 65                  70                  75                  80
Ala Asp Phe Leu Tyr Leu Cys Ser Gln Phe Val Ile Cys Leu Leu Ile
                 85                  90                  95
Ala Phe Tyr Ile Phe Tyr Ser Ile Asp Ile Asn Ile Pro Leu Val Leu
                100                 105                 110
Tyr Val Val Pro Ile Phe Ala Tyr Leu Ser Gly Leu Ser Ile Leu Ser
                115                 120                 125
Thr Ile Ser Ile Glu Arg Cys Leu Ser Val Ile Trp Pro Ile Trp Tyr
130                 135                 140
Arg Cys Lys Arg Pro Arg His Thr Ser Ala Ile Thr Cys Phe Val Leu
145                 150                 155                 160
Trp Val Met Ser Leu Leu Leu Gly Leu Leu Glu Gly Lys Ala Cys Gly
                165                 170                 175
Leu Leu Phe Asn Ser Phe Asp Ser Tyr Trp Cys Glu Thr Phe Asp Val
                180                 185                 190
Ile Thr Asn Ile Trp Ser Val Val Phe Phe Gly Val Leu Cys Gly Ser
                195                 200                 205
Ser Leu Thr Leu Leu Val Arg Ile Phe Cys Gly Ser Gln Arg Ile Pro
210                 215                 220
Met Thr Arg Leu Tyr Val Thr Ile Thr Leu Thr Val Leu Val Phe Leu
225                 230                 235                 240
Ile Phe Gly Leu Pro Phe Gly Ile Tyr Trp Ile Leu Tyr Gln Trp Ile
                245                 250                 255
Ser Asn Phe Tyr Tyr Val Glu Ile Cys Asn Phe Tyr Leu Glu Ile Leu
                260                 265                 270
Phe Leu Ser Cys Val Asn Ser Cys Met Asn Pro Ile Ile Tyr Phe Leu
                275                 280                 285
Val Gly Ser Ile Arg His Arg Arg Phe Arg Arg Lys Thr Leu Lys Leu
                290                 295                 300
Leu Leu Gln Arg Ala Met Gln Asp Thr Pro Glu Glu Gln Ser Gly
305                 310                 315                 320
Asn Lys Ser Ser Glu His Pro Glu Glu Leu Glu Thr Val Gln Ser
                325                 330                 335
Cys Ser

<210> SEQ ID NO 42
<211> LENGTH: 1009
<212> TYPE: DNA
<213> ORGANISM: Mus musculus

<400> SEQUENCE: 42
ttttctaagc atggctctaa gaacctcact aataaccacc acagcaccgg ataaaaccag      60
ccttccaatt tcaatttgta tcatcaagtt ccaagtcatg aatttgcttt ccatcaccat     120
ttcccctgtt gggatggtac tgaatatcat agtgctgtgg ttcctgggct tccagatatg     180
caggaatgcc ttctctgcct acatcctcaa cctggctgtg gctgattttc tcttcctgtg     240
```

| | | | |
|---|---|---|---|
| ttctcattct | atatttctt | ttcttattgt | ctgcaaactg | cactatttt | tattctacat | 300 |
| tagacagctt | ttggatactg | tgacaatgtt | tgcttatgtt | tttggcctga | gcattaccac | 360 |
| catcattagc | attgagtgct | gcctgtctat | catgtggccc | atctggtatc | actgccaacg | 420 |
| tccaagacac | acatcagctg | tcatttgtgt | cttgctttgg | gctctatctc | tgctgtttcc | 480 |
| tgctctgcag | atggaaaaat | gtagcgtcct | gtttaatact | tttgaatatt | cttggtgtgg | 540 |
| gataatcaat | ataatctctg | gtgcatggtt | agttgtttta | tttgtggttc | tctgtgggtt | 600 |
| cagcctcatc | ctgctcctca | ggatctcctg | tggatcacag | cagattcctg | tgaccaggct | 660 |
| gaatgtaact | attgcactca | gagtgctact | cctcctgatc | tttggtattc | cctttgggat | 720 |
| cttctggata | gttgacaaat | ggaatgaaga | aaattttttc | gttagagctt | gtggtttttc | 780 |
| acatcatata | ctatacgtat | actgtattaa | catctgtgtc | aatgctacca | tatacttcct | 840 |
| tgttggctcc | attaggcatg | gcaagtttca | gaagatgact | ctgaagctga | ttctgcagag | 900 |
| agctatacag | ggcaccccg | aggaagaagg | tggagagagg | ggtccttaag | gaaatactga | 960 |
| agaactggga | acagtctagt | gcagcaaccg | agagctgctt | taataataa | | 1009 |

<210> SEQ ID NO 43
<211> LENGTH: 312
<212> TYPE: PRT
<213> ORGANISM: Mus musculus

<400> SEQUENCE: 43

Met Ala Leu Arg Thr Ser Leu Ile Thr Thr Ala Pro Asp Lys Thr
1               5                   10                  15

Ser Leu Pro Ile Ser Ile Cys Ile Ile Lys Phe Gln Val Met Asn Leu
            20                  25                  30

Leu Ser Ile Thr Ile Ser Pro Val Gly Met Val Leu Asn Ile Ile Val
        35                  40                  45

Leu Trp Phe Leu Gly Phe Gln Ile Cys Arg Asn Ala Phe Ser Ala Tyr
    50                  55                  60

Ile Leu Asn Leu Ala Val Ala Asp Phe Leu Phe Leu Cys Ser His Ser
65                  70                  75                  80

Ile Phe Ser Phe Leu Ile Val Cys Lys Leu His Tyr Phe Leu Phe Tyr
                85                  90                  95

Ile Arg Gln Leu Leu Asp Thr Val Thr Met Phe Ala Tyr Val Phe Gly
            100                 105                 110

Leu Ser Ile Thr Thr Ile Ile Ser Ile Glu Cys Cys Leu Ser Ile Met
        115                 120                 125

Trp Pro Ile Trp Tyr His Cys Gln Arg Pro Arg His Thr Ser Ala Val
    130                 135                 140

Ile Cys Val Leu Leu Trp Ala Leu Ser Leu Leu Phe Pro Ala Leu Gln
145                 150                 155                 160

Met Glu Lys Cys Ser Val Leu Phe Asn Thr Phe Glu Tyr Ser Trp Cys
                165                 170                 175

Gly Ile Ile Asn Ile Ile Ser Gly Ala Trp Leu Val Val Leu Phe Val
            180                 185                 190

Val Leu Cys Gly Phe Ser Leu Ile Leu Leu Arg Ile Ser Cys Gly
        195                 200                 205

Ser Gln Gln Ile Pro Val Thr Arg Leu Asn Val Thr Ile Ala Leu Arg
    210                 215                 220

Val Leu Leu Leu Leu Ile Phe Gly Ile Pro Phe Gly Ile Phe Trp Ile
225                 230                 235                 240

```
Val Asp Lys Trp Asn Glu Glu Asn Phe Phe Val Arg Ala Cys Gly Phe
            245                 250                 255

Ser His His Ile Leu Tyr Val Tyr Cys Ile Asn Ile Cys Val Asn Ala
        260                 265                 270

Thr Ile Tyr Phe Leu Val Gly Ser Ile Arg His Gly Lys Phe Gln Lys
    275                 280                 285

Met Thr Leu Lys Leu Ile Leu Gln Arg Ala Ile Gln Gly Thr Pro Glu
290                 295                 300

Glu Glu Gly Gly Glu Arg Gly Pro
305                 310

<210> SEQ ID NO 44
<211> LENGTH: 1219
<212> TYPE: DNA
<213> ORGANISM: Mus musculus

<400> SEQUENCE: 44
tttatggacc tgtgccagat attcctacat aatcacatgg tcctgactga gactatcttg      60
tgttcatatc tcgatttctt tgcaggaatg ccagtggaaa attcctaagc atgggtacaa     120
ccaccctggc ctggaacatt aacaacaccg ctgaaaatgg aagttacact gaaatgttct     180
cctgtatcac aagttcaat acctgaatt tcttactgt catcatagct gtggttggcc        240
tgcaggaaa cggcatagtg ctatggcttc tagccttcca cctgcatagg aatgccttct     300
ctgtctatgt cctcaatctg ctggtgctg atttcttgta ccttttcact caagttgtgc     360
attccctgga atgtgtcctt cagttagata taactccctt ttatattctc ctcattgtaa     420
caatgtttgc ttaccttgca ggtttgtgta tgattgcagc catcagtgct gaacgctgcc     480
tatctgttat gtggcctatc tggtatcact gccaaagacc aagacacaca tcagccatca     540
tgtgtgctct ggtctggatt cctctctat tgttgagcct cgtggtaggg ctaggctgtg      600
gttttctgtt cagttattat gattattatt tctgtattac tttgaatttt atcactgctg     660
cattttaat agtgttatct gtggttcttt ctgtatctag cctggccctg ttggtgaaga     720
ttgtgtgggg gtcacacagg attcctgtga ccaggttctt tgtgaccatt gctctcacag     780
tggtggtctt catatacttt ggcatgccct ttggtatctg ctggttcctc ttatcaagga     840
ttatggagtt tgatagcatt ttcttaaca atgtttatga aataatagaa ttcctgtcct     900
gtgttaacag ctgtgccaat cccatcattt acttccttgt tggctccatt agacaacaca     960
ggttgcgatg gcagtctctg aagctacttc ttcagagagc catgcaggac actcctgagg    1020
aagagagtgg agagaggggt ccttcgcaaa ggtctgggga actggaaaca gtctagtaca    1080
gtagttgagt gagtccctgg tcaaacatag tttctgtgag agtcaatttt gcctttatct    1140
atataagcaa ttttcataat ttgtttaatc agtagagaat atagtcattt tatagaaatt    1200
aggagaaatg agcttgtta                                                  1219

<210> SEQ ID NO 45
<211> LENGTH: 321
<212> TYPE: PRT
<213> ORGANISM: Mus musculus

<400> SEQUENCE: 45

Met Gly Thr Thr Thr Leu Ala Trp Asn Ile Asn Asn Thr Ala Glu Asn
1               5                   10                  15

Gly Ser Tyr Thr Glu Met Phe Ser Cys Ile Thr Lys Phe Asn Thr Leu
            20                  25                  30
```

```
Asn Phe Leu Thr Val Ile Ile Ala Val Val Gly Leu Ala Gly Asn Gly
            35                  40                  45
Ile Val Leu Trp Leu Leu Ala Phe His Leu His Arg Asn Ala Phe Ser
 50                  55                  60
Val Tyr Val Leu Asn Leu Ala Gly Ala Asp Phe Leu Tyr Leu Phe Thr
 65                  70                  75                  80
Gln Val Val His Ser Leu Glu Cys Val Leu Gln Leu Asp Asn Asn Ser
                 85                  90                  95
Phe Tyr Ile Leu Leu Ile Val Thr Met Phe Ala Tyr Leu Ala Gly Leu
            100                 105                 110
Cys Met Ile Ala Ala Ile Ser Ala Glu Arg Cys Leu Ser Val Met Trp
            115                 120                 125
Pro Ile Trp Tyr His Cys Gln Arg Pro Arg His Thr Ser Ala Ile Met
130                 135                 140
Cys Ala Leu Val Trp Val Ser Ser Leu Leu Leu Ser Leu Val Val Gly
145                 150                 155                 160
Leu Gly Cys Gly Phe Leu Phe Ser Tyr Tyr Asp Tyr Tyr Phe Cys Ile
                165                 170                 175
Thr Leu Asn Phe Ile Thr Ala Ala Phe Leu Ile Val Leu Ser Val Val
            180                 185                 190
Leu Ser Val Ser Ser Leu Ala Leu Leu Val Lys Ile Val Trp Gly Ser
            195                 200                 205
His Arg Ile Pro Val Thr Arg Phe Phe Val Thr Ile Ala Leu Thr Val
210                 215                 220
Val Val Phe Ile Tyr Phe Gly Met Pro Phe Gly Ile Cys Trp Phe Leu
225                 230                 235                 240
Leu Ser Arg Ile Met Glu Phe Asp Ser Ile Phe Phe Asn Asn Val Tyr
                245                 250                 255
Glu Ile Ile Glu Phe Leu Ser Cys Val Asn Ser Cys Ala Asn Pro Ile
            260                 265                 270
Ile Tyr Phe Leu Val Gly Ser Ile Arg Gln His Arg Leu Arg Trp Gln
            275                 280                 285
Ser Leu Lys Leu Leu Leu Gln Arg Ala Met Gln Asp Thr Pro Glu Glu
290                 295                 300
Glu Ser Gly Glu Arg Gly Pro Ser Gln Arg Ser Gly Glu Leu Glu Thr
305                 310                 315                 320
Val

<210> SEQ ID NO 46
<211> LENGTH: 1281
<212> TYPE: DNA
<213> ORGANISM: Mus musculus

<400> SEQUENCE: 46
atggtcctga cagagagtat catgtgttca tatctctatt tttttgcggg aacaccactg        60
gaaacttcct aaacatgggt ctaaccactc cagcctggaa cattaacaac acagtagtga       120
atggaagtaa caatactgaa catttctcct gtgtcagcaa gttcaatacc ctgaactttc       180
ttactgtcat cattgccatg tttggcctgg caggaaatgc catagtccta tggcttctag       240
ccttccacct gcctaggaat gccttctctg tctatgtctg caacttggct tgtgctgatt       300
tcttgcaact tgcactcag attttaggtt ccctggaatg tttccttcag ttaaatagga       360
gacacacttt ttttctcacc gttgtattta tgtttgctta ccttgcaggt tgtgtgatga       420
ttgcagccat cagtgttgag cgctctctat ctgttatgtg gcccatctgg tatcactgcc       480
```

```
aaagaccaag acatacatca tccatcatgt gtgctctgct ctgggctttc tgtctactgt    540
tgaatttcct attagggaa ggctgtggcc ttctgttcag tgatcctaaa tattatttct    600
gtattacttg tgccttaatc actactgcac ttataatatt attaactgtg gttccttctg    660
tgtccagcct ggcccgttg gtcaagatga tctgtggatc acacaggatt cctgtgacca    720
ggttctatgt gaccattgct ctcacattgg tggtcttcat attcttgggt ctgcccttg    780 ggatttactc atctttcttg ataatgttta aggagtttca aagcattttc tcttaccatg    840
tccttgaagt gacaatattc ctgtcctgtg ttaacagctg tgccaatccc atcatttact    900
ttcttgttgg ctccattagg cagcacaggt tgcaatggca gtctctgaag ctacttcttc    960
agagagccat gcaggacact cctgaggaag atagtggaga gagggttccc tcacaaaggt   1020
ctggggaact ggaaagtgtt tagtgcagta gttgagtgag tctttgatca gacatggtta   1080
ctctgagagt cagttttgcc tttgtttatg taagcaattt tcacaatctt gtacaatttg   1140
taaagaaata gtcattttat agaaatttggg agaaagggc ttgttacaca gaaactgagt   1200
gcaacaccat aaagctgtct tatgtgggtc tcattacatt ctcttgtgat ataagccttg   1260
taatcacttg ggaacaaaac t                                             1281
```

<210> SEQ ID NO 47
<211> LENGTH: 322
<212> TYPE: PRT
<213> ORGANISM: Mus musculus

<400> SEQUENCE: 47

```
Met Gly Leu Thr Thr Pro Ala Trp Asn Ile Asn Asn Thr Val Val Asn
  1               5                  10                  15

Gly Ser Asn Asn Thr Glu His Phe Ser Cys Val Ser Lys Phe Asn Thr
             20                  25                  30

Leu Asn Phe Leu Thr Val Ile Ile Ala Met Phe Gly Leu Ala Gly Asn
         35                  40                  45

Ala Ile Val Leu Trp Leu Leu Ala Phe His Leu Pro Arg Asn Ala Phe
     50                  55                  60

Ser Val Tyr Val Cys Asn Leu Ala Cys Ala Asp Phe Leu Gln Leu Cys
 65                  70                  75                  80

Thr Gln Ile Leu Gly Ser Leu Glu Cys Phe Leu Gln Leu Asn Arg Arg
                 85                  90                  95

His Thr Phe Phe Leu Thr Val Val Phe Met Phe Ala Tyr Leu Ala Gly
            100                 105                 110

Leu Cys Met Ile Ala Ala Ile Ser Val Glu Arg Ser Leu Ser Val Met
        115                 120                 125

Trp Pro Ile Trp Tyr His Cys Gln Arg Pro Arg His Thr Ser Ser Ile
    130                 135                 140

Met Cys Ala Leu Leu Trp Ala Phe Cys Leu Leu Leu Asn Phe Leu Leu
145                 150                 155                 160

Gly Glu Gly Cys Gly Leu Leu Phe Ser Asp Pro Lys Tyr Tyr Phe Cys
                165                 170                 175

Ile Thr Cys Ala Leu Ile Thr Thr Ala Leu Ile Leu Leu Thr Val
            180                 185                 190

Val Pro Ser Val Ser Ser Leu Ala Leu Leu Val Lys Met Ile Cys Gly
        195                 200                 205

Ser His Arg Ile Pro Val Thr Arg Phe Tyr Val Thr Ile Ala Leu Thr
    210                 215                 220
```

```
Leu Val Val Phe Ile Phe Leu Gly Leu Pro Phe Gly Ile Tyr Ser Ser
225                 230                 235                 240

Phe Leu Ile Met Phe Lys Glu Phe Gln Ser Ile Phe Ser Tyr His Val
            245                 250                 255

Leu Glu Val Thr Ile Phe Leu Ser Cys Val Asn Ser Cys Ala Asn Pro
        260                 265                 270

Ile Ile Tyr Phe Leu Val Gly Ser Ile Arg Gln His Arg Leu Gln Trp
        275                 280                 285

Gln Ser Leu Lys Leu Leu Leu Gln Arg Ala Met Gln Asp Thr Pro Glu
        290                 295                 300

Glu Asp Ser Gly Glu Arg Val Pro Ser Gln Arg Ser Gly Glu Leu Glu
305                 310                 315                 320

Ser Val
```

<210> SEQ ID NO 48
<211> LENGTH: 1280
<212> TYPE: DNA
<213> ORGANISM: Mus musculus

<400> SEQUENCE: 48

```
ccccactagt tcataacaca gaatttaaca tgggttcttc ttccacccat aggaatgaac      60
tccactcttg acagcagccc agctccaggt ctgaccatca gtcccaccat ggaccttgtg     120
acctggatct acttttcagt gacattcctc gccatggcca cgtgtgtggg gggggatggc     180
aggcaactca ttggtgattt ggctcctgag ctgcaatggc atgcagaggt ctcccttctg     240
tgtctatgtg ctcaacctgg cggtggctga cttcctcttc ttattctgca tggcctccat     300
gctcagcctg gaaacagggc ccctgctcat agtcaacatt tctgccaaaa tctatgaagg     360
gatgaggaga atcaagtact tgcctatac agcaggcctg agcctgctga cagccatcag     420
cacccagcgc tgcctctccg tgcttttccc catctggtat aagtgccacc ggccccggca     480
cctgtcatca gtggtatctg gtgcactctg ggcactggcc ttcctgatga acttcctggc     540
ttctttcttc tgcgtccaat tctggcatcc caacaaacac cagtgcttca aggtggacat     600
tgttttcaac agtcttatcc tggggatctt catgccggtc atgatcctga ccagcaccat     660
cctcttcatc cgggtgcgga agaacagcct gatgcagaga cggcggcccc ggcggctgta     720
cgtggtcatc ctgacttcca tccttgtctt cctcacctgt tctctgccct tgggcatcaa     780
ctggttctta ctctactggg tggatgtgaa acgggatgtg aggctacttt atagctgcgt     840
atcacgcttc tcttcgtctt tgagcagcag tgccaacccg tcatttact cctcgtggg      900
cagccagaag agccaccggc tgcaggagtc cctgggtgct gtgctggggc gggcactgcg     960
ggatgagcct gagccagagg gcagagagac gccatccacg tgtactaatg atggggtctg    1020
aagggagccc aaccaggaac tcctccaaag ccccacccag cccttcccta aaagtaccca    1080
gcaagcctgc aatgcaaagg ccttgcacct caaaatgttt gggtcacgtt cctctctgcc    1140
agggagggtt caccactatc accttgtgtt cctaatctaa actaagaggt gaggcaatat    1200
atctttctgt tttacctgtt tagacacaga tcctaacttt gggtcccatc atgggcaagg    1260
ctgtctggga aatggagttt                                                 1280
```

<210> SEQ ID NO 49
<211> LENGTH: 281
<212> TYPE: PRT
<213> ORGANISM: Mus musculus

<400> SEQUENCE: 49

| | | | | | | | | | | | | | | |
|---|---|---|---|---|---|---|---|---|---|---|---|---|---|---|
| Met | Ala | Gly | Asn | Ser | Leu | Val | Ile | Trp | Leu | Leu | Ser | Cys | Asn | Gly | Met |
| 1 | | | | 5 | | | | | 10 | | | | | 15 |

Met Ala Gly Asn Ser Leu Val Ile Trp Leu Leu Ser Cys Asn Gly Met
 1               5                  10                  15

Gln Arg Ser Pro Phe Cys Val Tyr Val Leu Asn Leu Ala Val Ala Asp
            20                  25                  30

Phe Leu Phe Leu Phe Cys Met Ala Ser Met Leu Ser Leu Glu Thr Gly
        35                  40                  45

Pro Leu Leu Ile Val Asn Ile Ser Ala Lys Ile Tyr Glu Gly Met Arg
50                  55                  60

Arg Ile Lys Tyr Phe Ala Tyr Thr Ala Gly Leu Ser Leu Leu Thr Ala
65                  70                  75                  80

Ile Ser Thr Gln Arg Cys Leu Ser Val Leu Phe Pro Ile Trp Tyr Lys
                85                  90                  95

Cys His Arg Pro Arg His Leu Ser Ser Val Val Ser Gly Ala Leu Trp
                100                 105                 110

Ala Leu Ala Phe Leu Met Asn Phe Leu Ala Ser Phe Phe Cys Val Gln
            115                 120                 125

Phe Trp His Pro Asn Lys His Gln Cys Phe Lys Val Asp Ile Val Phe
        130                 135                 140

Asn Ser Leu Ile Leu Gly Ile Phe Met Pro Val Met Ile Leu Thr Ser
145                 150                 155                 160

Thr Ile Leu Phe Ile Arg Val Arg Lys Asn Ser Leu Met Gln Arg Arg
                165                 170                 175

Arg Pro Arg Arg Leu Tyr Val Val Ile Leu Thr Ser Ile Leu Val Phe
                180                 185                 190

Leu Thr Cys Ser Leu Pro Leu Gly Ile Asn Trp Phe Leu Leu Tyr Trp
            195                 200                 205

Val Asp Val Lys Arg Asp Val Arg Leu Leu Tyr Ser Cys Val Ser Arg
210                 215                 220

Phe Ser Ser Ser Leu Ser Ser Ser Ala Asn Pro Val Ile Tyr Phe Leu
225                 230                 235                 240

Val Gly Ser Gln Lys Ser His Arg Leu Gln Glu Ser Leu Gly Ala Val
                245                 250                 255

Leu Gly Arg Ala Leu Arg Asp Glu Pro Glu Pro Glu Gly Arg Glu Thr
            260                 265                 270

Pro Ser Thr Cys Thr Asn Asp Gly Val
        275                 280

<210> SEQ ID NO 50
<211> LENGTH: 1170
<212> TYPE: DNA
<213> ORGANISM: Mus musculus

<400> SEQUENCE: 50

```
gacttctgca gacatcagcc atgacgtccc tgagcgtgca cacagattct cccagcaccc      60
agggagaaat ggctttcaac ctgaccatcc tgtccctcac agagctcctc agcctgggcg     120
ggctgctggg caatggagtg gccctctggc tgctcaacca aaatgtctac aggaaccccct   180
tctccatcta tctcttggat gtggcctgcg ccgacctcat cttcctctgc tgccacatgg     240
tggccatcat ccctgagctg ctgcaggacc agctgaactt ccctgaattt gtacatatca    300
gcctgaccat gctgcggttc ttctgctaca ttgtgggcct gagcctcctg gcggccatca    360
gcacggagca gtgcctggcc actctcttcc ctgcctggta cctgtgccgc cgcccacgct    420
acctgaccac ctgtgtgtgt gcgctcatct gggtgctctg cctgctactg gacctgctgc    480
```

-continued

```
tgagcggcgc ctgcacccag ttctttggag cacccagcta ccacctgtgt gacatgctgt      540
ggctggtggt ggcagttctc ctggctgccc tgtgctgcac catgtgtgtg accagcctgc      600
tcctgctgct gcgggtggag cgtggtccag agagacacca gcctcggggc ttccccaccc      660
tggtcctgct ggccgtcctg ctcttcctct tctgcggcct gccctttggc atcttctggc      720
tgtccaagaa cctgtcctgg cacatccccc tctacttcta tcatttcagc ttcttcatgg      780
ccagtgtgca cagtgcagcc aagcctgcca tctactttt  cttgggcagc acacctggcc      840
agaggtttcg ggaacccctc cggctggtgc tccagcgggc acttggagat gaggctgagc      900
tgggagctgg gagagaggct tcccaagggg gacttgtgga catgactgtc taagcacagt      960
gggtcacaac tgcagcttca gcccatgggg gtccagggga gctgcctgat gtaggtaaag     1020
ctggatcag  agctccatca gtaagactct tgagggacat ctttgctgat gacccagtgc     1080
tgtgtccct  gggaggattc tgggaagggg caagcagaga gtgatgcttc tgtggagggc     1140
ctggggttgt gtgtgttagg cagagctcct                                       1170
```

```
<210> SEQ ID NO 51
<211> LENGTH: 310
<212> TYPE: PRT
<213> ORGANISM: Mus musculus

<400> SEQUENCE: 51

Met Thr Ser Leu Ser Val His Thr Asp Ser Pro Ser Thr Gln Gly Glu
1               5                   10                  15

Met Ala Phe Asn Leu Thr Ile Leu Ser Leu Thr Glu Leu Leu Ser Leu
            20                  25                  30

Gly Gly Leu Leu Gly Asn Gly Val Ala Leu Trp Leu Leu Asn Gln Asn
        35                  40                  45

Val Tyr Arg Asn Pro Phe Ser Ile Tyr Leu Leu Asp Val Ala Cys Ala
    50                  55                  60

Asp Leu Ile Phe Leu Cys Cys His Met Val Ala Ile Pro Glu Leu
65                  70                  75                  80

Leu Gln Asp Gln Leu Asn Phe Pro Glu Phe Val His Ile Ser Leu Thr
                85                  90                  95

Met Leu Arg Phe Phe Cys Tyr Ile Val Gly Leu Ser Leu Leu Ala Ala
            100                 105                 110

Ile Ser Thr Glu Gln Cys Leu Ala Thr Leu Phe Pro Ala Trp Tyr Leu
        115                 120                 125

Cys Arg Arg Pro Arg Tyr Leu Thr Thr Cys Val Cys Ala Leu Ile Trp
    130                 135                 140

Val Leu Cys Leu Leu Leu Asp Leu Leu Leu Ser Gly Ala Cys Thr Gln
145                 150                 155                 160

Phe Phe Gly Ala Pro Ser Tyr His Leu Cys Asp Met Leu Trp Leu Val
                165                 170                 175

Val Ala Val Leu Leu Ala Ala Leu Cys Cys Thr Met Cys Val Thr Ser
            180                 185                 190

Leu Leu Leu Leu Leu Arg Val Glu Arg Gly Pro Glu Arg His Gln Pro
        195                 200                 205

Arg Gly Phe Pro Thr Leu Val Leu Leu Ala Val Leu Leu Phe Leu Phe
    210                 215                 220

Cys Gly Leu Pro Phe Gly Ile Phe Trp Leu Ser Lys Asn Leu Ser Trp
225                 230                 235                 240

His Ile Pro Leu Tyr Phe Tyr His Phe Ser Phe Met Ala Ser Val
                245                 250                 255
```

His Ser Ala Ala Lys Pro Ala Ile Tyr Phe Phe Leu Gly Ser Thr Pro
            260                 265                 270

Gly Gln Arg Phe Arg Glu Pro Leu Arg Leu Val Leu Gln Arg Ala Leu
        275                 280                 285

Gly Asp Glu Ala Glu Leu Gly Ala Gly Arg Glu Ala Ser Gln Gly Gly
    290                 295                 300

Leu Val Asp Met Thr Val
305                 310

<210> SEQ ID NO 52
<211> LENGTH: 1519
<212> TYPE: DNA
<213> ORGANISM: Mus musculus

<400> SEQUENCE: 52

```
tgtgttccca gcagcaccca gtgcagggtt tctggcccta acatytyma gcctccacaa      60
tggcactcac aacaacaaaa tccaatggac gaaacccatc ccctggaagt accagcatca    120
agattctgat cccaaacttg atgatcatca tctttggact ggtcgggctg acaggaaacg    180
ccattgtgtt ctggctcctg gcttccact tgcgcaggaa tgccttctca gtctacatcc    240
taaacttggc cctggctgac ttcctcttcc tcctctgtcg catcatagct tccacgcaga    300
aacttctcac gttctcctca cccaacatta cctttctcat ttgcctttac acctttcaggg   360
tgattctcta catcgcaggc ctgagcatgc tcactgccat cagcattgag cgctgcctgt    420
ctgtcctgtg ccccatctgg tatcgctgcc accgcccaga acacacatca actgtcatgt    480
gtgctgcaat ctgggtcctg tccctgttga tctgcattct gaataggtat ttctgcggtt    540
tcttagatac caaatatgta aatgactatg ggtgtatggc atcaaatttc tttaatgctg    600
cataccctgat gttttgttt gtagtcctct gtgtgtccag cctggctctg ctggccaggt    660
tgttctgtgg cactgggcgg atgaagctta ccagattgta cgtgaccatc atgctgacca    720
ttttggtttt tctcctctgc gggttgccct gtggcttata ctggttcctg ttattctgga    780
ttaagaatgg ttttgctgta tttgatttta acttttatct agcatcaact gtcctgagtg    840
ctattaatag ctctgccaac cccatcattt acttcttcgt gggctcattc aggcatcggt    900
tgaagcacca gaccctcaaa atggttctcc agagtgcact gcaggatact cctgagacag    960
ctgaaaacat ggtggagatg tcaagaagca agcagagcc gtgatgaaga gcctctgcct   1020
ggacctcgga ggtagctttg gagtgagcac ttccctgctg caattgacca ctgtccactc   1080
tcctctcagc ttactgactc aacatgcctc agtggtccac caacatcttc aacagctctc   1140
cattgattta gtttttctaa ctctcccaag taatagcatt aatcagaaag tatcatgtct   1200
gcatccttct tgacattaat caaattctca aactaacttc ctctgaagct ttcttgctga   1260
ttctttggaa cttttgttgc catggaacta gcccaggtcc agaaccatga ctctcgtatc   1320
tgtgatggtt ctgtacctga atataaagac aaaggagcct agagatgatc ctgtccattc   1380
ccaaatacca cctagagagc tggtctccca ggattgcaga caagcctgtg agcacaggta   1440
agaccaccac ttctgctcaa agggacatgc ctggaactac tcaggacaca ggtacagagg   1500
agcattttgg gacaagata                                               1519
```

<210> SEQ ID NO 53
<211> LENGTH: 303
<212> TYPE: PRT
<213> ORGANISM: Mus musculus

<400> SEQUENCE: 53

```
Asn Pro Ser Pro Gly Ser Thr Ser Ile Lys Ile Leu Ile Pro Asn Leu
 1               5                   10                  15

Met Ile Ile Ile Phe Gly Leu Val Gly Leu Thr Gly Asn Ala Ile Val
             20                  25                  30

Phe Trp Leu Leu Gly Phe His Leu Arg Arg Asn Ala Phe Ser Val Tyr
         35                  40                  45

Ile Leu Asn Leu Ala Leu Ala Asp Phe Leu Phe Leu Cys Arg Ile
     50                  55                  60

Ile Ala Ser Thr Gln Lys Leu Leu Thr Phe Ser Ser Pro Asn Ile Thr
 65                  70                  75                  80

Phe Leu Ile Cys Leu Tyr Thr Phe Arg Val Ile Leu Tyr Ile Ala Gly
                 85                  90                  95

Leu Ser Met Leu Thr Ala Ile Ser Ile Glu Arg Cys Leu Ser Val Leu
             100                 105                 110

Cys Pro Ile Trp Tyr Arg Cys His Arg Pro Glu His Thr Ser Thr Val
         115                 120                 125

Met Cys Ala Ala Ile Trp Val Leu Ser Leu Leu Ile Cys Ile Leu Asn
     130                 135                 140

Arg Tyr Phe Cys Gly Phe Leu Asp Thr Lys Tyr Val Asn Asp Tyr Gly
145                 150                 155                 160

Cys Met Ala Ser Asn Phe Phe Asn Ala Ala Tyr Leu Met Phe Leu Phe
                 165                 170                 175

Val Val Leu Cys Val Ser Ser Leu Ala Leu Leu Ala Arg Leu Phe Cys
             180                 185                 190

Gly Thr Gly Arg Met Lys Leu Thr Arg Leu Tyr Val Thr Ile Met Leu
         195                 200                 205

Thr Ile Leu Val Phe Leu Leu Cys Gly Leu Pro Cys Gly Leu Tyr Trp
     210                 215                 220

Phe Leu Leu Phe Trp Ile Lys Asn Gly Phe Ala Val Phe Asp Phe Asn
225                 230                 235                 240

Phe Tyr Leu Ala Ser Thr Val Leu Ser Ala Ile Asn Ser Ser Ala Asn
                 245                 250                 255

Pro Ile Ile Tyr Phe Phe Val Gly Ser Phe Arg His Arg Leu Lys His
             260                 265                 270

Gln Thr Leu Lys Met Val Leu Gln Ser Ala Leu Gln Asp Thr Pro Glu
         275                 280                 285

Thr Ala Glu Asn Met Val Glu Met Ser Arg Ser Lys Ala Glu Pro
     290                 295                 300
```

<210> SEQ ID NO 54
<211> LENGTH: 2093
<212> TYPE: DNA
<213> ORGANISM: Mus musculus

<400> SEQUENCE: 54

```
tggtatgcac tcactgataa gcggatatag cccaaaagct gcaaacaacc aggataaaat    60
tcacagacca catgaagctc aataagaagg aagaacaaag tgtaggtgtt tcagtccttc   120
ttagaaggag aacaaaatac tcacaggagc aaatatggag atacagtata gagcagagac   180
taaaggaaag gtcattcaga gactgtccca actggggatt cattccatat agagatacca   240
aacccagact ctaaattgga tgcaaacaag tgcatgccaa aggagctag ataaggtaac    300 cctgtctcaa aaaaaaaaa aaggctgtca cctgaaaggc cctgtcaaag gcttacaaat   360
```

```
acagaagcag atgttagtag tcaacaattg gacagagcat ggggttccta atagaggagt      420
tagaggaagg aattagggag ttgaagggat ttgcagcccc ataagaacaa caatatcaac      480
caaccggaca ctcccccaga tatcacaggg tctaagccat caacaaagga gtacacatgg      540
ctccagatgc acatatagca gaggacggcc atgtcatgca tcaatggaag aagagatcct      600
tgtacctatg aaggatcgat agatgaccca gtgtagggga atcaaggaca gaaaggttgg      660
agtggatgtg tggactggcc ggactgcacag gaaatgccat tgtgttctgg ctcctgctct      720
tccacttgca caggaatgct ttctcaatct acatcttaaa tttggtcata gctgacttcc      780
ttttcctcct tggtcacatc atagcttcca caatgcaact tctcaaggtt cctacctca       840
acattatttt tctttaccgt ttttacacaa tcatgatggt gctctacaac acaggcctga      900
ccatgctcag tgccatcaac actaagcact gcctgtctgt cctgtgtccc atctggtatc      960
gctcccactg cacaaaacac acatcaactg tcatatgtgc tgctatacgg gacctgtccc     1020
tgttgatctg ctttctgaat acgtatttct gtggtctctt agataccaaa tataaaaatg     1080
acaatgggtg tctggcatcg aatttctttta ttaatgcata ccctgatgtt tttgtttgta     1140
gtcctactgt ctgtccactc tggctctgct ggccaggttg ttctgtggtg ctgggaagat     1200
gaaatttaca agattattcg tgaccatcat gctgacagtt ttagtttttc tcctctgtgg     1260
gttgccctct gccatctact ggttcctgtt aatctggatt aagattgatt atggtgtatt     1320
tgcttatgat gttttctgg catcactcgt cctgagtgct gttaacagct gtgccaaccc     1380
catcatttac ttcttcgtgg gctctttcag gcatcggttg aagcaccaaa ccctcaaaat     1440
ggttctccag aatgtactgc aggacactcc tgagacagct gaaaacatgg tagagatgtc     1500
aagaggcaaa gcagagccat gatgaagagc ctctgcctgg agctcagagg tggctttgga     1560
gtgagcactg ccctgatgta cttgaccact gtccactctc ctctcagctt actgactaga     1620
catgcctcag tggtccacca tctccaagag ctctccactg actttgtttt ctacctctcc     1680
tgaataatag cattaatcag aaagtatcat gtctacatcc ttcttgacat taatcaaatt     1740
ctcatgctat cttcccctga agctttcttg ctgtttcttt gggacttttt gttgccatgg     1800
aaataacaaa ggtccagaac catgactctc ttgcctgtga ttgttctgta cctgaatgta     1860
aagataaagg agccaggaga tgatcctgta tcacggtgct ccataccaaa ataccaccaa     1920
gagagctggt ctcccaggag tgcagacaag cctgtgagca caggtaagac caccatttct     1980
gctcaaaggg acatgcctgg aaccctcagt acacaggaac agaggagcct ggaactggat     2040
atttccagtt tccatctgca ccccagagct gactctgtac cacagctctc cat            2093
```

<210> SEQ ID NO 55
<211> LENGTH: 282
<212> TYPE: PRT
<213> ORGANISM: Mus musculus

<400> SEQUENCE: 55

Gly Leu Ala Gly Leu Thr Gly Asn Ala Ile Val Phe Trp Leu Leu
1               5                   10                  15

Phe His Leu His Arg Asn Ala Phe Ser Ile Tyr Ile Leu Asn Leu Val
            20                  25                  30

Ile Ala Asp Phe Leu Phe Leu Leu Gly His Ile Ile Ala Ser Thr Met
        35                  40                  45

Gln Leu Leu Lys Val Ser Tyr Leu Asn Ile Ile Phe Leu Tyr Arg Phe
    50                  55                  60

Tyr Thr Ile Met Met Val Leu Tyr Asn Thr Gly Leu Thr Met Leu Ser

```
                65                  70                  75                  80
Ala Ile Asn Thr Lys His Cys Leu Ser Val Leu Cys Pro Ile Trp Tyr
                        85                  90                  95

Arg Ser His Cys Thr Lys His Thr Ser Thr Val Ile Cys Ala Ala Ile
                100                 105                 110

Arg Asp Leu Ser Leu Leu Ile Cys Phe Leu Asn Thr Tyr Phe Cys Gly
                115                 120                 125

Leu Leu Asp Thr Lys Tyr Lys Asn Asp Asn Gly Cys Leu Ala Ser Asn
        130                 135                 140

Phe Phe Ile Asn Ala Tyr Leu Met Phe Leu Phe Val Val Leu Cys Leu
145                 150                 155                 160

Ser Thr Leu Ala Leu Leu Ala Arg Leu Phe Cys Gly Ala Gly Lys Met
                165                 170                 175

Lys Phe Thr Arg Leu Phe Val Thr Ile Met Leu Thr Val Leu Val Phe
                180                 185                 190

Leu Leu Cys Gly Leu Pro Ser Ala Ile Tyr Trp Phe Leu Leu Ile Trp
                195                 200                 205

Ile Lys Ile Asp Tyr Gly Val Phe Ala Tyr Asp Val Phe Leu Ala Ser
        210                 215                 220

Leu Val Leu Ser Ala Val Asn Ser Cys Ala Asn Pro Ile Ile Tyr Phe
225                 230                 235                 240

Phe Val Gly Ser Phe Arg His Arg Leu Lys His Gln Thr Leu Lys Met
                245                 250                 255

Val Leu Gln Asn Val Leu Gln Asp Thr Pro Glu Thr Ala Glu Asn Met
                260                 265                 270

Val Glu Met Ser Arg Gly Lys Ala Glu Pro
                275                 280

<210> SEQ ID NO 56
<211> LENGTH: 2401
<212> TYPE: DNA
<213> ORGANISM: Mus musculus

<400> SEQUENCE: 56
acttgctaac ttctgtaatt gatggccccc aaacaggaaa catcattata tctcacatga      60
ctataattaa tcacccactg tgttcatatc tttgactcaa atctttccc ttgtagttaa     120 cttcagacga gcactcgata gattatagta agatctgaga cttctcagag ttatgaccat     180
gttgggaatt tggttttccc aagctcagga atctgtccaa atggattgcc acaactacac     240
agagatggaa ggaaaggtag agaactttcc cagtgccatt acattctaca ggctacagga     300
gccttggctg gtcagaatgc aactttggtt ggcactcaga acaatgttaa ttttcctttt     360
caattctctc ctatctcttt ccactctgct catttgttct gttgcagcac atctgtgact     420
tccatgtatg aaagtagttt cttttcctac tctactctct caattatctt tttaattcta     480
ctatttctac tcacacatta aaatgtgtgt atgtgtgttt gtgttcatac gtgtgtgttg     540
aggctgattt tttccttatt tgctgtatat gaaactctac attctgttgt acacccaga     600 tgtcatgtgt taaattgtat ttcatgttct gctctctaaa acctacattc aggtacagaa     660
caatcacaga caagagagtc atggttttgg acctgggcta tttccatgrc aacaaaagtt     720
tcaaagaaac agcaagaaag cttcagagga agttagcacg acaatttgat taatgtcaag     780
aaggatgcag acatgatact ttctgattaa tgctttact caggagatgg agaaaaacta     840
agttatggaa gagctgttga aggtgttggt agaccactga ggcatgccaa gtaggtcagc     900
```

```
tgaaaggaga gtggacagtg tggtcaagtg cagcagggca gtgctcactc caaaactacc      960
tctgaaatcc aggcagaggc tcttcatcat ggctctgctt tgcttttga catctccact      1020 atgttttcag gtgtctcagg aatgtcctgc agtgcactct ggataaccat tttgagggtc      1080
tggtgctgca atcgatgcct gaaggagccc acgaagaagt aaatgatggg gttggcacag      1140
ctgttaagag cagtcaggac acttgatgcc ataaaagac taaaatcaaa tacaataaaa      1200
acattcttaa tcttggataa caggaaccag tagatgccac agggcaaccc gcagaggaga      1260
aaaaccaaaa tggtcagcat gatggtcacg tacaatctgg taagtttcat acgcccagcg      1320
ccacagaaca acctggccag cagagccagg ctggatagac agaggaccac aaacaaaaac      1380
atcaggtatg cagcagtaaa aagtttgat gccatacatc catagtcatt tacatatttg      1440
gtatctaaga aaacgcagaa atacttattc agaatgctga tcaacaggga caggacccag      1500
atcatagcac acgtgacagt tgatgtgtgt tctgggcggt ggcagcgata ccagatgggg      1560
cacagtacag acagacaccg ttcagtgccg atggcactga gtatgctcag gcctgcaatg      1620
tagagaacca gcatgatgct gaagaagcac ctgcgaaaga taatgttagg gtaggaaacc      1680
ttgagaagaa acagagtgga agctatgatg tgacagagga ggaagaggaa gtcagccaga      1740
gccaagttta ggatgtagac tgagaaggca ttcttgcgca agcggaagcc caggagccag      1800
aacacaatgg catttcctgt catcccaacc agtccgaaga tgatgatcat caagtgtggg      1860
atcagggtgc tgatgtcaat acttccaggg atggtttcgt ccattagatt tgttgtcgac      1920
ggtgccattg atgaggcaga ggtgtttagg gccagaaacc ctgcaccggt gctgctggga      1980
acacaaagaa gaaatgaggc tttccctatg aacacacctt ttgttttct tttcccttt       2040 ttgtttttgt tgttgttttt aaaaattttt ttctattgga tatttctttt atttaaattt      2100
caaatgttat cccctttcct gcttttccct ctccaggaaa tccccatctc atcctccctc      2160
cttctgcttc tatgatggtg ttcctcaacc cacacaccca cttccacctc tctgccctcg      2220
attcccatac actggagcat ctattgagcc ttcaaaggtc ctaggacctt tttttccatt      2280
gatgcatgac acagcaattc tctcatacat atacagctgg agccatgttt acttwctttg      2340
ttgatggctt attccatgga ggctggggcc aggggkgtg tctgatttgt tgatattggt      2400
t                                                                     2401
```

<210> SEQ ID NO 57  
<211> LENGTH: 305  
<212> TYPE: PRT  
<213> ORGANISM: Mus musculus

<400> SEQUENCE: 57

```
Met Asp Glu Thr Ile Pro Gly Ser Ile Asp Ile Ser Thr Leu Ile Pro
 1               5                  10                  15

His Leu Met Ile Ile Phe Gly Leu Val Gly Met Thr Gly Asn Ala
             20                  25                  30

Ile Val Phe Trp Leu Leu Gly Phe Arg Leu Arg Lys Asn Ala Phe Ser
         35                  40                  45

Val Tyr Ile Leu Asn Leu Ala Leu Ala Asp Phe Leu Phe Leu Leu Cys
     50                  55                  60

His Ile Ile Ala Ser Thr Leu Phe Leu Leu Lys Val Ser Tyr Pro Asn
 65                  70                  75                  80

Ile Ile Phe Arg Arg Cys Phe Phe Ser Ile Met Leu Val Leu Tyr Ile
                 85                  90                  95

Ala Gly Leu Ser Ile Leu Ser Ala Ile Gly Thr Glu Arg Cys Leu Ser
```

```
            100                 105                 110
Val Leu Cys Pro Ile Trp Tyr Arg Cys His Arg Pro Glu His Thr Ser
        115                 120                 125

Thr Val Thr Cys Ala Met Ile Trp Val Leu Ser Leu Leu Ile Ser Ile
            130                 135                 140

Leu Asn Lys Tyr Phe Cys Val Phe Leu Asp Thr Lys Tyr Val Asn Asp
145                 150                 155                 160

Tyr Gly Cys Met Ala Ser Asn Phe Phe Thr Ala Ala Tyr Leu Met Phe
                165                 170                 175

Leu Phe Val Val Leu Cys Leu Ser Ser Leu Ala Leu Leu Ala Arg Leu
            180                 185                 190

Phe Cys Gly Ala Gly Arg Met Lys Leu Thr Arg Leu Tyr Val Thr Ile
        195                 200                 205

Met Leu Thr Ile Leu Val Phe Leu Leu Cys Gly Leu Pro Cys Gly Ile
    210                 215                 220

Tyr Trp Phe Leu Leu Ser Lys Ile Lys Asn Val Phe Ile Val Phe Asp
225                 230                 235                 240

Phe Ser Leu Phe Met Ala Ser Ser Val Leu Thr Ala Leu Asn Ser Cys
                245                 250                 255

Ala Asn Pro Ile Ile Tyr Phe Phe Val Gly Ser Phe Arg His Arg Leu
            260                 265                 270

Gln His Gln Thr Leu Lys Met Val Ile Gln Ser Ala Leu Gln Asp Ile
        275                 280                 285

Pro Glu Thr Pro Glu Asn Ile Val Glu Met Ser Lys Ser Lys Ala Glu
    290                 295                 300

Pro
305

<210> SEQ ID NO 58
<211> LENGTH: 2110
<212> TYPE: DNA
<213> ORGANISM: Mus musculus

<400> SEQUENCE: 58
agaggtgtaa gtgggtatgt gggttgagga acacccttca tagaagcagg gggagggagg    60
atgagatggg gttttctggg aaggggcaaa agcaggaaag tggataacat ttgtaattta   120
aataaagaaa atatccaata caaaaaattt aaaaaaaaaa acacaaaacc acacaaaaaa   180
aagacaaaaa aaaagaaatt aaaagttgtg ttcatagtta atgcctcatt tttctttgtg   240
ttcccagcaa aaccagtgca gggtttctgg ccctaaacac cttcagcctt tcaatggca    300 cccaacgaca accaatacaa tggacgaaac catccctgga cgtattgaca tcgagaccct   360
gatcccaaac ttgatgatca tcatcttcgg actggtcggg ctgacaggaa atggcattgt   420
gttctggctc ctgggcttcc gcatgcacag gaatgccttc ttagtctaca tcctaaactt   480
ggccctggct gactttctct tccttctctg tcacatcatt aattccacaa tgcttcttct   540
caaggttctc ccactcaact ggatscttgt tccattgctt taacaccatc agaacggttc   600
tatacatcac aggcctgagc atgctcagcg ccatcagcac tgagcgctgc ctgtctgtcc   660
tgtgccccat ctggtatcga tgccgtcgcc gagaaaacac atcagctgtc atgtgtgctg   720
tgatctgggt cctgtccctg ttgatctgta ttctgaatag ttatttctgt tattactctg   780
gtcccaaaga tgtaaataac tctgtgtgtc tggtatcgaa attcttcatc agtacatacc   840
caatgttttt gtttgtagtc ctctgtctgt ccaccctgac tctgctggcc aggttgttct   900
```

```
gtggtgctgg gaagaggaaa tttaccagat tattcgtgac catcatactg accatttttgg    960 ttttcttct gtgtgggttg ccctgggct tctactggtt cctgttacac tgtattaagg      1020
gtagtttcag tgtactacat aatagactttt ttcaggcatc acttgtccta acttctgtta   1080
acagctgtgc caaccccatc atttacttct cgtgggctc cttcagggat cgggtgaagc     1140
accagaccct caaaatggta ctccagaatg cactgcagga cactcctgag acacctgaaa    1200
acaaggtgga gatgtcaaga agtaaagcag agccatgatg aagagactcg gccaggacct    1260
cagaggtagc tttggagtsa gwactgccct gctrcacttg accactgtcc actctcctct    1320
cagcttacts acttyggatg cctcagtggt ccaacaacam cttcaaawgc tctccactga    1380
cttagtattt atacctctcc caagtaatag cattaatcag aaagtatcat gtctgcatcc    1440
ttcttgacat taatccaatt ctcatactaa cttcatctga aactttcttg atgttccttt    1500 ggaactttg ttgccatggt aatagccyag gtccagcacc atgactctct tgtctgtgat     1560
tkttctgtac ctgaatgtaa agtcaaagga gccaggagat gatcctgtgt cacagtgctc    1620
attacccaaa caccaccaac agagcttgtc tcccaggagt gcagacacgc ctgtgaacac    1680
aggtaagacc accacttctg cttaaaggga catgcctgga accctcagaa cacaggaaga    1740
aaagagcagc cttggacagg atacttccag tttccaactg caccccggag ctgaccctgt    1800
gccacagctc tccatacccca aattcctccc agaaagaacy ggtcwaccaa gagtactgac   1860
acayaggctt gcaggaggga caagccacmg tcagagatag caaggaccag ctaacaccag    1920
agataaccag atggcaagag gcaagggcaa aaatataagc aatgggaacc aagactatttt    1980 ggcatcatca gaacctagtt ctctcaacat ggtgagccat ggctactcca acagacaaga   2040
aaagcatgac tctgatttaa tgtcacagat gatgatgatg atgatgatga tgatgatgat   2100
gatgatgatg                                                           2110
```

<210> SEQ ID NO 59
<211> LENGTH: 305
<212> TYPE: PRT
<213> ORGANISM: Mus musculus

<400> SEQUENCE: 59

```
Met Asp Glu Thr Ile Pro Gly Arg Ile Asp Ile Glu Thr Leu Ile Pro
1               5                   10                  15

Asn Leu Met Ile Ile Ile Phe Gly Leu Val Gly Leu Thr Gly Asn Gly
            20                  25                  30

Ile Val Phe Trp Leu Leu Gly Phe Arg Met His Arg Asn Ala Phe Leu
        35                  40                  45

Val Tyr Ile Leu Asn Leu Ala Leu Ala Asp Phe Leu Phe Leu Leu Cys
    50                  55                  60

His Ile Ile Asn Ser Thr Met Leu Leu Leu Lys Val Leu Pro Pro Thr
65                  70                  75                  80

Gly Ser Leu Phe His Cys Phe Asn Thr Ile Arg Thr Val Leu Tyr Ile
                85                  90                  95

Thr Gly Leu Ser Met Leu Ser Ala Ile Ser Thr Glu Arg Cys Leu Ser
            100                 105                 110

Val Leu Cys Pro Ile Trp Tyr Arg Cys Arg Arg Glu Asn Thr Ser
        115                 120                 125

Ala Val Met Cys Ala Val Ile Trp Val Leu Ser Leu Leu Ile Cys Ile
    130                 135                 140

Leu Asn Ser Tyr Phe Cys Tyr Tyr Ser Gly Pro Lys Asp Val Asn Asn
145                 150                 155                 160
```

```
Ser Val Cys Leu Val Ser Lys Phe Phe Ile Ser Thr Tyr Pro Met Phe
            165                 170                 175
Leu Phe Val Val Leu Cys Leu Ser Thr Leu Thr Leu Leu Ala Arg Leu
                180                 185                 190
Phe Cys Gly Ala Gly Lys Arg Lys Phe Thr Arg Leu Phe Val Thr Ile
            195                 200                 205
Ile Leu Thr Ile Leu Val Phe Leu Leu Cys Gly Leu Pro Leu Gly Phe
        210                 215                 220
Tyr Trp Phe Leu Leu His Cys Ile Lys Gly Ser Phe Ser Val Leu His
225                 230                 235                 240
Asn Arg Leu Phe Gln Ala Ser Leu Val Leu Thr Ser Val Asn Ser Cys
                245                 250                 255
Ala Asn Pro Ile Ile Tyr Phe Phe Val Gly Ser Phe Arg Asp Arg Val
            260                 265                 270
Lys His Gln Thr Leu Lys Met Val Leu Gln Asn Ala Leu Gln Asp Thr
        275                 280                 285
Pro Glu Thr Pro Glu Asn Lys Val Glu Met Ser Arg Ser Lys Ala Glu
    290                 295                 300
Pro
305

<210> SEQ ID NO 60
<211> LENGTH: 740
<212> TYPE: DNA
<213> ORGANISM: Mus musculus

<400> SEQUENCE: 60
cagggtttct ggccctaaac acctcagcct cggcaatgac acccacgaca aacaattcaa    60
tggacgaaac catccctgga agtattggca ctgagaccct gattcaaaac ttgatgatca   120
tcatcttcgg actggtcggg ctgacaggaa atgccattgt gttctggctc ctgggcttcc   180
acttgcacag gaatgccttt ttagtctaca tcctaaactt ggccctggct gatttcctct   240
tccttctctg tcacatcata gattccacag tgtttcttct caaggttccc ccacccaacc   300
ggatcttggt ccattgcttt aacatcatca gaattgtact ctacatcaca ggcttgagca   360
tgctcagtgc catcagcatg gagcgctgcc tgtctgtcct gtgccccatc tggtatcgct   420
gccgccgccc agaaaacaca tcaactgtca tttgtgctgt gatctggatc ctgtccctgt   480
tgttctgcat tctgaatgga tatttctgtt atttctctgg tcccaactat gtaaatgact   540
atgtgtgttt tgcatcggac atctttatca gaacataccc aatgttttg tttgtagtcc    600
tctgtctgtc cactctggct ctgctggcca ggttgttctg tggtgctggg aagacgaaat   660
ttaccagatt attcgtcacc atcatactga ccgttttggt tttcttctc tgtgggttgc   720
ccctgggctt cttctggttc                                                740

<210> SEQ ID NO 61
<211> LENGTH: 227
<212> TYPE: PRT
<213> ORGANISM: Mus musculus

<400> SEQUENCE: 61

Met Asp Glu Thr Ile Pro Gly Ser Ile Gly Thr Glu Thr Leu Ile Gln
1               5                   10                  15
Asn Leu Met Ile Ile Ile Phe Gly Leu Val Gly Leu Thr Gly Asn Ala
            20                  25                  30
```

```
Ile Val Phe Trp Leu Leu Gly Phe His Leu His Arg Asn Ala Phe Leu
             35                  40                  45

Val Tyr Ile Leu Asn Leu Ala Leu Ala Asp Phe Leu Phe Leu Leu Cys
 50                  55                  60

His Ile Ile Asp Ser Thr Val Phe Leu Leu Lys Val Pro Pro Pro Asn
 65                  70                  75                  80

Arg Ile Leu Val His Cys Phe Asn Ile Ile Arg Ile Val Leu Tyr Ile
                 85                  90                  95

Thr Gly Leu Ser Met Leu Ser Ala Ile Ser Met Glu Arg Cys Leu Ser
                100                 105                 110

Val Leu Cys Pro Ile Trp Tyr Arg Cys Arg Arg Pro Glu Asn Thr Ser
            115                 120                 125

Thr Val Ile Cys Ala Val Ile Trp Ile Leu Ser Leu Leu Phe Cys Ile
        130                 135                 140

Leu Asn Gly Tyr Phe Cys Tyr Phe Ser Gly Pro Asn Tyr Val Asn Asp
145                 150                 155                 160

Tyr Val Cys Phe Ala Ser Asp Ile Phe Ile Arg Thr Tyr Pro Met Phe
                165                 170                 175

Leu Phe Val Val Leu Cys Leu Ser Thr Leu Ala Leu Leu Ala Arg Leu
            180                 185                 190

Phe Cys Gly Ala Gly Lys Thr Lys Phe Thr Arg Leu Phe Val Thr Ile
        195                 200                 205

Ile Leu Thr Val Leu Val Phe Leu Leu Cys Gly Leu Pro Leu Gly Phe
    210                 215                 220

Phe Trp Phe
225

<210> SEQ ID NO 62
<211> LENGTH: 1979
<212> TYPE: DNA
<213> ORGANISM: Mus musculus

<400> SEQUENCE: 62
aatacacaaa attaaaaaca acaacaacaa caacacgccc cacaaaaaaa gaaaacaaaa      60
acaaaaaaga aattaaaagt tgtggtcata gtaaaggcct cacttcttct ttgtgttccc     120
agcaacacca gtgcagggtt tctggcccga acacctcag  cctcgacaat gacacccaca     180
acaacaaatc caatgaacga aaccatccct ggaagtattg acatcgagac cctgatacca     240
aacttgatga tcatcatctt cggactggtc gggctgacag gaaatgccat tgtgttctgg     300
ctcctgggct tccgcatgca caggactgcc ttctcagtct acatcctaaa cttggccctg     360
gctgacttcc tcttccttct ctgtcacatc ataaattcca cagtgcttct tctccaggtt     420
tccccaccca acagtacctt ggtccattgc tttgacacca tcagaatggt tctctacatc     480
gcaggcctga gcatgctcag tgccattagc actgagcact gcctgtctgt cctgtgcccc     540
atctggtatc gctgccgccg cccagaacat acttcaactg tcatgtgtgc tgtgatctgg     600
gtcctgtccc tgttgatctg cattctaagt ggatatttct gtaattttt  tcttcacaaa     660 tatgtatatt actctgtgtg tcgggcattg gaattctgta tcggaacata ccccgatgtt     720
tttgttttgt agtcctctgt ctgtccaccc tggctctgct ggtcaggttg ttctgtggta     780
ctgggaaggc aaaatttacc agattattcg tgaccatcat gctgactgtt ttggttttc     840 ttctctgtgg gttgccctg tgtttcttct ggttcctggt agtctggatt aagcgtcctc     900
tcagtgtact aaatattaca ttttattttg catccattgt cctaactgtt gttaacagct     960
```

-continued

```
gtgccaaccc catcatttac ttcttcgtgg gctccttcag gcatcggttg aagcaacaga    1020
acctcaaaat ggttctccag aatgcactgc aggacactgc tgagcacct gaaacgtgg      1080 cagagatttc aagaagcaaa gcagagccct gatgaggagc ctctgcctgg acctcagagg   1140
tggctttggc actgagcact gccctgctgc acttgcccac tgtccactct cctctcagct    1200
tactgactgg caataactca gtggtacaac aacaccttca aaagctcacc actgacttag    1260
tatttctacc tatcccaagt aatagcatta atcagaaagt atcatgtctg catccttcta    1320
gacattattc aaattctcat ccaacttcat ctgaaacttt cttgctattt ctttggaaca    1380
ttttttgcca tggtaatagc ccaggtccag catcatgcct ctcttacctt tgattgttct    1440
gtacctgaat gtaaagaaaa aggagagaga agatgatcct ctgtcacagt gctcattacc   1500
caagcaccac taagagagct tgtctcccag gagtgcagac aaacctgtga gcacaggtaa   1560
gactaccact tctgcttaaa ggggcatgcc tggaacccac aggacacagg taaagaggag   1620
cagcctgaga aaggatactt tccagtttcc aactgcaccc tggagctgac cctgtgccac   1680
agctctcccc accttaattc ttcccagaaa gaactggtct mccaggaagt actgacacat   1740
agccttgcag gaggtacaag acactgtcac agatagcaag accagctaac accagagata   1800
accagatggc aagaggcaag ggcaaaaaca taagcaatgg gaaccaaggc tacttggcat   1860
catcagaacc tagttctctc aacaaagtga gccctggata ctccaacaca caagaaaagt   1920
atgactgtga ttaaaagtca ccgatgatga tgatgatgat gatgatgatg atgatgatg    1979
```

<210> SEQ ID NO 63
<211> LENGTH: 305
<212> TYPE: PRT
<213> ORGANISM: Mus musculus

<400> SEQUENCE: 63

```
Met Asn Glu Thr Ile Pro Gly Ser Ile Asp Ile Glu Thr Leu Ile Pro
  1               5                  10                  15

Asn Leu Met Ile Ile Ile Phe Gly Leu Val Gly Leu Thr Gly Asn Ala
                 20                  25                  30

Ile Val Phe Trp Leu Leu Gly Phe Arg Met His Arg Thr Ala Phe Ser
             35                  40                  45

Val Tyr Ile Leu Asn Leu Ala Leu Ala Asp Phe Leu Phe Leu Leu Cys
         50                  55                  60

His Ile Ile Asn Ser Thr Val Leu Leu Leu Gln Val Ser Pro Pro Asn
 65                  70                  75                  80

Ser Thr Leu Val His Cys Phe Asp Thr Ile Arg Met Val Leu Tyr Ile
                 85                  90                  95

Ala Gly Leu Ser Met Leu Ser Ala Ile Ser Thr Glu His Cys Leu Ser
            100                 105                 110

Val Leu Cys Pro Ile Trp Tyr Arg Cys Arg Arg Pro Glu His Thr Ser
        115                 120                 125

Thr Val Met Cys Ala Val Ile Trp Val Leu Ser Leu Leu Ile Cys Ile
    130                 135                 140

Leu Ser Gly Tyr Phe Cys Asn Phe Phe Leu His Lys Tyr Val Tyr Tyr
145                 150                 155                 160

Ser Val Cys Arg Ala Leu Glu Phe Cys Ile Gly Thr Tyr Pro Met Phe
                165                 170                 175

Leu Phe Val Val Leu Cys Leu Ser Thr Leu Ala Leu Leu Val Arg Leu
            180                 185                 190

Phe Cys Gly Thr Gly Lys Ala Lys Phe Thr Arg Leu Phe Val Thr Ile
```

|  | 195 |  |  |  | 200 |  |  |  |  | 205 |  |  |
|---|---|---|---|---|---|---|---|---|---|---|---|---|

Met Leu Thr Val Leu Val Phe Leu Leu Cys Gly Leu Pro Leu Cys Phe
210                     215                     220

Phe Trp Phe Leu Val Val Trp Ile Lys Arg Pro Leu Ser Val Leu Asn
225                     230                     235                     240

Ile Thr Phe Tyr Phe Ala Ser Ile Val Leu Thr Val Val Asn Ser Cys
                245                     250                     255

Ala Asn Pro Ile Ile Tyr Phe Phe Val Gly Ser Phe Arg His Arg Leu
                260                     265                     270

Lys Gln Gln Asn Leu Lys Met Val Leu Gln Asn Ala Leu Gln Asp Thr
            275                     280                     285

Ala Glu Thr Pro Glu Asn Val Ala Glu Ile Ser Arg Ser Lys Ala Glu
        290                     295                     300

Pro
305

<210> SEQ ID NO 64
<211> LENGTH: 1485
<212> TYPE: DNA
<213> ORGANISM: Mus musculus

<400> SEQUENCE: 64

```
aacaacacaa aaccctgaaa aaaaaaaaga aattaaaagt tttgttcata gtaaaggcct      60
catttcttct ttgtgttcac agcaacatca gtgcacggtt aatggcaata aacacctcag     120
cctcggcaat ggcacccacg acaacaaatc caagggaag caaacaatcc ctgggaagta     180
ttgacatcga gaccctgatc tcaaacttga tgatcatcat tttcgggctg gtagggctgc     240
caggaaatgc cattgtgttc tggctcctgg gcttctgctt gcacaggaat gccttcttag     300
tctacatcct aaacttggcc ctggctgacg tcctcttcct tctctgtcac atcataaatt     360
ccacagtgct tcttctcaag gttcccccac ccaacggtaa tattggtcca ttgcttcaac     420
atcatcagaa ttgttctcta catcacaggc ctgagcatgc tcagtgccat catcactgag     480
cgctgcctgt ctatcctgtg ccccatctgg tatcgctgcc accgcccaga acacacatca     540
actgccatgt gtgctgtgat ctgggtcctg tctctgttga tctgcattct tggaagaata     600
tttctgtaat ttttttcctt c acaaatatgt aaattactct gtgtgtctgg cattggactc     660
ctttatcgga acatacccaa tgttttttgct tgtagtcctc tgtctgtcca ccatggctct     720
gctggccagg ttgttctgtg gttctgggaa gacgaaattt accagattat tgtgaccat      780
catgcttacc gttttggttt ttcttctctg cttggtttgc ccctgggctt cttctggttc     840
ctgttactct ggattaaggg tgcttacagt gtactaggtt atagatttta ttttgcatca     900
attgtcctaa ctgctgttaa cagctgtgcc aaccccatca tttacttctt catgggctca     960
ttcaggcaac gattgcagca caagaccctc aaaatcgttc tccagagtgc actgcacgac    1020
actcctgaga cacctgaaaa catggtggag atgtcaagaa gcaaagcaga gccataatga    1080
agagcctctg cctggacctc agaggtggat ttggagtgag aactgcccta cgcttgacca    1140
ctgtccactc tcctctcagc ttactgactt tggatgccta agtggtccaa caacaacttc    1200
aaaatctctc cactgactta gtatttatac ctctcccaag taatagcatt aatcagaaag    1260
tatcatgtct gcatccttct tgacattaat ccaattctca tactaacttc atctgaaact    1320
ttcttgctgt ttctttggaa cttttgttgc catagtaata gcccagatcc agcaccatga    1380
ctcacttgtc tgtgattatt ctgtacctga atgtaaagaa aaaggcagga gatgatcctg    1440
```
tatcacagtg ctcattacac aaacaccacc aagaaagctc gtctc        1485

<210> SEQ ID NO 65
<211> LENGTH: 300
<212> TYPE: PRT
<213> ORGANISM: Mus musculus

<400> SEQUENCE: 65

| | | | | | | | | | | | | | | |
|---|---|---|---|---|---|---|---|---|---|---|---|---|---|---|
| Gly | Ser | Ile | Asp | Ile | Glu | Thr | Leu | Ile | Ser | Asn | Leu | Met | Ile | Ile |
| 1 | | | | 5 | | | | | 10 | | | | | 15 |
| Phe | Gly | Leu | Val | Gly | Leu | Pro | Gly | Asn | Ala | Ile | Val | Phe | Trp | Leu | Leu |
| | | | 20 | | | | | 25 | | | | | 30 | | |
| Gly | Phe | Cys | Leu | His | Arg | Asn | Ala | Phe | Leu | Val | Tyr | Ile | Leu | Asn | Leu |
| | | 35 | | | | | 40 | | | | | 45 | | | |
| Ala | Leu | Ala | Asp | Val | Leu | Phe | Leu | Leu | Cys | His | Ile | Ile | Asn | Ser | Thr |
| 50 | | | | | 55 | | | | | 60 | | | | | |
| Val | Leu | Leu | Leu | Lys | Val | Pro | His | Pro | Thr | Val | Ile | Leu | Val | His | Cys |
| 65 | | | | | 70 | | | | | 75 | | | | | 80 |
| Phe | Asn | Ile | Ile | Arg | Ile | Val | Leu | Tyr | Ile | Thr | Gly | Leu | Ser | Met | Leu |
| | | | | 85 | | | | | 90 | | | | | 95 | |
| Ser | Ala | Ile | Ile | Thr | Glu | Arg | Cys | Leu | Ser | Ile | Leu | Cys | Pro | Ile | Trp |
| | | | 100 | | | | | 105 | | | | | 110 | | |
| Tyr | Arg | Cys | His | Arg | Pro | Glu | His | Thr | Ser | Thr | Ala | Met | Cys | Ala | Val |
| | | 115 | | | | | 120 | | | | | 125 | | | |
| Ile | Trp | Val | Leu | Ser | Leu | Leu | Ile | Cys | Ile | Leu | Gly | Lys | Tyr | Phe | Cys |
| 130 | | | | | 135 | | | | | 140 | | | | | |
| Asn | Phe | Phe | Leu | His | Lys | Tyr | Val | Asn | Tyr | Ser | Val | Cys | Leu | Ala | Leu |
| 145 | | | | | 150 | | | | | 155 | | | | | 160 |
| Asp | Ser | Phe | Ile | Gly | Thr | Tyr | Pro | Met | Phe | Leu | Leu | Val | Val | Leu | Cys |
| | | | | 165 | | | | | 170 | | | | | 175 | |
| Leu | Ser | Thr | Met | Ala | Leu | Leu | Ala | Arg | Leu | Phe | Cys | Gly | Ser | Gly | Lys |
| | | | 180 | | | | | 185 | | | | | 190 | | |
| Thr | Lys | Phe | Thr | Arg | Leu | Phe | Val | Thr | Ile | Met | Leu | Thr | Val | Leu | Val |
| | | 195 | | | | | 200 | | | | | 205 | | | |
| Phe | Leu | Leu | Cys | Leu | Gly | Leu | Pro | Leu | Gly | Phe | Trp | Phe | Leu | Leu |
| 210 | | | | | 215 | | | | | 220 | | | | | |
| Leu | Trp | Ile | Lys | Gly | Ala | Tyr | Ser | Val | Leu | Gly | Tyr | Arg | Phe | Tyr | Phe |
| 225 | | | | | 230 | | | | | 235 | | | | | 240 |
| Ala | Ser | Ile | Val | Leu | Thr | Ala | Val | Asn | Ser | Cys | Ala | Asn | Pro | Ile | Ile |
| | | | | 245 | | | | | 250 | | | | | 255 | |
| Tyr | Phe | Phe | Met | Gly | Ser | Phe | Arg | Gln | Arg | Leu | Gln | His | Lys | Thr | Leu |
| | | | 260 | | | | | 265 | | | | | 270 | | |
| Lys | Ile | Val | Leu | Gln | Ser | Ala | Leu | His | Asp | Thr | Pro | Glu | Thr | Pro | Glu |
| | | 275 | | | | | 280 | | | | | 285 | | | |
| Asn | Met | Val | Glu | Met | Ser | Arg | Ser | Lys | Ala | Glu | Pro |
| | | 290 | | | | | 295 | | | | | 300 |

<210> SEQ ID NO 66
<211> LENGTH: 1518
<212> TYPE: DNA
<213> ORGANISM: Mus musculus

<400> SEQUENCE: 66
aacaacaaaa aaaaaaaaca gaaaagaaa ttaaaagttg tgtccatagt gaaggcctca    60
tttcttcttt gtgtttccag caacaccagt gcagggtttc tggacctaaa cacctcagcc    120

```
tcggcaatag cacccacaac aaccaaacca atggacgaaa ccatccctgg aagtattgac    180
actgagaccc tgtatccaac acttgatgat catcatcttc ggactggtcg ggctgacagg    240
aaatggcatt gtgttgtggc tcctgggctt ccacttgcaa aggaatgcct ttttagtcta    300
catcctaaac ttggcctag ctgacttcct tacttctc tgtcacatca tagattccac    360
aatgcttctt ctcaaggttc ccccacccaa ctggatcttg gtccattgct ttaggaccat    420
ccaaattttt ctctacatca caggcctgag catgctcagt gccatcagca cagagcgctg    480
cctgtctgtc ctgtgcccca tctggtatcg ctgccgccgc cagaaaaca catcaactgt    540 gatgtgtgct gtgatctggg tcctgtcctt gttgatctgc attctgcatg atatttttc    600 tgttatttct ctggtctcag ttatgaaaat tactctgtgt gttttgcatc agcgatcatt    660
atcagttcat acccaacgtt tttgcttgta gtcctctgtc tgtccaccct ggctctgctg    720
gccaggttgt tctgtggtgc tgggaagagg aaatttccca gattattcgt gaccatcata    780
cttaccgttt tggtttttct tctctgtggg ttgccctggg gagccctctg gttcccatta    840
ctctggattc agggtggttt ctggaaaaga ctttttcagg catcaattgt cctatcttct    900
gttaacagct gtgccaaccc catcatttat ttcttcgtgg gctcattcag gcatcgattg    960
aagcaccaga cccttaaaat ggttctccag aatgcactgc aggacactcc tgagacaact   1020
gaaaacatgg tggagatgtc aagaagtaaa gcagagccat gatgaagagc ctctgcctgg   1080
acctcagagg tggatttgga gtgagcactg ccctgctgca cttgaccact gtccactctc   1140
ctctcagctt actgacttgg aatgcctcag tggtccaaaa acaccttcaa aagctctcca   1200
ctgactaagt atttctacct atcccaagta atagcattaa tcagaaagta ccatgtctgc   1260
atccttcttg acattaatca aattctctta ctatcttcat ctgaaacttt cttgttgttt   1320
ctttggaact tttgttgcca tggtaatagc ccaagtccag caccatgact ttcttatctg   1380
tgattgttct atacctgaat gtaaaggcaa aggagccagg agatgatcct gtgttacagt   1440
gctcattacc caaacaccac caagagagct tgtctcccag gagtgcagac acgcctgtga   1500
acacaggtaa gaccacca                                                  1518
```

<210> SEQ ID NO 67
<211> LENGTH: 303
<212> TYPE: PRT
<213> ORGANISM: Mus musculus

<400> SEQUENCE: 67

```
Met Asp Glu Thr Ile Pro Gly Ser Ile Asp Thr Glu Thr Leu Tyr Pro
  1               5                  10                  15

Asn Leu Met Ile Ile Phe Gly Leu Val Gly Leu Thr Gly Asn Gly
                 20                  25                  30

Ile Val Leu Trp Leu Leu Gly Phe His Leu Gln Arg Asn Ala Phe Leu
             35                  40                  45

Val Tyr Ile Leu Asn Leu Ala Leu Ala Asp Phe Leu Tyr Leu Cys
         50                  55                  60

His Ile Ile Asp Ser Thr Met Leu Leu Leu Lys Val Pro Pro Asn
 65                  70                  75                  80

Trp Ile Leu Val His Cys Phe Arg Thr Ile Gln Ile Phe Leu Tyr Ile
                 85                  90                  95

Thr Gly Leu Ser Met Leu Ser Ala Ile Ser Thr Glu Arg Cys Leu Ser
            100                 105                 110

Val Leu Cys Pro Ile Trp Tyr Arg Cys Arg Arg Pro Glu Asn Thr Ser
        115                 120                 125
```

```
Thr Val Met Cys Ala Val Ile Trp Val Leu Ser Leu Leu Cys Ile
    130                 135                 140

Leu His Gly Tyr Phe Cys Tyr Phe Ser Gly Leu Ser Tyr Glu Asn
145                 150                 155                 160

Tyr Ser Val Cys Phe Ala Ser Ala Ile Ile Ser Ser Tyr Pro Thr
                165                 170                 175

Phe Leu Leu Val Val Leu Cys Leu Ser Thr Leu Ala Leu Leu Ala Arg
                180                 185                 190

Leu Phe Cys Gly Ala Gly Lys Arg Lys Phe Ser Arg Leu Phe Val Thr
            195                 200                 205

Ile Ile Leu Thr Val Leu Val Phe Leu Leu Cys Gly Leu Pro Trp Gly
    210                 215                 220

Ala Leu Trp Phe Pro Leu Leu Trp Ile Gln Gly Gly Phe Trp Lys Arg
225                 230                 235                 240

Leu Phe Gln Ala Ser Ile Val Leu Ser Ser Val Asn Ser Cys Ala Asn
                245                 250                 255

Pro Ile Ile Tyr Phe Phe Val Gly Ser Phe Arg His Arg Leu Lys His
                260                 265                 270

Gln Thr Leu Lys Met Val Leu Gln Asn Ala Leu Gln Asp Thr Pro Glu
            275                 280                 285

Thr Thr Glu Asn Met Val Glu Met Ser Arg Ser Lys Ala Glu Pro
    290                 295                 300

<210> SEQ ID NO 68
<211> LENGTH: 1500
<212> TYPE: DNA
<213> ORGANISM: Mus musculus

<400> SEQUENCE: 68
cattttcgga ctggtcgggc tgacaggaaa taccattgtg ttctggctcc tgggcttctg      60
cttgcacagg aatgcctttt tagtctacat cctaaacttg gccctggctg acttcctctt     120
ccttctctgc cacatcataa attccacagt acttcttctc aaggttcccc tacccaactg     180
gatcttgttc cattgcttta acaccatcag aattgttctt tacatcacag gcctgaacat     240
gctcagtgcc atcaacatgg agcactgcct gtctgtcctg tgccccatct ggtatcactg     300
ctgccgccca gaacacacat caactgtcat gtgtgctgtg atctgggtcc tgtccctgtt     360
gatctgcatt ctgaatgaat atttctgtga tttctttggt accaaattgg taaattacta     420
tgtgtgtctg gcatcgaact tctttatggg agcatacctg ttgttttgt ttgtagtcct     480 ctgtctgtcc accctggctc tgctggccag gttgttctgt ggtgctggga atacgaaatt     540
taccagattt cacatgacca tcttgctgac ccctttgttc tttctcctct gcggggttgcc     600 ctttgccatc taatgcttcc tgttattcaa gattaaggat gatttccatg tattttatat     660
taaccttttt ctagcattag aagtcctgac ttctattaac agctgtgaca accccatcat     720
ctatttcttc ctggactcct tcagacatca ggagaagcac cagaccctca aaatggttct     780
ccagagtgca ctgcaggata ctccytgagac acctgaaaac atggcagaga tgtcaagaag     840
caaagcagag ccgtgatgaa gagcctctgc ctggatgtca gaggtggctt tggagtgagc     900
actgccctgc tgcacttgac cactgtcaac tctactctca gcttactgac ttgtcatgcc     960
tcagtggttc aacaacacct tcaaaagctc tccactgact tagtattttt acctctccca    1020
agtagtagca ttaatcagaa agtatcatgt ctgcatcctt cttgacatta ttcaaattct    1080
catctaactt catctgaaac tttctcccta tttctttgga acttttgttg ccatggkaat    1140
```

```
agcccagatc cagcaccatg actctcttgt ctgtgattgt tctgaacctg aatgtaaaga    1200
caaaggagag agaagatgat cctgtgtcac agtgctcatt acccaagcac cgccaagaga    1260
tcttgtctcc caggagtgca gacaagcctg tgcgcactgg taagaccacc acttttgctt    1320
aaagggacat gcctggaact ttcaagacag agtaacagag gagcaccctg aacaggata     1380 cttccagttt ccaactgcac accggagctg accctatgca acagctctcc atacccaact    1440
tcttcccaca aagaactggt gctaccagga gtactgacac acaggttttc aggaaggaca    1500
```

<210> SEQ ID NO 69
<211> LENGTH: 283
<212> TYPE: PRT
<213> ORGANISM: Mus musculus

<400> SEQUENCE: 69

Ile Phe Gly Leu Val Gly Leu Thr Gly Asn Thr Ile Val Phe Trp Leu
1               5                   10                  15

Leu Gly Phe Cys Leu His Arg Asn Ala Phe Leu Val Tyr Ile Leu Asn
            20                  25                  30

Leu Ala Leu Ala Asp Phe Leu Phe Leu Leu Cys His Ile Ile Asn Ser
        35                  40                  45

Thr Val Leu Leu Leu Lys Val Pro Leu Pro Asn Trp Ile Leu Phe His
    50                  55                  60

Cys Phe Asn Thr Ile Arg Ile Val Leu Tyr Ile Thr Gly Leu Asn Met
65                  70                  75                  80

Leu Ser Ala Ile Asn Met Glu His Cys Leu Ser Val Leu Cys Pro Ile
                85                  90                  95

Trp Tyr His Cys Cys Arg Pro Glu His Thr Ser Thr Val Met Cys Ala
            100                 105                 110

Val Ile Trp Val Leu Ser Leu Leu Ile Cys Ile Leu Asn Glu Tyr Phe
        115                 120                 125

Cys Asp Phe Phe Gly Thr Lys Leu Val Asn Tyr Tyr Val Cys Leu Ala
    130                 135                 140

Ser Asn Phe Phe Met Gly Ala Tyr Leu Leu Phe Leu Phe Val Val Leu
145                 150                 155                 160

Cys Leu Ser Thr Leu Ala Leu Leu Ala Arg Leu Phe Cys Gly Ala Gly
                165                 170                 175

Asn Thr Lys Phe Thr Arg Phe His Met Thr Ile Leu Leu Thr Pro Leu
            180                 185                 190

Phe Phe Leu Leu Cys Gly Leu Pro Phe Ala Ile Cys Phe Leu Leu Phe
        195                 200                 205

Lys Ile Lys Asp Asp Phe His Val Phe Tyr Ile Asn Leu Phe Leu Ala
    210                 215                 220

Leu Glu Val Leu Thr Ser Ile Asn Ser Cys Asp Asn Pro Ile Ile Tyr
225                 230                 235                 240

Phe Phe Leu Asp Ser Phe Arg His Gln Glu Lys His Gln Thr Leu Lys
                245                 250                 255

Met Val Leu Gln Ser Ala Leu Gln Asp Thr Pro Glu Thr Pro Glu Asn
            260                 265                 270

Met Ala Glu Met Ser Arg Ser Lys Ala Glu Pro
        275                 280

<210> SEQ ID NO 70
<211> LENGTH: 2504
<212> TYPE: DNA

<213> ORGANISM: Mus musculus

<400> SEQUENCE: 70

```
gtgtgtgcct tggtttttat tgcttatgtt tttgtccttg catcttgcca tctggttatc      60
tctggtatta gctggtcttg atgtctctga ttgtccttgt ccctcctgca agcctgtgtg     120
tcatttctcc tgggagacca gttatttcta gaagaaattt aggtatgggg agttgtggca     180
cagggtcagc cccagggtgc agatgaaaac tggaaggatc ctgtcccagg tcgctcctct     240
atttctgtgt cctgcgggtt ctgggcatgt ccctttgagc agaagtgttg gtcttacctg     300
tgctcacagg cttgtctgca ctgtggcaca agatcatctc ctggctcctt tgtctttaca     360
ttcaggtaca gamcaatcmc cagacaagag agtcatgctt ctggacttgg gctatttcca     420
tggcaacaaa agttccaaag aaacamcaag aaaggttcag aggaagttag catgagaatt     480
tgattaatgt cataaaggat gcagacatga tactttctga ttaatgatat tactcgagag     540
aggtagaaaa tctaagtcag tggagagctt ttgaagatgt tggtggacca ctgaggcatg     600
tcaagtcagt cagcggagag cagagtggac agtgataaag tgcagcaggg cattcttcac     660
tccaaagcca cctctgaggt ccaggcagag gctcttcatc atggctctgc tttacttctt     720
gacatcccca ccatgttttc aggtgtctca ggagtgtcct acattgtcct ctggagaacc     780
attttcagtg tctggtgctg caaccgaagc ctgaaggagc ccgtgaagaa gtaaatgatg     840
gagttggcac aactgttaat agcagtcatg acaagtgatt ccagataaaa tacaagagta     900
aatacatgaa aagcatcctt aatcttgcat aacagaaacc agtagatgcc aaagttcaat     960
ctgcaaagga gaaaaccaga gcagtcagca ggatggtcac atactatctg gtaagcttca    1020
tttgcccaac atcacagaac aacctggcca gcagagccag gctggaaaga cagagatcca    1080
caaacaaaac atcaggtatg cagaagtaaa gaagttcaat gccagacacc cattgtcatt    1140
ttcatatttg ctatgtaaga aacctcagaa ataactattc agaatgcaga tcaacaggga    1200
cagtacccag atcacagcac acatggcagc tgatgtatgt tctgggtggt gacagcaatc    1260
ccagatgggc acagtacaga caggccgtgc tcagtgctga tggcagtgag catgctcagg    1320
cctgcgatgt agagaaccat catgatgatg taaaagcaca agataaagat aatggggtag    1380
aaaacattga gaagaagcag tatggaatct atggtgtgac ctaggaggaa gaagaagtca    1440
gccaggtcca agtttaggat gtagaccttg aaagcattcc tgcgcaaggg gaagtgcagg    1500
atccagaaga caatggaatt tcctgtcagc ccaaccagtc cgaagatgat ggttatcaag    1560
tttgggatca gaatcctgat gttgatacct ccagggatgg ttttgtccat tggatttgct    1620
gttgtgggtg ctgttggtga ggctgatgtg tttagggcca gaaactctgc accagtgctg    1680
ctggaacac aaagaaaaaa tgaggccttc cctatgaact cacctttgt tttccttttt    1740
gttggatttt taatttcttc tattgcatat tttaaattat ttgctttcct gtgtccccc    1800
ccctcccttt cctgaaaacc cctatcccac cctccctcta ccctgcttac tattgaggat    1860
attcctccac ccactcccac ctctctgccc tctattgccc tacactgggg caactatcaa    1920
gccttcatag atccatagaa ctcttctccc atttattcat gacagggcca tcctctgcta    1980
catatgcagc tggagccatg tgtacttctt tgctgatggc ttgtcccctg ggtgctgggg    2040
gattggtact ggttggttga tattgttttt cttacctatg ggcttgcaaa ccccttcaac    2100
tcccttagtc ctttctctaa ttcttctatt agggaccctg ttctcagtct aatggctgga    2160
tgctaacatc tgcctctgta tttgtaaggc tctgacagtc cctctcaaga aacagccata    2220
ttaggctcct gtcagcatgc acttcttgca atccacaata gtgtctggtt ttggtaactg    2280
```

```
tatatggtac gaatccccag gtgggacagt gtctgtgtga tctttccttt agtctttgct    2340
ctagacttta tctccataaa aagtattttg ttctccttct aaaaagcact gaagcaccca    2400
ctctttggtc tttcttcttc atggacttca tgtggtctgt gaattttaac ctggttattt    2460
ttcagttttt gagctcctat tcacttatca gtgagtgcat acca                     2504
```

<210> SEQ ID NO 71
<211> LENGTH: 301
<212> TYPE: PRT
<213> ORGANISM: Mus musculus

<400> SEQUENCE: 71

```
Met Asp Lys Thr Ile Pro Gly Gly Ile Asn Ile Arg Ile Leu Ile Pro
  1               5                  10                  15

Asn Leu Ile Thr Ile Ile Phe Gly Leu Val Gly Leu Thr Gly Asn Ser
                 20                  25                  30

Ile Val Phe Trp Ile Leu His Phe Pro Leu Arg Arg Asn Ala Phe Lys
             35                  40                  45

Val Tyr Ile Leu Asn Leu Asp Leu Ala Asp Phe Phe Phe Leu Leu Gly
         50                  55                  60

His Thr Ile Asp Ser Ile Leu Leu Leu Asn Val Phe Tyr Pro Ile
 65                  70                  75                  80

Ile Phe Ile Leu Cys Phe Tyr Ile Ile Met Met Val Leu Tyr Ile Ala
                 85                  90                  95

Gly Leu Ser Met Leu Thr Ala Ile Ser Thr Glu His Gly Leu Ser Val
                100                 105                 110

Leu Cys Pro Ile Trp Asp Cys Cys His His Pro Glu His Thr Ser Ala
            115                 120                 125

Ala Met Cys Ala Val Ile Trp Val Leu Ser Leu Leu Ile Cys Ile Leu
        130                 135                 140

Asn Ser Tyr Phe Gly Phe Leu His Ser Lys Tyr Glu Asn Asp Asn Gly
145                 150                 155                 160

Cys Leu Ala Leu Asn Phe Phe Thr Ser Ala Tyr Leu Met Phe Leu Phe
                165                 170                 175

Val Asp Leu Cys Leu Ser Ser Leu Ala Leu Leu Ala Arg Leu Phe Cys
            180                 185                 190

Asp Val Gly Gln Met Lys Leu Thr Arg Tyr Val Thr Ile Leu Leu Thr
        195                 200                 205

Ala Leu Val Phe Leu Leu Cys Arg Leu Asn Phe Gly Ile Tyr Trp Phe
    210                 215                 220

Leu Leu Cys Lys Ile Lys Asp Ala Phe His Val Phe Thr Leu Val Phe
225                 230                 235                 240

Tyr Leu Glu Ser Leu Val Met Thr Ala Ile Asn Ser Cys Ala Asn Ser
                245                 250                 255

Ile Ile Tyr Phe Phe Thr Gly Ser Phe Arg Leu Arg Leu Gln His Gln
            260                 265                 270

Thr Leu Lys Met Val Leu Gln Arg Thr Met Asp Thr Pro Glu Thr Pro
        275                 280                 285

Glu Asn Met Val Gly Met Ser Arg Ser Lys Ala Glu Pro
    290                 295                 300
```

<210> SEQ ID NO 72
<211> LENGTH: 2758
<212> TYPE: DNA
<213> ORGANISM: Mus musculus

<400> SEQUENCE: 72

```
aattttgtg tttcctcttt aagggcttct accaatttat ctgtgttctc ctgtattatt      60
ttaagggagt tatttatgtc tttcttaatg tcctctatca tcatcatcat catccttatc     120
attttcatca tcatcaccag aggtgacttt aaatcagagt catgcttttc tggtgtgttg     180
gagtatccag ggctcaccat gttgagagaa ctaggttctg atgatgccaa gtagccttgg    240
ttcccattgc ttatgttttt gcccttgcct cttgccatct gattatctct ggagtaagct    300
ggtcttgctc tctctaactg tggcttgtcc ctcctgcaag cctatgtgtc agtactcctg    360
gtagaccagt tctttctggg agaaatttgg gtatggagag ctgtggcaca gggtcagctc    420
cggggtacag ttggaaactg aagtatcct gtcccaggct gctcctctgt tcctgtgtcc     480
tgaggattcc aggcatgtcc atttaagcag aagtggtggt cttacctatg ttcacaggca    540
tatctgcact cctgggagac aagctttctt ggtggtgttt gggtaatgag cactgggaca    600
caggaacatc tcctggctcc tttgtcttta catttgggta cagaacaatc acagacaaga    660
gagtaattgt gctgaaccta agctattacc atggcaacaa aagttccaaa gaaacagcaa    720
gaatgtttca gatgaagtta gtatgagaat tggattaatg tcaggaagga tgcagacatg    780
gtactttctg attaatgcta ttacttggga gaggtagaaa tactaagtca gtggagagct    840
tttgaaggtg ttgttggacc actgaggaat gccaagtcag taagctgaga ggaaagtgga    900
cagtggtcta gtgcagcatg gcagtgctca ctccaaagcc acctctgagg tccaggcaga    960
ggctcttcat catggctctg ctttgcttct tgatatatcc accatgtttt caggtgtctc   1020
aggagtgtcc tgcaatgcac tctggagaac cattttgagg gtcttgtgct tcaacggatg   1080
cctgtatgag cccacgaaga agtaaatgat ggggttggca cagctgttaa cagcagttag   1140
gacaagtgat gccagaaaga atctatagtc tagtatactg aaaccaccct caatccaggg   1200
taacaggaac cagaggaagc ccaggggcaa cccacagaga agaaaaacca aaatggtcac   1260
catgatggtc atgaataatc tggtaaattt cttctttcca gcaccacaga acaacctggc   1320
cagcagagtc agggtagaaa aacagaggac tacaaacaaa aaaatagggt atattctgat   1380
gaagaattct gatgcctgac acacagagtt aatttcatat ttgggaccaa ataaatcaca   1440
gaaatatctg ttcagaaggc agatcaacag gggacaggac ccagatcacg acacacatga   1500
tggttgatgt gtgttmtggg cggtggcagc gataccagat ggggcacagg acagacaggc   1560
agcgmtcagt gctgatggca ctgagcatgc tcaggcctgt gatgtagaga accgttctga   1620
tggtgtcaaa gcaatggatg aagatactgt tgtgtgggcg aaccttgaaa agatgcattg   1680
tggaatttat gatgtgacag agaagaaaga aggaagtcag ccagggccaa gtttaggatg   1740
tagactaaga tggcattcct gtgaaatcgg aagcccagga tccagaatac aatggcattt   1800
ccagtcagcc caaccagtcc gaagatgatg atcatcaagt gtgggataag ggtctcgatt   1860
tcaatacttc cagagatggt ttcatccatt ggatttgttg tcgtgggtgc cattgctgag   1920
gctgaggtgt ttagggccag aaaccctgca ctggtattgc tggaaacaca acaagaaat   1980
gaggccttca ctgtgaacac aactttaat ttctttcttt ttgtttgttt gtttgtttgt   2040
ttgtggggtt ttgttttttt ttttaatttt tttttgtatt agatattttc ttcatttaat   2100
tttcaaatgt tatccctttt cctggctttc cccctccca gaaacccct tctgatcctc    2160
ccaccctctt caacccacac acccacttcc acctctctgc ccctgattcc cttacactgg   2220
agcatctata gaaccttcat aggttcaagg acctcttctt ccatccatgc aagacatggc   2280
```

```
catcatctgc tacatatgca tctggagcca cacgtactcc tttgttgatg gcttagtccc    2340
tgggagttca gggggtgggg gtgggggtgg gggcagtggt ctcttggttc atactgttgc    2400
tcttcttatg gagcttcaaa ccacttcaac tccctcaggc ctttctctaa ctcctctatt    2460
agggaccctg tgctcagttt aattgttggc tgctaacatc agactctgca tttgaaaggc    2520
cctgacatgg cctcttagga aacagctata tcaggttcct gtcagcattc actccttgac    2580
atccacaata gtgtctgcat ttggtaactg tgtatgagat gaatcccag gtggaacatt     2640 ctctgggtga ctttccttt agtgtctgtt ctacacatta tctccatatt tgctcttgtg     2700
agtattttgt tcttcttcta agaaggtctg aaacacccac actttcgtct tccttgtt      2758
```

<210> SEQ ID NO 73
<211> LENGTH: 304
<212> TYPE: PRT
<213> ORGANISM: Mus musculus

<400> SEQUENCE: 73

```
Met Asp Glu Thr Ile Ser Gly Ser Ile Glu Ile Glu Thr Leu Ile Pro
 1               5                  10                  15

His Leu Met Ile Ile Ile Phe Gly Leu Val Gly Leu Thr Gly Asn Ala
             20                  25                  30

Ile Val Phe Trp Ile Leu Gly Phe Arg Phe His Arg Asn Ala Ile Leu
         35                  40                  45

Val Tyr Ile Leu Asn Leu Ala Leu Ala Asp Phe Phe Phe Leu Leu Cys
     50                  55                  60

His Ile Ile Asn Ser Thr Met His Leu Phe Lys Val Arg Pro His Asn
 65                  70                  75                  80

Ser Ile Phe Ile His Cys Phe Asp Thr Ile Arg Thr Val Leu Tyr Ile
                 85                  90                  95

Thr Gly Leu Ser Met Leu Ser Ala Ile Ser Thr Asp Arg Cys Leu Ser
            100                 105                 110

Val Leu Cys Pro Ile Trp Tyr Arg Cys His Arg Pro His Thr Ser Thr
        115                 120                 125

Ile Met Cys Val Val Ile Trp Val Leu Ser Leu Leu Ile Cys Leu Leu
    130                 135                 140

Asn Arg Tyr Phe Cys Asp Leu Phe Gly Pro Lys Tyr Glu Ile Asn Ser
145                 150                 155                 160

Val Cys Gln Ala Ser Glu Phe Phe Ile Arg Ile Tyr Pro Ile Phe Leu
                165                 170                 175

Phe Val Val Leu Cys Phe Ser Thr Leu Thr Leu Leu Ala Arg Leu Phe
            180                 185                 190

Cys Gly Ala Gly Lys Lys Lys Phe Thr Arg Leu Phe Met Thr Ile Met
        195                 200                 205

Val Thr Ile Leu Val Phe Leu Leu Cys Gly Leu Pro Leu Gly Phe Leu
    210                 215                 220

Trp Phe Leu Leu Pro Trp Ile Glu Gly Gly Phe Ser Ile Leu Asp Tyr
225                 230                 235                 240

Arg Phe Phe Leu Ala Ser Leu Val Leu Thr Ala Val Asn Ser Cys Ala
                245                 250                 255

Asn Pro Ile Ile Tyr Phe Phe Val Gly Ser Tyr Arg His Pro Leu Lys
            260                 265                 270

His Lys Thr Leu Lys Met Val Leu Gln Ser Ala Leu Gln Asp Thr Pro
        275                 280                 285

Glu Thr Pro Glu Asn Met Val Asp Ile Ser Arg Ser Lys Ala Glu Pro
```

<210> SEQ ID NO 74
<211> LENGTH: 1738
<212> TYPE: DNA
<213> ORGANISM: Mus musculus

<400> SEQUENCE: 74

```
cacccacaac aaccaaatcc aatggacgaa accatcccct ggaagtattg acatcaagac      60
cctgatcgca aatttgatga tcatcatctt cggactggtc gggctgacag aaactgcctt     120
tgtgttctga ctcctgggct tccacttgca caggaacgcc ttcttagtct acatcctaaa     180
cttggccctg actgacttcc tcttccttct ctgtcacatc ataaattcca cagtgattct     240
tctcaatgtt ccctaccta acatgatctt ggtccattgc tttagcacca tcagaatatt     300
tctcaacatc acaggcctaa gcattctcag tgccatcagc actgagcgct gcctgtctgt     360
cctgtgcccc atctggtatc gctgccacca cccagaacac acatcaactg tcatgtgtgc     420
tgtgatctga gtcctgtccc tgttgatttg cactctgtat agatatttct gttttttctt     480
tggtcccaaa tatgtatttg actctgtgtg tctggcaacg acctacttta tcagaacata     540
cccaatgttt ttgtttatgg tcctctgtct gtccactctg gctctgctgg ccaggttgtt     600
ctgtggtgct gggaagamra aatttaccag gattattcgt gaccatcatg ctgacygttt     660
tggtttttct tctctgtggg atgccccctag gcttcttctg gttcgtgttc ccatggatta     720
actgtgattt cagtgtacta gattatagac tttttctggc atcaattgta ctaactgctg     780
ttaacagtta tggcaacccc atcatttact tcttcgtggg ctccttcagg aatcggttga     840
agcaccagac cctccaaaag gttctccaga gtgcactgca cgacactcct gagacacctg     900
aaaacatggt agagatgtca agaagcaaag cagagccatg atgaagagtc tctgacagga     960
cttcagaggt ggctttggag tgagcactgc cctgctgcac ttaaccacac tccactctcc    1020
tctcagctta ctgactatgg atgcctcagt ggtccaacaa tgccttcaaa agctctccac    1080
tgacttagta tttctacctc tcccaagtaa tagcattaat cagaaagtac catgtctgca    1140
tccttcttga cattaatcca attctcatac taacttcatc tgtaactttc ttgctgtttc    1200
tttggaactt ttgttaccat agtaatagcc taggtccagc accatgattc ccttgtctgt    1260
gattgttctg tacctacctg aatgtaaagc aaagtagcca ggagatgttc ctgtgtycca    1320
gtgctcatta cccaaacacc accaagaaag cttgtctccc aggagtgcag acaagcctgt    1380
gaacacaggt aagaccacca cttctgctta aaggggcatg cctggaaccc tcaggacaca    1440
ggaacagagg agcagcctgg gacaggatac ttccagtttc caactgcact ccagagctga    1500
ccctgtgcca cagctctcca tacccaaatt cctcccagaa agaattggtg taccaggagt    1560
actgacacac aggcttgcag aaggaacaag ccacagtcaa agttagcaag acctgctaac    1620
accagagata accagatggc aagacacaag ggcaaaaaca taagcaatgg gaaccaagac    1680
tacttggcat catcagaaac tagttctctc aacatggtga gccatggata cttcaaca     1738
```

<210> SEQ ID NO 75
<211> LENGTH: 303
<212> TYPE: PRT
<213> ORGANISM: Mus musculus

<400> SEQUENCE: 75

Met Asp Glu Thr Ile Pro Gly Ser Ile Asp Ile Lys Thr Leu Ile Ala
1               5                   10                  15

Asn Leu Met Ile Ile Ile Phe Gly Leu Val Gly Leu Thr Glu Thr Ala
            20                  25                  30

Phe Val Phe Leu Leu Gly Phe His Leu His Arg Asn Ala Phe Leu Val
            35                  40                  45

Tyr Ile Leu Asn Leu Ala Leu Thr Asp Phe Leu Phe Leu Leu Cys His
 50                  55                  60

Ile Ile Asn Ser Thr Val Ile Leu Leu Asn Val Pro Leu Pro Asn Met
 65                  70                  75                  80

Ile Leu Val His Cys Phe Ser Thr Ile Arg Ile Phe Leu Asn Ile Thr
                85                  90                  95

Gly Leu Ser Ile Leu Ser Ala Ile Ser Thr Glu Arg Cys Leu Ser Val
            100                 105                 110

Leu Cys Pro Ile Trp Tyr Arg Cys His His Pro Glu His Thr Ser Thr
            115                 120                 125

Val Met Cys Ala Val Ile Val Leu Ser Leu Leu Ile Cys Thr Leu Tyr
            130                 135                 140

Arg Tyr Phe Cys Phe Phe Phe Gly Pro Lys Tyr Val Phe Asp Ser Val
145                 150                 155                 160

Cys Leu Ala Thr Thr Tyr Phe Ile Arg Thr Tyr Pro Met Phe Leu Phe
                165                 170                 175

Met Val Leu Cys Leu Ser Thr Leu Ala Leu Leu Ala Arg Leu Phe Cys
            180                 185                 190

Gly Ala Gly Lys Lys Phe Thr Arg Leu Phe Val Thr Ile Met Leu
            195                 200                 205

Thr Val Leu Val Phe Leu Leu Cys Gly Met Pro Leu Gly Phe Phe Trp
            210                 215                 220

Phe Val Phe Pro Trp Ile Asn Cys Asp Phe Ser Val Leu Asp Tyr Arg
225                 230                 235                 240

Leu Phe Leu Ala Ser Ile Val Leu Thr Ala Val Asn Ser Tyr Gly Asn
                245                 250                 255

Pro Ile Ile Tyr Phe Phe Val Gly Ser Phe Arg Asn Arg Leu Lys His
            260                 265                 270

Gln Thr Leu Gln Lys Val Leu Gln Ser Ala Leu His Asp Thr Pro Glu
            275                 280                 285

Thr Pro Glu Asn Met Val Glu Met Ser Arg Ser Lys Ala Glu Pro
            290                 295                 300

<210> SEQ ID NO 76
<211> LENGTH: 1011
<212> TYPE: DNA
<213> ORGANISM: Mus musculus

<400> SEQUENCE: 76
aagaggaaac acatatattt gggatgttaa ccaaggtttt ctatagggaa caatggaaaa        60
ctgttcactt caagattaca gtttagctgc atgattaaac tttaaattga cattaacatt       120
taattactgg gttttataaa ggtcctgaga tatttaaggt tggattgtct tttatattat       180
gatattaata tgcttagaac aaagaaagaa aagtttattg ttcaatggtg aagtgtcttt       240
taaatagaag tgggcagagt gtcctggcaa acctcaattt ttaccttgac acagattaaa       300
gtcgtatgag aggagaaatc acaacagcag aaatgacaac tgaggaattg tctagattat       360
cttggcctgt gggcatgatt atgaggaatt atctttaaca taaattaatg taagcaaaca       420
tggtctatgg taggttgcac caataagcta cttaagcagg acctgtaatc atccagaatt       480
ggagcttgga aggagtgttt cttgtagata ctgttccttg tgttccttga gttcctgaca       540

-continued

```
tgacttccct cactgatgga gtctgtacta agagtataag ccagataacc cattttattt        600
tctaggatgt ttgtggtcaa aatgttttcc catgaaacag aaaaggaaac tagaacatgc        660
acaaattacc taacagatat ttattaagtt agagaatatt ctaagttata caaatactaa        720
aggaaactac aaatgtggat ctattaaatt cttatttaaa caaaatctgt agagatgata        780
aattgttaaa aatgtcataa attttcaatc actatcaagt tcagttacca atgaaattca        840
gttattaact gaaaactcct gatctttgga tgaagaaggg gcttgtcaaa aatgggagca        900
gtcttggacc tataattatt acagtgggtc tcatctcaag gggatccagt gaagtgtcat        960
taagaggaga gtaggaaagt tcaacatagt atttctatta aaagtggtgt a               1011
```

<210> SEQ ID NO 77
<211> LENGTH: 274
<212> TYPE: PRT
<213> ORGANISM: Mus musculus

<400> SEQUENCE: 77

```
Leu Leu Ser Ile Ile Ile Ala Phe Ile Gly Leu Ala Glu Asn Ala Ile
1               5                   10                  15

Val Leu Trp Leu Leu Gly Phe His Met His Arg Asn Ala Phe Ser Val
            20                  25                  30

Tyr Ile Leu Asn Ala Gly Ala Asn Phe Leu Phe Leu Cys Pro Tyr Ile
        35                  40                  45

Val Phe Ser Leu Val Thr Ile Thr Val Asn Phe His Ser Ile Asn Ser
    50                  55                  60

His Ile Ile Leu Phe Leu Asn Thr Val Phe Thr Leu Ala Tyr Leu Ala
65                  70                  75                  80

Gly Val Ser Met Ile Thr Ala Ile Ser Val Glu Tyr Trp Leu Ser Val
                85                  90                  95

Ile Trp Ser Asn Trp Tyr His Gly Arg His Pro Lys His Thr Ser Ala
            100                 105                 110

Phe Ile Cys Thr Leu Leu Trp Ala Val Ser Leu Leu Ser Leu Pro
        115                 120                 125

His Glu Ile Ile Cys Gly Leu Leu Asp His Ile Tyr Asn Trp Asp Met
    130                 135                 140

Cys Trp Lys Cys Lys Leu Ile Ile Val Val Trp Leu Leu Ile Glu Phe
145                 150                 155                 160

Val Val Leu Ser Gln Ser Asn Gln Ala Met Met Phe Arg Ile Phe Cys
                165                 170                 175

Gly Ser Gln Gln Thr Pro Met Thr Arg Leu Phe Val Thr Ile Val Leu
            180                 185                 190

Thr Ala Leu Val Val Leu Ile Cys Gly Phe Pro Leu Gly Ile Tyr Ile
        195                 200                 205

Tyr Phe Leu Tyr Trp Thr Thr Asp Val Tyr Phe Ile Met Pro Cys Asn
    210                 215                 220

Ser Phe His Glu Thr Ile Leu Leu Leu Ser Ala Val Asn Ser Cys Ala
225                 230                 235                 240

Asn Pro Ile Ile Cys Leu Leu Val Gly Ser Ile Lys His Cys Gln Phe
                245                 250                 255

Gln Cys Gly Thr Leu Arg Leu Ile Leu Gln Arg Ala Ile Gln Asp Thr
            260                 265                 270

Pro Glu
```

<210> SEQ ID NO 78
<211> LENGTH: 1358
<212> TYPE: DNA
<213> ORGANISM: Mus musculus

<400> SEQUENCE: 78

```
taaattactg aatctctgtg atcctgattc cctctctttta tggacctgtg cctgacatac      60
ccacatagtc acatggtcct gacagaaact atcatgtgtt catatctcta tgtcttttca     120
ggaatgtcag tggaaaattc ctaagcatgg gtacaactag cctggcctgg aacattaaca     180
acacagctga aaatggaagc tacactgaaa tgttctcctg tatcaccacg ttcaataccc     240
tgaattttct tactgtcatc attgctgtgg ttgtcctggc aggaaattcc atagtgctat     300
ggcttctagc cttccacctg cacaggaatg ccttcttcgt ctatgtcctc aatctggctg     360
gtgctgattt cttgtacctt tgcactcaga ttgtgtattc cctggagtgt gtcattcagt     420
ttgataaaag ctcctttttat attctcctca ttttatcaat gtttgcttac cttgcaggat     480
tgagtatgat tgcaaccatc agtactgagc gctgcctatc tgttatgtgg cccatctggt     540
atcactgcca aagaccaaga cacacatcag ccatcatgtc tgttctgctc tgggtttttct     600
ctatactgtt gagcctcctg gtaggactag gctgtggttt tctgttcaga tattctgaat     660
attatttctg tattactttg aactttatca ctgctgcatt tatcataggg ttatctgtgg     720
ttctttctgt atctagcctg accctgttgg tcaagatcat ctgtggatca cacaggatac     780
ctgtgaccag gttgtttgtt accatttgct ctcacagtgg tggtcttcat aatctttggc     840
atgccccttg gaatctgctg gttcctcttt ccaagtatta ttgagtttca taaaattttc     900
tctaacaatt tttatgaaat gatagcattc ctgtcatgta ttaatagttg tgccaatccc     960
atcatttact tccttgttgg ctctattagg caccacaggt tgaaatggca gtctcttaag    1020
ctacttcttc agagagccat gcaggacact cctgaggaag tgagtggaga gagggggtcct   1080
tcagaaaggt ctggggaact ggaaagagtc tagtgcagta gtggagtgag tccttgatca   1140
gatatagttt ctctgagagt caattttgcc tttatctatt taggcaattt tcacagtctt   1200
gttcaatcag tagagaaaat agtcatttta tagaaattag gaggaacagg cttgttacac   1260
agaaactgac ttgcagcacc ataaagctgc cttatgtggt gctcagtgca tcccctcgtg   1320
atataagcct tgtaatcact tggggccaga acagctcc                           1358
```

<210> SEQ ID NO 79
<211> LENGTH: 268
<212> TYPE: PRT
<213> ORGANISM: Mus musculus

<400> SEQUENCE: 79

Phe Leu Thr Val Ile Ile Ala Val Val Val Leu Ala Gly Asn Ser Ile
1               5                   10                  15

Val Leu Trp Leu Leu Ala Phe His Leu His Arg Asn Ala Phe Phe Val
                20                  25                  30

Tyr Val Leu Asn Leu Ala Gly Ala Asp Phe Leu Tyr Leu Cys Thr Gln
            35                  40                  45

Ile Val Tyr Ser Leu Glu Cys Val Ile Gln Phe Asp Lys Ser Ser Phe
        50                  55                  60

Tyr Ile Leu Leu Ile Leu Ser Met Phe Ala Tyr Leu Ala Gly Leu Ser
65                  70                  75                  80

Met Ile Ala Thr Ile Ser Thr Glu Arg Cys Leu Ser Val Met Trp Pro
                85                  90                  95

```
Ile Trp Tyr His Cys Gln Arg Pro Arg His Thr Ser Ala Ile Met Ser
            100                 105                 110

Val Leu Leu Trp Val Phe Ser Ile Leu Leu Ser Leu Leu Val Gly Leu
        115                 120                 125

Gly Cys Gly Phe Leu Phe Arg Tyr Ser Glu Tyr Tyr Phe Cys Ile Thr
    130                 135                 140

Leu Asn Phe Ile Thr Ala Ala Phe Ile Ile Gly Leu Ser Val Val Leu
145                 150                 155                 160

Ser Val Ser Ser Leu Thr Leu Leu Val Lys Ile Ile Cys Gly Ser His
                165                 170                 175

Arg Ile Pro Val Thr Arg Leu Val Thr Ile Cys Phe Thr Val Val
            180                 185                 190

Val Phe Ile Ile Phe Gly Met Pro Leu Gly Ile Cys Trp Phe Leu Phe
        195                 200                 205

Pro Ser Ile Ile Glu Phe His Lys Ile Phe Ser Asn Asn Phe Tyr Glu
    210                 215                 220

Met Ile Ala Phe Leu Ser Cys Ile Asn Ser Cys Ala Asn Pro Ile Ile
225                 230                 235                 240

Tyr Phe Leu Val Gly Ser Ile Arg His His Arg Leu Lys Trp Gln Ser
                245                 250                 255

Leu Lys Leu Leu Leu Gln Arg Ala Met Gln Asp Thr
            260                 265

<210> SEQ ID NO 80
<211> LENGTH: 2387
<212> TYPE: DNA
<213> ORGANISM: Mus musculus

<400> SEQUENCE: 80
gggcctgagg cacaaacctc tcgggctggc agatccctgc gcactcacca tgtaaggtgg      60
ccggttgtct ggacgaggaa ttatctttaa cacatgttaa tgcaagcaaa catggcctat     120
ggtaagttgc accaaaaagc tacctaagca ggacctgtaa ccaatccaga attgcagcta     180
ggaaggagag tttcctgtag acactgttcc ttgtgctgct tgagtttctg acatgacttc     240
cttcactgat ggactctgta ctgagaggat aagccagata acccatttta tctcctagga     300
tgtttgtggt caaatgtttt tcccatgaaa tagaaaagga aactagaaca ggcacaaatt     360
gcctaaaaga tatttattaa gttagagaat attctaagtc atacaaatac taaggaaac     420 tacaaatgtg gatctattaa attcttattt atcatctgta gagatgataa attgttaaaa     480
atgtcatata ccttcatca ctatcaagtt cagtgaccaa tgataatcag ttattacctg      540
aagactattg atctttggat gaagaagggg cttgtcaaaa atgggagcag tcctggaccc      600
ataattatta cagtgggtct catctcaagg ggatccagtg aagcgtcatt aagaggagag     660
taggaacgtt caacacacta tttctattaa aagtggtgta ctgatctact ttcaagggaa     720
tggttaatat cccaactgat ttcacctcag gccatcaact cagcagggtt gtagaaatgc     780
cccaaaagga taagggcaaa tttgtcctat aagttctctt gtgtatcatc acagcagctc     840
tcagttgcat cactagagtg tagtactctc ttcatcttct tcacctcctt cttgttctac     900
aacttcttca acttcttcat cttcttcctc agggctctct tgaatggctc tctgaagaat     960
cagcctgaga gtcccacact ggaattggca gtgcttaatt gagccaacaa ataagcaaat    1020
gataggattg gcacagctgt taacaccgga tagtaggaga attgtctcat aaaaataacc    1080
acaaggcata attgaattct cttctttctt ccagtaaaag aagcatatgc caatcccaaa    1140
```

-continued

```
gccacagatc aagacgacca gtgctgtaag cataatggtc acaagcagcc tggtcacagg    1200
tgtctgctgt gaaccacaga agaccctgaa cagcagggct tgattggatc tagaaagaac    1260
cacaaataaa acaagtaacc atacaactat gatgagagca agtttccaac acatatccca    1320
gttataaata taatccagca ctttacaaat tatccaattc caagggtca acagaagggg     1380 aaaaaaccca gagcagagta caaatgacag ttgatgtgtg ttttgggcgt tgggcatgat    1440
accaagtggg ccaaaggaca gacaaccagt actccacact aatggctgtg atcatgctca    1500
cccctgcaag gtatgccagt atggtcacat tgacagaaaa caacgcccat gtgaatgtcg    1560
atgtagtgaa actgcctaat gagattttcc agggaaaata caatgtgagt gcagaggaag    1620
aggaagtttg ccccagacag gttgaagatg tagacagaga aggcattcct gtgcatgtgg    1680
aagcccagaa gctgcagcac tatgacattt cctgtcagtc caatgatggc aatgataatg    1740
gaaagcaaac tcatggcaag ggacatgtca caagatgaag attccatgaa gtagctttca    1800
ttctgttctc tgaattcaat attccagtct gggaagcttg aatccatgtt tgggaacact    1860
cctggaataa aaacaagac ataatcgcat gctttgcatt ctctaattca caagaccacc     1920
ctgatatttg taagctgata tggcacaaaa tgatggaaaa tgagcttaag aaatttatca    1980
aaaccagtat gtttagagac ttctttaaa accagtctga atttatttgg gttatctaca     2040
atccatgtca tgtactaaca cgaatgtagt tgatggtcca agtatacacc ccaagtgtct    2100
catgttgtgt ggcagaatga aatggaacac tgaacctgta ggggtttgag tataatggca    2160
tccatcaatc catacatttg aatatacagt cactgtttgg tggaactgtt tggagaaggg    2220
ttatatgtag gggtaattct gatgctaagg tcctgctccc caatcagtta ttgatatgtt    2280
gctaaagaaa gacattggcc ctctgctggt caggggggag ggcaaagggt gatttacagg    2340
actttgggta cctggagtca agcagagaga tgcaagagag gaaagga                  2387
```

<210> SEQ ID NO 81
<211> LENGTH: 273
<212> TYPE: PRT
<213> ORGANISM: Mus musculus

<400> SEQUENCE: 81

```
Leu Leu Ser Ile Ile Ala Ile Ile Gly Leu Thr Gly Asn Val Ile
1               5                   10                  15

Val Leu Gln Leu Leu Gly Phe His Met His Arg Asn Ala Phe Ser Val
            20                  25                  30

Tyr Ile Phe Asn Leu Ser Gly Ala Asn Phe Leu Phe Leu Cys Thr His
        35                  40                  45

Ile Val Phe Ser Leu Glu Ile Ser Leu Gly Ser Phe Thr Thr Ser Thr
    50                  55                  60

Phe Thr Trp Ala Leu Phe Ser Val Asn Val Thr Ile Leu Ala Tyr Leu
65                  70                  75                  80

Ala Gly Val Ser Met Ile Thr Ala Ile Ser Val Glu Tyr Trp Leu Ser
                85                  90                  95

Val Leu Trp Pro Thr Trp Tyr His Ala Gln Arg Pro Lys His Thr Ser
            100                 105                 110

Thr Val Ile Cys Thr Leu Leu Trp Val Phe Ser Leu Leu Leu Thr Leu
        115                 120                 125

Trp Asn Trp Ile Ile Cys Lys Val Leu Asp Tyr Ile Tyr Asn Trp Asp
    130                 135                 140

Met Cys Trp Lys Leu Ala Leu Ile Ile Val Val Trp Leu Leu Val Leu
145                 150                 155                 160
```

```
                Phe Val Val Leu Ser Arg Ser Asn Gln Ala Leu Leu Phe Arg Val Phe
                                165                 170                 175

Cys Gly Ser Gln Gln Thr Pro Val Thr Arg Leu Leu Val Thr Ile Met
                            180                 185                 190

Leu Thr Ala Leu Val Val Leu Ile Cys Gly Phe Gly Ile Gly Ile Cys
                        195                 200                 205

Phe Phe Tyr Trp Lys Lys Glu Glu Asn Ser Ile Met Pro Cys Gly Tyr
                    210                 215                 220

Phe Tyr Glu Thr Ile Leu Leu Ser Gly Val Asn Ser Cys Ala Asn
                225                 230                 235                 240

Pro Ile Ile Cys Leu Phe Val Gly Ser Ile Lys His Cys Gln Phe Gln
                                245                 250                 255

Cys Gly Thr Leu Arg Leu Ile Leu Gln Arg Ala Ile Gln Glu Ser Pro
                            260                 265                 270

Glu

<210> SEQ ID NO 82
<211> LENGTH: 1319
<212> TYPE: DNA
<213> ORGANISM: Mus musculus

<400> SEQUENCE: 82
tttataaacc aggtcagtaa ttaccacata gcaggatgtt cctgaatcag aaagaacata        60
gcatgtgctc attgttttgt ttattttgtt ccagaaatag tactggagac ttcctaaaca       120
aggatctaag catctcaacc ttggaagcta actccagaac atctactgaa cccaatgata       180
cttcaggttg tggcatcaag ttccaaacca agatgttgct ttccctcatt tccctgtttg       240
ggatggtact aaatcccata gtgctgtgat tgctgagctt ccaggtgcac aggaatgcct       300
tgtttgtcta catcctcaac cttgctgtgg ttgacatttt cttccggttt gatcagtttg       360
cattttgtgt ttttgttatc atttacacta tcaagtccat ttccaatgat atcctatcat       420 ttttatttt tgtgccagca tttctgtatc ttttaagcct gagcattctc ataaccatta       480
gcattgaacg atgcctgtat gtcatgtggc ccatctggta tcactgtcaa tgtccaagac       540
acacatcagc tgtcatttgt gtcttgcttt gggctctgtc ccttgtgttt atgtttctgg       600
atgggaaggc atattttta ctgttttctg accctaactc ttttttggtat cagacatttg       660 atatcatcat tactgtatag acaattgttt tatttgtggt tctctgtggg tccagcttaa       720
tcctacttgt cagaatcttc tgtggctccc agcagatccc tgtaaccagg ctggatgtga       780
tcattgcact cagagtgctt tcttcctga tatttagttt tcccttttgg atctactggc       840
tccttgacca acggattggg agacgttgta atttttgat gaaatgattt tcttatcctg       900
tattaagagc tgtgtcaact ccatcattta ctttcttgtt gcctccatta tgcacagtag       960
tggattcaag gtgaagagtc tcaaactatt tccagagaga gccatgcagg acattcctga      1020
agaaggagaa ggtgttgaga atagttctta aggaaatcat gaagaactgg agaaatctag      1080
tgcagcagac gacagctact tgattagac agagtggtcg ttttctat ctttgtggac       1140 taatttaatg accttattca gtttgttact taatcttcaa tcagttaaaa atgacaatca      1200 ttttgtaat agttgaaaga tacagtactt gtcacacaaa tattaactgt gccatttctc      1260
ttgctgtgtt tttgaggcct ttaccatttc cttttgatgg gagtacttgc aagtattct       1319

<210> SEQ ID NO 83
<211> LENGTH: 264
```

<212> TYPE: PRT
<213> ORGANISM: Mus musculus

<400> SEQUENCE: 83

```
Leu Ile Ser Leu Phe Gly Met Val Leu Asn Pro Ile Val Leu Leu
 1               5                  10                  15

Ser Phe Gln Val His Arg Asn Ala Leu Phe Val Tyr Ile Leu Asn Leu
                20                  25                  30

Ala Val Val Asp Ile Phe Phe Arg Phe Asp Gln Phe Ala Phe Cys Val
            35                  40                  45

Phe Val Ile Ile Tyr Thr Ile Lys Ser Ile Ser Asn Asp Ile Leu Ser
     50                  55                  60

Phe Phe Ile Phe Val Pro Ala Phe Leu Tyr Leu Ser Leu Ser Ile
65                  70                  75                  80

Leu Ile Thr Ile Ser Ile Glu Arg Cys Leu Tyr Val Met Trp Pro Ile
                85                  90                  95

Trp Tyr His Cys Gln Cys Pro Arg His Thr Ser Ala Val Ile Cys Val
                100                 105                 110

Leu Leu Trp Ala Leu Ser Leu Val Phe Met Phe Leu Asp Gly Lys Ala
            115                 120                 125

Tyr Phe Leu Leu Phe Ser Asp Pro Asn Ser Phe Trp Tyr Gln Thr Phe
     130                 135                 140

Asp Ile Ile Ile Thr Val Thr Ile Val Leu Phe Val Val Leu Cys Gly
145                 150                 155                 160

Ser Ser Leu Ile Leu Leu Phe Arg Ile Phe Cys Gly Ser Gln Gln Ile
                165                 170                 175

Pro Val Thr Arg Leu Asp Val Ile Ile Ala Leu Arg Val Leu Phe Phe
            180                 185                 190

Leu Ile Phe Ser Phe Pro Phe Trp Ile Tyr Trp Leu Leu Asp Gln Arg
     195                 200                 205

Ile Gly Arg Arg Cys Asn Phe Leu Asn Glu Met Ile Phe Leu Ser Cys
210                 215                 220

Ile Lys Ser Cys Val Asn Ser Ile Ile Tyr Phe Leu Val Ala Ser Ile
225                 230                 235                 240

Met His Ser Ser Gly Phe Lys Val Lys Ser Leu Lys Leu Phe Pro Glu
                245                 250                 255

Arg Ala Met Gln Asp Thr Pro Glu
            260
```

<210> SEQ ID NO 84
<211> LENGTH: 2349
<212> TYPE: DNA
<213> ORGANISM: Mus musculus

<400> SEQUENCE: 84

```
tttctttctg agaaatagtt tgttttaaaa taggaatttt aaaacagctt gagacactga      60
gagtttatac tggaaccatc aactactcta atgtcaatac aggatatggg ttgtagataa     120
cccaaatata tatgaatgat atatttaaat taaggctcca gaaatattga ttttgataaa     180
ttgcttcatg tctaccaccc tgtttcacca ttttaagaac taggtaaacc gttaacatct     240
ataatggtga tcctaagaat cagagaacaa aaagcatgtg ttcatgtctt gttttttctttt    300 ccagaaacat cagtggaagg gatctaagag tggattcaaa cataacatac tggggaacaa     360
acatcacagc tgtgaatgaa agcaaccaya ctggaatgtc attttgtgaa gtcgtgtctt     420
gtaccatgkt tttctttcc ctcattgttg ccctagttgg gctggttgga aatgccacag      480
```

```
tgctgtggtt cctgggcttc cagatgcgca ggaatgcatt ctctgtttac atcctcaacc    540
tcgctggtgc tgactttctc ttcatttgct ttcaaattgg atattgtttt cacatgatct    600
tggacattga ttccatcccc attgaaattg atctgtttta ccttgttgtg ttaaactttc    660 cttattttg tggcctgagt atcctcagtg ctattagcat tgaacgttgc ctgtctgtca     720
tgtggcccat ttggtatcac tgccaacgcc caaggcacac atcagctgtc atatgtaccc    780
tgctttgggt cttgtcccta gtgtgtagcc tcctggaagg gaaggaatgt ggcttcctat    840
attacactag tgaccctggt tggtgtaaga catttgattt aatcactgct acatggttaa    900
ttgttttatt tgtagctctc ttgggatcca gtctggcctt agtgattacc atcttctggg    960
gcttacacaa gattcctgtg accaggctgt atgtggccat tgtgttcaca gtgcttgttt   1020
tcctgctctt tggtctgccc tatgggatct actggttcct cttagtgtgg attgagaaat   1080
tttattatgt tttaccttgt agtatatatc cggtcacagt atttctctcc tgtgttaaca   1140
gctctgcaaa acccatcatt tattgccttg taggctccat taggcatcat cgatttcaac   1200
ggaagactct caagctattt ctgcagagag ccatgcaaga cactcctgag gaggaagaat   1260
gtggagagat gggttcctca ggaagatcta gagaaataaa aacaatctgg aaaggactga   1320
gagctgcttt gatcaggcat aaagagctct gaagagaact atgtttttat cactttgttg   1380
cattttcata acgttgttta gttgatgacc caaggttaac tcagtgggga agtagtcaa    1440 tgttgtagaa gttgattgat attggacttg ttacaaatac tgggtacaac atttctgcag   1500
ctatcttgct cagggtttta ccaacttctt ttgatgttac tccttgcaag ctctgtgggg   1560
tccaggaaag ctgttgacca caattgataa atcccttctt cagaagaaag cttaagaaag   1620
tacaggaaag ggttgcattt cttaacttcac ttaacttgat agtggataaa ttcatgttat   1680
attttgcaaa aaaattattc tgtttcaagg caaacttttc ttcagtgttg aagggttaaa    1740
tagatacatt atataatccc agactttatt aatttctgta tgttttaaag aatatgtgga   1800
gcaatagttt ttcttataca catttcttaa taaagaagta aacattctca agagaagtgt   1860
taaacatcca tgtacatagg aaggtgcagt gtcctctgtg gttctattca cagtttcctt   1920
tttagcatcc catagttgag tattgtcttt gatatgatcc tcatgctctc tgactgtgta   1980
atccctcatg aaaagtttcc aatgaggtcc tctataaaga ctcccttgaa atacaactta   2040
ttttaaattt ataccatttc aaggagccca cagcatctat taacttagct atatgcacag   2100
tttagtaaaa ttttctataa aataatattc cttttataaa gctgcagtaa taatttcaat   2160
ttttctacaa ttaagagaat aaaatatcaa caaattaaat aaaactaatc agtaggtttt   2220
cttaagttaa tgtagctgca tgactctgta cctaatcaag acacaaaata ctacactata   2280
tcttttaatt ttcatttctt ctcctgtcat aatttttat cacagataaa tatgatatcc    2340
atacttctg                                                           2349
```

<210> SEQ ID NO 85
<211> LENGTH: 273
<212> TYPE: PRT
<213> ORGANISM: Mus musculus

<400> SEQUENCE: 85

Phe Leu Ser Leu Ile Val Ala Leu Val Gly Leu Val Gly Asn Ala Thr
1               5                   10                  15

Val Leu Trp Phe Leu Gly Phe Gln Met Arg Arg Asn Ala Phe Ser Val
            20                  25                  30

```
Tyr Ile Leu Asn Leu Ala Gly Ala Asp Phe Leu Phe Ile Cys Phe Gln
             35                  40                  45

Ile Gly Tyr Cys Phe His Met Ile Leu Asp Ile Asp Ser Ile Pro Ile
         50                  55                  60

Glu Ile Asp Leu Phe Tyr Leu Val Val Leu Asn Phe Pro Tyr Phe Cys
 65                  70                  75                  80

Gly Leu Ser Ile Leu Ser Ala Ile Ser Ile Glu Arg Cys Leu Ser Val
                 85                  90                  95

Met Trp Pro Ile Trp Tyr His Cys Gln Arg Pro Arg His Thr Ser Ala
            100                 105                 110

Val Ile Cys Thr Leu Leu Trp Val Leu Ser Leu Val Cys Ser Leu Leu
            115                 120                 125

Glu Gly Lys Glu Cys Gly Phe Leu Tyr Tyr Thr Ser Asp Pro Gly Trp
130                 135                 140

Cys Lys Thr Phe Asp Leu Ile Thr Ala Thr Trp Leu Ile Val Leu Phe
145                 150                 155                 160

Val Ala Leu Leu Gly Ser Ser Leu Ala Leu Val Ile Thr Ile Phe Trp
                165                 170                 175

Gly Leu His Lys Ile Pro Val Thr Arg Leu Tyr Val Ala Ile Val Phe
            180                 185                 190

Thr Val Leu Val Phe Leu Leu Phe Gly Leu Pro Tyr Gly Ile Tyr Trp
            195                 200                 205

Phe Leu Leu Val Trp Ile Glu Lys Phe Tyr Val Leu Pro Cys Ser
    210                 215                 220

Ile Tyr Pro Val Thr Val Phe Leu Ser Cys Val Asn Ser Ser Ala Lys
225                 230                 235                 240

Pro Ile Ile Tyr Cys Leu Val Gly Ser Ile Arg His His Arg Phe Gln
                245                 250                 255

Arg Lys Thr Leu Lys Leu Phe Leu Gln Arg Ala Met Gln Asp Thr Pro
            260                 265                 270

Glu

<210> SEQ ID NO 86
<211> LENGTH: 1313
<212> TYPE: DNA
<213> ORGANISM: Mus musculus

<400> SEQUENCE: 86
tttatttaat tattttgtta ttgttgtttc aggtagcaag tatttcctaa gcatgggata      60
tagacatttc gagcctgggc atttacatca tagcaccgaa tggaagcagc tacactaata     120
gtgttgattg tttcttcaaa atccaagtca tgggttttct ttccctcatc atttcccctg     180
ttgggatggt attaaattcc acagtgctgt ggtttctggg cttccagata cgtaggaatg     240
ccttctctgt ctacatcctc aacctggccg gggctgactt tctcttcctg cactctcagt     300
ttttatttta ccttcttgct atttttccct ccattcctat ccagatccct ctctttttg      360 atatgttgac aaaatttgca tatctttctg ggctgagcat tctcagcacc attagcattg     420
agcgctgcct gtgtgtcatg tggcccatct ggtaccgctg tcaaagacca agacacacat     480
catctgtaac ctgttccttg ctttgggctt tgtccctgtt gtttgctctt ctggatggga     540
tgggatgtgg cttactgttt aatagttttg accagtcttg gtgtttgaaa tttgatttaa     600
tcatttgtgc gtggtcaatt gttttatttg tggttctctg tgggtccagt ctcatcctac     660
ttgttaggat cttctgtggc tcccagcaga tccctgtgac caggctgtat gtgaccattg     720
```

-continued

```
cactcacagt gttattcttc ctaatctgct gtcttccctt tggaatctcc tggatcatcc    780
aatggagtga aactttgata tatgttggat tttgtgatta ttttcacgag gaactattcc    840
tatcctgtat taacagctgt gccaacccta tcatttactt ccttgttggt tttattcgtc    900
agcgaaagtt ccaacagaag tctctgaagg tgcttcttca aagagcgatg gaggacactc    960
ctgaagaaga aaatgaagac atgggtcctt caagaaatcc agaagaattt gaaacagtct   1020
gtagcaactg agaggttctt tgatcagaca gaaatggttt tttagagaaa aaaattttt    1080 ctcatttctg tgggccattt tcacagtttt gyacagtttg tttcctgata ttcaatcagt   1140
taaaaaataa gcattttgt gaaagtggat agatacaaga cttgtcatac aaatactgac    1200
tgtagtattt ttggagctgt tactcagact ttcatcatct ccttttgatg ggattccatg   1260
taagtgtctg gagttgagga gatgtgttga ccactattga caaagccctc att          1313
```

<210> SEQ ID NO 87
<211> LENGTH: 270
<212> TYPE: PRT
<213> ORGANISM: Mus musculus

<400> SEQUENCE: 87

```
Phe Leu Ser Leu Ile Ile Ser Pro Val Gly Met Val Leu Asn Ser Thr
 1               5                  10                  15

Val Leu Trp Phe Leu Gly Phe Gln Ile Arg Arg Asn Ala Phe Ser Val
            20                  25                  30

Tyr Ile Leu Asn Leu Ala Gly Ala Asp Phe Leu Phe Leu His Ser Gln
        35                  40                  45

Phe Leu Phe Tyr Leu Leu Ala Ile Phe Pro Ser Ile Pro Ile Gln Ile
    50                  55                  60

Pro Leu Phe Phe Asp Met Leu Thr Lys Phe Ala Tyr Leu Ser Gly Leu
65                  70                  75                  80

Ser Ile Leu Ser Thr Ile Ser Ile Glu Arg Cys Leu Cys Val Met Trp
                85                  90                  95

Pro Ile Trp Tyr Arg Cys Gln Arg Pro Arg His Thr Ser Ser Val Thr
            100                 105                 110

Cys Ser Leu Leu Trp Ala Leu Ser Leu Leu Phe Ala Leu Leu Asp Gly
        115                 120                 125

Met Gly Cys Gly Leu Leu Phe Asn Ser Phe Asp Gln Ser Trp Cys Leu
    130                 135                 140

Lys Phe Asp Leu Ile Ile Cys Ala Trp Ser Ile Val Leu Phe Val Val
145                 150                 155                 160

Leu Cys Gly Ser Ser Leu Ile Leu Leu Val Arg Ile Phe Cys Gly Ser
                165                 170                 175

Gln Gln Ile Pro Val Thr Arg Leu Tyr Val Thr Ile Ala Leu Thr Val
            180                 185                 190

Leu Phe Phe Leu Ile Cys Cys Leu Pro Phe Gly Ile Ser Trp Ile Ile
        195                 200                 205

Gln Trp Ser Glu Thr Leu Ile Tyr Val Gly Phe Cys Asp Tyr Phe His
    210                 215                 220

Glu Glu Leu Phe Leu Ser Cys Ile Asn Ser Cys Ala Asn Pro Ile Ile
225                 230                 235                 240

Tyr Phe Leu Val Gly Phe Ile Arg Gln Arg Lys Phe Gln Gln Lys Ser
                245                 250                 255

Leu Lys Val Leu Leu Gln Arg Ala Met Glu Asp Thr Pro Glu
            260                 265                 270
```

<210> SEQ ID NO 88
<211> LENGTH: 1883
<212> TYPE: DNA
<213> ORGANISM: Mus musculus

<400> SEQUENCE: 88

```
cgtgtgccac caccaccaac aggtgggaca tttcttaaag tatactattc atttaatctt      60
tatcaagttt aattaccaaa gcaattctga cacttcttgc actaccttga tccttttcct     120
gagggaggca tttgttccca gtgagagctg ttctgacccc aagagattac aagggttaca     180
tcacaagggg gtgcagtaag gcatacataa ggcagtttga tggtgctgca gtgaatttct     240
gagtaacaag ctccatttct cctaatttga ataaaatgac tattttctct accaattaaa     300
caagattgtg aaaactgcct acatagataa agcaaaatt gactctcaga gaaactatgt      360
ctcatcaagt actctttcaa agcctgcact agactctttc cagttcccta gcctttgtga     420
aggacccctc tctcctctct tttcctcact actgtcctac atggttctct gcagaagttg     480
cttcaaactc tgacattgca acctacggtg cctaacagag ccaaggagag agtaaataat     540
gggattggca cagctgttaa cacaggaatg ctatcacttc aaaaacattg tatgagaaca     600
tgctatgtaa gtccataaac attgtcaaga ggaatgtgca gattccaatg gcataccaa      660
agaatatgaa gaccatcaat gtgagggcaa tggacacata gaacatggtc acaggaatcc     720
tgagtgatac acagaacatt tgacaaacag ggccaggcta gacacaaaak aaaccacaga     780
taatactatt atcaatgcag tagygatata gtggcatrta atacagaaat tgtgttcwta     840
ataacttaac agaaagccac agccttgtrc aaasrgaagg atcarcagta tagagaaaac     900
ccagagcaga gcacacatga cagctgatgt gtgtcttggt cttcagcagt gataccagat     960
gggacacata acagataggc agtgctcagc actgattgtt gmaatcatac acaaacctgc    1020
aagttaagca atcataaatc ctgtgaggat aaaatgatag tagatcataa gtatcttaag    1080
gaaacactgc aggggaatgt acaaactgtg tgcaaatttg caagaaatca gcacaagaca    1140
ggtttaagac atagacagag aaggcattcc tatgcaggtg gaaggctaga agccatagca    1200
ctatggcatt tcctgccagg ccaagcacag caatgatgac aataagaaaa ttgaatgtgg    1260
tgaaacagga taaatttttc agtgcattaa cttccattga cttctgtgtt tttaaatttc    1320
cattccaggt tggttggatc catgcttagg aatttttccac tggcattcct gcaaagaaat    1380
agagatatga atctagggta ctctttgtag ggactatgtg actatgtagg aatgtatggc    1440
acaggtacat aaggagggag aaacaggatc acagagatta agtaatttac caacattcca    1500
aaagtgctac acatttttga aatccatttt gtactattca gtctaactgc agaccagtat    1560
gatgtaaggt agttgatggt cccagtacag ttgctaggca tttatttcag gttatgtgag    1620
gaagagacag aactctgaaa ccaacattct ttttgttcta gggctgagat tcttctctg     1680
gtgtaggaaa atggaagttc ttggtgcaag ccatatcttc cctcagtcac tgggaggaat    1740
ctatcaaaca ggcaaaatag aatcatgaat gagagtcatg aatgagattc acgaagggaa    1800
tggtacttgc tatgaagacc tgtaggggaa tagccatgct tcttatgctt gaaagggtag    1860
ttgctcattt aacaattta aaa                                             1883
```

<210> SEQ ID NO 89
<211> LENGTH: 263
<212> TYPE: PRT
<213> ORGANISM: Mus musculus

<400> SEQUENCE: 89

```
Phe Leu Ile Val Ile Ala Val Leu Gly Leu Ala Gly Asn Ala Ile
  1               5                  10                  15

Val Leu Trp Leu Leu Ala Phe His Leu His Arg Asn Ala Phe Ser Val
             20                  25                  30

Tyr Val Leu Asn Leu Ser Cys Ala Asp Phe Leu Gln Ile Cys Thr Gln
                 35                  40                  45

Phe Val His Ser Pro Ala Val Phe Leu Lys Ile Leu Met Ile Tyr Tyr
         50                  55                  60

His Phe Ile Leu Thr Gly Phe Met Ile Ala Leu Ala Gly Leu Cys Met
 65              70                  75                  80

Ile Ser Thr Ile Ser Ala Glu His Cys Leu Ser Val Met Trp Pro Ile
                 85                  90                  95

Trp Tyr His Cys Arg Pro Arg His Thr Ser Ala Val Met Cys Ala Leu
            100                 105                 110

Leu Trp Val Phe Ser Ile Leu Leu Ile Leu Phe Val Gln Gly Cys
            115                 120                 125

Gly Phe Leu Leu Ser Tyr Tyr Glu His Asn Phe Cys Ile Ile Cys His
    130                 135                 140

Tyr Ile Ala Thr Ala Leu Ile Ile Val Leu Ser Val Val Ser Phe Val
145                 150                 155                 160

Ser Ser Leu Ala Leu Phe Val Thr Met Phe Cys Val Ser Leu Arg Ile
            165                 170                 175

Pro Val Thr Met Phe Tyr Val Ser Ile Ala Leu Thr Leu Met Val Phe
                180                 185                 190

Ile Phe Phe Gly Met Pro Ile Gly Ile Cys Thr Phe Leu Leu Thr Met
            195                 200                 205

Phe Met Asp Leu His Ser Ser Ser His Thr Met Phe Leu Lys His Ser
    210                 215                 220

Cys Val Asn Ser Cys Ala Asn Pro Ile Ile Tyr Ser Leu Leu Gly Ser
225                 230                 235                 240

Val Arg His Arg Arg Leu Gln Cys Gln Ser Leu Lys Gln Leu Leu Gln
                245                 250                 255

Arg Thr Met Asp Ser Ser Glu
            260

<210> SEQ ID NO 90
<211> LENGTH: 1219
<212> TYPE: DNA
<213> ORGANISM: Mus musculus

<400> SEQUENCE: 90
ttataaatga tttttattaag ccatattgac aataatatct atattatatg atgattgcca    60
gaagaagggt aaatgttaag gtgatcaaat atggtctgtg ttctcagaga caccactgga   120
agatttgtga gcatggatcc aaccatctca tcccacaaca cagaatctac accactgaat   180
gaaactggtc attccaaatg cagtccaatc ctgactctgt cctttctggt cctcatcact   240
gtcctggtgg aactaggagg aagcaccatt gtactctggc tcctggaatt cagcatgccc   300
aggaaagcca tctcagtcta tgtcctcaat ctggctctgg cagactcctt cttcctcggc   360
tgcgatttca ttgaatttct gctacggatc attgacttca tctatgccca taaattaagc   420
aaagatatct taggcaatac agcaatcatt ccttatatcg caggacagaa cgttctcagt   480
gctattagca tggagcactg cctgtctgta ttgtggccaa tctggtacca ctaccaccac   540
ccaagaaaca tgtcagctat catatgtgcc ctaatctggg ttctgtactt tctcatgggc   600
```

```
atcctccatt ggttcttctc agtattcctg ggtgaggctc atcatcattt gaggaaaaag    660
gttgacttta ctataactgc atttctgaat ttttatttat gcttcactct gtgtccagtc    720 tggcccctact gctgaggatc ctctgtggct ccaggaggaa acccctgtcc aggctgtatg    780
ttaccatcgc tctcacagtg atggtcacct catctctggc ctgcctcttg ggctttactt    840
gttcctgtta tactggtttg gggttcattt gcatcatccc tcttgtcaca attaccaagt    900
tacttcagtc ctgccctgtg taaacagcta taacaacccc atcatttact tcattgtagg    960
ctcctttagg cctcttagaa agcattaatc cctccaaact attcttaaga gggctctgga   1020
ggacactcct gaggagcatg aatatacagc cagccatctt cagaaaacca ctgagatgtc   1080
agaaagcatt tttgagagtc aaaacaacat taacttaatc ttctctcaga aaccccctcag  1140 tgattgcact gctttcaatt gattattttt tatccaattt tcttatactt ctcaaagtag   1200
tcataaataa gaatttctc                                                 1219
```

<210> SEQ ID NO 91
<211> LENGTH: 270
<212> TYPE: PRT
<213> ORGANISM: Mus musculus

<400> SEQUENCE: 91

```
Phe Leu Val Leu Ile Thr Val Leu Val Glu Leu Gly Gly Ser Thr Ile
1               5                   10                  15

Val Leu Trp Leu Leu Glu Phe Ser Met Pro Arg Lys Ala Ile Ser Val
            20                  25                  30

Tyr Val Leu Asn Leu Ala Leu Ala Asp Ser Phe Leu Gly Cys Asp
        35                  40                  45

Phe Ile Glu Phe Leu Leu Arg Ile Ile Asp Phe Ile Tyr Ala His Lys
    50                  55                  60

Leu Ser Lys Asp Ile Leu Gly Asn Thr Ala Ile Ile Pro Tyr Ile Ala
65                  70                  75                  80

Gly Gln Asn Val Leu Ser Ala Ile Ser Met Glu His Cys Leu Ser Val
                85                  90                  95

Leu Trp Pro Ile Trp Tyr His Tyr His His Pro Arg Asn Met Ser Ala
            100                 105                 110

Ile Ile Cys Ala Leu Ile Trp Val Leu Tyr Phe Leu Met Gly Ile Leu
        115                 120                 125

His Trp Phe Phe Ser Val Phe Leu Gly Glu Ala His His Leu Arg
    130                 135                 140

Lys Lys Val Asp Phe Thr Ile Thr Ala Phe Leu Ile Phe Leu Phe Met
145                 150                 155                 160

Leu His Ser Val Ser Ser Leu Ala Leu Leu Arg Ile Leu Cys Gly
                165                 170                 175

Ser Arg Arg Lys Pro Leu Ser Arg Leu Tyr Val Thr Ile Ala Leu Thr
            180                 185                 190

Val Met Val Tyr Leu Ile Ser Gly Leu Pro Leu Gly Leu Tyr Leu Phe
        195                 200                 205

Leu Leu Tyr Trp Phe Gly Val His Leu His His Pro Ser Cys His Asn
    210                 215                 220

Tyr Gln Val Thr Ser Val Leu Pro Cys Val Asn Ser Tyr Asn Asn Pro
225                 230                 235                 240

Ile Ile Tyr Phe Ile Val Gly Ser Phe Arg Pro Leu Arg Lys His Ser
                245                 250                 255
```

Leu Gln Thr Ile Leu Lys Arg Ala Leu Glu Asp Thr Pro Glu
         260                 265                 270

<210> SEQ ID NO 92
<211> LENGTH: 1178
<212> TYPE: DNA
<213> ORGANISM: Mus musculus

<400> SEQUENCE: 92

| | |
|---|---|
| ttaaggtgat gaaatatggt ctgtgttctc agggacacca ctggaagatt tgtgagcatg | 60 |
| gatccaatca tctcatccca aacagagaaa tcacaccact gaatgaaact gcaatcattc | 120 |
| caactgcagt ccaatcctga ctctgtcctt tctggtcctc atcactatcc tggtggaact | 180 |
| ggcaggaaac accattgtcc tctggctctt gggattccgc atgcacagga aagccatctc | 240 |
| agtttatgtc ctcaatctgg ctctggcaga ctccgtattc ctctgctgtc atttcattga | 300 |
| ctctctgcta tgcatcattg acttcatcta tgcccataaa ttaagcagat accttaggca | 360 |
| atgcagaaat cattccctat atcacagggc tgagcatcct cagtgctatt agcatggagg | 420 |
| actacctgtc tgtattgtgg ccaatctggt accactgcca tcacccaagg aacatgtcaa | 480 |
| ctatcctatg tgccctaatc tgggttctat cctttctcat gggcatcctc gattggttct | 540 |
| tctcaggatt cctgggtgag actcatcatt atttgtgaaa aaatgttgac tttattataa | 600 |
| ctgcatttct gatttttttt tttatttatg cttctctctg ggtccagtct ggccctactg | 660 |
| ctgaggatcc tctgtggctc caggaggaaa ccactgtcca ggttgtatgc taccatctca | 720 |
| ctcacagtga tggtctacct catctgtggc ctacctcttg gctttacttt gtttctgtta | 780 |
| cactcctttg gggttaattt gcatcatccc ttttgtcacc tttacaaagt tactgcagtc | 840 |
| ctgtcctgtg taaacatctc taccaaccc atcaatcatt taattcattg gcatttcttt | 900 |
| ttttttaat taggtatttt cctcgtttac attttcaatg ctatcccaaa ggtcccccat | 960 |
| acccaccccc cccaatccct acccaccccac tgcccctttt tggcactggc gttcccctgt | 1020 |
| actggggcat ataagtttg caagtccaat gggcctctct ttgcagtgat gaccgactag | 1080 |
| gccatctttt gatacatatg cagctaaaga catgagctcc cgggtactgg ttagttcata | 1140 |
| ttgttgttcc acctataggg ttgcagttcc ctttagct | 1178 |

<210> SEQ ID NO 93
<211> LENGTH: 243
<212> TYPE: PRT
<213> ORGANISM: Mus musculus

<400> SEQUENCE: 93

Phe Leu Val Leu Ile Thr Ile Leu Val Glu Leu Ala Gly Asn Thr Ile
 1               5                  10                  15

Val Leu Trp Leu Leu Gly Phe Arg Met His Arg Lys Ala Ile Ser Val
            20                  25                  30

Tyr Val Leu Asn Leu Ala Leu Ala Asp Ser Val Phe Leu Cys Cys His
        35                  40                  45

Phe Ile Asp Ser Leu Leu Cys Ile Ile Asp Phe Tyr Leu Cys Pro Asp
    50                  55                  60

Ala Asp Thr Leu Gly Asn Ala Glu Ile Ile Pro Tyr Ile Thr Gly Leu
65                  70                  75                  80

Ser Ile Leu Ser Ala Ile Ser Met Glu Asp Tyr Leu Ser Val Leu Trp
            85                  90                  95

Pro Ile Trp Tyr His Cys His His Pro Arg Asn Met Ser Thr Ile Leu
           100                 105                 110

```
Cys Ala Leu Ile Trp Val Leu Ser Phe Leu Met Gly Ile Leu Asp Trp
        115                 120                 125

Phe Phe Ser Gly Phe Leu Gly Glu Thr His His Tyr Leu Lys Asn Val
130                 135                 140

Asp Phe Ile Ile Thr Ala Phe Leu Ile Phe Phe Ile Leu Leu Leu
145                 150                 155                 160

Ser Gly Ser Ser Leu Ala Leu Leu Arg Ile Leu Cys Gly Ser Arg
            165                 170                 175

Arg Lys Pro Leu Ser Arg Leu Tyr Ala Thr Ile Ser Leu Thr Val Met
            180                 185                 190

Val Tyr Leu Ile Cys Gly Leu Pro Leu Gly Leu Tyr Leu Phe Leu Leu
            195                 200                 205

His Ser Phe Gly Val Asn Leu His His Pro Phe Cys His Leu Tyr Lys
        210                 215                 220

Val Thr Ala Val Leu Ser Cys Val Asn Ile Ser Thr Asn Pro Ile Asn
225                 230                 235                 240

His Leu Ile

<210> SEQ ID NO 94
<211> LENGTH: 2416
<212> TYPE: DNA
<213> ORGANISM: Mus musculus

<400> SEQUENCE: 94
atggagggac ccatggctcc agttgcatgt gtagcagagg atggccttgt agctcatcaa      60
tgggaggaga gacttttggt cctgtgaagg ccctataccc cagtgttggg ggttgccagg     120
gagaagaagt gggagtgggt gggttggtgt acagagggag ggcgataatg ggttttcaaa     180
ggaaaaatca ggaaaaggga taacatttga atgtaaaata agaaaatat ttaataaaaa      240 gcaaaaatga aaaaaaagtg caaaaacatg ttctattatg ggagtgggtg tgttgaggag     300
cagtggggga gggttaaata gagaggggac tgttggaggg gaaactagga aaggggataa     360
cattggaaat gtaaataaag aaaatatcta ataaaaaata aaataaaaaa ttttggaaga     420
tatttgaaaa attcattgac aagggcaaga atgttggaga aattcttatt tttgactact     480
ttgagaagta taagaaaatt agattaaaaa taatcaattg aaagcactgc aatcactgag     540
gcgtttctga gagaagagta agttaatgtt gtcttgactc tcaacatatg ctttctgaca     600
tctcagtggt tttctgaaga tggctgtctg tatattcatc ctcttcagga gtgtctttca     660
gagccctatt aagaatagtt tggaaggaac aacactttct acaatgccta aggagccta      720 caatgaagta aatgatggga ttggcagagc tgtttacaca ggacaggact gcagttactt     780
ggtaaatgtg acaagaggga taatgcaaat gaaccccaaa ccagtgtagc aggaaaaagt     840
aaagcccaag aggcaggcca cagatgagat agaccatcac tgtgagagag atggtaactt     900
acagcctgga caggggtttc ttcctaggac cacagaggat cctcagcagt agggccagac     960
tggacacaga gagaagcata ataaaaaaa tcagaaatgc agttataata aaggcaacat    1020
tttccacaaa tgatgattag tctcacccag gaatcctaag aagaaccaat ccaggatgcc    1080
tatgagaatg acagaaccc agattagggc atataggata gctgacatgt tactttggtg    1140
gtggaagtca taccagattg gccacaatac agacaggcag tgctccatgc taatagcact    1200
gagcaggctg tgccctgcca tagggaatg attgctgca ttgcctaaga tatctttgtt    1260
taatttatgg gcatagatga agtcaatgat ccatagcaga gagtcaatga aatggcagca    1320
```

```
gaggaagaag gagtcgccca gagccagatt gaggacatag cctgagatgg gtttcctgtg    1380
cattcagaat cccaggagcc agagaacaat cgtgtttcct gccagttcca ccaggacagt    1440
gatgaggacc agaaaggacg gagtcaggat tggactgcag ttgggatgac cagtttcatt    1500
cagtggtatg attcctgtgt tgtgtgatga gatgattgga tccatgctca caaatctttc    1560
agtggtgtta ctgagaacac agaccacatt taatcacctt aaaattgacc cttcttctgg    1620
aaatcataat ataatataga tattttttgtc aatatgcctt aataaaatca tttataaata    1680
aaaggaaagt aacatgacca tatggatcaa gaattctggg ctgtgaattc aaattcagag    1740
cttgtgtata ctctatagtg tgggtcatac ttcctgtgta taactcagga cttttttaatc   1800
gcgtggaaat ggttccattc tctcatggac aaggttggat ccatttcctg ctctcctgta    1860
accccagaaa gggaagcacc agatttgcct cccagggct taaaataaca caggaaagat     1920
gaagatatca gggtattgtc gaggtacatt aagggaaata tccttctgca tggtcaaaag    1980
aatgtattct gagttatgca cctaactctc ggtcgagaca tgacactggt ctgtgcaaca    2040
gattacagat cacatgcatt tacctcctcc cttgagatga ccaagctgca cctatcagtc    2100
acttcaccag gggattgctg aggtggcaga aggaatgaca actcactcat ctttcacagg    2160
agttatacct tctctgcagc catctctgac cttccctcag ctggtacagt taagcctgtc    2220
tgcttttctg aaagcactta aggttccttt ttctttcttt agatctcctt ttcttttgaa    2280
catgggtcaa aagaccaagc aacatttccc tgagagtctg gactctctca atcatttctg    2340
aaacccacat ctctttccac catgaaagtt ttttcccaac ttccattgct ggacatacca    2400
gctttcttgg ggatgt                                                     2416

<210> SEQ ID NO 95
<211> LENGTH: 269
<212> TYPE: PRT
<213> ORGANISM: Mus musculus

<400> SEQUENCE: 95

Phe Leu Val Leu Ile Thr Val Leu Val Glu Leu Ala Gly Asn Thr Ile
 1               5                  10                  15

Val Leu Trp Leu Leu Gly Phe Met His Arg Lys Pro Ile Ser Gly Tyr
             20                  25                  30

Val Leu Asn Leu Ala Leu Gly Asp Ser Phe Phe Leu Cys Cys His Phe
         35                  40                  45

Ile Asp Ser Leu Leu Trp Ile Ile Asp Phe Ile Tyr Ala His Lys Leu
     50                  55                  60

Asn Lys Asp Ile Leu Gly Asn Ala Ala Ile Ile Pro Tyr Met Ala Gly
 65                  70                  75                  80

His Ser Leu Leu Ser Ala Ile Ser Met Glu His Cys Leu Ser Val Leu
                 85                  90                  95

Trp Pro Ile Trp Tyr Asp Phe His His Gln Ser Asn Met Ser Ala Ile
            100                 105                 110

Leu Tyr Ala Leu Ile Trp Val Leu Ser Ile Leu Ile Gly Ile Leu Asp
        115                 120                 125

Trp Phe Phe Leu Gly Phe Leu Gly Glu Thr Asn His His Leu Cys Glu
    130                 135                 140

Asn Val Ala Phe Ile Ile Thr Ala Phe Leu Ile Phe Leu Phe Met Leu
145                 150                 155                 160

Leu Ser Val Ser Ser Leu Ala Leu Leu Leu Arg Ile Leu Cys Gly Pro
                165                 170                 175
```

```
Arg Lys Lys Pro Leu Ser Arg Leu Val Thr Ile Ser Leu Thr Val Met
                180                 185                 190

Val Tyr Leu Ile Cys Gly Leu Pro Leu Gly Leu Tyr Phe Phe Leu Leu
        195                 200                 205

His Trp Phe Gly Val His Leu His Tyr Pro Ser Cys His Ile Tyr Gln
    210                 215                 220

Val Thr Ala Val Leu Ser Cys Val Asn Ser Ser Ala Asn Pro Ile Ile
225                 230                 235                 240

Tyr Phe Ile Val Gly Ser Phe Arg His Cys Arg Lys Cys Cys Ser Phe
                245                 250                 255

Gln Thr Ile Leu Asn Arg Ala Leu Lys Asp Thr Pro Glu
                260                 265

<210> SEQ ID NO 96
<211> LENGTH: 1954
<212> TYPE: DNA
<213> ORGANISM: Mus musculus

<400> SEQUENCE: 96
tggcattcgg tacctgcctc ctggcagaag atgaaggccc gaaatagggc atgtcccagt      60
aagctgttag cttctgtatt ccaaactctc acctacacag actagtctca gagggatcgg     120
ggaaccaaga tggcttcccc atggtactcc agcaaaacac tcccaggtga ggtggacacc     180
tctcctctga cagggaaggt gcccggatat ctggagcctg aaacgggtc tgcctcagaa      240 gctgttagct tctgtagtcc acactctcac atgtgtaggc tagtctcagc aggatccagg     300
aaccaagatc agaagggtca atgttcaggt gatcaaatgt agtctgtgtt cacagggata     360
ccactggaag atttgtgagc atggatccaa tcatctcatc ccacaacaca gaatcacacc     420
actgaatgaa actggtcatc ccaactgcag tacaatcctg actccatcct ttctggtcct     480
catcactgtc ctggtggaac tgcaggaaaa taccattgta ctctggctcc tgagattcca     540
catgcacagg atagcccatc tcagactatg tcctcaatct ggctctggca gattccttct     600
tcctctcctg ccagttcatt gactctctgc tatggatcct tgacttcatc taggcccata     660
aattaagcaa agatatctta tggaatgcag caatcattcc caataatgca gggctgagct     720
acctcagtgc tattagcatg gagcactgcc tgcctgtatt gtggccaatc tggcaccact     780
gccaccacac aagaaacatg tcagctatca tatgtgccct aatctgggtt ctgtcctttc     840
tcatgggcat cctcgattag tacttctcag gattcctggg tgagactcat catcagttgt     900
ggaaaaatgt tgattttatt ctaactgcat ttctgatttc ttttttttt tatttatgct      960 tctctctggg tccagtctgg ccctacgact gaggatcctc tgtggctcca ggaggaaacc    1020
cctgtccttg ctgtatgtta tcatctctct cacagtgatg gtctacctca tctgtggcct    1080
acctgttggg ctttacttgt tcctgttaaa ctggtttggg gttcatttgc atcatcccat    1140
ttgtcacatt tatcaagtta ctgcactcct gccctttgta aacagctttg ccaaacccat    1200
catttccttc attgtaggct cctttaggca ttgtagaaag cattggtccc gccaaactat    1260
tattaagagg gctctggagg acactcctga ggaggatgaa tatacagata gccatcttca    1320
gaaaactact gagatgtcag aaagcagatg ttgagagtca agacaacatt aacttaatct    1380
tctctcagaa acacctcact ggttgcagtg ctttcaattg attattttt aatccaattt     1440 tcttataagt ctcaaagtag tcataaataa gaatttctcc aacattcttg gccttgtcaa    1500
tgaatttctc aaatatcctc caaaacattt tgtatataat ttaattttt tagatatttt     1560 ctatatttat atttccaatg ttatccccctt yccttagttt ccctccaaa agccccctct    1620
```

```
ccccttcccc cccccactgc tcctcaatat actcactccc ataattgaac accttttttgc   1680 acttttttct ttttttttcac ttttttgtttt ttattagata ttttctttat ttacatttca   1740
aatgttgtcc cttttcctga ttttccctct gaaaacccat tactgtcatc ccctgtaca    1800 ccatccctcc cacttctact tctatcctag gcattccccct acactggggt atagggcctt   1860
cacaggacca agagtctctc ctcccattga tgagctacaa ggccatcctc tgctacacat   1920
ggcaactgga gccatgggtc cctccatgtg tact                               1954
```

<210> SEQ ID NO 97
<211> LENGTH: 272
<212> TYPE: PRT
<213> ORGANISM: Mus musculus

<400> SEQUENCE: 97

```
Phe Leu Val Leu Ile Thr Val Leu Val Glu Leu Ala Gly Asn Thr Ile
 1               5                  10                  15

Val Leu Trp Leu Leu Arg Phe His Met His Arg Ile Ala Leu Ser Asp
            20                  25                  30

Tyr Val Leu Asn Leu Ala Leu Ala Asp Ser Phe Phe Leu Ser Cys Gln
        35                  40                  45

Phe Ile Asp Ser Leu Leu Trp Ile Leu Asp Phe Ile Ala His Lys Leu
    50                  55                  60

Ser Lys Asp Ile Leu Trp Asn Ala Ala Ile Ile Pro Asn Asn Ala Gly
65                  70                  75                  80

Leu Ser Tyr Leu Ser Ala Ile Ser Met Glu His Cys Leu Pro Val Leu
                85                  90                  95

Trp Pro Ile Trp His His Cys His His Thr Arg Asn Met Ser Ala Ile
            100                 105                 110

Ile Cys Ala Leu Ile Trp Val Leu Ser Phe Leu Met Gly Ile Leu Asp
        115                 120                 125

Tyr Phe Ser Gly Phe Leu Gly Glu Thr His His Gln Leu Trp Lys Asn
    130                 135                 140

Val Asp Phe Ile Leu Thr Ala Phe Leu Ile Val Phe Phe Phe Leu Phe
145                 150                 155                 160

Met Leu Leu Ser Gly Ser Ser Leu Ala Leu Arg Leu Arg Ile Leu Cys
                165                 170                 175

Gly Ser Arg Arg Lys Pro Leu Ser Leu Leu Tyr Val Ile Ile Ser Leu
            180                 185                 190

Thr Val Met Val Tyr Leu Ile Cys Gly Leu Pro Val Gly Leu Tyr Leu
        195                 200                 205

Phe Leu Leu Asn Trp Phe Gly Val His Leu His Pro Ile Cys His
    210                 215                 220

Ile Tyr Gln Val Thr Ala Leu Leu Pro Phe Val Asn Ser Phe Ala Lys
225                 230                 235                 240

Pro Ile Ile Ser Phe Ile Val Gly Ser Phe Arg His Cys Arg Lys His
                245                 250                 255

Trp Ser Arg Gln Thr Ile Ile Lys Arg Ala Leu Glu Asp Thr Pro Glu
            260                 265                 270
```

<210> SEQ ID NO 98
<211> LENGTH: 1893
<212> TYPE: DNA
<213> ORGANISM: Mus musculus

<400> SEQUENCE: 98

```
ttagcaatcc cctggccagg tgactgacag gtgcagctta gtctttctca agggatgagg      60
taattgcatg tgatctgtaa tctgttgcac agaccagtgt catgtctcaa cccagagtta     120
ggtgtataac tcagaatcca ttttttgac catgcagaag catctttcct ttaatgtact      180
tcaacaaaac cctgatatct tcatcttttc tgcgttattt taagccctgg ggaggcaaat    240
atgatgcttc ccctttctag gggttacagg ggagcaggaa atggatgcag ccctgaccat    300
gatagtaggg aatcatttcc atgtgattta aaggtcctga gttatacaca ggaagaatga    360
cccagactag agtatgtaca agctctgaat ttgaatccaa atccagaatt cttgatccac    420
atggtcatgt tattctcctt tttttataaa tgatttatt aagccatatt gacaacaata     480
tctatattac attatgattg ccagaagaag ggtcaatgtt aaggtgatga aatatggtct    540
gtgttcctca ggcacaacac tggaagattt ttgagcatgg atccaaccat ctcattccac    600
aacacagaat ctacaccact gaatgaaact tgtcatccaa atacagtcca atcctgactc    660
cgtcctttct ggtcctcatc actgtcctgg tggacctggc aggaaacacc attgttctct    720
ggctcctggg attccgcatg cacaggaaac ccatctcagt ctatgtcctc aacctggctc    780
tgggcgactc cttcttctgc tgccatttca ttgactctct gctatggatc attgacttca    840
tctatgccca taaattaagc aaagatatct taggcaatgt agcaatcgtt ccctatatcg    900
cagggctgag cgtcctcagt gctattagca tggagaactg actgtttata ttgtggccaa    960
tctggtacca ctgccaccac ccaagaaaca tgtcagctat cctatgtgcc ctaatctggg   1020
ttctgttctt tctcatgggc atcctcggtt ggttcttctt aagattttg ggtgaaactc   1080
atcattgact ttattatacc tgcatttctg atttttttt tatttatgct tctctctggg   1140
tccattctgg ccctactgct gaggatcctc tatggttcca ggaggaaatc cctgtccagg   1200
ttgtatgtta acatctctct cacagtgatg gtctacctca tctgtggcct gcctcttgga   1260
ctttacttgg tcctgttata ctgctttggg gttcatttac atcatccctc tcctcacatt   1320
taccaagtta ctgtggtctt gtcctatgtg gacagctctg ccaaccacat cttttatttc   1380
cttgcaggtt cctttaggta ttgtagaaag cattggtccc tccaaactct tctaaagagg   1440
actctagagg acactcctgg ggaggatgaa atacagaca gccatcttca gaaaaccact     1500
gagatgtcag aaagcagatg ttgagagtca acacattaac ttactcttct ctaagaaacg   1560
cctcagtgat tgcaatgctt tcaattggtt tttcttttta atcaaatttt cttatacttc   1620
tcaaagtagt cagaaatgag aatttctcga aaattcttgg cactgtcaat gaattttca    1680
aatatcttcc aaaactttct tatttattt tatttattt ttattagaca ttttcttat      1740
ttacatttca aatgttatcc cctttactag tttcccctcc aaaaaagcac tatcccctca   1800
cccctctacc tgctccccac attacccact cccataattg aacactttt tctttttta    1860
acttattatt tttattagat attttctta ttt                                 1893
```

<210> SEQ ID NO 99
<211> LENGTH: 262
<212> TYPE: PRT
<213> ORGANISM: Mus musculus

<400> SEQUENCE: 99

Phe Leu Val Leu Ile Thr Val Leu Val Asp Leu Ala Gly Asn Thr Ile
 1               5                  10                  15

Val Leu Trp Leu Leu Gly Phe Arg Met His Arg Lys Pro Ile Ser Val
            20                  25                  30

```
Tyr Val Leu Asn Leu Ala Leu Gly Asp Ser Phe Phe Cys Cys His Phe
             35                  40                  45

Ile Asp Ser Leu Leu Trp Ile Ile Asp Phe Ile Tyr Ala His Lys Leu
 50                  55                  60

Ser Lys Asp Ile Leu Gly Asn Val Ala Ile Val Pro Tyr Ile Ala Gly
 65                  70                  75                  80

Leu Ser Val Leu Ser Ala Ile Ser Met Glu Asn Leu Phe Ile Leu Trp
                 85                  90                  95

Pro Ile Trp Tyr His Cys His Pro Arg Asn Met Ser Ala Ile Leu
            100                 105                 110

Cys Ala Leu Ile Trp Val Leu Phe Leu Met Gly Ile Leu Gly Gly
            115                 120                 125

Ser Ser Asp Phe Trp Val Lys Leu Ile Ile Asp Phe Ile Ile Pro Ala
130                 135                 140

Phe Leu Ile Phe Phe Leu Phe Met Leu Leu Ser Gly Ser Ile Leu Ala
145                 150                 155                 160

Leu Leu Leu Arg Ile Leu Tyr Gly Ser Arg Arg Lys Ser Leu Ser Arg
                165                 170                 175

Leu Tyr Val Asn Ile Ser Leu Thr Val Met Val Tyr Leu Ile Cys Gly
            180                 185                 190

Leu Pro Leu Gly Leu Tyr Leu Val Leu Leu Tyr Cys Phe Gly Val His
            195                 200                 205

Leu His His Pro Ser Pro His Ile Tyr Gln Val Thr Val Val Leu Ser
            210                 215                 220

Tyr Val Asp Ser Ser Ala Asn His Ile Phe Tyr Phe Leu Ala Gly Ser
225                 230                 235                 240

Phe Arg Tyr Cys Arg Lys His Trp Ser Leu Gln Thr Leu Leu Lys Arg
                245                 250                 255

Thr Leu Glu Asp Thr Pro
            260

<210> SEQ ID NO 100
<211> LENGTH: 1290
<212> TYPE: DNA
<213> ORGANISM: Mus musculus

<400> SEQUENCE: 100
cctctggcta ggtgactgac aggtgcagct tggtcatctc aagggaggag gttactgcat      60
ttgatctata atctgttgca cagaccagtg tcttgtctcg acccagagtt aggtgtataa     120
ctcagaatcc attcttttga ccgtgcaaaa gtatctttct cttgatgtac ctcaacaaaa     180
ccctgatatc ttcatctttc ctgtgttatt ttaagccctg ggggagtaca atctgatgc      240 ttccctttct gtggttacag gtagagcagg aaatggatcc tacctgacc atgagagaag     300 ggaatcattt ccatgtgatt aaaaggtcct gagttataca ctggaagtat gacccagact    360
acagagtata cacaagctct gaatttgaat ccacagtcca gaattcttga tcaatgtagt    420
catgttactc tcctttttt tataaatgat tttagcaagc catattgaca acaatatcta     480
tattacatta tgatcgccag aagaaaggtc aatgttaagg tgatcaaaca tggtcttgtt    540
ctcagggaca ccactggaag atttgtgcgc atggatccaa tcatcttatc ccacaacaca    600
gaatcacact gctgaatgaa actggtcaac ccaacttcag tccaatcctg actctgtctc    660
tctggtcctc atcactgtcc tgtttgaact ggcaggaaac accattgtac tctggctcct    720
gggattccac atgcacaagg aaagtcatct cagtctatgt cctcaatctg gctcttgcag    780
```

| | |
|---|---|
| actccttctt cctcagctgc caattcattg actctctgct ttgaagcatt gacttcctct | 840 |
| atgcatataa attaagcaaa gatatcttag gcaatgcagc aatcgttccc tatatcgcag | 900 |
| ggctgagtat cctcagtgct attagcatgg agcactgcct gtctgtatag tggcaaatgc | 960 |
| ggtaccactg ccactaccca agaaacatgt cagctatcct atgtgcccta atctgggttc | 1020 |
| tgtcttttct catggacatc ctggattggt tcttctcagg attcctgggt gagactcatc | 1080 |
| atcatttatg gaaaaatatt gacttcatta taactgcatt tctgattttt ttatttatgc | 1140 |
| ttctctctgg ctccagtctg gccctactgc tgaggattct ttatggcttc aagaggaaac | 1200 |
| ccctgtccag gctatatatt atcatctctc tcacagtgat ggtctacctc atctgggcct | 1260 |
| gccccttggg ctttcatttt tcctgttaca | 1290 |

```
<210> SEQ ID NO 101
<211> LENGTH: 207
<212> TYPE: PRT
<213> ORGANISM: Mus musculus

<400> SEQUENCE: 101
```

Leu Val Leu Ile Thr Val Leu Phe Glu Leu Ala Gly Asn Thr Ile Val
1               5                   10                  15

Leu Trp Leu Leu Gly Phe His Met Thr Arg Lys Val Ile Ser Val Tyr
            20                  25                  30

Val Leu Asn Leu Ala Leu Ala Asp Ser Phe Phe Leu Ser Cys Gln Phe
        35                  40                  45

Ile Asp Ser Leu Leu Ser Ile Asp Phe Leu Tyr Ala Tyr Lys Leu Ser
    50                  55                  60

Lys Asp Ile Leu Gly Asn Ala Ala Ile Val Pro Tyr Ile Ala Gly Leu
65                  70                  75                  80

Ser Ile Leu Ser Ala Ile Ser Met Glu His Cys Leu Ser Val Trp Gln
                85                  90                  95

Met Arg Tyr His Cys His Tyr Pro Arg Asn Met Ser Ala Ile Leu Cys
            100                 105                 110

Ala Leu Ile Trp Val Leu Ser Phe Leu Met Asp Ile Leu Asp Trp Phe
        115                 120                 125

Phe Ser Gly Phe Leu Gly Glu Thr His His His Leu Trp Lys Asn Ile
    130                 135                 140

Asp Phe Ile Ile Thr Ala Phe Leu Ile Phe Leu Phe Met Leu Leu Ser
145                 150                 155                 160

Gly Ser Ser Leu Ala Leu Leu Leu Arg Ile Leu Tyr Gly Phe Lys Arg
                165                 170                 175

Lys Pro Leu Ser Arg Leu Tyr Ile Ile Ile Ser Leu Thr Val Met Val
            180                 185                 190

Tyr Leu Ile Leu Gly Leu Pro Leu Gly Leu Ser Phe Phe Leu Leu
        195                 200                 205

```
<210> SEQ ID NO 102
<211> LENGTH: 1389
<212> TYPE: DNA
<213> ORGANISM: Mus musculus

<400> SEQUENCE: 102
```

| | |
|---|---|
| ttaaggtgat caaatatggc ctgttttctc agggacacca ctggaagatt tttaaacatg | 60 |
| gatccaaaca tctcatccca caacacagaa tctactccac tgaatgaaac tggtcatcca | 120 |
| aacttcagta caatactcac gctgtccttt ctggtcctcg tcactgtcct cgtggaactg | 180 |

```
gcaggaaaca ccattgtact ctggctcctg ggattccgca tgcacaggaa agccatctca    240
gtctatgtcc tcaatctggc tctggcagac tccttcttct gctgccattt cattgactct    300
ctgctatgga tcactgactt catctatacc cataaattaa gcaaagatat cttacgcaat    360
gcagcaattg ttccctatat cgcaagactg agcgtcctca gtgctattag aatggagcac    420
ttactgttta tattgtggcc aatctggtac cactgccacc acccaagaaa catatcagct    480
atcctatgtg ccctaatctg ggttctgttc tttctcatgg gcatccttga ttggttcttc    540
ttaggattcc tgggtgagac tcatcatcat ttgtggaaaa atattgactt tattataccc    600
gcatttctga ttttttttaat gctgctttct gggtccactc tggccctact gctgaggata    660
ctttgtggtt ccaggaggaa actcctgtcc aggctgtatg ttaccatctc tctcacagtg    720
atggtctacc tcatctgtgg catgcctctt gggctttact tgttcctgtt atactggttt    780
gggattcatt tacactatcc ctcttgtcac atttaccaag ttactgcact cttgtcctat    840
gtggacagct ctgccaacca catcttttat ttccttgtag gctcctttag gcattttaga    900
aagcattggt ccctctaaac tattctaaag aggaccctgg agaacattcc tgaggaggat    960
gaatatacag acagctatct tcagaatacc actgagatgt cagaaatcag atgttgagag   1020
tcaacacatt aacttactct tctctcagaa acgcctcagt gattgcaacg ctttcaattt   1080
ttttgtttgt ttggtttttt ttttttggga ttgttttaaa ttaggtattt tggtatttta   1140
catttccaaa tttatattta tacttccaaa agtccccat accttccct gccaatcccc   1200 tacccacttt ttggccctgg cgtttccctg tactggggca tataaagttt gcaagtccag   1260
tgggcctctc tttccagtga tggcctacta agccatcttt tgatacatat gcagctagag   1320
tcaagagctc cagggtactg attaattcat aatgttgttc cacctatagg gttgcagatc   1380
cctttagca                                                          1389
```

<210> SEQ ID NO 103
<211> LENGTH: 206
<212> TYPE: PRT
<213> ORGANISM: Mus musculus

<400> SEQUENCE: 103

```
Phe Phe Cys Cys His Phe Ile Asp Ser Leu Leu Trp Ile Thr Asp Phe
 1               5                  10                  15

Ile Tyr Thr His Lys Leu Ser Lys Val Tyr Leu Thr Gln Cys Ser Asn
            20                  25                  30

Phe Pro Tyr Ile Ala Arg Leu Ser Val Leu Ser Ala Ile Arg Met Glu
        35                  40                  45

His Leu Leu Phe Ile Leu Trp Pro Ile Trp Tyr Cys His His Pro
    50                  55                  60

Arg Asn Ile Ser Ala Ile Leu Cys Ala Leu Ile Trp Val Leu Phe Phe
65                  70                  75                  80

Leu Met Gly Ile Leu Asp Trp Phe Phe Leu Gly Phe Leu Gly Glu Thr
                85                  90                  95

His His His Leu Trp Lys Asn Ile Asp Phe Ile Ile Pro Ala Phe Leu
            100                 105                 110

Ile Phe Leu Met Leu Leu Ser Gly Ser Thr Leu Ala Leu Leu Leu Arg
        115                 120                 125

Ile Leu Cys Gly Ser Arg Arg Lys Leu Leu Ser Arg Leu Tyr Val Thr
    130                 135                 140

Ile Ser Leu Thr Val Met Val Tyr Leu Ile Cys Gly Met Pro Leu Gly
145                 150                 155                 160
```

Leu Tyr Leu Phe Leu Leu Tyr Trp Phe Gly Ile His Leu His Tyr Pro
            165                 170                 175

Ser Cys His Ile Tyr Gln Val Thr Ala Leu Leu Ser Tyr Val Asp Ser
            180                 185                 190

Ser Ala Asn His Ile Phe Tyr Phe Leu Val Gly Ser Phe Arg
            195                 200             205

<210> SEQ ID NO 104
<211> LENGTH: 1420
<212> TYPE: DNA
<213> ORGANISM: Mus musculus

<400> SEQUENCE: 104
aaaaaggaac cttacacttt tctgagttag tgtgcattca gagaatcaga cagtcttaac      60
tgtaccccct gagggaaggt cagagatggc tgcatagagg gtgcaactcc tgtgaaggat     120
gagtgaattg tcattccttc tgccatctta gcaatcccct ggccaggtga ctgacaggta     180
caacattgtc aactcaaggg aggakrtaaa tgyrtgtgat ccttaatcta gagcacagac     240
cagagtcaca tmtcaaccca gagttagggg tagaaytcag aatccattct tttgatgatg     300
aggaagtatc tttcccttaa tatgcctcaa caaaaccctg atatcatcat cttttctgtg     360
tcattttaag ccctggggag gtaaatgtga tgcttccctt tctggagtta ccaaggtggc     420
aggaaatgga tccaaccctg accatgaaaa aggaaatcg tttccatgtg aattaaagat      480
cctgagttat acacaggaag aatgatgcag actatagagt aaacacaagc tctaaatttg     540
aatccacagt ccagaattct taatcccatg tggtcatgtt actttccttt tatttataaa     600
tcattttatt taataatgtt gacaagaata tctatattay rttatgattg ccagaagaag     660
ggtcagtgtt aatgtgctca aatatggtct gtgttctcag ggacacaact ggaagatttg     720
tgagcatgga ttcaaccatc tcatcccaca acacaawatc tacacaactg aatgaaactg     780
stratcctaa ctgcagtcca atcctgacmc tgyccttcct ggccctcatc actgccctgg     840
tttgactggc agaaaacact attatactct gactcctggg attccccatg cacaggaaag     900
ccatctcagt ctatatcctc aaccaggctc tggcagactc cttcttcctc tgctgtcact     960
tccttgactc tatgctacag atcattgact tctatggcat ctatggccat aaattaagca    1020
aagatatctt aggcaatgca gcaatcattc cctatatcac agggctgagc gtcctcagtg    1080
ctattagcac tgcctgtcta tattgtggcc aatctggtac cattgccacc acccaagaaa    1140
catgtcaggt atcatatgtg ccctaatctg ggttctgtcc tttctcatgg gcatccttga    1200
ttggttcttc tcaggattcc tgggtgagac tcattatcat ttgtgggaaa atgttgactt    1260
tattataact gcattttta tttatgcttc tctctgggtc tactcatgag atcctctgt     1320
ggaggaaacc cctgtccagg ctgtatgtta ccatctctct cacagtgatg ggctacctca    1380
tctgtggcct gcctcttggg ctttacttgt ctctgttaca                          1420

<210> SEQ ID NO 105
<211> LENGTH: 200
<212> TYPE: PRT
<213> ORGANISM: Mus musculus

<400> SEQUENCE: 105

Phe Leu Ala Leu Ile Thr Ala Leu Val Leu Ala Glu Asn Thr Ile Ile
  1               5                  10                  15

Leu Leu Leu Gly Phe Pro Met His Arg Lys Ala Ile Ser Val Tyr Ile
             20                  25                  30

Leu Asn Gln Ala Leu Ala Asp Ser Phe Phe Leu Cys Cys His Phe Leu
          35                  40                  45

Asp Ser Met Leu Gln Ile Ile Asp Phe Tyr Gly Ile Tyr Gly His Lys
     50                  55                  60

Leu Ser Lys Asp Ile Leu Gly Asn Ala Ala Ile Ile Pro Tyr Ile Thr
 65                  70                  75                  80

Gly Leu Ser Val Leu Ser Ala Ile Ser Thr Asp Leu Ser Ile Leu Trp
                 85                  90                  95

Pro Ile Trp Tyr His Cys His His Pro Arg Asn Met Ser Gly Ile Ile
            100                 105                 110

Cys Ala Leu Ile Trp Val Leu Ser Phe Leu Met Gly Ile Leu Asp Trp
        115                 120                 125

Phe Phe Ser Gly Phe Leu Gly Glu Thr His Tyr His Leu Trp Glu Asn
    130                 135                 140

Val Asp Phe Ile Ile Thr Ala Phe Pro Ile Val Cys Phe Ser Leu Gly
145                 150                 155                 160

Leu Leu Met Arg Ile Leu Cys Gly Gly Ile Pro Leu Ser Arg Leu Tyr
                165                 170                 175

Val Thr Ile Ser Leu Thr Val Met Gly Tyr Leu Ile Cys Gly Leu Pro
            180                 185                 190

Leu Gly Leu Tyr Leu Ser Leu Leu
        195                 200

<210> SEQ ID NO 106
<211> LENGTH: 730
<212> TYPE: DNA
<213> ORGANISM: Mus musculus

<400> SEQUENCE: 106
tgtgatctgt gttctcaggg acaccgctgg aagcatttgt gagcatggat ccaatcatct      60
catcccacaa cacagaatca caccactgaa tgaaactggt catcccaact gcagtccaat     120
cctgacacca ttctttctgg tcctcatcac tgtactggtg gaattggcag gggaacacca     180
ttatactctg gctcctggga tttcgcatga acaggaaagc aatctcagtt tatgtcctca     240
atctggctct ggcagactcc ttcttttcct ctgttgccat tcattgact ctctgctaca      300
gaacattgac ttcatcaatg cccataaatt aagcaaacat atcttaggaa atgcagcaat     360
cattccctat attgcagggc tgagcctcct cagtgctatt agcatggagc actgcctgtt     420
tatattatgg ccaatctggt accactgcca ccacatgtca gctatcatat gtgccctaat     480
ctgggttccg tcctttctca agggcatcct caatttgttc ttctcaggat tcctgggtga     540
gactcatcat catttgtggg aaaatattga ctttattata actgcatttc tgatttttt      600
atttatgctt ctctgtgggt gcactttggc cctagagctg aggatactct gtggctccag     660
gaagaaaccc ctgtccaggc tgtaagttac catctctctc acagcgatgg tctacctcat     720
ctgtggcctg                                                           730

<210> SEQ ID NO 107
<211> LENGTH: 198
<212> TYPE: PRT
<213> ORGANISM: Mus musculus

<400> SEQUENCE: 107

Phe Leu Val Leu Ile Thr Val Leu Val Glu Leu Ala Gly Asn Thr Ile
 1               5                  10                  15

```
Ile Leu Trp Leu Leu Gly Phe Arg Met Asn Arg Lys Ala Ile Ser Val
             20                  25                  30

Tyr Val Leu Asn Leu Ala Leu Ala Asp Ser Phe Val Phe Leu Cys Cys
         35                  40                  45

His Phe Ile Asp Ser Leu Leu Gln Asn Ile Asp Phe Ile Asn Ala His
     50                  55                  60

Lys Leu Ser Lys His Ile Leu Gly Asn Ala Ala Ile Ile Pro Tyr Ile
 65                  70                  75                  80

Ala Gly Leu Ser Leu Ser Ala Ile Ser Met Glu His Cys Leu Phe
             85                  90                  95

Ile Leu Trp Pro Ile Trp Tyr His Cys His His Met Ser Ala Ile Ile
            100                 105                 110

Cys Ala Leu Ile Trp Val Pro Ser Phe Leu Lys Gly Ile Leu Asn Leu
        115                 120                 125

Phe Phe Ser Gly Phe Leu Gly Glu Thr His His His Leu Trp Glu Asn
        130                 135                 140

Ile Asp Phe Ile Ile Thr Ala Phe Leu Ile Phe Leu Phe Met Leu Leu
145                 150                 155                 160

Cys Gly Cys Thr Leu Ala Leu Glu Leu Arg Ile Leu Cys Gly Ser Arg
                165                 170                 175

Lys Lys Pro Leu Ser Arg Leu Val Thr Ile Ser Leu Thr Ala Met Val
            180                 185                 190

Tyr Leu Ile Cys Gly Leu
        195

<210> SEQ ID NO 108
<211> LENGTH: 847
<212> TYPE: DNA
<213> ORGANISM: Mus musculus

<400> SEQUENCE: 108
ttcagaattc ttgatccatg tggtcatgtt actccccttt tattaataaa tgagtacatt      60
aagccatatt gaaaacaata tctatattat attatgattg cccgaagaag ggtcaatgtt     120
aaggtgatca aatatggcct gttttcctca gggacaccaa tgggtgattt gtttagcatg     180
gatccaacca tctcatccca caacacagaa tcacaccact gaatgaacct ggcccatccc     240
gactgcaatc caatcctggt tctgtccttt ctggtcctca tcgctgtcct ggtgaactg      300
gcaggaaaca ccattgttct ctggctcctg ggattccgca tgcacaggaa acccatctca     360
gtctatgtcc tcaatctggc tctggcagac tccttcttcc tctgctgcca tttcattgac     420
tctctgctac aaatcattga cttcacctat gcccataaat taagcaaaga tatcttagac     480
aatgcagcaa ttgttccctt tatcacaggg ctgagggtcc tcagtgctat tagcatggag     540
cactgcctgt ctgtattgtg ctaatctggg taccactgcc accacctgag aaatatgtca     600
gctatcctat gtgccctaat ctgggttctg tcctttctca tgtccatcct ggactagttc     660
ttctcagaat tcctgcatga gactcatcat catttgtggg aaaatgttga ctttattata     720
actgcatttc tgatttttttt atttatgctt ctctttaggt ccagtctggc cctactgcgg     780
aggatcctcc tgtggctcca ggaggaaata cctgtccacg ctatatgtta tcatttctct     840
cacagtg                                                              847

<210> SEQ ID NO 109
<211> LENGTH: 192
<212> TYPE: PRT
<213> ORGANISM: Mus musculus
```

```
<400> SEQUENCE: 109

Phe Leu Val Leu Ile Ala Val Leu Val Glu Leu Ala Gly Asn Thr Ile
1               5                   10                  15

Val Leu Trp Leu Leu Gly Phe Arg Met His Arg Lys Pro Ile Ser Val
            20                  25                  30

Tyr Val Leu Asn Leu Ala Leu Ala Asp Ser Phe Phe Leu Cys Cys His
            35              40              45

Phe Ile Asp Ser Leu Leu Gln Ile Ile Asp Phe Thr Tyr Ala His Lys
        50              55              60

Leu Ser Lys Asp Ile Leu Asp Asn Ala Ala Ile Val Pro Phe Ile Thr
65              70              75                          80

Gly Leu Arg Val Leu Ser Ala Ile Ser Met Glu His Cys Leu Ser Val
                85              90                  95

Leu Trp Leu Ile Trp Tyr His Cys His His Leu Arg Asn Met Ser Ala
            100             105                 110

Ile Leu Cys Ala Leu Ile Trp Val Leu Ser Phe Leu Met Ser Ile Leu
            115             120                 125

Asp Phe Phe Ser Glu Phe Leu His Glu Thr His His His Leu Trp Glu
        130             135                 140

Asn Val Asp Phe Ile Ile Thr Ala Phe Leu Ile Phe Leu Phe Met Leu
145                 150                 155                 160

Leu Phe Arg Ser Ser Leu Ala Leu Leu Arg Arg Ile Leu Cys Gly Ser
                165             170                 175

Arg Arg Lys Tyr Leu Ser Thr Leu Tyr Val Ile Ile Ser Leu Thr Val
            180             185                 190
```